(12) United States Patent
Singer et al.

(10) Patent No.: US 12,195,725 B2
(45) Date of Patent: Jan. 14, 2025

(54) COMPOSITIONS AND METHODS FOR MODULATING AND DETECTING TISSUE SPECIFIC TH17 CELL PATHOGENICITY

(71) Applicants: Dana-Farber Cancer Institute, Inc., Boston, MA (US); The Broad Institute, Inc., Cambridge, MA (US); Massachusetts Institute of Technology, Cambridge, MA (US); The Brigham and Women's Hospital, Inc., Boston, MA (US)

(72) Inventors: Meromit Singer, Boston, MA (US); Alexandra Schnell, Boston, MA (US); Aviv Regev, Cambridge, MA (US); Vijay K. Kuchroo, Boston, MA (US)

(73) Assignees: Dana-Farber Cancer Institute, Inc., Boston, MA (US); The Brigham and Women's Hospital, Inc., Boston, MA (US); The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 597 days.

(21) Appl. No.: 17/063,617

(22) Filed: Oct. 5, 2020

(65) Prior Publication Data
US 2021/0102166 A1    Apr. 8, 2021

Related U.S. Application Data

(60) Provisional application No. 62/968,981, filed on Jan. 31, 2020, provisional application No. 62/910,451, filed on Oct. 3, 2019.

(51) Int. Cl.
| | | |
|---|---|---|
| *C12N 5/0783* | (2010.01) |
| *A61K 39/00* | (2006.01) |
| *A61P 37/06* | (2006.01) |
| *C12Q 1/6881* | (2018.01) |
| *G01N 33/50* | (2006.01) |

(52) U.S. Cl.
CPC ........ *C12N 5/0637* (2013.01); *A61K 39/4611* (2023.05); *A61K 39/4621* (2023.05); *A61K 39/46433* (2023.05); *A61P 37/06* (2018.01); *C12N 5/0636* (2013.01); *C12Q 1/6881* (2013.01); *G01N 33/5091* (2013.01); *C12Q 2600/106* (2013.01); *C12Q 2600/158* (2013.01); *G01N 2800/52* (2013.01)

(58) Field of Classification Search
CPC ..... C12N 5/0637; C12N 5/0636; A61P 37/06; A61K 35/17
See application file for complete search history.

(56) References Cited

U.S. PATENT DOCUMENTS

| | | |
|---|---|---|
| 4,737,323 A | 4/1988 | Martin et al. |
| 4,837,028 A | 6/1989 | Allen |
| 5,143,854 A | 9/1992 | Pirrung et al. |
| 5,288,644 A | 2/1994 | Beavis et al. |
| 5,324,633 A | 6/1994 | Fodor et al. |
| 5,432,049 A | 7/1995 | Fischer et al. |
| 5,470,710 A | 11/1995 | Weiss et al. |
| 5,492,806 A | 2/1996 | Ormanac et al. |
| 5,503,980 A | 4/1996 | Cantor |
| 5,510,270 A | 4/1996 | Fodor et al. |
| 5,525,464 A | 6/1996 | Drmanac et al. |
| 5,547,839 A | 8/1996 | Dower et al. |
| 5,580,732 A | 12/1996 | Grossman et al. |
| 5,580,737 A | 12/1996 | Polisky et al. |
| 5,641,870 A | 6/1997 | Rinderknecht et al. |
| 5,660,985 A | 8/1997 | Pieken et al. |
| 5,661,028 A | 8/1997 | Foote |
| 5,686,281 A | 11/1997 | Roberts |
| 5,800,992 A | 9/1998 | Fodor et al. |
| 5,811,097 A | 9/1998 | Allison et al. |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |

(Continued)

FOREIGN PATENT DOCUMENTS

| | | |
|---|---|---|
| EP | 0 404 097 A2 | 12/1990 |
| EP | 0 785 280 A2 | 7/1997 |

(Continued)

OTHER PUBLICATIONS

Deng et al., CXCR6/CXCL16 functions as a regulator in metastasis and progression of cancer, Biochimica et Biophysica Acta 1806, pp. 42-49, Publication Date: Feb. 1, 2010 (Year: 2010).*

Cheng et al., Selective organ targeting (SORT) nanoparticles for tissue-specific mRNA delivery and CRISPR-Cas gene editing, Nature Nanotechnology, vol. 15, pp. 313-320, Publication Date: Apr. 2020 (Year: 2020).*

(Continued)

*Primary Examiner* — Peter J Reddig
*Assistant Examiner* — Cheng Lu
(74) *Attorney, Agent, or Firm* — Wenderoth, Lind & Ponack, L.L.P.

(57) ABSTRACT

The subject matter disclosed herein is generally directed to tissue specific modulation of Th17 differentiation and pathogenicity by targeting tissue specific Th17 gene programs and gene targets. The tissue specific modulation may be used therapeutically to treat a disease or condition in the tissue where it arises. The subject matter disclosed herein is also directed to detecting tissue specific Th17 cells for diagnostic and therapeutic methods.

15 Claims, 133 Drawing Sheets

Specification includes a Sequence Listing.

(56) References Cited

U.S. PATENT DOCUMENTS

| | | | |
|---|---|---|---|
| 6,004,811 A | 12/1999 | Seed et al. | |
| 6,040,177 A | 3/2000 | Riddell et al. | |
| 6,284,240 B1 | 9/2001 | Seed et al. | |
| 6,352,694 B1 | 3/2002 | June et al. | |
| 6,392,013 B1 | 5/2002 | Seed et al. | |
| 6,410,014 B1 | 6/2002 | Seed et al. | |
| 6,479,626 B1 | 11/2002 | Kim et al. | |
| 6,489,458 B2 | 12/2002 | Hackett et al. | |
| 6,534,055 B1 | 3/2003 | June et al. | |
| 6,534,261 B1 | 3/2003 | Cox et al. | |
| 6,607,882 B1 | 8/2003 | Cox et al. | |
| 6,746,838 B1 | 6/2004 | Choo et al. | |
| 6,753,162 B1 | 6/2004 | Seed et al. | |
| 6,794,136 B1 | 9/2004 | Eisenberg et al. | |
| 6,797,514 B2 | 9/2004 | Berenson et al. | |
| 6,824,978 B1 | 11/2004 | Cox et al. | |
| 6,866,997 B1 | 3/2005 | Choo et al. | |
| 6,867,041 B2 | 3/2005 | Berenson et al. | |
| 6,887,466 B2 | 5/2005 | June et al. | |
| 6,903,185 B2 | 6/2005 | Kim et al. | |
| 6,905,680 B2 | 6/2005 | June et al. | |
| 6,905,681 B1 | 6/2005 | June et al. | |
| 6,905,874 B2 | 6/2005 | Berenson et al. | |
| 6,933,113 B2 | 8/2005 | Case et al. | |
| 6,979,539 B2 | 12/2005 | Cox et al. | |
| 7,013,219 B2 | 3/2006 | Case et al. | |
| 7,030,215 B2 | 4/2006 | Liu et al. | |
| 7,144,575 B2 | 12/2006 | June et al. | |
| 7,148,203 B2 | 12/2006 | Hackett et al. | |
| 7,160,682 B2 | 1/2007 | Hackett et al. | |
| 7,175,843 B2 | 2/2007 | June et al. | |
| 7,208,152 B2 | 4/2007 | Briskin et al. | |
| 7,220,719 B2 | 5/2007 | Case et al. | |
| 7,232,566 B2 | 6/2007 | June et al. | |
| 7,241,573 B2 | 7/2007 | Choo et al. | |
| 7,241,574 B2 | 7/2007 | Choo et al. | |
| 7,446,190 B2 | 11/2008 | Sadelain et al. | |
| 7,572,631 B2 | 8/2009 | Berenson et al. | |
| 7,585,849 B2 | 9/2009 | Liu et al. | |
| 7,595,376 B2 | 9/2009 | Kim et al. | |
| 7,741,465 B1 | 6/2010 | Eshhar et al. | |
| 7,985,739 B2 | 7/2011 | Kay et al. | |
| 8,021,867 B2 | 9/2011 | Smith et al. | |
| 8,034,334 B2 | 10/2011 | Dudley et al. | |
| 8,088,379 B2 | 1/2012 | Robbins et al. | |
| 8,119,361 B2 | 2/2012 | Smith et al. | |
| 8,119,381 B2 | 2/2012 | Smith et al. | |
| 8,124,369 B2 | 2/2012 | Smith et al. | |
| 8,129,134 B2 | 3/2012 | Smith et al. | |
| 8,133,697 B2 | 3/2012 | Smith et al. | |
| 8,163,514 B2 | 4/2012 | Smith et al. | |
| 8,211,422 B2 | 7/2012 | Eshhar et al. | |
| 8,227,432 B2 | 7/2012 | Hackett et al. | |
| 8,399,645 B2 | 3/2013 | Campana et al. | |
| 8,637,307 B2 | 1/2014 | June et al. | |
| 8,697,854 B2 | 4/2014 | Schendel et al. | |
| 8,735,553 B1 | 5/2014 | Li et al. | |
| 8,906,682 B2 | 12/2014 | June et al. | |
| 8,911,993 B2 | 12/2014 | June et al. | |
| 8,916,381 B1 | 12/2014 | June et al. | |
| 8,975,071 B1 | 3/2015 | June et al. | |
| 9,062,111 B2 | 6/2015 | Nichol et al. | |
| 9,101,584 B2 | 8/2015 | June et al. | |
| 9,102,760 B2 | 8/2015 | June et al. | |
| 9,102,761 B2 | 8/2015 | June et al. | |
| 9,132,281 B2 | 9/2015 | Zeng et al. | |
| 9,233,125 B2 | 1/2016 | Davila et al. | |
| 9,320,811 B2 | 4/2016 | Jure-Kunkel | |
| 9,327,014 B2 | 5/2016 | Gurney et al. | |
| 2004/0224402 A1 | 11/2004 | Bonyhadi et al. | |
| 2010/0104509 A1 | 4/2010 | King et al. | |
| 2012/0244133 A1 | 9/2012 | Rosenberg et al. | |
| 2013/0071414 A1 | 3/2013 | Dotti et al. | |
| 2015/0368342 A1 | 12/2015 | Wu et al. | |
| 2015/0368360 A1 | 12/2015 | Liang et al. | |
| 2016/0046724 A1 | 2/2016 | Brogdon et al. | |
| 2016/0129109 A1 | 5/2016 | Davila et al. | |
| 2016/0166613 A1 | 6/2016 | Spencer et al. | |
| 2016/0175359 A1 | 6/2016 | Spencer et al. | |
| 2017/0283504 A1 | 10/2017 | Wiltzius et al. | |
| 2017/0349950 A1* | 12/2017 | Regev | C12Q 1/6881 |
| 2018/0085444 A1 | 3/2018 | Morgan et al. | |
| 2019/0045582 A1 | 2/2019 | He | |

FOREIGN PATENT DOCUMENTS

| | | | |
|---|---|---|---|
| EP | 0 373 203 B2 | 2/2007 | |
| WO | 92/15322 A1 | 9/1992 | |
| WO | 93/11161 A1 | 6/1993 | |
| WO | 95/21265 A1 | 8/1995 | |
| WO | 96/31622 A1 | 10/1996 | |
| WO | 96/40281 A2 | 12/1996 | |
| WO | 97/10365 A1 | 3/1997 | |
| WO | 97/27317 A1 | 7/1997 | |
| WO | 03/020763 A2 | 3/2003 | |
| WO | 03/057171 A2 | 7/2003 | |
| WO | 2004/033685 A1 | 4/2004 | |
| WO | 2004/044004 A2 | 5/2004 | |
| WO | 2004/074322 A1 | 9/2004 | |
| WO | 2005/113595 A2 | 12/2005 | |
| WO | 2005/114215 A2 | 12/2005 | |
| WO | 2006/000830 A2 | 1/2006 | |
| WO | 2006/125962 A2 | 11/2006 | |
| WO | 2008/038002 A2 | 4/2008 | |
| WO | 2008/039818 A2 | 4/2008 | |
| WO | WO-2008146272 A2 * | 12/2008 | C07K 14/7158 |
| WO | 2009/012418 A2 | 1/2009 | |
| WO | 2011/146862 A1 | 11/2011 | |
| WO | 2012/048265 A2 | 4/2012 | |
| WO | 2012/058460 A2 | 5/2012 | |
| WO | 2012/079000 A1 | 6/2012 | |
| WO | 2012/082470 A2 | 6/2012 | |
| WO | 2013/039889 A1 | 3/2013 | |
| WO | 2013/040371 A2 | 3/2013 | |
| WO | 2013/044225 A1 | 3/2013 | |
| WO | 2013/154760 A1 | 10/2013 | |
| WO | 2013/166321 A1 | 11/2013 | |
| WO | 2013/176915 A1 | 11/2013 | |
| WO | 2014/011987 A1 | 1/2014 | |
| WO | 2014/018863 A1 | 1/2014 | |
| WO | 2014/059173 A2 | 4/2014 | |
| WO | 2014/083173 A1 | 6/2014 | |
| WO | 2014/093622 A2 | 6/2014 | |
| WO | 2014/133567 A1 | 9/2014 | |
| WO | 2014/133568 A1 | 9/2014 | |
| WO | 2014/134165 A1 | 9/2014 | |
| WO | 2014/134351 A2 | 9/2014 | |
| WO | 2014/145631 A1 | 9/2014 | |
| WO | 2014/172606 A1 | 10/2014 | |
| WO | 2014/184744 A1 | 11/2014 | |
| WO | 2014/191128 A1 | 12/2014 | |
| WO | 2014/204725 A1 | 12/2014 | |
| WO | 2014/210353 A2 | 12/2014 | |
| WO | 2015/057834 A1 | 4/2015 | |
| WO | 2015/057852 A1 | 4/2015 | |
| WO | 2015/120096 A2 | 8/2015 | |
| WO | 2015/130968 A2 | 9/2015 | |
| WO | 2015/142675 A2 | 9/2015 | |
| WO | 2015/158671 A1 | 10/2015 | |
| WO | 2015/187528 A1 | 12/2015 | |
| WO | 2016/000304 A1 | 1/2016 | |
| WO | 2016/011210 A2 | 1/2016 | |
| WO | 2016/014789 A2 | 1/2016 | |
| WO | 2016/040476 A1 | 3/2016 | |
| WO | 2016/070061 A1 | 5/2016 | |
| WO | 2016/106236 A1 | 6/2016 | |
| WO | 2016/138488 A2 | 9/2016 | |
| WO | 2016/168584 A1 | 10/2016 | |
| WO | 2016/191756 A1 | 12/2016 | |
| WO | 2016/196388 A1 | 12/2016 | |
| WO | 2017/004916 A1 | 1/2017 | |
| WO | 2017/011804 A1 | 1/2017 | |
| WO | 2017/070395 A1 | 4/2017 | |
| WO | 2017/164936 A1 | 9/2017 | |

(56) References Cited

FOREIGN PATENT DOCUMENTS

| WO | 2017/211900 A1 | 12/2017 |
| WO | 2018/028647 A1 | 2/2018 |
| WO | 2018/191553 A1 | 10/2018 |
| WO | 2018/213708 A1 | 11/2018 |
| WO | 2018/213726 A1 | 11/2018 |
| WO | 2019/005884 A1 | 1/2019 |
| WO | 2019/005886 A1 | 1/2019 |
| WO | 2019/018423 A1 | 1/2019 |
| WO | 2019/060746 A1 | 3/2019 |
| WO | 2019/071048 A1 | 4/2019 |
| WO | 2019/094984 A1 | 5/2019 |
| WO | 2019/126709 A1 | 6/2019 |
| WO | 2019/126716 A1 | 6/2019 |
| WO | 2019/126762 A2 | 6/2019 |
| WO | 2020/033601 A1 | 2/2020 |
| WO | 2020/077236 A1 | 4/2020 |
| WO | 2020/131862 A1 | 6/2020 |

OTHER PUBLICATIONS

O'Connor et al., Adjuvant Immunotherapy of Experimental Autoimmune Encephalomyelitis, Journal of Immunology, 188(5): 2093-2101, (Year: 2011).*

Kim et al., Two-photon laser scanning microscopy imaging of intact spinal cord and cerebral cortex reveals requirement for CXCR6 and neuroinflammation in immune cell infiltration of cortical injury sites, Journal of Immunological Methods, 352, 89-100, Publication Date: Oct. 2, 2009 (Year: 2009).*

Butcher et al., CXCR6 regulates the recruitment of pro-inflammatory IL-17A-producing T cells into atherosclerotic aortas, International Immunology, vol. 28, No. 5, pp. 255-261, Publication Date: Nov. 27, 2015 (Year: 2015).*

Selplg genecards downloaded from: https://www.genecards.org/cgi-bin/carddisp.pl?gene=SELPLG, on Feb. 20, 2024 (Year: 2024).*

\* cited by examiner

Intestinal Th17 cell heterogeneity at single-cell resolution

Th17 self-renewing

Th17-pre Th1 like effector

Spleen Cluster 0 is related to all Th17 clusters in CNS and dLN

Hashing information:
- 5' hashing 10X with TCR information
- 2 channels- each one EAE mouse
- 7 tissues per mouse

IL-17A

IL-2

SEQUENCE LISTING

```
<160> NUMBER OF SEQ ID NOS: 21

<210> SEQ ID NO 1
<211> LENGTH: 288
<212> TYPE: PRT
<213> ORGANISM: Artificial
<220> FEATURE:
<223> OTHER INFORMATION: Synthetic

<400> SEQUENCE: 1

Met Asp Pro Ile Arg Ser Arg Thr Pro Ser Pro Ala Arg Glu Leu Leu
1               5                   10                  15

Ser Gly Pro Gln Pro Asp Gly Val Gln Pro Thr Ala Asp Arg Gly Val
            20                  25                  30

Ser Pro Pro Ala Gly Gly Pro Leu Asp Gly Leu Pro Ala Arg Arg Thr
        35                  40                  45

Met Ser Arg Thr Arg Leu Pro Ser Pro Ala Pro Ser Pro Ala Phe
    50                  55                  60

Ser Ala Asp Ser Phe Ser Asp Leu Leu Arg Gln Phe Asp Pro Ser Leu
```

```
              65                  70                  75                  80
          Phe Asn Thr Ser Leu Phe Asp Ser Leu Pro Pro Phe Gly Ala His His
                              85                  90                  95
          Thr Glu Ala Ala Thr Gly Glu Trp Asp Glu Val Gln Ser Gly Leu Arg
                          100                 105                 110
          Ala Ala Asp Ala Pro Pro Thr Met Arg Val Ala Val Thr Ala Ala
                      115                 120                 125
          Arg Pro Pro Arg Ala Lys Pro Ala Pro Arg Arg Ala Ala Gln Pro
              130                 135                 140
          Ser Asp Ala Ser Pro Ala Ala Gln Val Asp Leu Arg Thr Leu Gly Tyr
          145                 150                 155                 160
          Ser Gln Gln Gln Glu Lys Ile Lys Pro Lys Val Arg Ser Thr Val
                              165                 170                 175
          Ala Gln His His Glu Ala Leu Val Gly His Gly Phe Thr His Ala His
                          180                 185                 190
          Ile Val Ala Leu Ser Gln His Pro Ala Ala Leu Gly Thr Val Ala Val
                      195                 200                 205
          Lys Tyr Gln Asp Met Ile Ala Ala Leu Pro Glu Ala Thr His Glu Ala
              210                 215                 220
          Ile Val Gly Val Gly Lys Gln Trp Ser Gly Ala Arg Ala Leu Glu Ala
          225                 230                 235                 240
          Leu Leu Thr Val Ala Gly Glu Leu Arg Gly Pro Pro Leu Gln Leu Asp
                              245                 250                 255
          Thr Gly Gln Leu Leu Lys Ile Ala Lys Arg Gly Gly Val Thr Ala Val
                          260                 265                 270
          Glu Ala Val His Ala Trp Arg Asn Ala Leu Thr Gly Ala Pro Leu Asn
                      275                 280                 285

<210> SEQ ID NO 2
<211> LENGTH: 183
<212> TYPE: PRT
<213> ORGANISM: Artificial
<220> FEATURE:
<223> OTHER INFORMATION: Synthetic

<400> SEQUENCE: 2

Arg Pro Ala Leu Glu Ser Ile Val Ala Gln Leu Ser Arg Pro Asp Pro
          1               5                   10                  15
          Ala Leu Ala Ala Leu Thr Asn Asp His Leu Val Ala Leu Ala Cys Leu
                          20                  25                  30
          Gly Gly Arg Pro Ala Leu Asp Ala Val Lys Lys Gly Leu Pro His Ala
                      35                  40                  45
          Pro Ala Leu Ile Lys Arg Thr Asn Arg Arg Ile Pro Glu Arg Thr Ser
              50                  55                  60
          His Arg Val Ala Asp His Ala Gln Val Arg Val Leu Gly Phe Phe
          65                  70                  75                  80
          Gln Cys His Ser His Pro Ala Gln Ala Phe Asp Asp Ala Met Thr Gln
                              85                  90                  95
          Phe Gly Met Ser Arg His Gly Leu Leu Gln Leu Phe Arg Arg Val Gly
                          100                 105                 110
          Val Thr Glu Leu Glu Ala Arg Ser Gly Thr Leu Pro Pro Ala Ser Gln
                      115                 120                 125
          Arg Trp Asp Arg Ile Leu Gln Ala Ser Gly Met Lys Arg Ala Lys Pro
              130                 135                 140
          Ser Pro Thr Ser Thr Gln Thr Pro Asp Gln Ala Ser Leu His Ala Phe
```

```
                145                 150                 155                 160
Ala Asp Ser Leu Glu Arg Asp Leu Asp Ala Pro Ser Pro Met His Glu
                165                 170                 175

Gly Asp Gln Thr Arg Ala Ser
            180

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
1               5

<210> SEQ ID NO 4
<211> LENGTH: 10
<212> TYPE: PRT
<213> ORGANISM: Simian virus 40

<400> SEQUENCE: 4

Pro Lys Lys Lys Arg Lys Val Glu Ala Ser
1               5                   10

<210> SEQ ID NO 5
<211> LENGTH: 16
<212> TYPE: PRT
<213> ORGANISM: Artificial
<220> FEATURE:
<223> OTHER INFORMATION: Nucleoplasmin bipartite NLS from Homo sapiens

<400> SEQUENCE: 5

Lys Arg Pro Ala Ala Thr Lys Lys Ala Gly Gln Ala Lys Lys Lys Lys
1               5                   10                  15

<210> SEQ ID NO 6
<211> LENGTH: 9
<212> TYPE: PRT
<213> ORGANISM: Artificial
<220> FEATURE:
<223> OTHER INFORMATION: c-myc NLS from Homo sapiens

<400> SEQUENCE: 6

Pro Ala Ala Lys Arg Val Lys Leu Asp
1               5

<210> SEQ ID NO 7
<211> LENGTH: 11
<212> TYPE: PRT
<213> ORGANISM: Artificial
<220> FEATURE:
<223> OTHER INFORMATION: c-myc NLS from Homo sapiens

<400> SEQUENCE: 7

Arg Gln Arg Arg Asn Glu Leu Lys Arg Ser Pro
1               5                   10

<210> SEQ ID NO 8
<211> LENGTH: 38
<212> TYPE: PRT
<213> ORGANISM: Artificial
<220> FEATURE:
<223> OTHER INFORMATION: hRNPA1 M9 NLS from Homo sapiens

<400> SEQUENCE: 8
```

```
Asn Gln Ser Ser Asn Phe Gly Pro Met Lys Gly Gly Asn Phe Gly
1               5                   10                  15

Arg Ser Ser Gly Pro Tyr Gly Gly Gly Gln Tyr Phe Ala Lys Pro
            20                  25                  30

Arg Asn Gln Gly Gly Tyr
        35
```

<210> SEQ ID NO 9
<211> LENGTH: 42
<212> TYPE: PRT
<213> ORGANISM: Artificial
<220> FEATURE:
<223> OTHER INFORMATION: IBB domain from importin-alpha from Homo
      sapiens

<400> SEQUENCE: 9

```
Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40
```

<210> SEQ ID NO 10
<211> LENGTH: 8
<212> TYPE: PRT
<213> ORGANISM: Artificial
<220> FEATURE:
<223> OTHER INFORMATION: Myoma T protein from Homo sapiens

<400> SEQUENCE: 10

```
Val Ser Arg Lys Arg Pro Arg Pro
1               5
```

<210> SEQ ID NO 11
<211> LENGTH: 8
<212> TYPE: PRT
<213> ORGANISM: Artificial
<220> FEATURE:
<223> OTHER INFORMATION: Myoma T protein from Homo sapiens

<400> SEQUENCE: 11

```
Pro Pro Lys Lys Ala Arg Glu Asp
1               5
```

<210> SEQ ID NO 12
<211> LENGTH: 8
<212> TYPE: PRT
<213> ORGANISM: Homo sapiens

<400> SEQUENCE: 12

```
Pro Gln Pro Lys Lys Lys Pro Leu
1               5
```

<210> SEQ ID NO 13
<211> LENGTH: 12
<212> TYPE: PRT
<213> ORGANISM: Mus sp.

<400> SEQUENCE: 13

```
Ser Ala Leu Ile Lys Lys Lys Lys Lys Met Ala Pro
1               5                   10
```

<210> SEQ ID NO 14

```
<211> LENGTH: 5
<212> TYPE: PRT
<213> ORGANISM: Influenza virus

<400> SEQUENCE: 14

Asp Arg Leu Arg Arg
1               5

<210> SEQ ID NO 15
<211> LENGTH: 7
<212> TYPE: PRT
<213> ORGANISM: Influenza virus

<400> SEQUENCE: 15

Pro Lys Gln Lys Lys Arg Lys
1               5

<210> SEQ ID NO 16
<211> LENGTH: 10
<212> TYPE: PRT
<213> ORGANISM: Hepatitis D virus

<400> SEQUENCE: 16

Arg Lys Leu Lys Lys Lys Ile Lys Lys Leu
1               5                   10

<210> SEQ ID NO 17
<211> LENGTH: 10
<212> TYPE: PRT
<213> ORGANISM: Mus sp.

<400> SEQUENCE: 17

Arg Glu Lys Lys Lys Phe Leu Lys Arg Arg
1               5                   10

<210> SEQ ID NO 18
<211> LENGTH: 20
<212> TYPE: PRT
<213> ORGANISM: Homo sapiens

<400> SEQUENCE: 18

Lys Arg Lys Gly Asp Glu Val Asp Gly Val Asp Glu Val Ala Lys Lys
1               5                   10                  15

Lys Ser Lys Lys
            20

<210> SEQ ID NO 19
<211> LENGTH: 17
<212> TYPE: PRT
<213> ORGANISM: Homo sapiens

<400> SEQUENCE: 19

Arg Lys Cys Leu Gln Ala Gly Met Asn Leu Glu Ala Arg Lys Thr Lys
1               5                   10                  15

Lys

<210> SEQ ID NO 20
<211> LENGTH: 107
<212> TYPE: PRT
<213> ORGANISM: Homo sapiens

<400> SEQUENCE: 20

Ile Glu Val Met Tyr Pro Pro Pro Tyr Leu Asp Asn Glu Lys Ser Asn
1               5                   10                  15
```

```
Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
 50                  55                      60

Trp Val Arg Ser Lys Arg Ser Arg Leu Leu His Ser Asp Tyr Met Asn
 65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 21
<211> LENGTH: 9
<212> TYPE: PRT
<213> ORGANISM: Homo sapiens

<400> SEQUENCE: 21

Ile Glu Val Met Tyr Pro Pro Pro Tyr
1               5
```

COMPOSITIONS AND METHODS FOR MODULATING AND DETECTING TISSUE SPECIFIC TH17 CELL PATHOGENICITY

This application claims the benefit of U.S. Provisional Application Nos. 62/910,451, filed Oct. 3, 2019 and, 62/968,981, filed Jan. 31, 2020. The entire contents of the above-identified applications are hereby fully incorporated herein by reference.

REFERENCE TO AN ELECTRONIC SEQUENCE LISTING

The contents of the electronic sequence listing ("BROD_4960US_ST25.txt"; Size is 10 kilobytes and it was created on Sep. 29, 2020) is herein incorporated by reference in its entirety.

TECHNICAL FIELD

The subject matter disclosed herein is generally directed to modulation and detection of Th17 pathogenicity by use of tissue specific Th17 targets.

BACKGROUND

The immune system must strike a balance between mounting proper responses to pathogens and avoiding uncontrolled, autoimmune reaction. Pro-inflammatory IL-17-producing Th17 cells are a prime case in point: as a part of the adaptive immune system, Th17 cells mediate clearance of fungal infections, but they are also strongly implicated in the pathogenesis of autoimmunity (Korn et al., IL-17 and Th17 Cells. Annu Rev Immunol. 2009; 27:485-517). In mice, although Th17 cells are present at sites of tissue inflammation and autoimmunity (Korn et al., 2009), they are also normally present at mucosal barrier sites, where they maintain barrier functions without inducing tissue inflammation (Blaschitz and Raffatellu, 2010). Th17 cells are pathogenic drivers of multiple autoimmune diseases, including multiple sclerosis (MS), psoriasis, rheumatoid arthritis, and inflammatory bowel disease (Korn et al. 2009; and Weaver et al. The Th17 pathway and inflammatory diseases of the intestines, lungs, and skin. Annu Rev Pathol. 2013 Jan. 24; 8:477-512). Th17 are also involved in Host defense against extracellular bacterial and fungal infections (Bedoya, et al., Th17 cells in immunity and autoimmunity. Clin Dev Immunol. 2013; 2013:986789) and contribute to intestinal barrier integrity by secreting IL-17, IL-21, and IL-22 inducing expression of anti-microbial peptides, tight junction proteins, and the secretion of IgA (Blaschitz et al. Th17 cytokines and the gut mucosal barrier. J Clin Immunol. 2010 March; 30(2):196-203; and Kinugasa, et al., Claudins regulate the intestinal barrier in response to immune mediators. Gastroenterology. 2000 June; 118(6): 1001-11).

Interleukin (IL)-17-producing helper T cells (Th17 cells) have been identified as a distinct lineage of CD4+ T helper cells producing IL-17A and IL-17F and are critical drivers of autoimmune tissue inflammation in experimental autoimmune encephalomyelitis (EAE) and in other autoimmune conditions (Korn et al., 2009). In a recent study, it has been shown that the Th17 cell differentiation program is regulated through two self-reinforcing and mutually antagonistic modules of positive and negative regulators (Yosef et al., 2013). This model was supported by transcriptional silencing and genetic ablation experiments (Yosef et al., 2013), as well as by chromatin immunoprecipitation (ChIP)-seq data (Xiao et al., 2014). The positive regulators promote the Th17 cell program while inhibiting the transcriptional programs of other T helper (Th) cell lineages (Th1, Treg). This suggests that there is not only a need for positive regulators to push the differentiation into a positive direction but also for concurrent inhibition of opposing differentiation programs to achieve unidirectional T cell differentiation. Other studies also support such a mutually antagonistic design in other Th lineages (O'Shea and Paul, 2010). However, how this is achieved for Th17 cells has not been elucidated.

In humans, functionally distinct Th17 cells have been described; for instance, Th17 cells play a protective role in clearing different types of pathogens like *Candida albicans* (Hernandez-Santos and Gaffen, 2012) or *Staphylococcus aureus* (Lin et al., 2009), and promote barrier functions at the mucosal surfaces (Symons et al., 2012), despite their pro-inflammatory role in autoimmune diseases such as IBD, rheumatoid arthritis, multiple sclerosis, psoriasis systemic lupus erythematous and asthma (Waite and Skokos, 2012). IL-17 is increased in multiple autoimmune diseases, such as, multiple sclerosis, rheumatoid arthritis, psoriasis, and IBD (Lock et al. 2002, Aarvak 1999, Teunissen 1998, Burkett 2015). IL-23R is susceptibility gene for IBD (Duerr et al. 2006). Transfer of autoantigen-specific Th17 cells is sufficient to induce autoimmune disease (Jaeger 2009). Loss of Th17 differentiation cytokines (IL-6, IL-1, IL-23) results in inhibition of the development of autoimmunity (Levesque 2016, Okuda 1999, Thakker 2007). Overall, Th17 cells are heterogenous, plastic, shaped by the environment and migratory. Thus, there is considerable diversity in the biological function of Th17 cells and in their ability to induce tissue inflammation or provide tissue protection.

Accordingly, there exists a need for a better understanding of the dynamic regulatory network that modulates, controls, or otherwise influences T cell balance, including Th17 cell differentiation, maintenance and function, and means for exploiting this network in a variety of therapeutic and diagnostic methods.

SUMMARY

In one aspect, the present invention provides for a method of shifting tissue specific T cell balance in a population of cells comprising T cells, said method comprising contacting the population of cells with one or more agents capable of binding to or modulating expression, activity, and/or function of one or more gene products in Tables 1-4 or FIG. 17. In certain embodiments, the one or more gene or gene products is selected from the group consisting: Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1; or Slamf6, Ccr6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411N06Rik, Ndufa4, Ctss and Adk; or Cxcr6, AA467197, Plac8, Ifitm2, Ifitm1, Ifitm3, Bhlhe40, Nkg7, Ifngr1, Ermn, Ctsw, Ggt1, Pglyrp1, Klrd1, Sema4a, Gramd3, Il18rap, Ccr2, Zyx, 2810001G20Rik, AC163354.1, Serpinb6b, Itgb1, Ras111a, Syt13, Klrc1, Id2, Bbc3, Ostf1, Car5b, Paox, Gcnt2, Furin, Slc2a3, Lilr4b, Rom1, Satb1, Il2rb, Hcst, Lgals3, Nptn, Ly6a, Serpinb9, Dnajc15, Anxa1, Ctsd, Crip1, Gzmb, Atp8b4 and Coxl7; or Slamf6, Ifi2712a, Izumo1r, Tcrg-C2, Timp2, Ikzf2, Cd27, Ccr6, Tnfsf8, Tbc1d4, Nav2, Cldndl, Tspan32, Rtp4, Lag3, Ighm, Trbcl, Cd9, Ctss, Ctla4, Jaml, Iigpl, St3gal6, Ccr7, Klf3, Rgs10, Zbtb20, Id3, Nt5e, Asb2, Hmgnl, Tox, Adk, Maf, Lmo4, Ifitl, Ar, Ndufa4, Aqp3, Il6ra, Chd3, Stat1, Tcrg-C4, Rflnb, Bcl2, Arl5c, Ikzf3, Isg15, Mtssl, Art2b, Cpe, Foxp1 and Ifi203; or Jmjd3, Prdm1, cMaf, Areg, Ramp3, and/or Sat1.

In certain embodiments, Th17 cell balance is shifted towards Treg-like cells and/or is shifted away from Th17 cells, or is shifted towards Th17 cells and/or is shifted away from Treg-like cells. In certain embodiments, Th17 cell balance is shifted towards non-pathogenic Th17 cells and/or is shifted away from pathogenic Th17 cells; or is shifted towards pathogenic Th17 cells and/or is shifted away from non-pathogenic Th17 cells.

In certain embodiments, the one or more agents bind to one or more surface markers on one or more Th17 cells and modulate the activity or function of the one or more Th17 cells. In certain embodiments, the one or more surface markers are selected from CXCR6 and SLAM1F6. In certain embodiments, the one or more agents comprise a small molecule, small molecule degrader, genetic modifying agent, antibody, antibody fragment, antibody-like protein scaffold, aptamer, protein, or any combination thereof. In certain embodiments, the antibody is a bi-specific antibody. In certain embodiments, the bi-specific antibody is specific for CXCR6 and another surface marker on Th17 cells expressing CXCR6. In certain embodiments, the genetic modifying agent comprises a CRISPR system, RNAi system, zinc finger nuclease system, TALE system, or a meganuclease. In certain embodiments, the CRISPR system comprises a CRISPR-Cas base editing system, a prime editor system, or a CAST system.

In certain embodiments, the population of cells comprises naïve T cells, Th1 cells and/or Th17 cells. In certain embodiments, the population of cells are in vitro cells. In certain embodiments, the population of cells is an in vivo population of cells in a subject at risk for or suffering from a disease or condition characterized by an aberrant immune response, whereby the one or more agents are used to treat the disease or condition. In certain embodiments, the one or more agents is targeted to the spleen. In certain embodiments, the population of cells are ex vivo cells obtained from a healthy donor subject or from a subject at risk for or suffering from a disease or condition characterized by an aberrant immune response.

In certain embodiments, the disease is an inflammatory and/or autoimmune disorder. In certain embodiments, the inflammatory disorder is selected from the group consisting of Multiple Sclerosis (MS), Irritable Bowel Disease (IBD), Crohn's disease, ulcerative colitis, spondyloarthritides, Systemic Lupus Erythematosus (SLE), Vitiligo, rheumatoid arthritis, psoriasis, Sjögren's syndrome, diabetes, psoriasis, Irritable bowel syndrome (IBS), allergic asthma, food allergies and rheumatoid arthritis.

In certain embodiments, the condition is an autoimmune response. In certain embodiments, the subject at risk for or suffering from an autoimmune response is a subject undergoing immunotherapy. In certain embodiments, the immunotherapy is checkpoint blockade therapy and/or adoptive cell transfer. In certain embodiments, the checkpoint blockade therapy comprises anti-PD1, anti-CTLA4, anti-PD-L1, anti-TIM3, anti-TIGIT, anti-LAG3, or combinations thereof. In certain embodiments, the one or more agents are administered before, during or after administering the immunotherapy. In certain embodiments, the subject undergoing immunotherapy is suffering from cancer.

In certain embodiments, the population of T cells comprises naïve T cells that are differentiated into Th17 cells, Th1 cells and/or Treg cells. In certain embodiments, the one or more agents are administered to the population of cells during differentiation.

In another aspect, the present invention provides for a population of T cells obtained by the method according to any embodiment herein. In another aspect, the present invention provides for a pharmaceutical composition comprising the population of T cells according to any embodiment herein. In another aspect, the present invention provides for a method of treating a disease or condition characterized by an aberrant immune response comprising administering the pharmaceutical composition according to any embodiment herein to a subject in need thereof.

In another aspect, the present invention provides for a method of monitoring a Th17 immune response in a subject in need thereof comprising detecting one or more Th17 cells characterized by expression of a gene program selected from proliferating, Treg-like, effector-like, $T_{FH}$-like, Naïve-like and ISG-high, wherein the gene programs comprise expression of one or more genes according to FIG. 4C. In certain embodiments, the ISG-high Th17 cells are detected by detecting the expression of PDL1 (CD274) on Th17 cells.

In another aspect, the present invention provides for a method of monitoring a Th17 immune response in a subject in need thereof comprising detecting one or more pathogenic and/or stem-like Th17 cells in a sample obtained from the subject, wherein pathogenic Th17 cells have increased expression of one or more genes selected from the group consisting of Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1; and wherein stem-like Th17 cells have increased expression of one or more genes selected from the group consisting of Slamf6, Ccr6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411 N06Rik, Ndufa4, Ctss and Adk. In certain embodiments, the sample is obtained from the spleen. In certain embodiments, the sample is obtained from the colon. In certain embodiments, the subject was treated or is currently being treated with antibiotics. In certain embodiments, the pathogenic Th17 cells are detected by detecting the expression of Cxcr6. In certain embodiments, the stem-like Th17 cells are detected by detecting the expression of Slamf6. In certain embodiments, the one or more Th17 cells are detected in a tissue sample. In certain embodiments, the detection comprises immunohistochemistry or cell sorting. In certain embodiments, the one or more Th17 cells are quantitated.

In another aspect, the present invention provides for a method of treating an autoimmune disease or condition in a subject in need thereof comprising (a) determining whether the disease in the subject to be treated has expansion of a pathogenic Th17 population in the spleen; and (b) administering an agent that reduces the pathogenic Th17 cell population or shifts the Th17 population to a non-pathogenic state. In certain embodiments, determining expansion of a pathogenic population in the spleen comprises detecting expression of one or more biomarkers from selected from the group consisting of Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1. In certain embodiments, determining expansion of a pathogenic population of Th17 cells comprises detecting increased expression of Cxcr6 relative to a control. In certain embodiments, the one or more agents decreases Cxcr6 expression. In certain embodiments, the one or more agents comprises an antibody that binds to Cxcr6. In certain embodiments, the one or more agents is a CRISPR-Cas system comprising a guide molecule configured to bind to a target sequence of Cxcr6. In certain embodiments, the CRISPR system comprises a CRISPR-Cas base editing system, a prime editor system, or a CAST system. In certain embodiments, the agent reduces IFN-gamma signaling in the pathogenic Th17 population. In certain embodiments, Th17 cells characterized by expression of one or more genes selected from the group consisting of Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1 are targeted. In certain embodiments, Cxcr6 is targeted on the Th17 cells. In certain embodiments, the one or more agents are targeted to the spleen.

In another aspect, the present invention provides for a population of CD4 T cells modified ex vivo to comprise reduced expression, activity or function of CXCR6. In another aspect, the present invention provides for a population of CD4 T cells enriched for cells expressing SLAMF6. In another aspect, the present invention provides for a method of treating a subject suffering from an autoimmune disease comprising administering the population of cells according to any embodiment herein to the subject.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 1B. UMAP analysis of single Th17 cells labeled by tissue. Single cell analysis performed with 10× genomics. The tissues were labeled using 5' hashing antibodies. TCR information was also obtained. FIG. 1C. Cells from each tissue were sorted from the mouse by FACS to select for Th17 cells that express tdTomato+ and GFP+/−. FIG. 1D. Detailed gating strategy for isolating Th17 cells from the mouse.

FIG. 2B. Graph showing the percentage of TdTomato positive CD4 T cells that are also GFP positive or negative in each tissue. GFP+Th17 cells are current Th17 cells because they are currently expressing Il17 and GFP− Th17 cells are ex-Th17 cells because they at one point expressed Il17, but are not expressing at the time of sorting.

FIG. 3B. Projection of Foxp3 and Mki67 expression on UMAP plot. FIG. 3C. Heatmap showing genes that are up (top) and downregulated (bottom) in Th17 cells from 1. all tissues, 2. multiple tissues and 3. single tissues. FIG. 3D. UMAP labeled by clusters. FIG. 3E. Heatmap showing differential expression of genes labeled by cluster and tissue. FIG. 3F. Average expression of the indicated genes in untreated tissues and the percentage of Th17 cells expressing the gene in each tissue. FIG. 3G. Tissue expression of the indicated pathways and processes shows tissue specific expression.

FIG. 4B. Heatmaps showing that the tissues share specific clusters for proliferating, Treg-like, effector-like, $T_{FH}$-like, Naïve-like and ISG-high (interferon stimulated genes) expression programs. FIG. 4C. Average expression of the indicated genes for each program and the percentage of Th17 cells expressing the gene in each tissue.

FIG. 5A. tSNE plots of spleen and mLN (mesenteric lymph nodes) labeled for CD274 expression. FIG. 5B. Graphs showing expression levels of ISG-high genes in PDL1− and PDL1+ Th17 cells.

FIG. 6A. Diagram of Il17Cre$^{TdT}$×Foxp3$^{GFP}$ mouse used to select for Treg-like Th17 cells and FACS showing isolation of Treg-like Th17 cells. FIG. 6B. Graphs showing the percentage of Treg-like Th17 cells in each tissue as determined by FACS and 10× scRNA-seq. FIG. 6C. UMAP of Th17 cells from the mouse labeled by tissue. FIG. 6D. UMAP of Th17 cells from the mouse labeled by cluster. FIG. 6E. Pie charts showing the number of cells identified for each cluster and the percentage that the cluster is identified in each tissue. FIG. 6F. Diagrams showing the possible origin of the Treg-like Th17 cells and the origin of the Treg-like Th17 cells. The Treg-like Th17 cells originate mainly from Treg cells. FIG. 6G. Graphs showing TCR clonal overlap of Treg cells and non-Treg cells in the spleen and colon. FIG. 6H. Plots from 2 mice showing TCR clonal overlap of colon Treg cells and colon Th17 cells as compared to non-Treg cells. FIG. 6I. Heatmaps from 2 mice showing TCR clonal overlap of colon Treg cells and colon Th17 cells as compared to non-Treg cells.

FIG. 7B. UMAP of intestinal Th17 cells labeled by Il17$^{eGFP}$ FIG. 7C. UMAP of intestinal Th17 cells labeled by EAE or untreated. FIG. 7D. Graph showing the percentage of each cluster in the colon and small intestine.

FIG. 10A. UMAP of Th17 cells from the mouse labeled by tissue. FIG. 10B. UMAP of Th17 cells from the mouse labeled by EAE or untreated (UT). The spleen EAE cluster is circled. FIG. 10C. Heatmap showing that clusters are shared across tissues in EAE. FIG. 10D. Average expression of the indicated genes and the percentage of Th17 cells expressing the gene in each untreated or EAE tissue. FIG. 10E. Comparison of EAE and UT tissues in cells order by monocle pseudotime. FIG. 10F. Diffusion map for EAE.

FIG. 12A. Heatmaps for 2 mice showing top 20 TCR clones in EAE and tissue expression of TCR clones. FIG. 12B. Charts showing TCR clones expressed in greater than 5 cells that are expressed in each tissue.

FIG. 13B. Graph showing the percentage of Th17 cells in each tissue during EAE. FIG. 13C. UMAP plots of Th17 cells in the spleen in EAE and UT labeled by treatment and cluster showing EAE specific clusters. FIG. 13D. UMAP plots labeled by expression of Tbx21, Ifng, Bhlhe40, Sell, Tcf7, and Slamf6. FIG. 13E. Violin plots showing expression of the indicated gene signature for clusters 0 and 1. FIG. 13F. Violin plot showing expression of a proliferation gene signature for clusters 0 and 1. FIG. 13G. Pie charts and graphs showing the number of cells expressing unique TCRs in each of cluster 0 and 1. Cluster 0 has greater clonal expansion and less unique TCRs.

FIG. 14B. Violin plots showing cluster 0 and 1 expression in CNS and LN.

FIG. 15B. Graphs showing similarity between spleen cluster 0 and 1 as compared to all Th17 clusters in the CNS and dLN. UMAP plot showing similarity between spleen cluster 0 and Th17 cells in the CNS.

FIG. 16B. UMAP plot of spleen, CNS and dLN Th17 cells labeled by CNS and spleen. FIG. 16C. UMAP plot of spleen, CNS and dLN Th17 cells labeled by CNS, spleen and dLN.

FIG. 18B. Graph showing percentage of Th17 cells in EAE that are Slamf6+ and Cxcr6+. FIG. 18C. FACS sorting showing the percentage of Cxcr6+ and Slamf6+Th17 cells in EAE and UT. FIG. 18D. Bar graph of FACs experiment in C. Cxcr6+ cells increase in EAE.

FIG. 22B. UMAP plot of Th17 cells labeled by cluster, Areg expression and Ramp3 expression.

FIG. 23B. Heatmap showing differential gene expression for each tag. FIG. 23C. tSNE plots showing clustering of Th17 cells by tissue and plots showing each tag.

FIG. 24B. Graph showing the percentage of current Th17 cells in each tissue.

FIG. 42B. CXCR6+ cell recipients show an exacerbated disease course.

FIG. 47B. Microbiota dependency of the SLAMF6+ subpopulation.

Figure 1A:
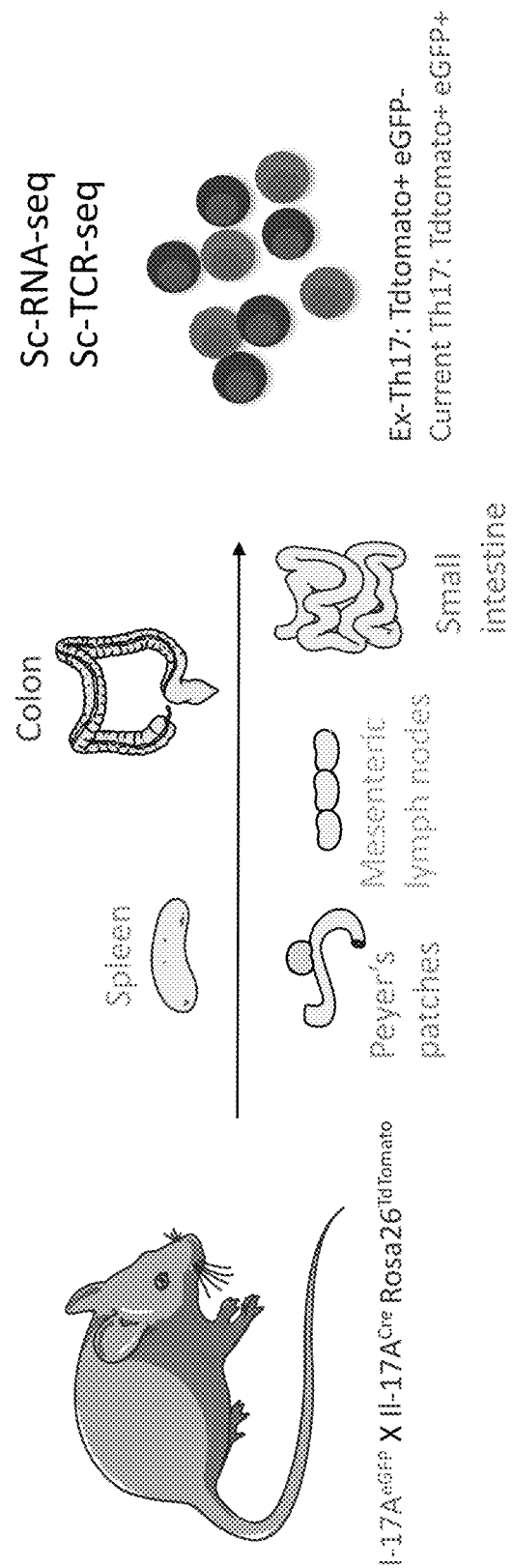
FIGS. 1A-1D— FIG. 1A. Diagram showing experimental system.
Figure 1B:
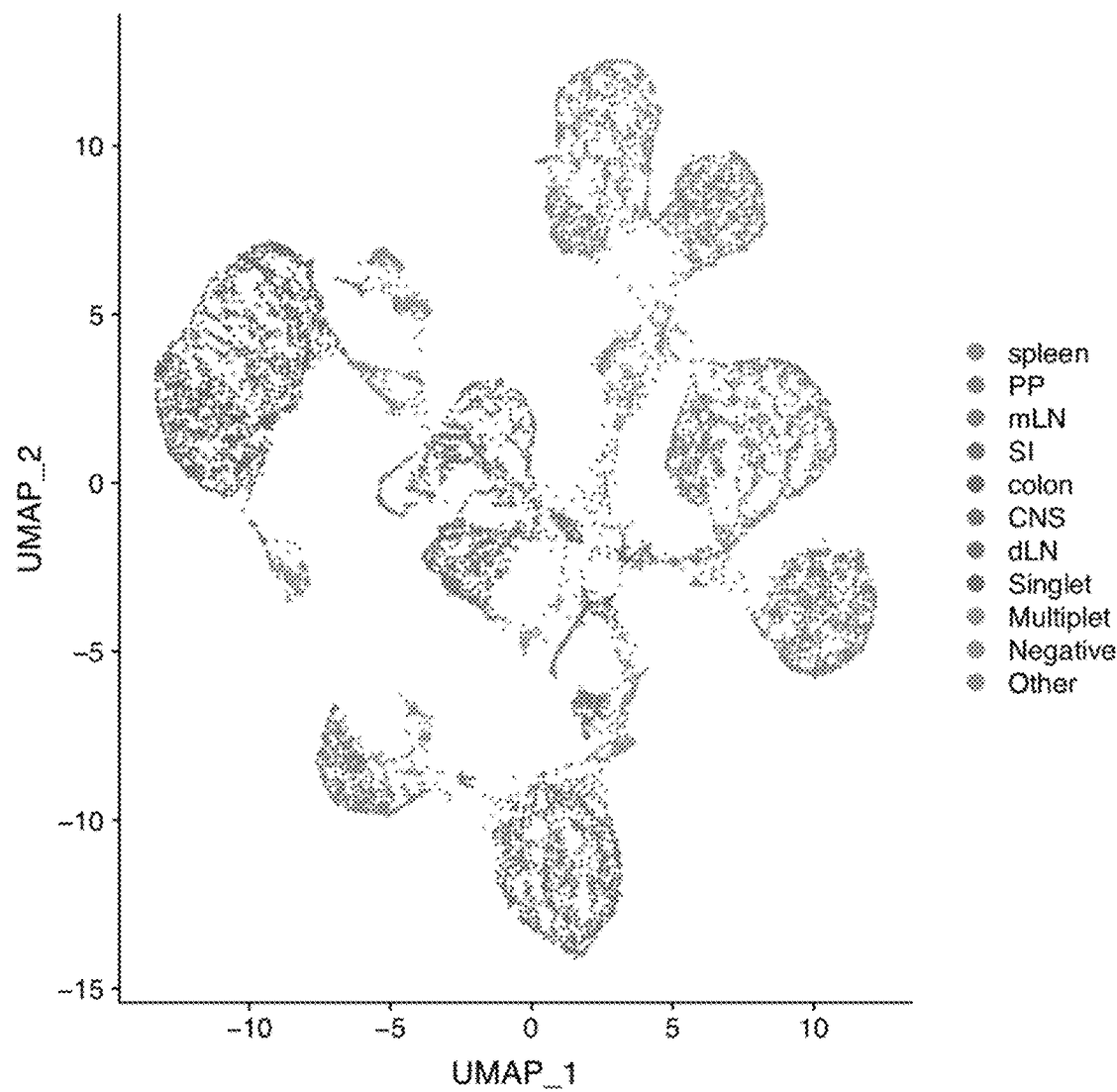
Figure 1C:
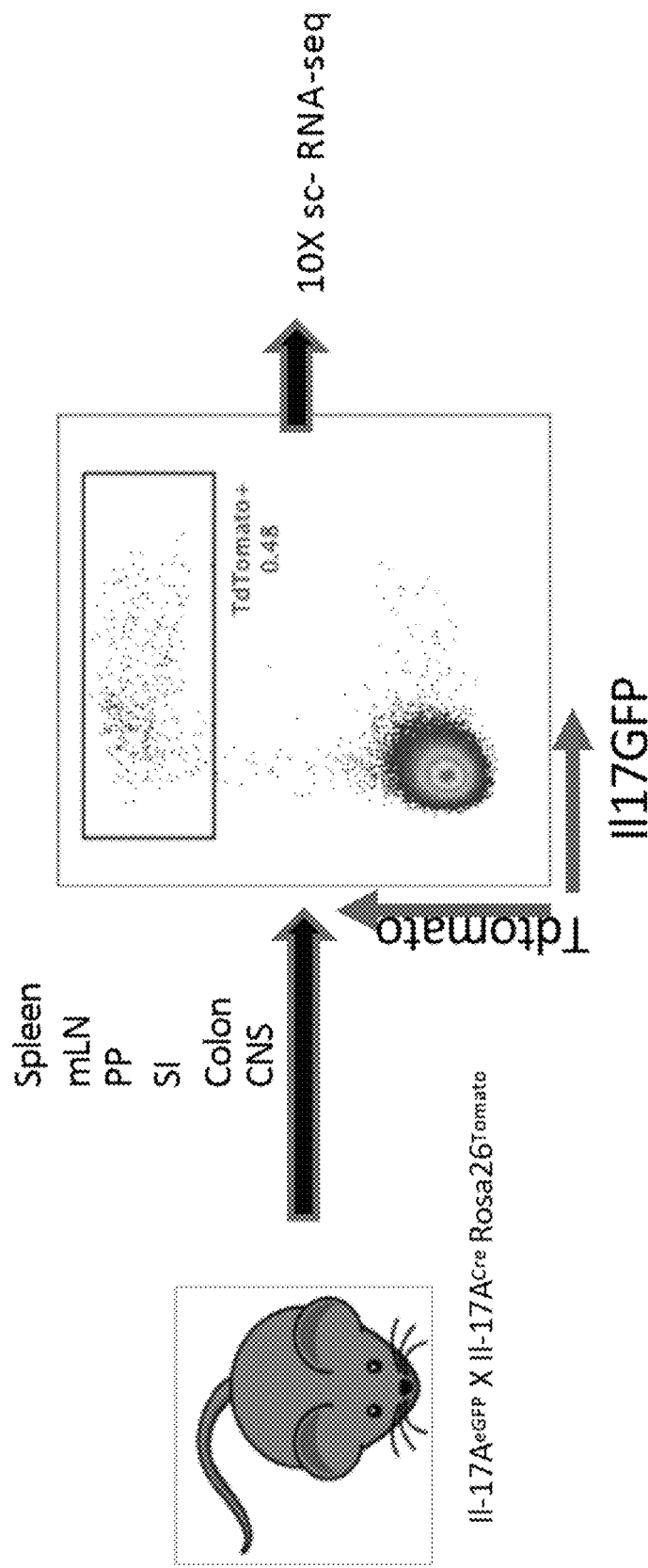
Figure 1D:
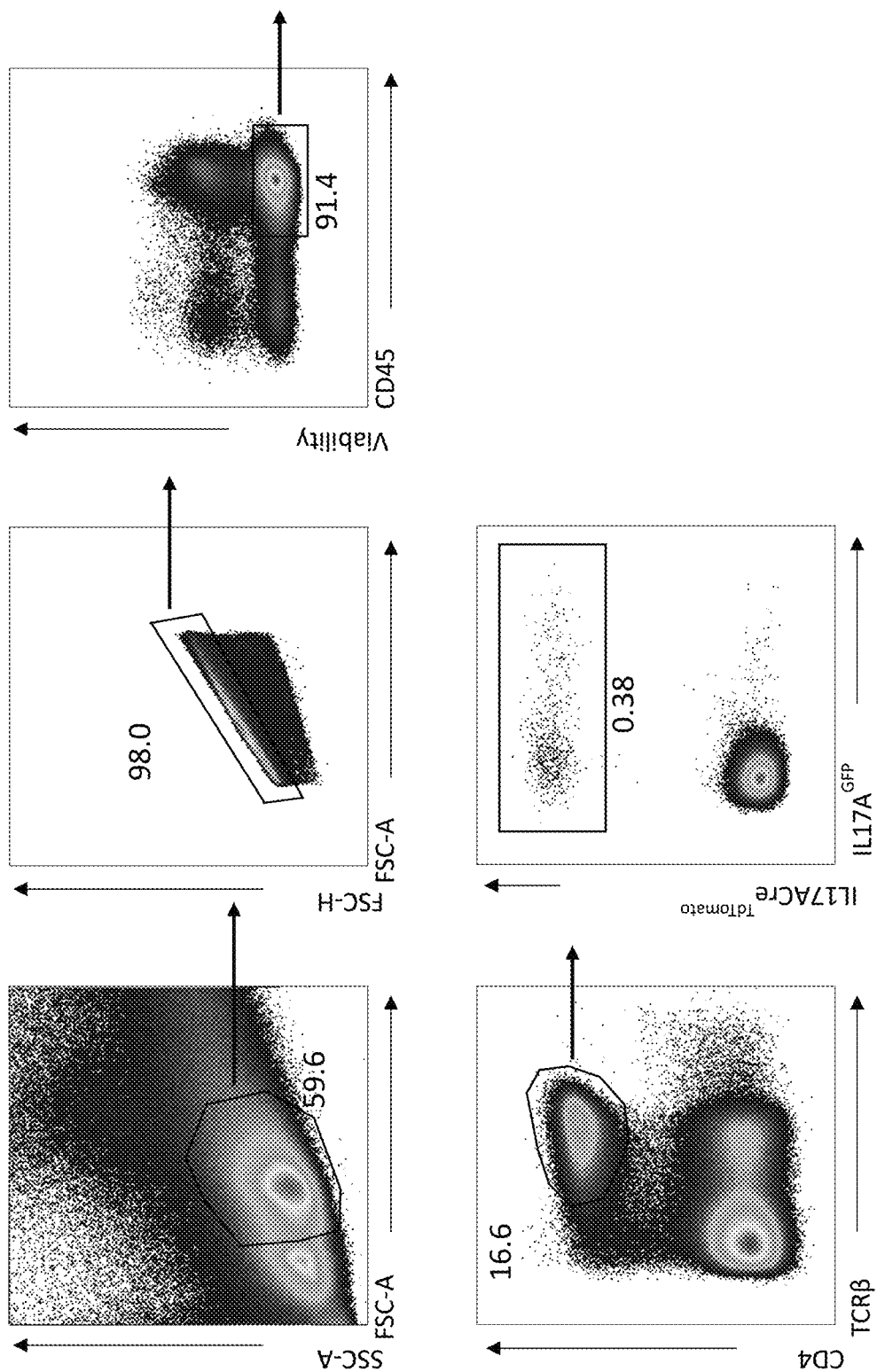

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Figure 3A:
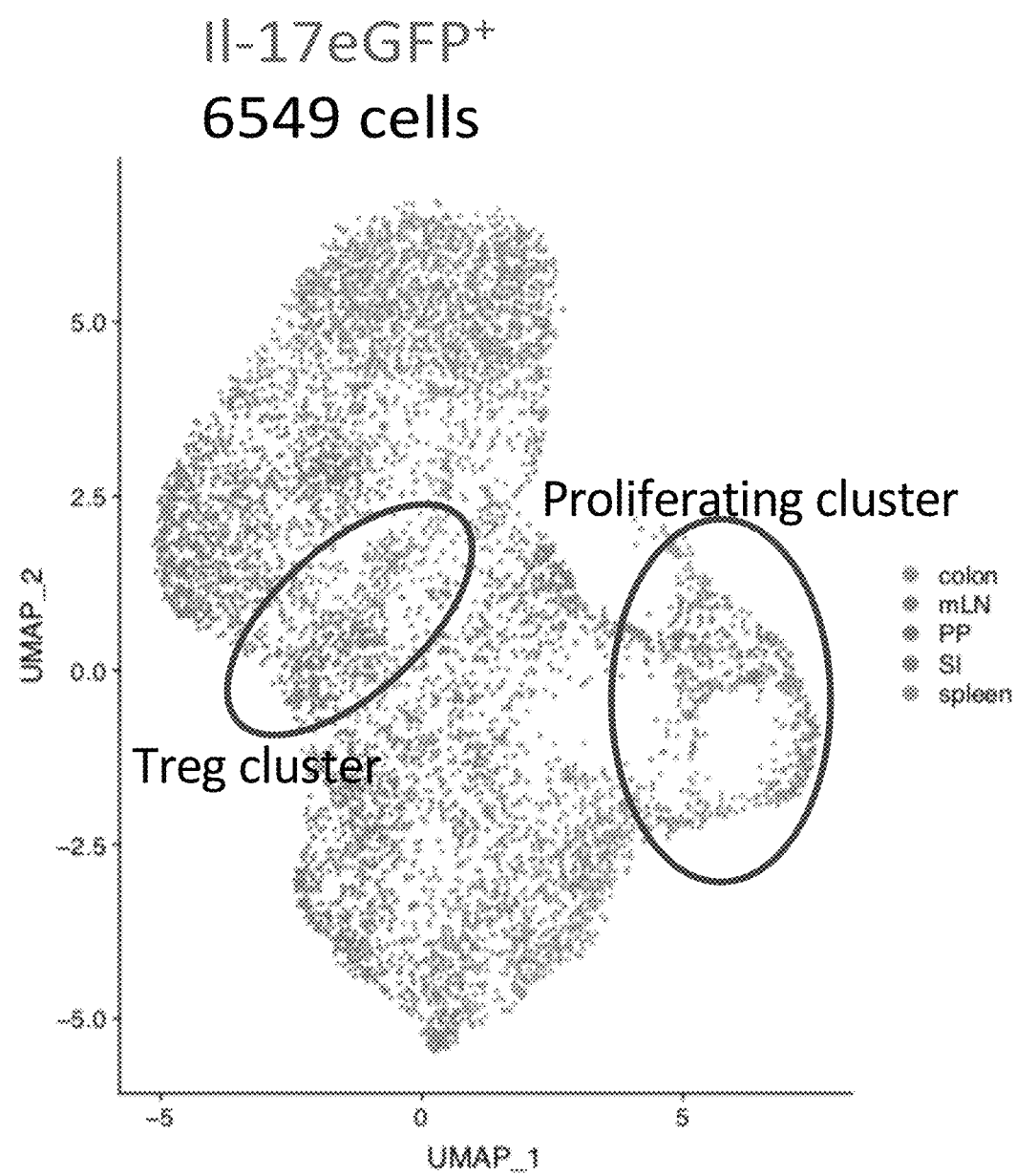
FIGS. 3A-3G— FIG. 3A. UMAP labeled by tissue shows tissue specific Th17 signatures.
Figure 3B:
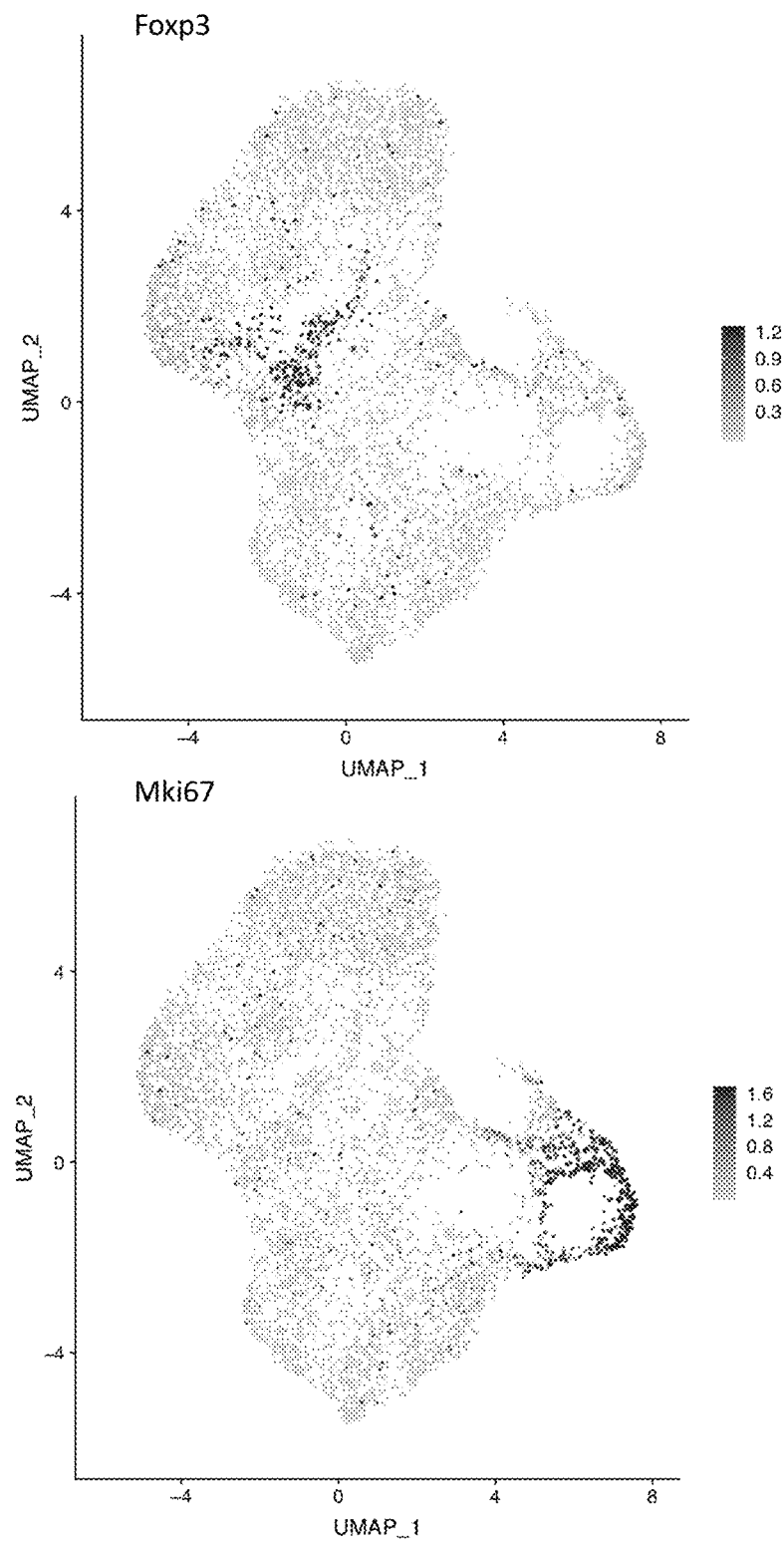
Figure 3C:
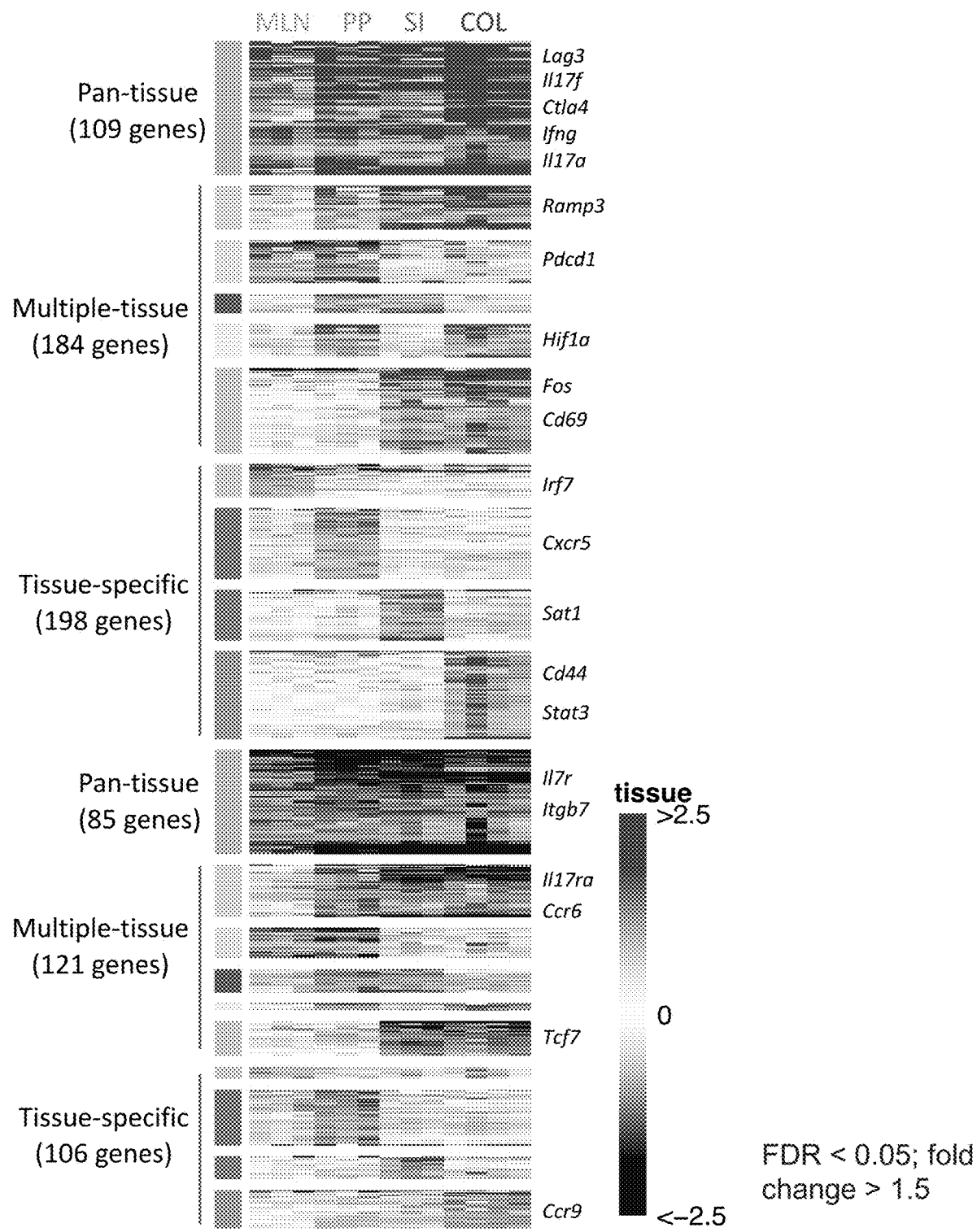
Figure 3D:
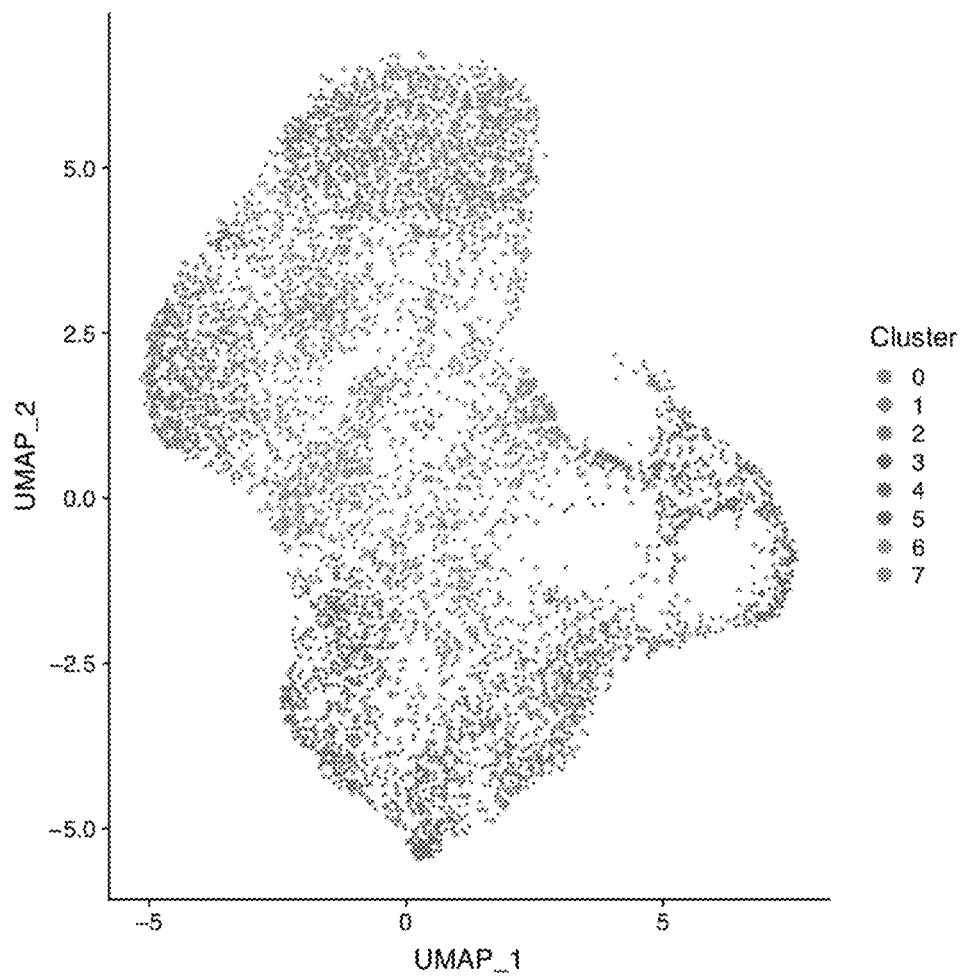
Figure 3E:
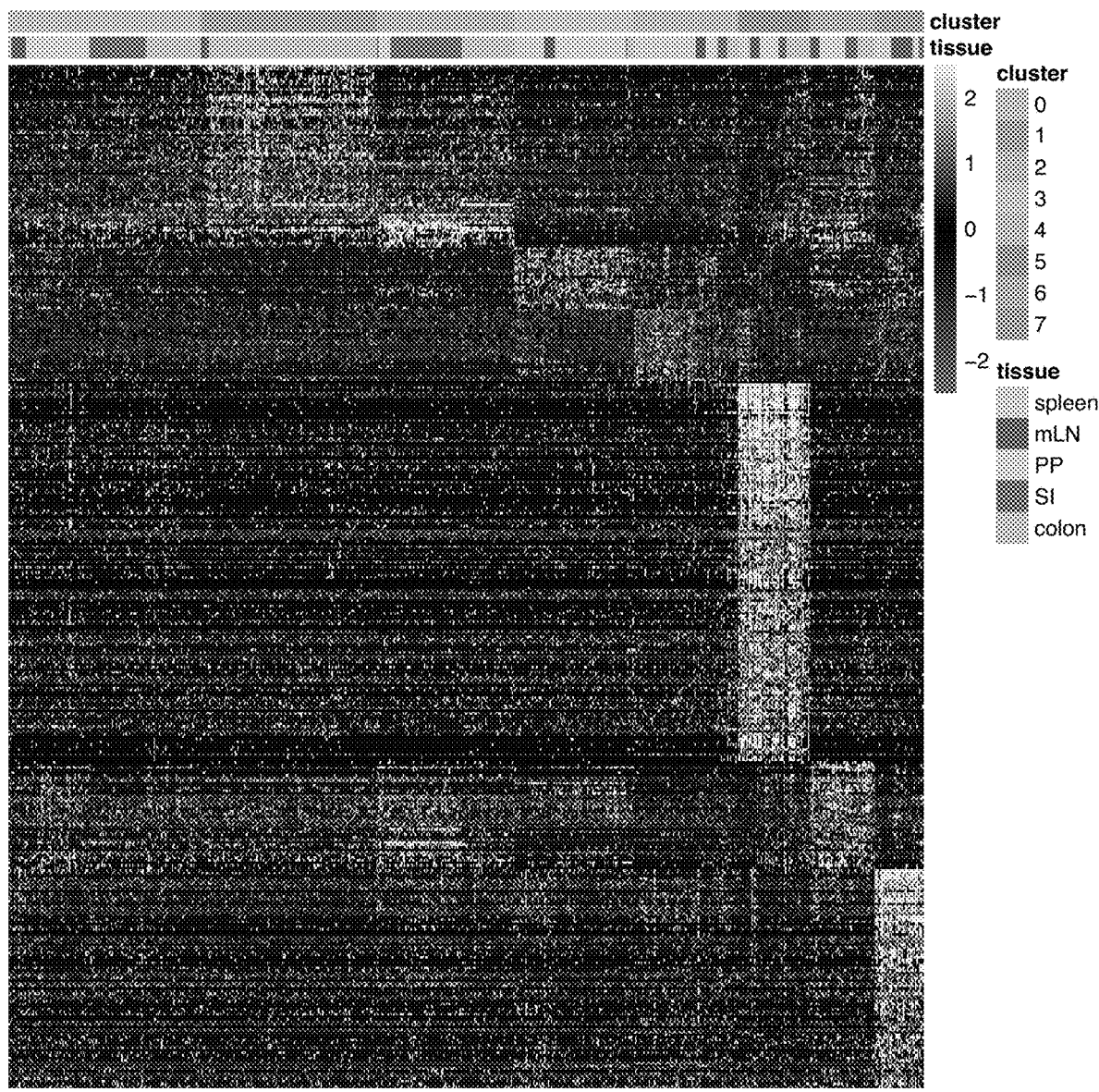
Figure 3F:
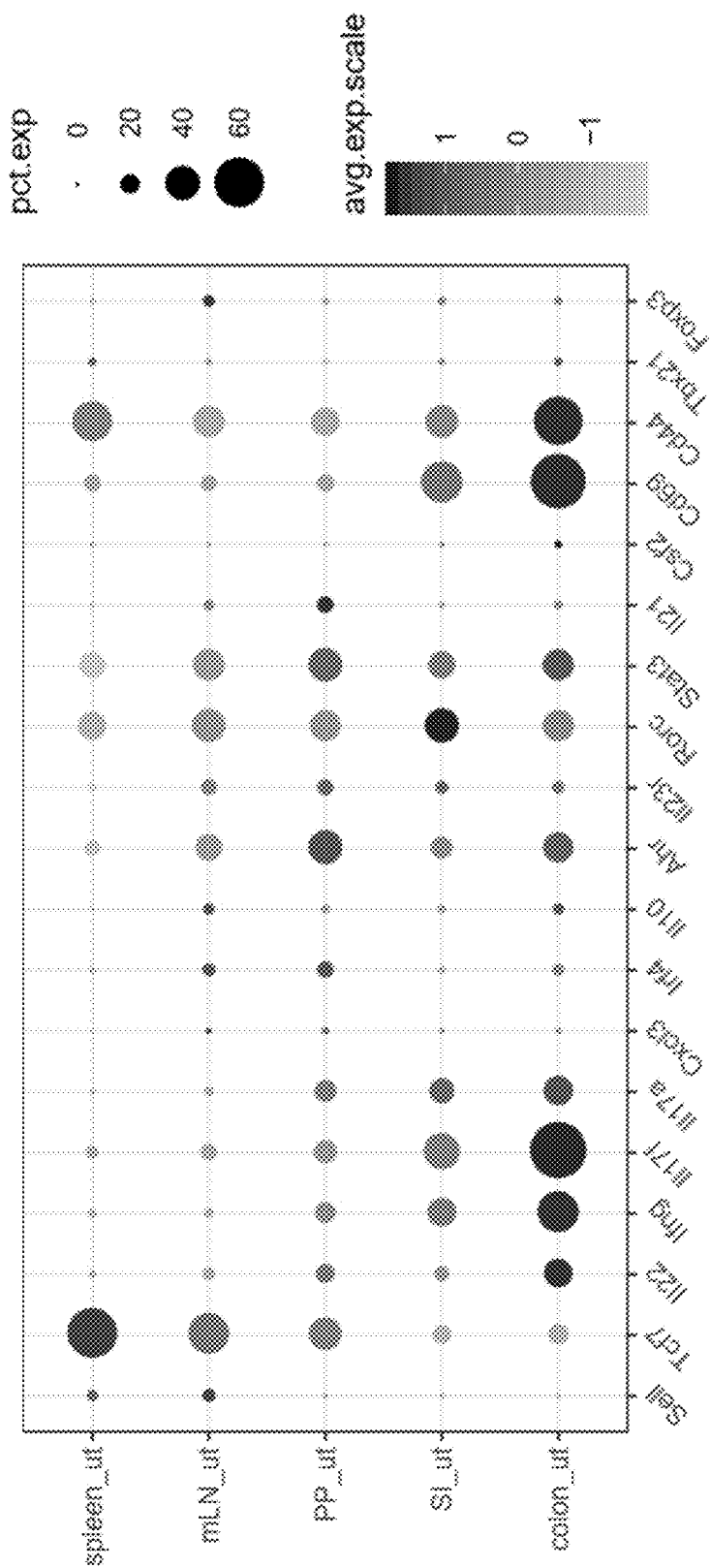
Figure 3G:
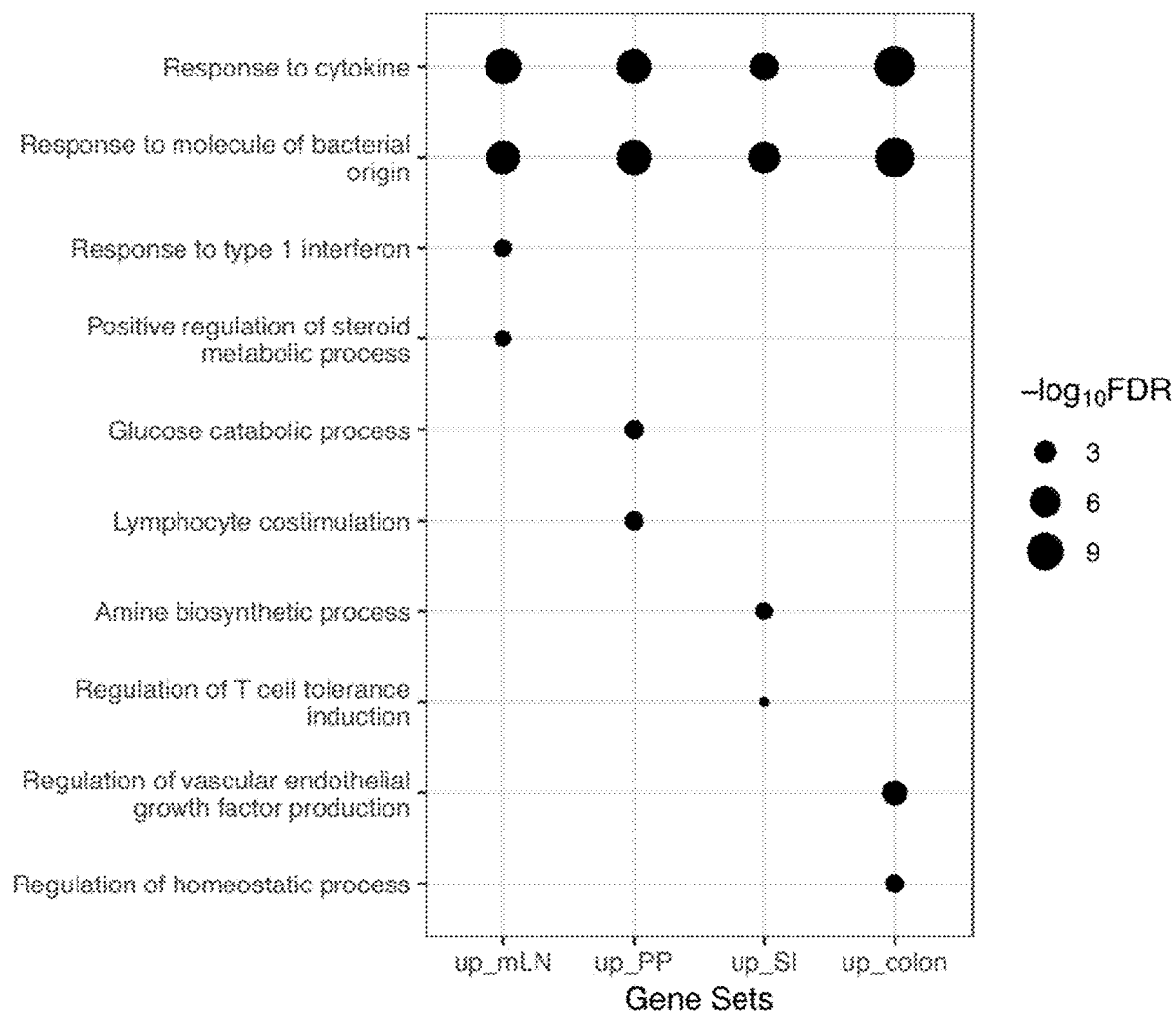
Figure 4A:
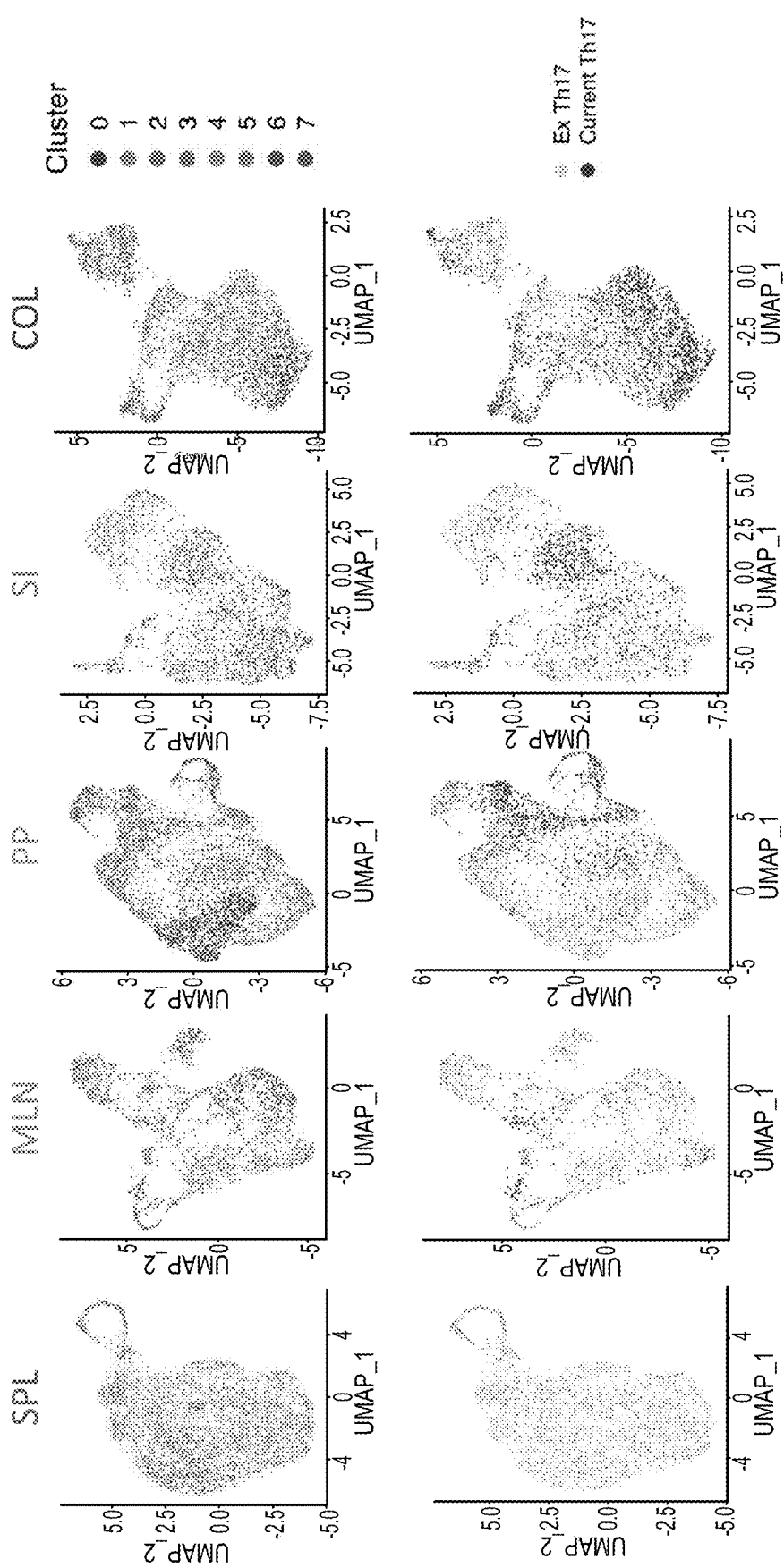
FIGS. 4A-4C— FIG. 4A. UMAP plots labeled by cluster for each tissue show similar intra-tissue clusters and the UMAPs labeled by current Th17 cells.
Figure 4B:
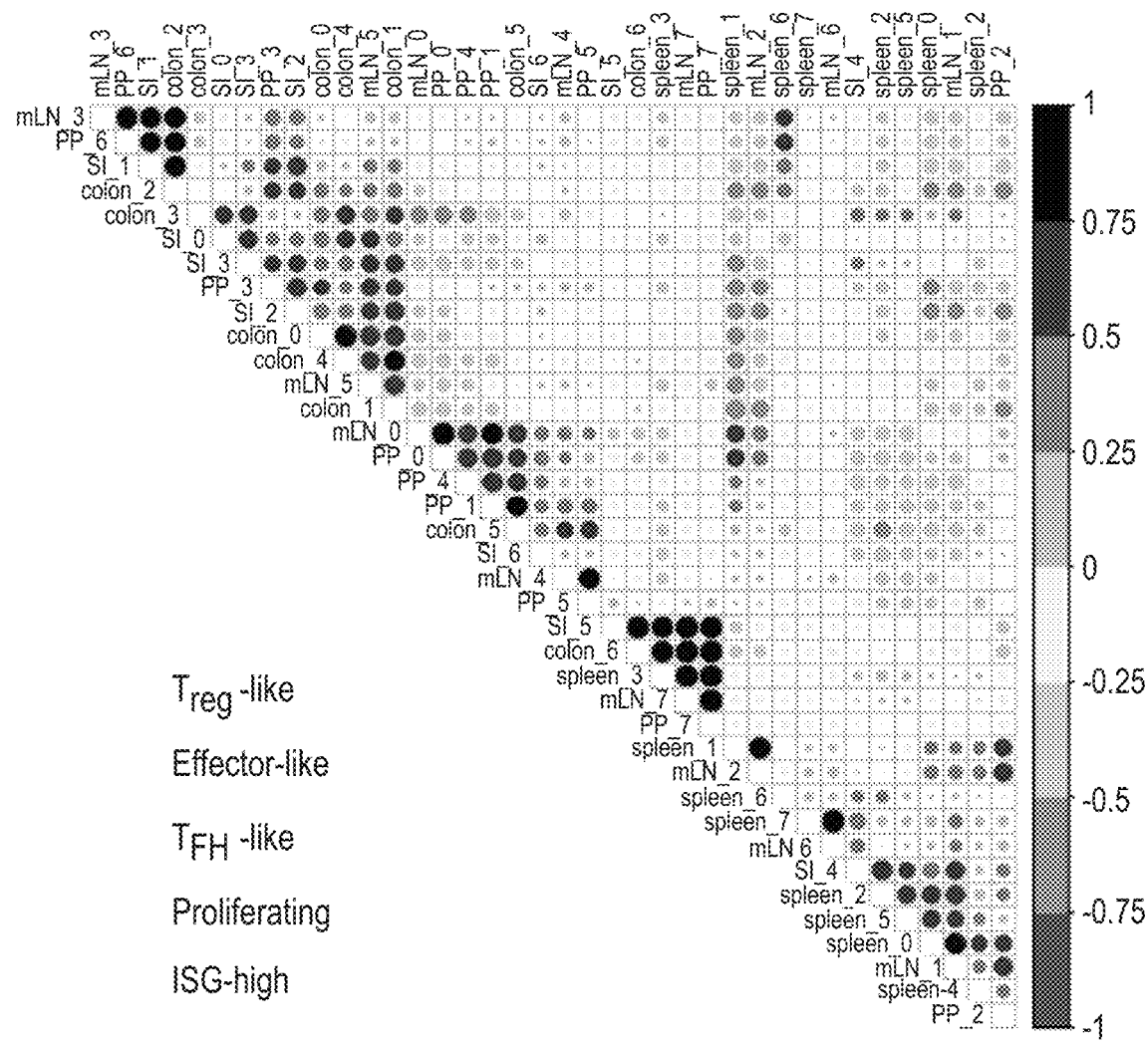
Figure 4B:
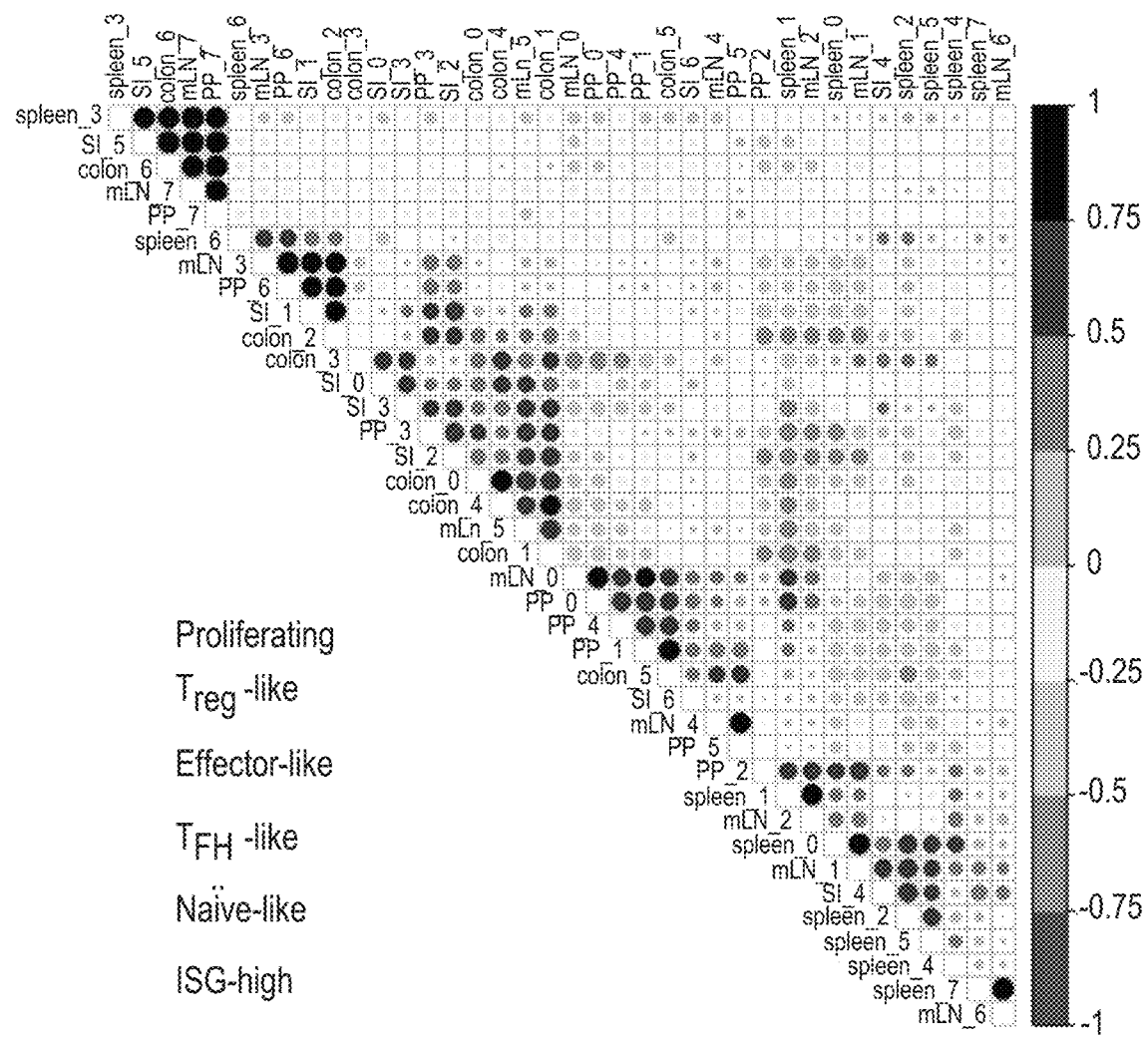
Figure 4C:
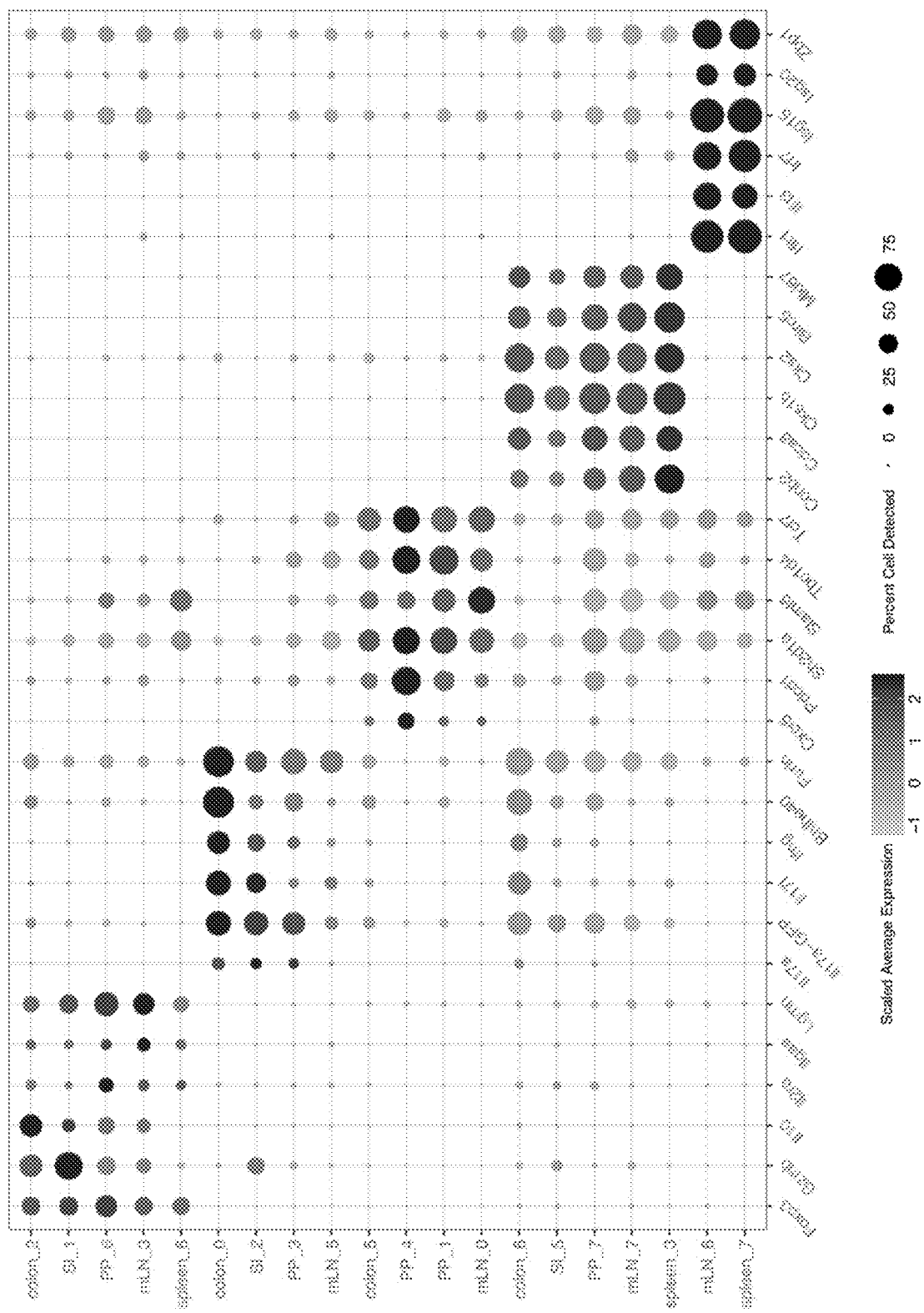
Figure 4C:
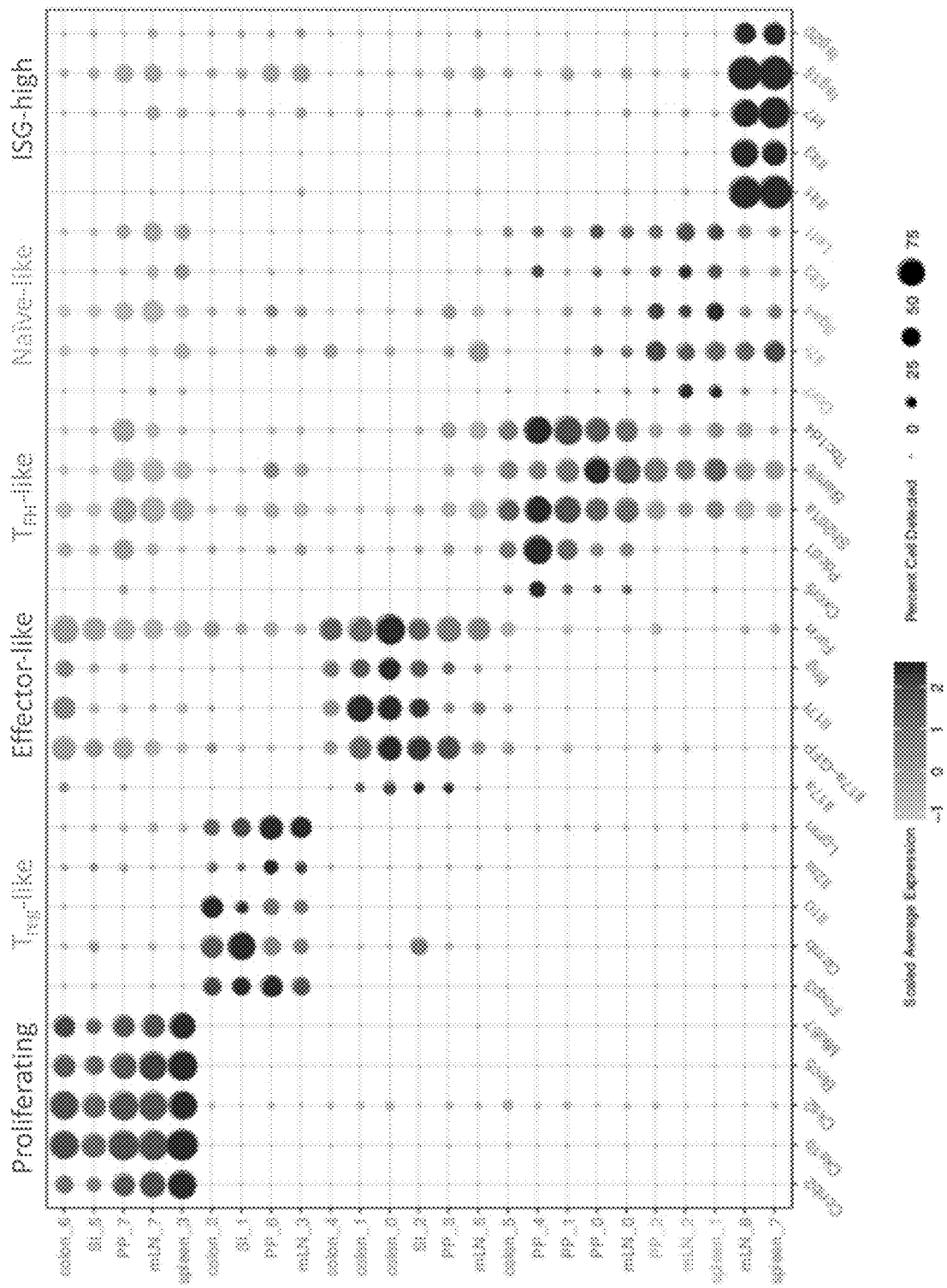
Figure 17:
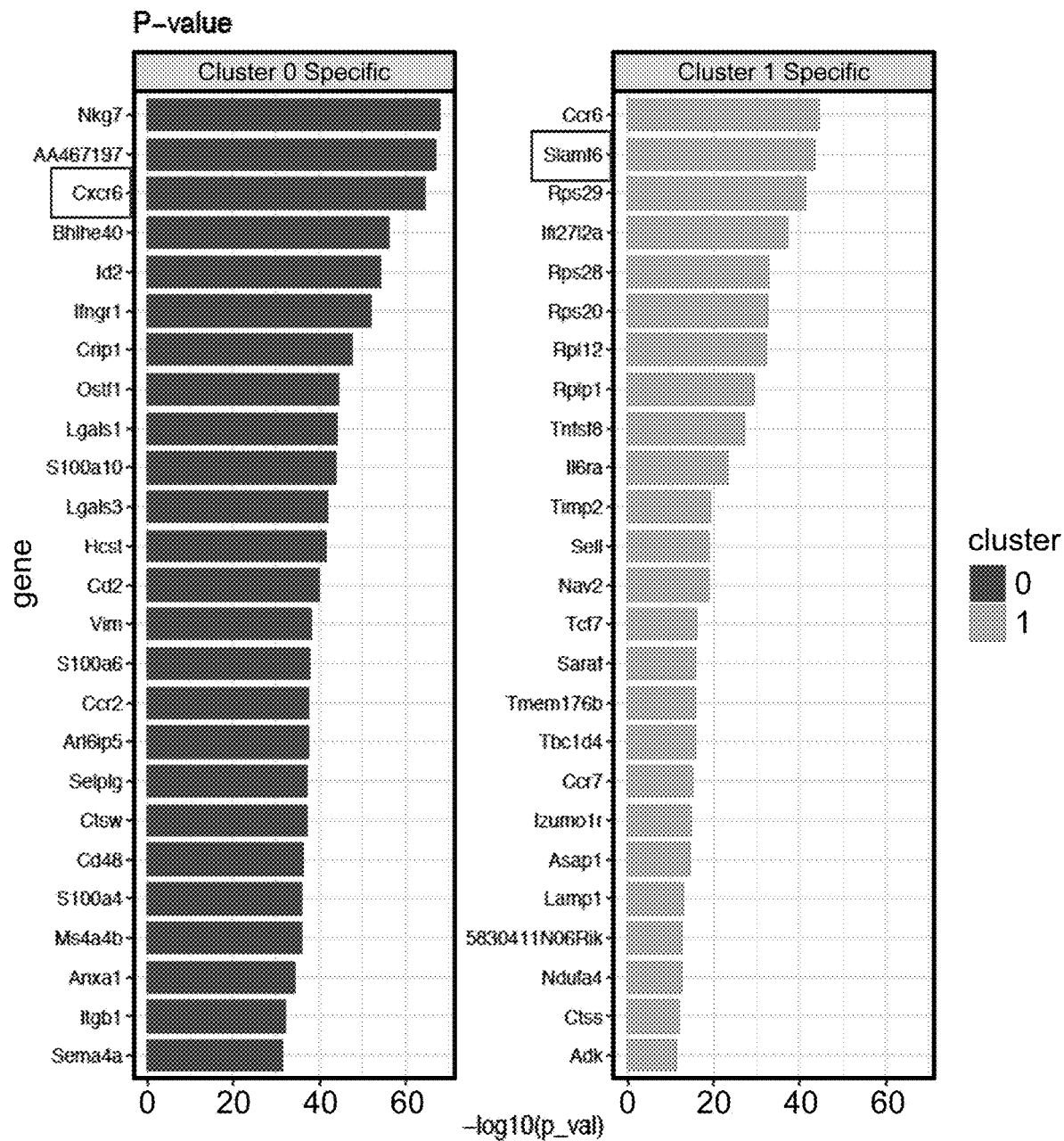
FIG. 17— Graphs showing differentially expressed genes between cluster 0 and 1. Cxcr6 and Slamf6 are highlighted.
Figure 18A:
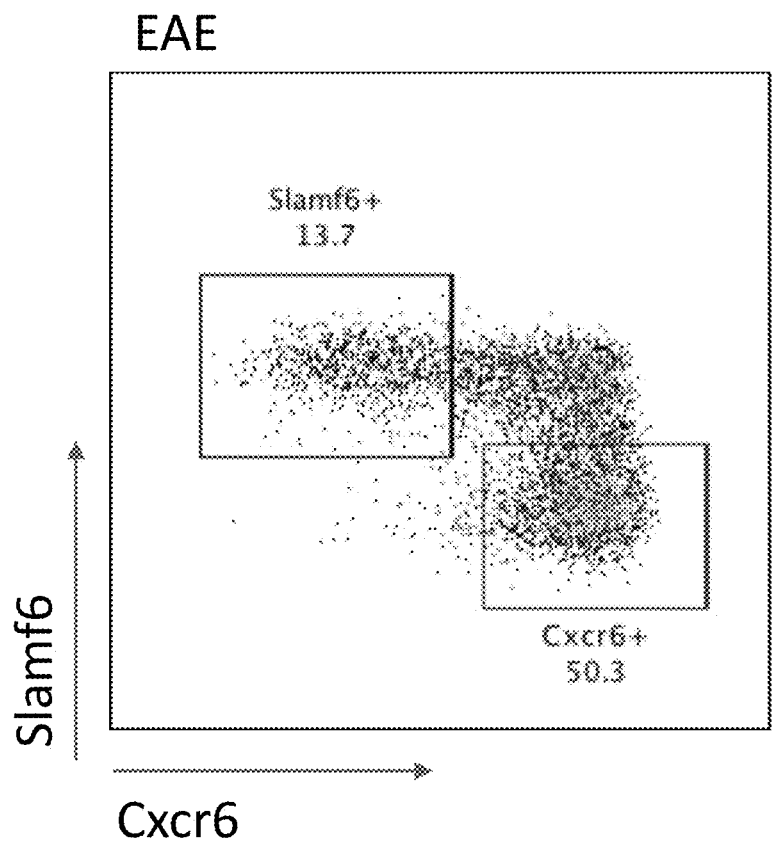
FIGS. 18A-18D— FIG. 18A. FACS sorting of EAE Th17 cells by Cxcr6 (cluster 0) and Slamf6 (cluster 1).
Figure 18B:
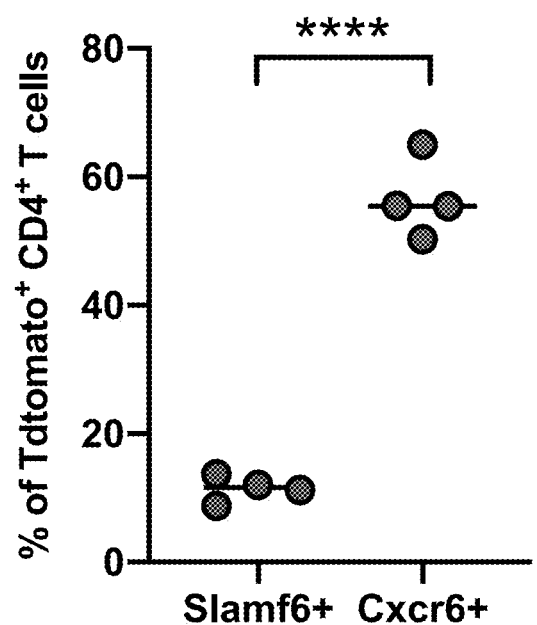
Figure 18C:
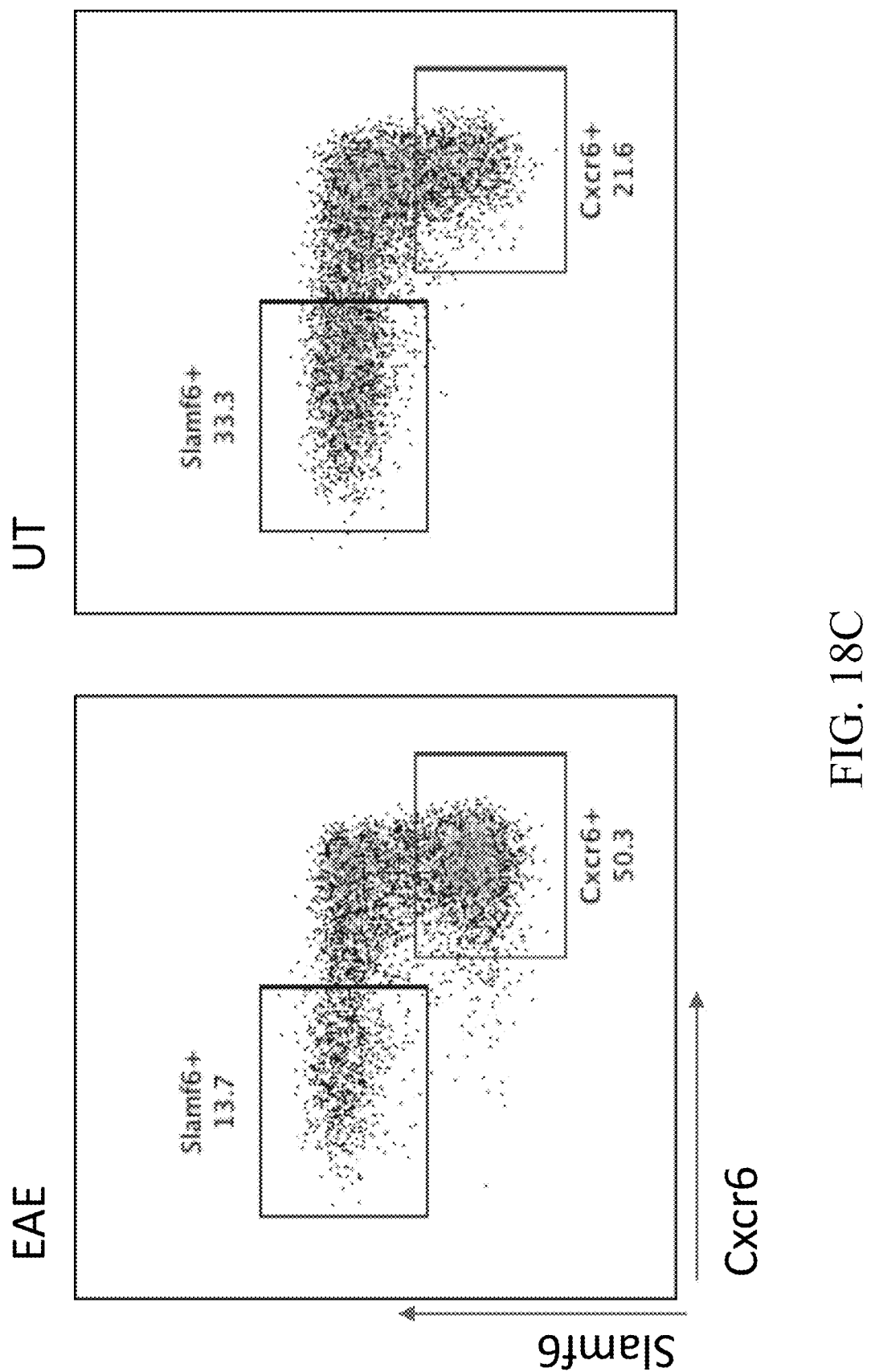
Figure 18D:
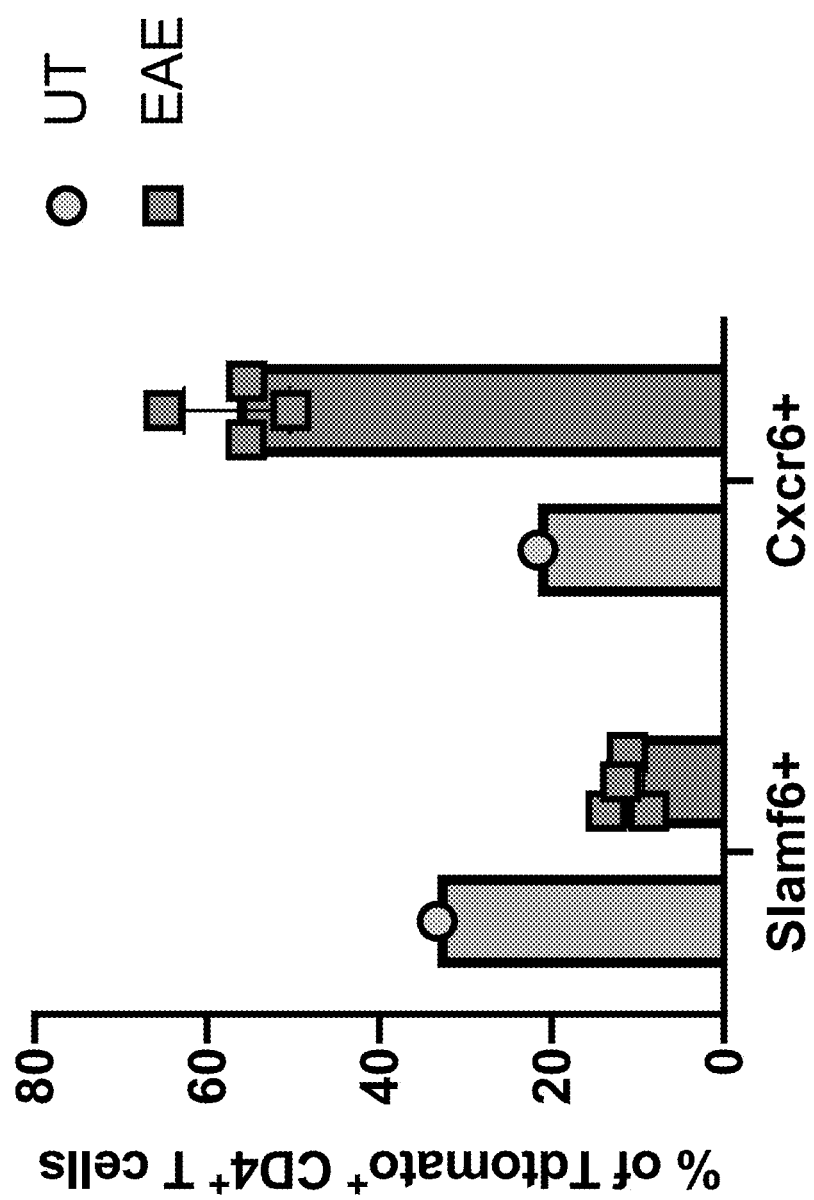

Embodiments disclosed herein provide methods of shifting T cell balance in a population of cells comprising T cells and therapeutic compositions thereof. Embodiments disclosed herein also provide for methods of treating inflammatory diseases and autoimmune responses. In certain embodiments, T cell differentiation is shifted towards or away from pathogenic Th17 cell subpopulations or homeostatic Th17 cell subpopulations. In certain embodiments, T cell differentiation is shifted towards or away from pathogenic Th17 cell gene expression or homeostatic Th17 cell gene expression. In certain embodiments, T cell balance is shifted by contacting the T cells with a one or more agents that modulate the expression of one or more genes or gene products in Tables 1-4, FIG. 3C,F, FIG. 4C, FIG. 10D, or FIG. 17, in particular genes or genes products expressed in Th17 cells specific to a tissue type or migratory Th17 subpopulation described herein, and/or differentially expressed in a tissue during autoimmune responses. Applicants have identified a specific subset of Th17 cells in the spleen that may be the pathogenesis driving Th17 population that migrates to the CNS during an autoimmune response. This subset increases in the spleen during EAE. Applicants also identified a stem-like Th17 population in the spleen that decreases during EAE and antibiotic treatment. These spleen specific populations have not been previously identified because the subsets could only be identified by a tissue specific analysis as described herein for the first time. FIG. 17 genes that are differentially expressed in the spleen specific pathogenic Th17 cells (cluster 0) as compared to spleen specific stem-like Th17 cells (cluster 1) include: Nkg7, AA467197, Cxcr6, Bhlhe40, Id2, Ifngr1, Crip1, Ostf1, Lgals1, S100a10, Lgals3, Hcst, Cd2, Vim, S100a6, Ccr2, Arl6ip5, Selplg, Ctsw, Cd48, S100a4, Ms4a4b, Anxa1, Itgb1 and Sema4a. FIG. 17 genes that are differentially expressed in the spleen specific stem-like Th17 cells (cluster 1) as compared to spleen specific pathogenic Th17 cells (cluster 0) include: Ccr6, Slamf6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411N06Rik, Ndufa4, Ctss and Adk. In certain embodiments, genes upregulated in the spleen specific pathogenic Th17 cells include Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1. In certain embodiments, genes upregulated in spleen specific stem-like Th17 cells include Slamf6, Ccr6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411N06Rik, Ndufa4, Ctss and Adk. In certain embodiments, genes upregulated in the spleen during EAE include Cxcr6, AA467197, Plac8, Ifitm2, Ifitm1, Ifitm3, Bhlhe40, Nkg7, Ifngr1, Ermn, Ctsw, Ggt1, Pglyrp1, Klrd1, Sema4a, Gramd3, Il18rap, Ccr2, Zyx, 2810001G20Rik, AC163354.1, Serpinb6b, Itgb1, Ras11a, Syt13, Klrc1, Id2, Bbc3, Ostf1, Car5b, Paox, Gcnt2, Furin, Slc2a3, Lilr4b, Rom1, Satb1, Il2rb, Hcst, Lgals3, Nptn, Ly6a, Serpinb9, Dnajcl5, Anxa1, Ctsd, Crip1, Gzmb, Atp8b4 and Cox17. In certain embodiments, genes downregulated in the spleen during EAE include Slamf6, Ifi2712a, Izumo1r, Tcrg-C2, Timp2, Ikzf2, Cd27, Ccr6, Tnfsf8, Tbc1d4, Nav2, Cldndl, Tspan32, Rtp4, Lag3, Ighm, Trbcl, Cd9, Ctss, Ctla4, Jaml, Iigpl, St3gal6, Ccr7, Klf3, Rgs10, Zbtb20, Id3, Nt5e, Asb2, Hmgnl, Tox, Adk, Maf, Lmo4, Ifitl, Ar, Ndufa4, Aqp3, Il6ra, Chd3, Stat1, Tcrg-C4, Rflnb, Bcl2, Arl5c, Ikzf3, Isg15, Mtssl, Art2b, Cpe, Foxp1 and Ifi203. In certain embodiments, additional genes differentially expressed in tissue specific Th17 cells include Jmjd3, Prdm1, cMaf, Areg, Ramp3, and/or Sat1. The genes described herein can be used as therapeutic targets and as diagnostic biomarkers.

All gene name symbols refer to the gene as commonly known in the art. The examples described herein that refer to the mouse gene names are to be understood to also encompasses human genes, as well as genes in any other organism (e.g., homologous, orthologous genes). Mouse gene symbols are generally italicized, with only the first letter in upper-case (e.g., Il17). Mouse protein symbols are generally not italicized, and all letters are in upper-case (e.g., IL-17). As used herein mouse gene symbols may be shown with only the first letter in upper-case and not italicized (e.g., Il17). Any reference to the gene symbol is a reference made to the entire gene or variants of the gene. Any reference to the gene symbol is also a reference made to the gene product (e.g., protein). The term, homolog, may apply to the relationship between genes separated by the event of speciation (e.g., ortholog). Orthologs are genes in different species that evolved from a common ancestral gene by speciation. Normally, orthologs retain the same function in the course of evolution. Gene symbols may be those referred to by the HUGO Gene Nomenclature Committee (HGNC) or National Center for Biotechnology Information (NCBI). The signature as described herein may encompass any of the genes described herein.

T Cells

In certain embodiments, T cells are modulated or detected in vitro, ex vivo or in vivo to shift T cell immune responses, such as pathogenic immune responses (e.g., autoimmune responses). T lymphocytes include a variety of T cell types, e.g., Th17, regulatory T cells (Tregs), Treg-like cells, Th1 cells or Th1-like cells, or naïve T cells. As used herein, terms such as "Th17 cell" and/or "Th17 phenotype" and all grammatical variations thereof refer to a differentiated T helper cell that expresses one or more cytokines selected from the group the consisting of interleukin 17A (IL-17A), interleukin 17F (IL-17F), and interleukin 17A/F heterodimer (IL17-AF). As used herein, terms such as "Th1 cell" and/or "Th1 phenotype" and all grammatical variations thereof refer to a differentiated T helper cell that expresses interferon gamma (IFNγ). As used herein, terms such as "Th2 cell" and/or "Th2 phenotype" and all grammatical variations thereof refer to a differentiated T helper cell that expresses one or more cytokines selected from the group the consisting of interleukin 4 (IL-4), interleukin 5 (IL-5) and interleukin 13 (IL-13). As used herein, terms such as "Treg cell" and/or "Treg phenotype" and all grammatical variations thereof refer to a differentiated T cell that expresses Foxp3. "Naïve T cells" and/or "naïve T cell phenotype" and all grammatical variations thereof as used herein are typically unable to produce proinflammatory cytokines, and are precursors for T-effector subsets. Naïve T cells typically lack expression of previous activation, such as, for example, CD25, CD44, CD69, CD45RO, or HLA-DR. (see, e.g. T. Eagar and S. Miller, 2019, Helper T-Cell Subsets and Control of the Inflammatory Response, Clinical Immunology (Fifth Edition), 2019).

As used herein, terms such as "pathogenic Th17 cell" and/or "pathogenic Th17 phenotype" and all grammatical variations thereof refer to Th17 cells that, when induced in the presence of TGF-β3 or TGF-β1+IL-6+IL-23, express an elevated level of one or more genes selected from Cxcl3, IL22, IL3, Ccl4, Gzmb, Lrmp, Cc15, Casp1, Csf2, Ccl3, Tbx21, Icos, 1117r, Stat4, Lgals3 and Lag, as compared to the level of expression in TGF-β1+IL-6-induced Th17 cells. As used herein, terms such as "non-pathogenic Th17 cell" and/or "non-pathogenic Th17 phenotype" and all grammatical variations thereof refer to Th17 cells that, when induced in the presence of TGF-β1+IL-6, express an increased level of one or more genes selected from IL6st, IL1rn, Ikzf3, Maf, Ahr, I19 and Il10, as compared to the level of expression in a TGF-β3-induced or TGF-β1+IL-6+IL-23-induced Th17 cells.

Depending on the cytokines used for differentiation (pathogenic conditions are TGF-33 or TGF-β1+IL-6+IL-23 and non-pathogenic conditions are TGF-β1+IL-6), in vitro polarized Th17 cells can either cause severe autoimmune responses upon adoptive transfer ('pathogenic Th17 cells') or have little or no effect in inducing autoimmune disease ('non-pathogenic cells') (Ghoreschi et al., 2010; Lee et al., 2012). In vitro differentiation of naïve CD4 T cells in the presence of TGF-β1+IL-6 induces an IL-17A and IL-10 producing population of Th17 cells, that are generally non-pathogenic, whereas activation of naïve T cells in the presence IL-1β+IL-6+IL-23 induces a T cell population that produces IL-17A and IFN-7, and are potent inducers of autoimmune disease induction (Ghoreschi et al., 2010).

Therapeutic Methods

Methods of Shifting T Cell Balance

The invention also provides compositions and methods for modulating T cell balance. The invention provides T cell modulating agents that modulate T cell balance. For example, in some embodiments, the invention provides T cell modulating agents and methods of using these T cell modulating agents to regulate, influence, shift or otherwise impact the level of and/or balance between T cell types, e.g., between Th17 and other T cell types, for example, regulatory T cells (Tregs), Treg-like cells, Th1 cells or Th1-like cells. For example, in some embodiments, the invention provides T cell modulating agents and methods of using these T cell modulating agents to regulate, influence, shift, or otherwise impact the level of and/or balance between Th17 activity and inflammatory potential. Shifting the balance in a population of cells comprising T cells can comprise a change in T cell differentiation. T cell differentiation can shift towards non-pathogenic Th17 cells, Th1 cells, Treg cells, and/or is shifted away from pathogenic Th17 cells, Treg cells, or Th1 cells. Methods of shifting the T cell balance can comprise differentiation of naïve T cells into Th17 cells, Th1 cells and/or Treg cells.

A dynamic regulatory network controls Th17 differentiation (See e.g., Yosef et al., Dynamic regulatory network controlling Th17 cell differentiation, Nature, vol. 496: 461-468 (2013); Wang et al., CD5L/AIM Regulates Lipid Biosynthesis and Restrains Th17 Cell Pathogenicity, Cell Volume 163, Issue 6, p1413-1427, 3 Dec. 2015; Gaublomme et al., Single-Cell Genomics Unveils Critical Regulators of Th17 Cell Pathogenicity, Cell Volume 163, Issue 6, p1400-1412, 3 Dec. 2015; and International Patent Publication Nos. WO2016138488A2, WO2015130968, WO/2012/048265, WO/2014/145631 and WO/2014/134351 the contents of which are hereby incorporated by reference in their entirety). Accordingly, shifting the T cell balance in a population of cells may include contacting the population of cells with IL-6 and TGF-β1 or IL-1β, IL-6, and IL-23. In certain embodiments, the IL-6 and TGF-β1 or IL-1β, IL-6, and IL-23 supplement a cell culture media. In one embodiment, the administration of the agents differentiates naïve T cells into Th17 cells. Optionally, the agents are administered to the population of cells during differentiation.

Modulating Agents

In certain embodiments, a population of T cells may be contacted with one or more modulating agents. As used herein, a population of cells can be contacted in vivo or in vitro or ex vivo. In certain embodiments, one or more genes or gene products are modulated. The one or more genes may be selected from the group consisting of Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a and Crip1. The one or more genes may be selected from the group consisting of Slamf6, Ccr6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411N06Rik, Ndufa4, Ctss and Adk. As used herein, "modulating" or "to modulate" generally means either reducing or inhibiting the expression or activity of, or alternatively increasing the expression or activity of a target. In particular, "modulating" or "to modulate" can mean either reducing or inhibiting the activity of, or alternatively increasing a (relevant or intended) biological activity of, a target or antigen as measured using a suitable in vitro, cellular or in vivo assay (which will usually depend on the target involved), by at least 5%, at least 10%, at least 25%, at least 50%, at least 60%, at least 70%, at least 80%, at least 90%, or more, compared to activity of the target in the same assay under the same conditions but without the presence of an agent. An "increase" or "decrease" refers to a statistically significant increase or decrease respectively. For the avoidance of doubt, an increase or decrease will be at least 10% relative to a reference, such as at least 10%, at least 20%, at least 30%, at least 40%, at least 50%, a t least 60%, at least 70%, at least 80%, at least 90%, at least 95%, at least 97%, at least 98%, or more, up to and including at least 100% or more, in the case of an increase, for example, at least 2-fold, at least 3-fold, at least 4-fold, at least 5-fold, at least 6-fold, at least 7-fold, at least 8-fold, at least 9-fold, at least 10-fold, at least 50-fold, at least 100-fold, or more. "Modulating" can also involve effecting a change (which can either be an increase or a decrease) in affinity, avidity, specificity and/or selectivity of a target or antigen. "Modulating" can also mean effecting a change with respect to one or more biological or physiological mechanisms, effects, responses, functions, pathways or activities in which the target or antigen (or in which its substrate(s), ligand(s) or pathway(s) are involved, such as its signaling pathway or metabolic pathway and their associated biological or physiological effects) is involved. Again, as will be clear to the skilled person, such an action as an agonist or an antagonist can be determined in any suitable manner and/or using any suitable assay known or described herein (e.g., in vitro or cellular assay), depending on the target or antigen involved.

Modulating can, for example, also involve allosteric modulation of the target and/or reducing or inhibiting the binding of the target to one of its substrates or ligands and/or competing with a natural ligand, substrate for binding to the target. Modulating can also involve activating the target or the mechanism or pathway in which it is involved. Modulating can for example also involve effecting a change in respect of the folding or confirmation of the target, or in respect of the ability of the target to fold, to change its conformation (for example, upon binding of a ligand), to associate with other (sub)units, or to disassociate. Modulating can for example also involve effecting a change in the ability of the target to signal, phosphorylate, dephosphorylate, and the like.

Therapeutic Agents

In certain embodiments, the present invention provides for one or more therapeutic agents targeting identified cell types and genes expressed thereof. In certain embodiments, the present invention provides for one or more therapeutic agents against combinations of targets identified. Targeting combinations may provide for enhanced or otherwise previously unknown activity in the treatment of disease. In certain embodiments, an agent against is administered in a combination with an agent already known or used clinically. In certain embodiments, targeting the combination may require less of the known agent as compared to the current standard of care and provide for less toxicity and improved treatment. In certain embodiments, the agents are used to modulate cell types. For example, the agents may be used to modulate cells for adoptive cell transfer. In certain embodiments, the one or more agents comprises a small molecule inhibitor, small molecule degrader (e.g., ATTEC, AUTAC, LYTAC, or PROTAC), genetic modifying agent, antibody, antibody fragment, antibody-like protein scaffold, aptamer, protein, or any combination thereof.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. As used herein "treating" includes ameliorating, curing, preventing it from becoming worse, slowing the rate of progression, or preventing the disorder from re-occurring (i.e., to prevent a relapse).

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

For example, in methods for treating autoimmunity in a subject, an effective amount of an agent or a combination of agents is any amount that reduces the autoimmune effect, such as reduces or prevents inflammatory responses in immune cells (e.g., Th17 pathogenic immune response).

CXCR6

In certain embodiments, inhibitors of CXCR6 are used to reduce Th17 pathogenicity or to reduce the CXCR6+ subpopulation of Th17 cells. In certain embodiments, the inhibitor targets CXCR6. In certain embodiments, the inhibitor targets CXCL16. In certain embodiments, the inhibitor is a blocking antibody, described further herein. (see, e.g., WO2012082470A2; and U.S. Pat. No. 7,208,152B2). As used herein CXCR6 refers to C-X-C motif chemokine receptor 6 (Also known as: BONZO, CD186, CDw186, STRL33, TYMSTR). Example sequences can be accessed using the following NCBI accession numbers: NM_006564.2, NM 001386435.1, NM_001386436.1, NM_001386437.1, NP 006555.1, NP_001373364.1, NP_001373365.1, and NP_001373366.1.

Small Molecules

In certain embodiments, the one or more agents is a small molecule. The term "small molecule" refers to compounds, preferably organic compounds, with a size comparable to those organic molecules generally used in pharmaceuticals. The term excludes biological macromolecules (e.g., proteins, peptides, nucleic acids, etc.). Preferred small organic molecules range in size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. In certain embodiments, the small molecule may act as an antagonist or agonist (e.g., blocking an enzyme active site or activating a receptor by binding to a ligand binding site).

One type of small molecule applicable to the present invention is a degrader molecule (see, e.g., Ding, et al., Emerging New Concepts of Degrader Technologies, Trends Pharmacol Sci. 2020 July; 41(7):464-474). The terms "degrader" and "degrader molecule" refer to all compounds capable of specifically targeting a protein for degradation (e.g., ATTEC, AUTAC, LYTAC, or PROTAC, reviewed in Ding, et al. 2020). Proteolysis Targeting Chimera (PROTAC) technology is a rapidly emerging alternative therapeutic strategy with the potential to address many of the challenges currently faced in modern drug development programs. PROTAC technology employs small molecules that recruit target proteins for ubiquitination and removal by the proteasome (see, e.g., Zhou et al., Discovery of a Small-Molecule Degrader of Bromodomain and Extra-Terminal (BET) Proteins with Picomolar Cellular Potencies and Capable of Achieving Tumor Regression. J. Med. Chem. 2018, 61, 462-481; Bondeson and Crews, Targeted Protein Degradation by Small Molecules, Annu Rev Pharmacol Toxicol. 2017 Jan. 6; 57: 107-123; and Lai et al., Modular PROTAC Design for the Degradation of Oncogenic BCR-ABL Angew Chem Int Ed Engl. 2016 Jan. 11; 55(2): 807-810). In certain embodiments, LYTACs are particularly advantageous for cell surface proteins as described herein (e.g., CXCR6).

Genetic Modifying Agents

In certain embodiments, the one or more modulating agents may be a genetic modifying agent. The genetic modifying agents may manipulate nucleic acids (e.g., genomic DNA or mRNA). The genetic modulating agent can be used to up- or downregulate expression of a gene either by targeting a nuclease or functional domain to a DNA or RNA sequence. The genetic modifying agent may comprise a CRISPR system, a zinc finger nuclease system, a TALEN, a meganuclease or RNAi system.

CRISPR-Cas Modification

In some embodiments, a polynucleotide of the present invention described elsewhere herein can be modified using a CRISPR-Cas and/or Cas-based system (e.g., genomic DNA or mRNA, preferably, for a disease gene). The nucleotide sequence may be or encode one or more components of a CRISPR-Cas system. For example, the nucleotide sequences may be or encode guide RNAs. The nucleotide sequences may also encode CRISPR proteins, variants thereof, or fragments thereof.

In general, a CRISPR-Cas or CRISPR system as used herein and in other documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g., tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g., CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g., Shmakov et al. (2015) "Discovery and Functional Characterization of Diverse Class 2 CRISPR-Cas Systems", Molecular Cell, DOI: dx.doi.org/10.1016/j.molcel.2015.10.008.

CRISPR-Cas systems can generally fall into two classes based on their architectures of their effector molecules, which are each further subdivided by type and subtype. The two classes are Class 1 and Class 2. Class 1 CRISPR-Cas systems have effector modules composed of multiple Cas proteins, some of which form crRNA-binding complexes, while Class 2 CRISPR-Cas systems include a single, multi-domain crRNA-binding protein.

In some embodiments, the CRISPR-Cas system that can be used to modify a polynucleotide of the present invention described herein can be a Class 1 CRISPR-Cas system. In some embodiments, the CRISPR-Cas system that can be used to modify a polynucleotide of the present invention described herein can be a Class 2 CRISPR-Cas system.

Class 1 CRISPR-Cas Systems

Figure 5A:
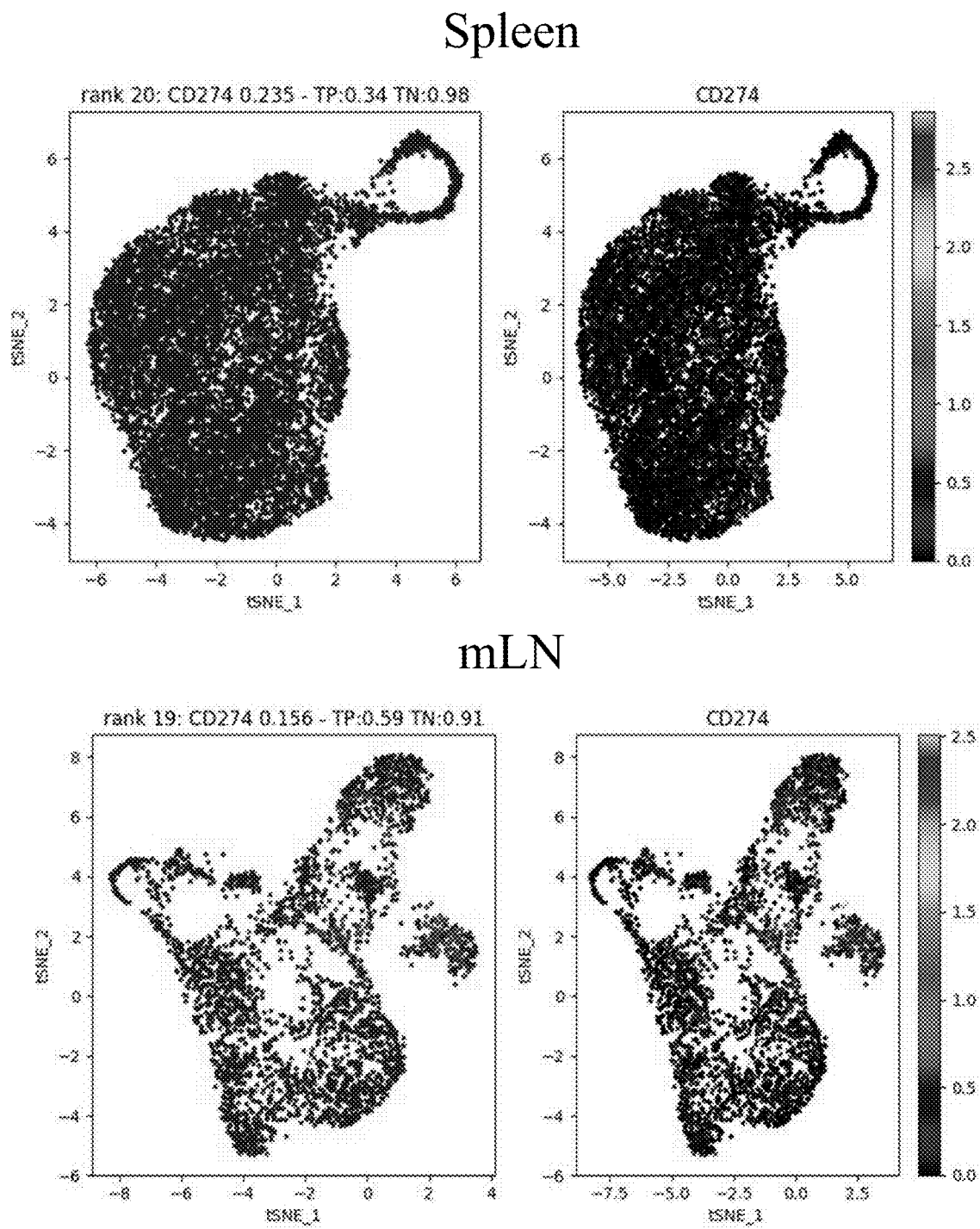
FIGS. 5A-5B— Validation of novel ISG-high Th17 cluster. COMET (Delaney et al., 2019, Combinatorial prediction of marker panels from single-cell transcriptomic data, Molecular Systems Biology 15: e9005, DOI 10.15252/msb.20199005) was used to identify CD274 as a marker specific for the ISG-high Th17 cluster.
Figure 5B:
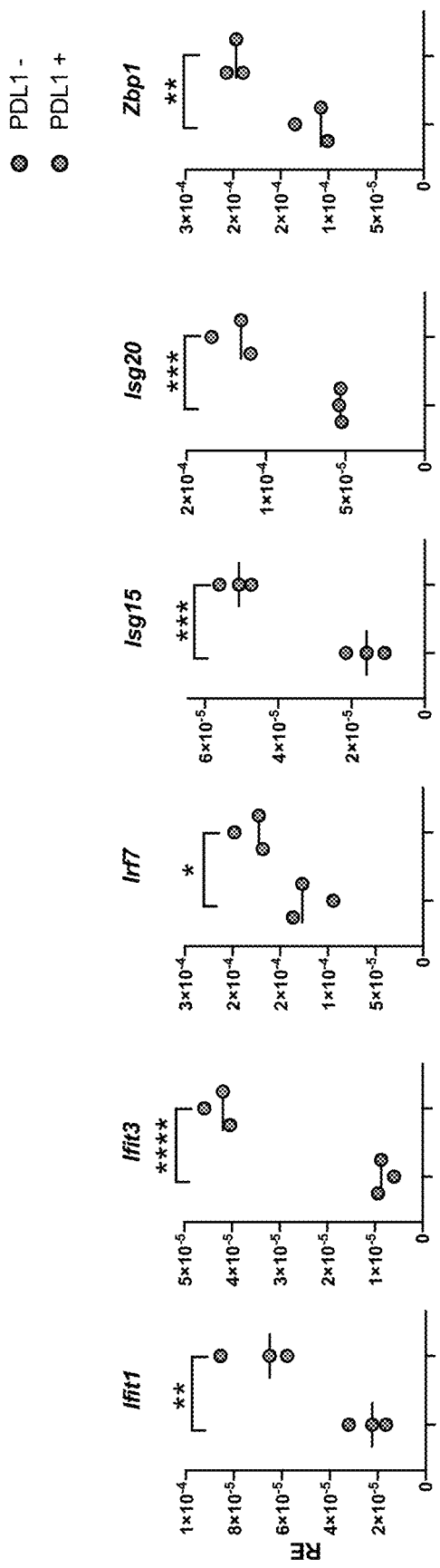
Figure 6A:
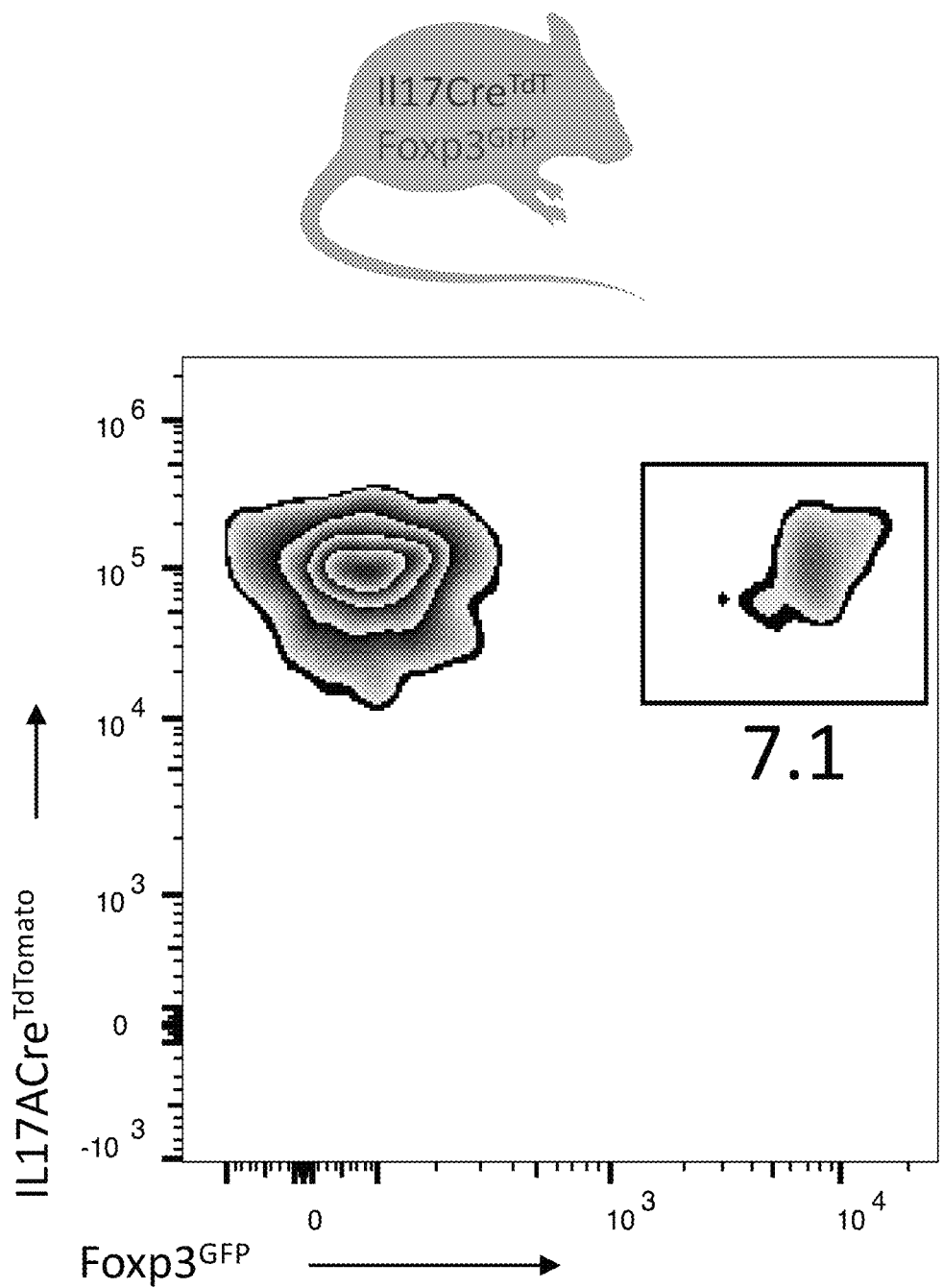
FIGS. 6A-6I— Validation of Treg-like Th17 cluster.
Figure 6B:
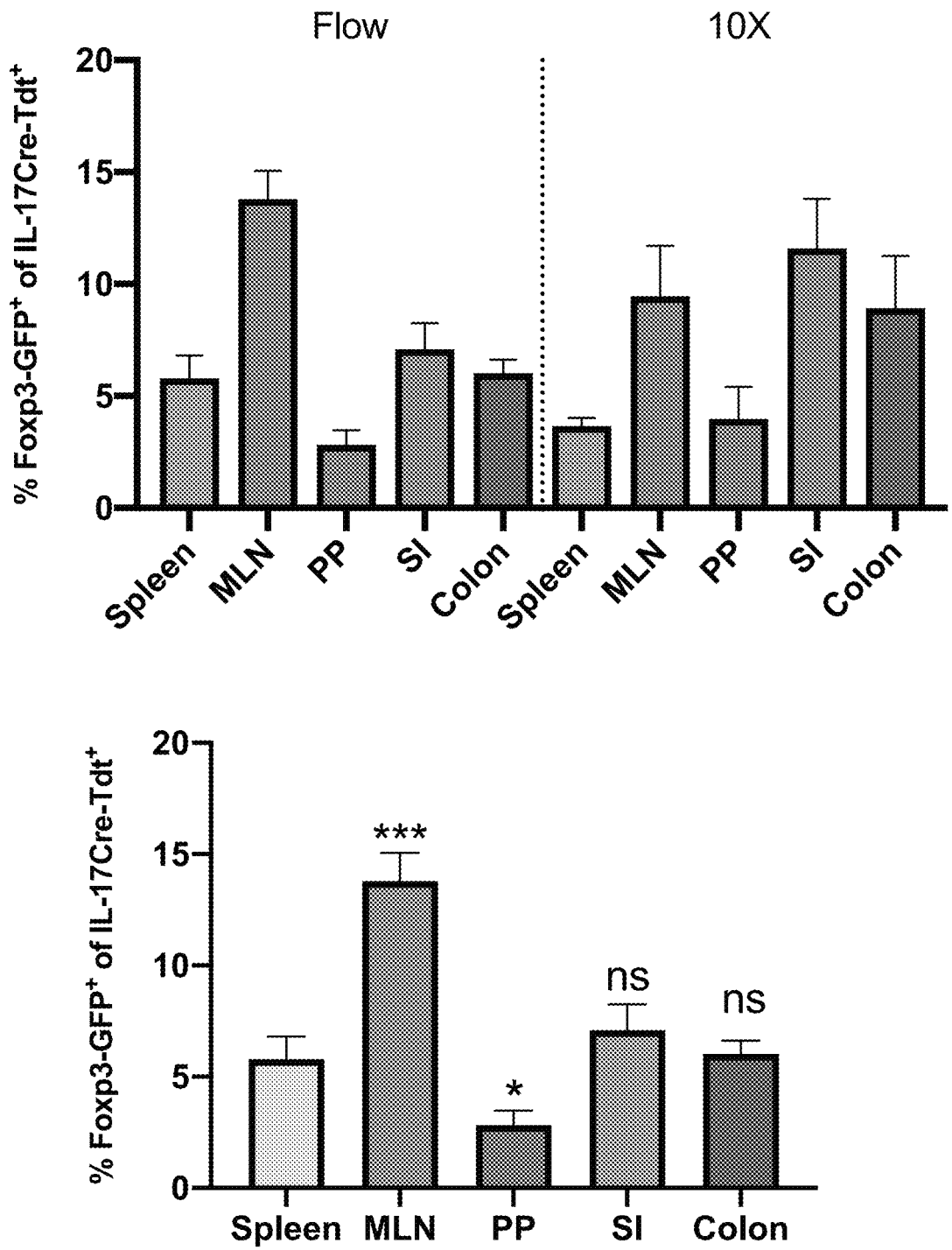
Figure 6C:
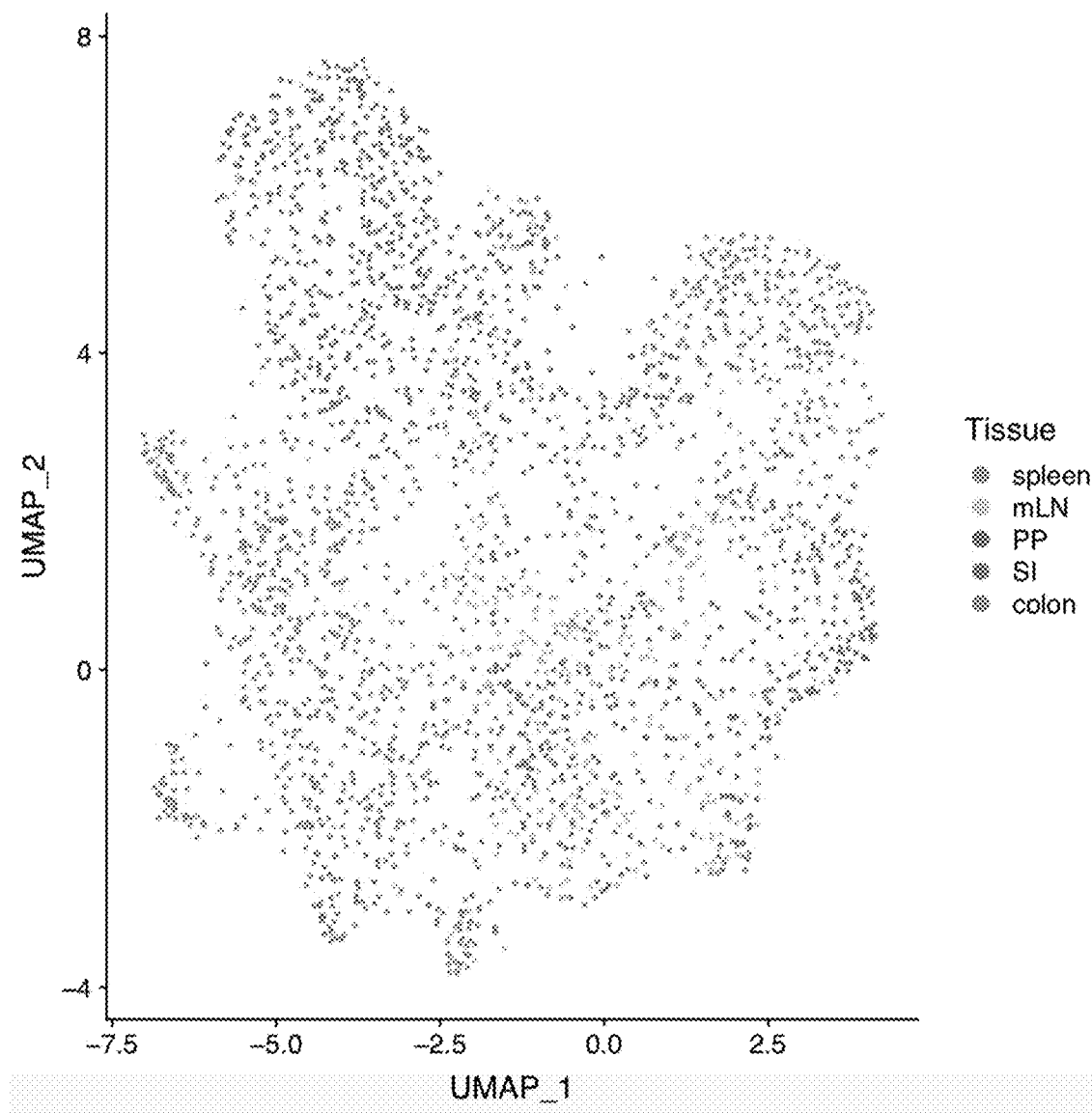
Figure 6D:
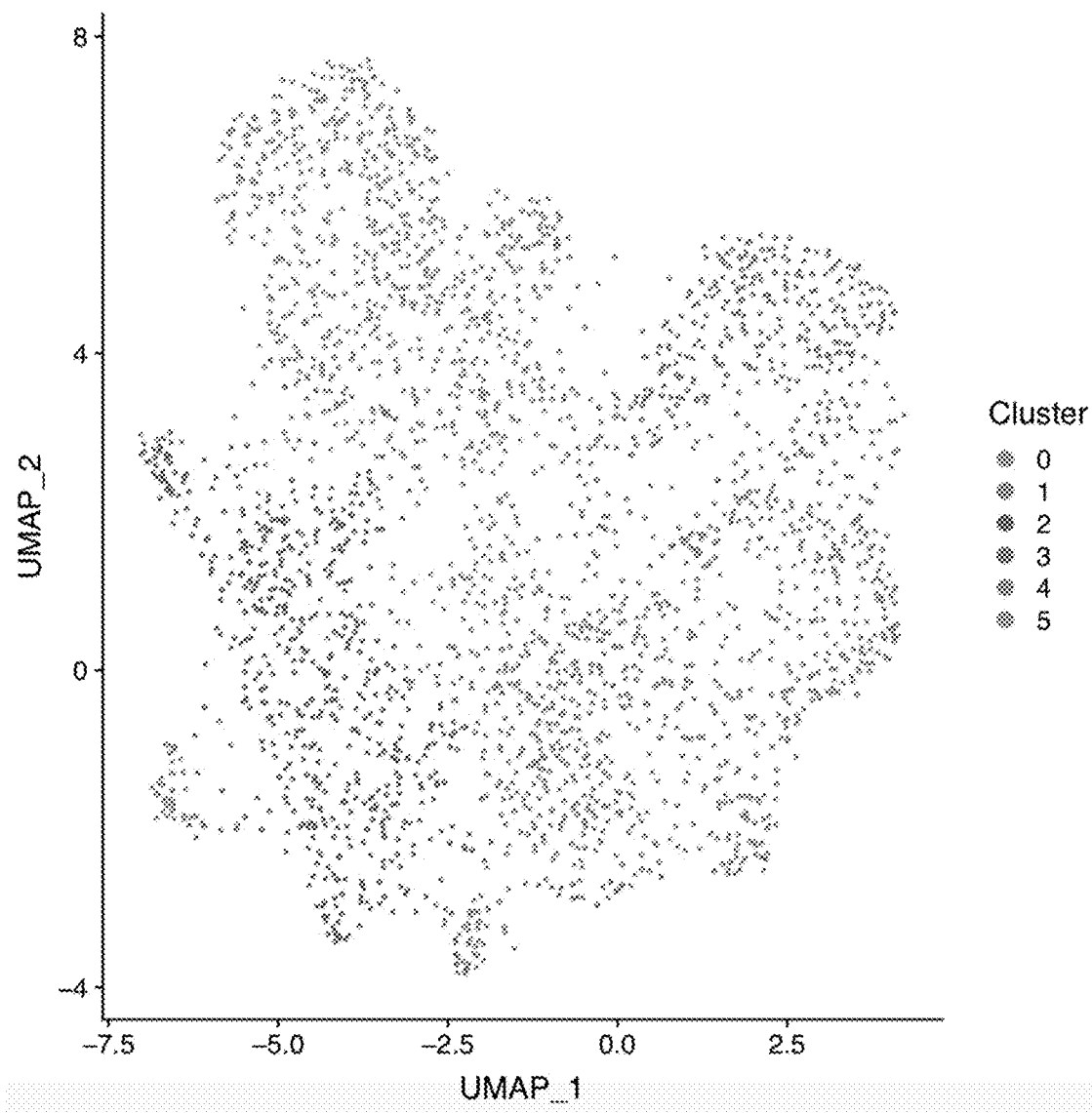
Figure 6E:
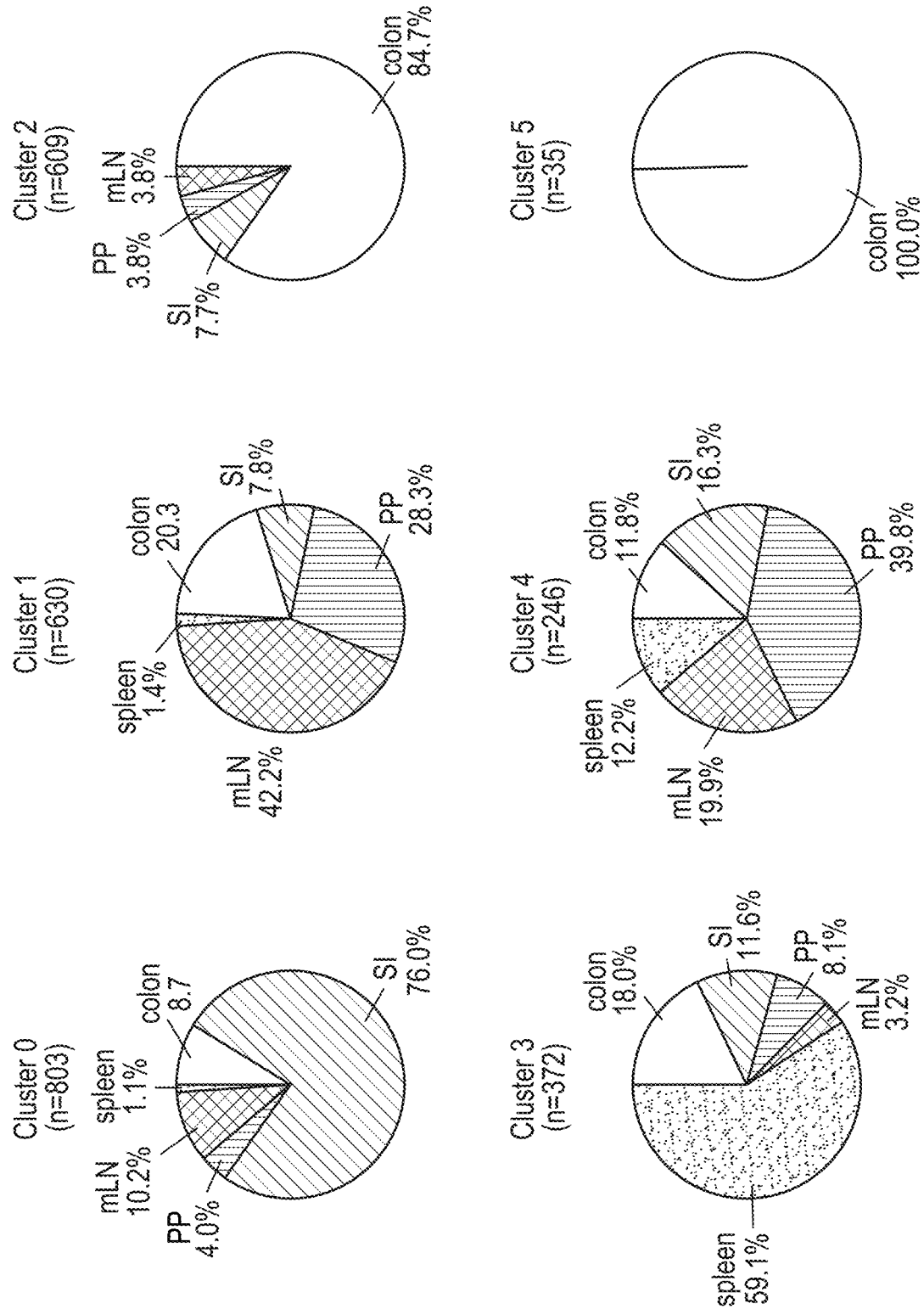
Figure 6F:
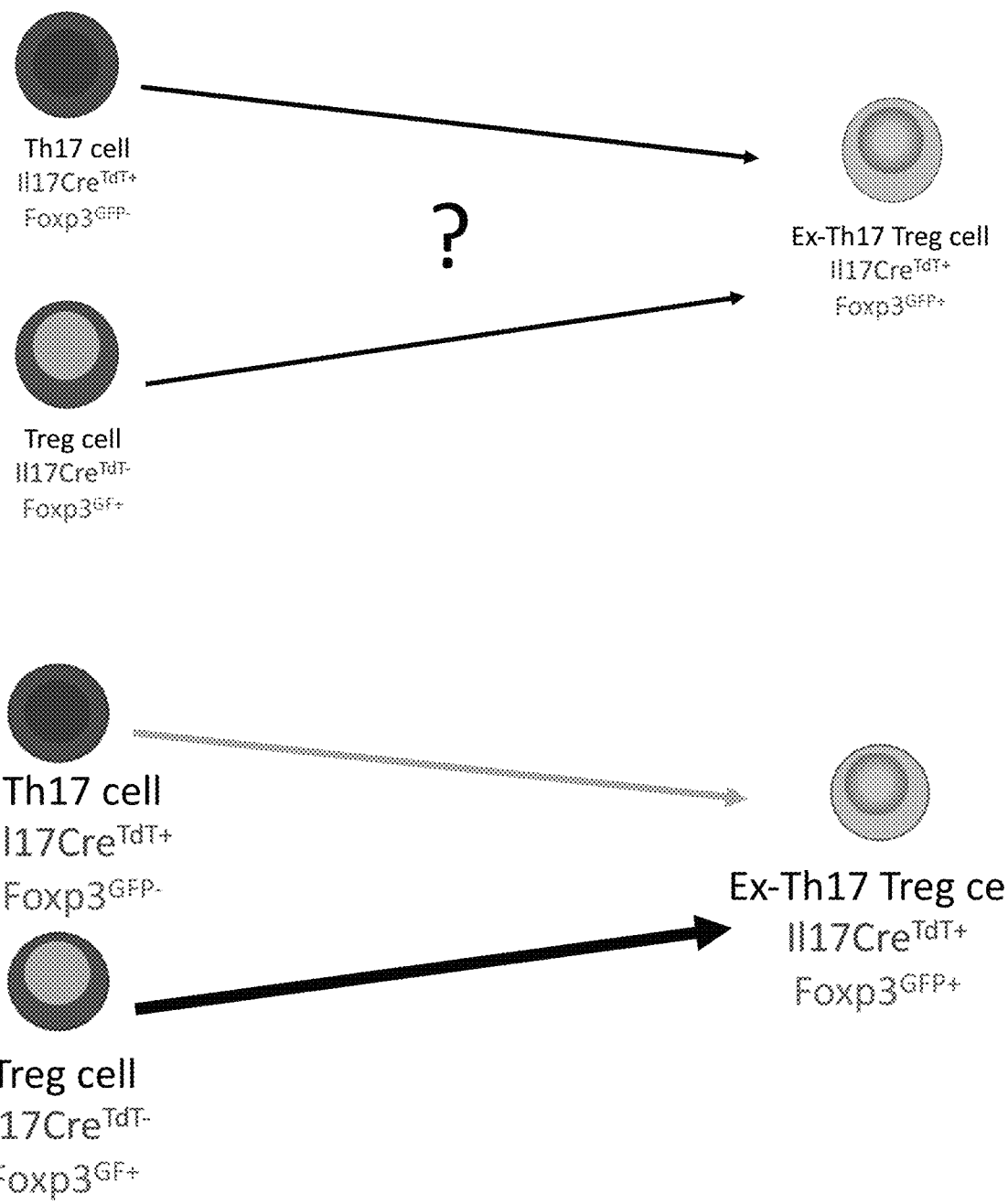
Figure 6G:
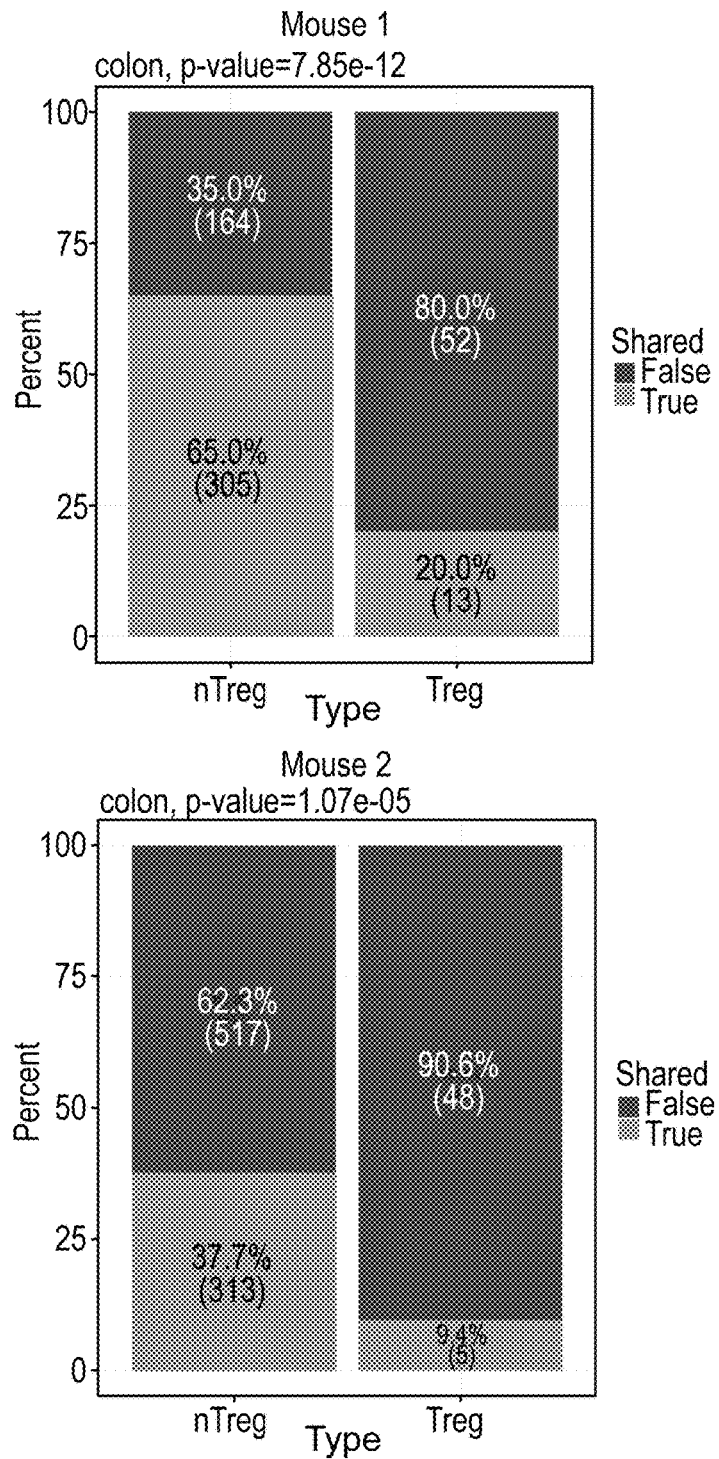
Figure 6H:
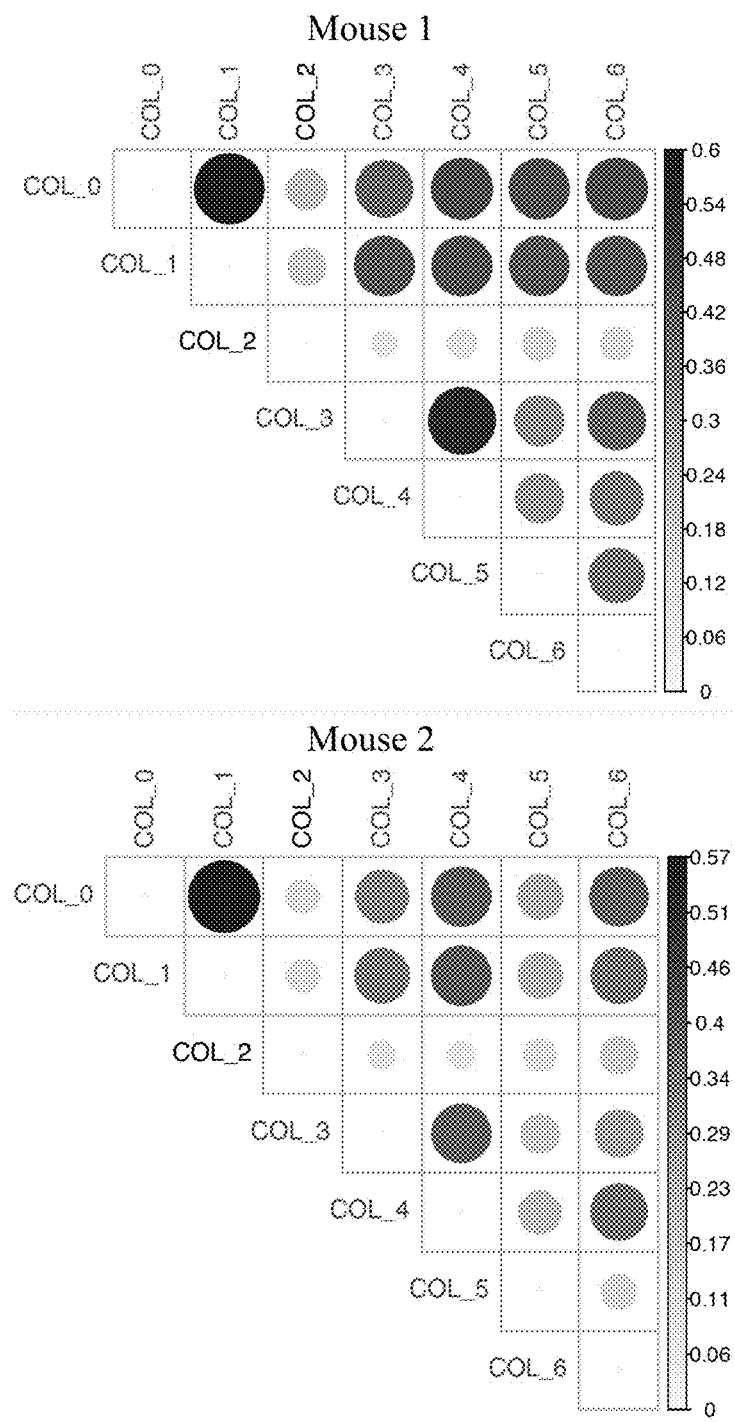
Figure 6I:
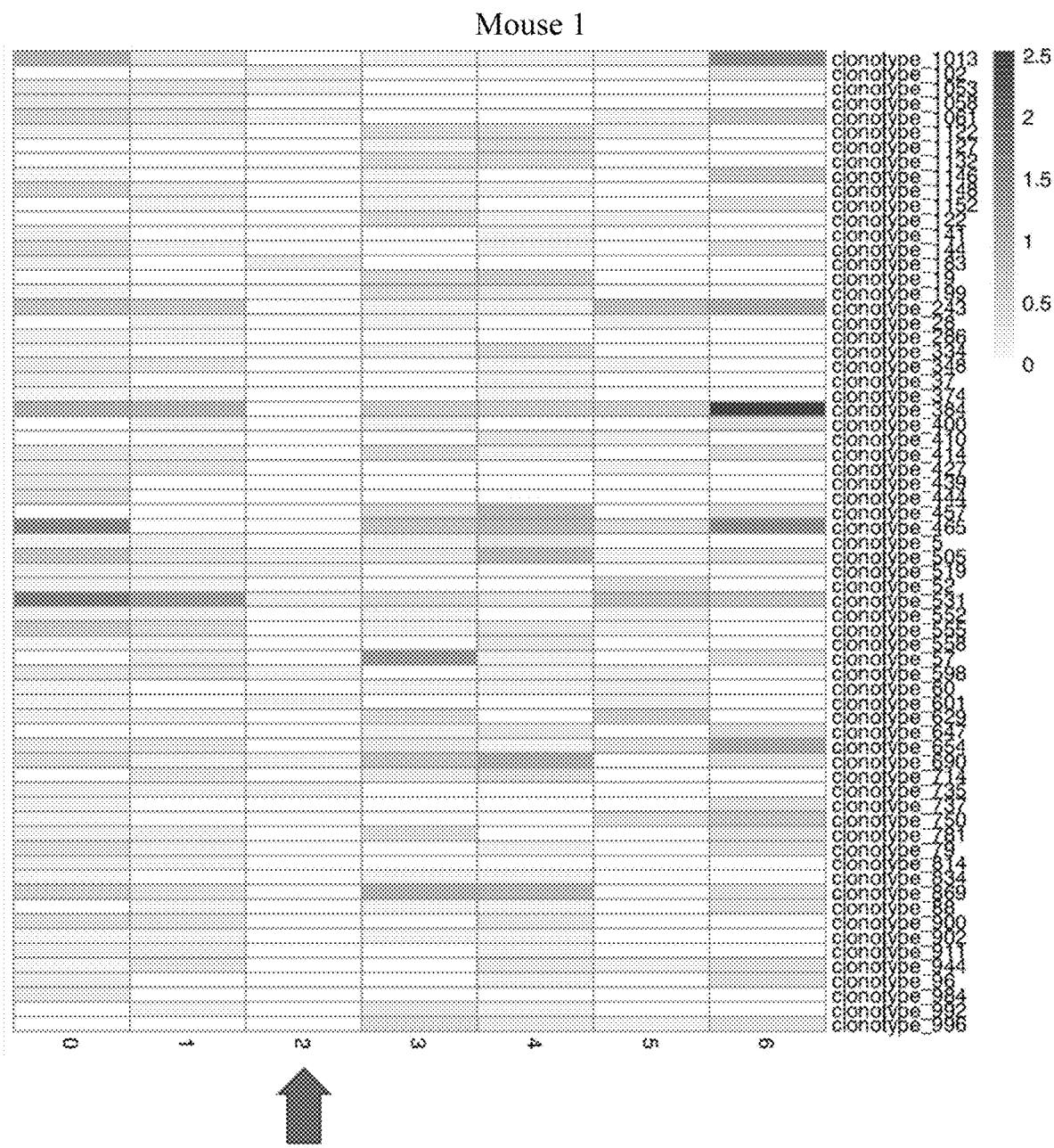
Figure 6I:
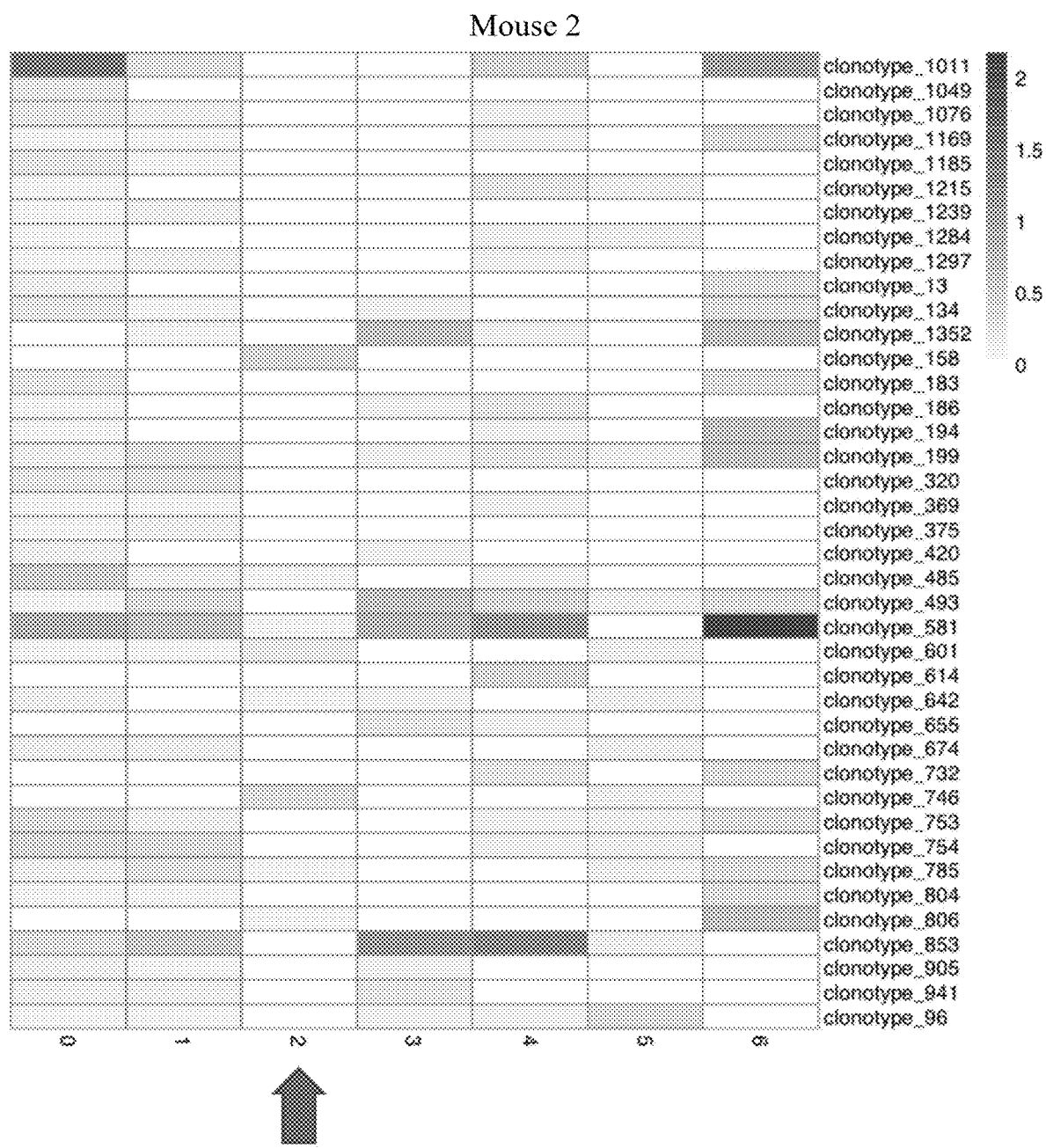
Figure 7A:
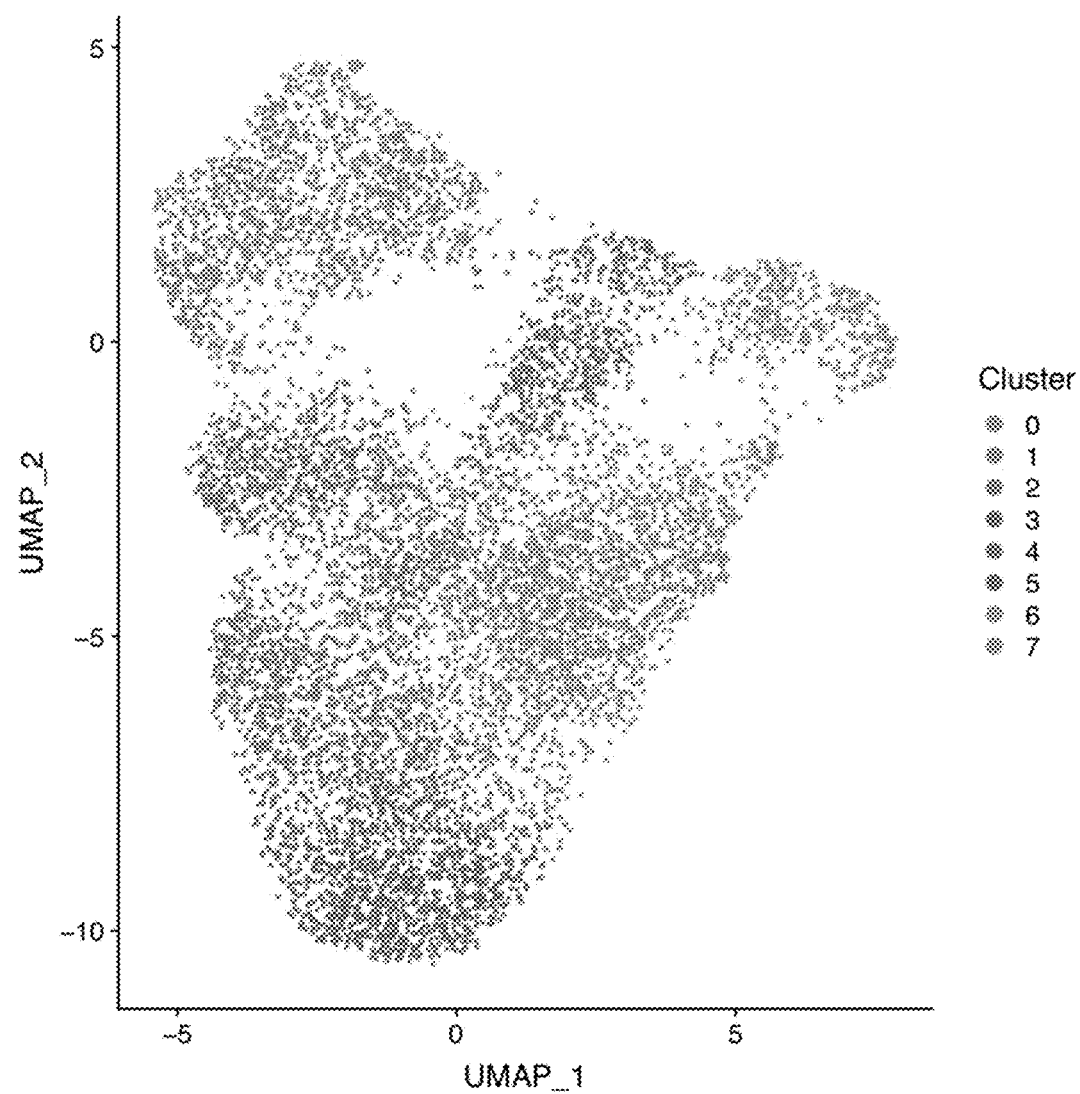
FIGS. 7A-7D— Intestinal Th17 cell heterogeneity at single-cell resolution FIG. 7A. UMAP of intestinal Th17 cells labeled by cluster.
Figure 7B:
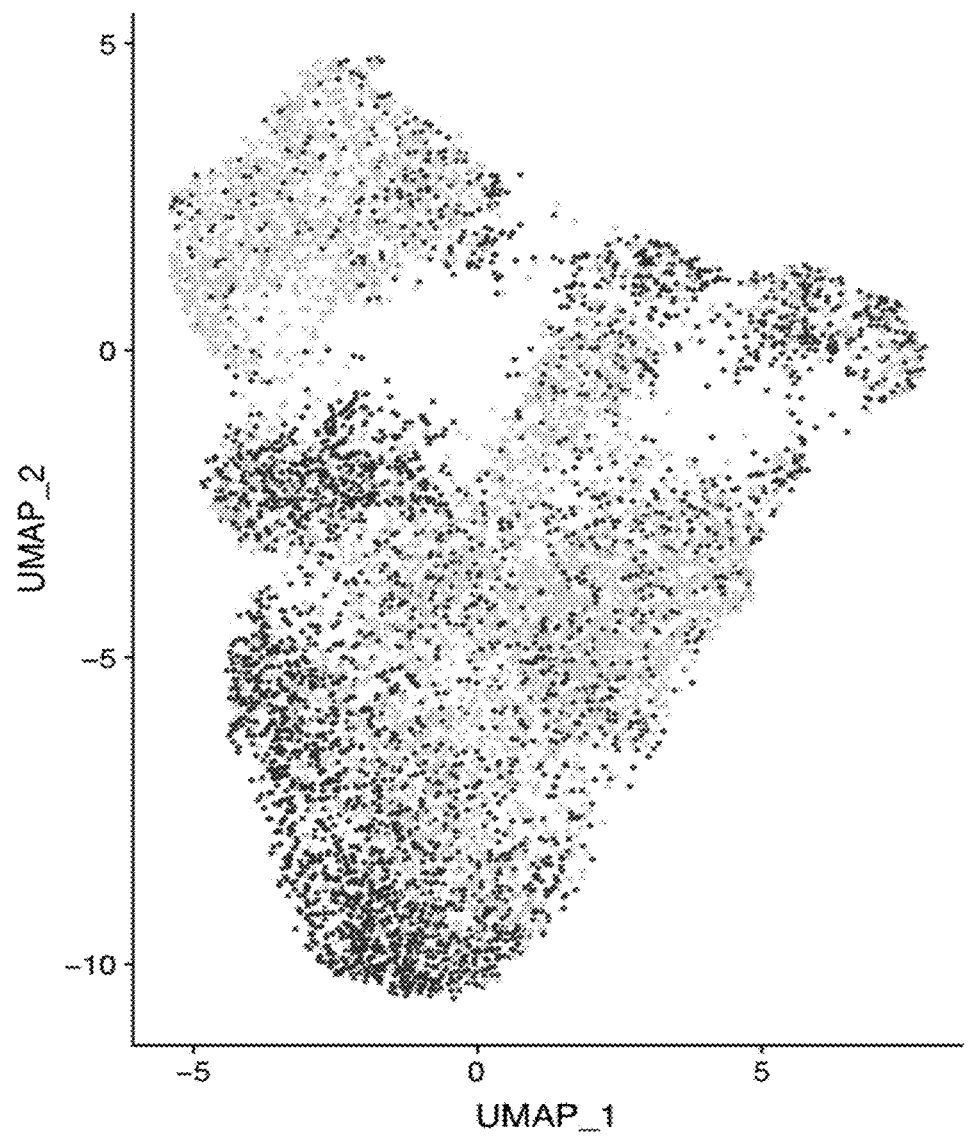
Figure 7C:
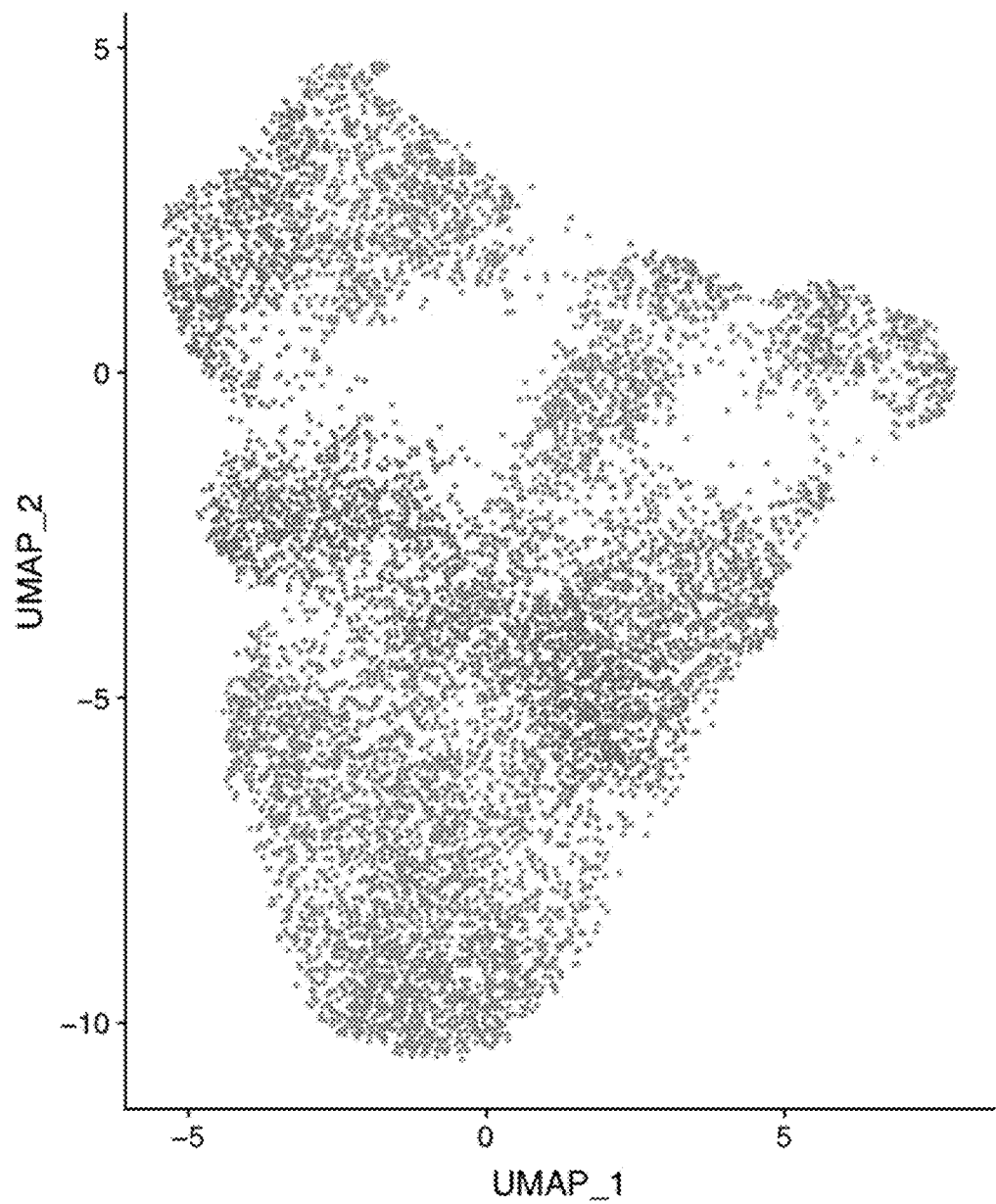
Figure 7D:
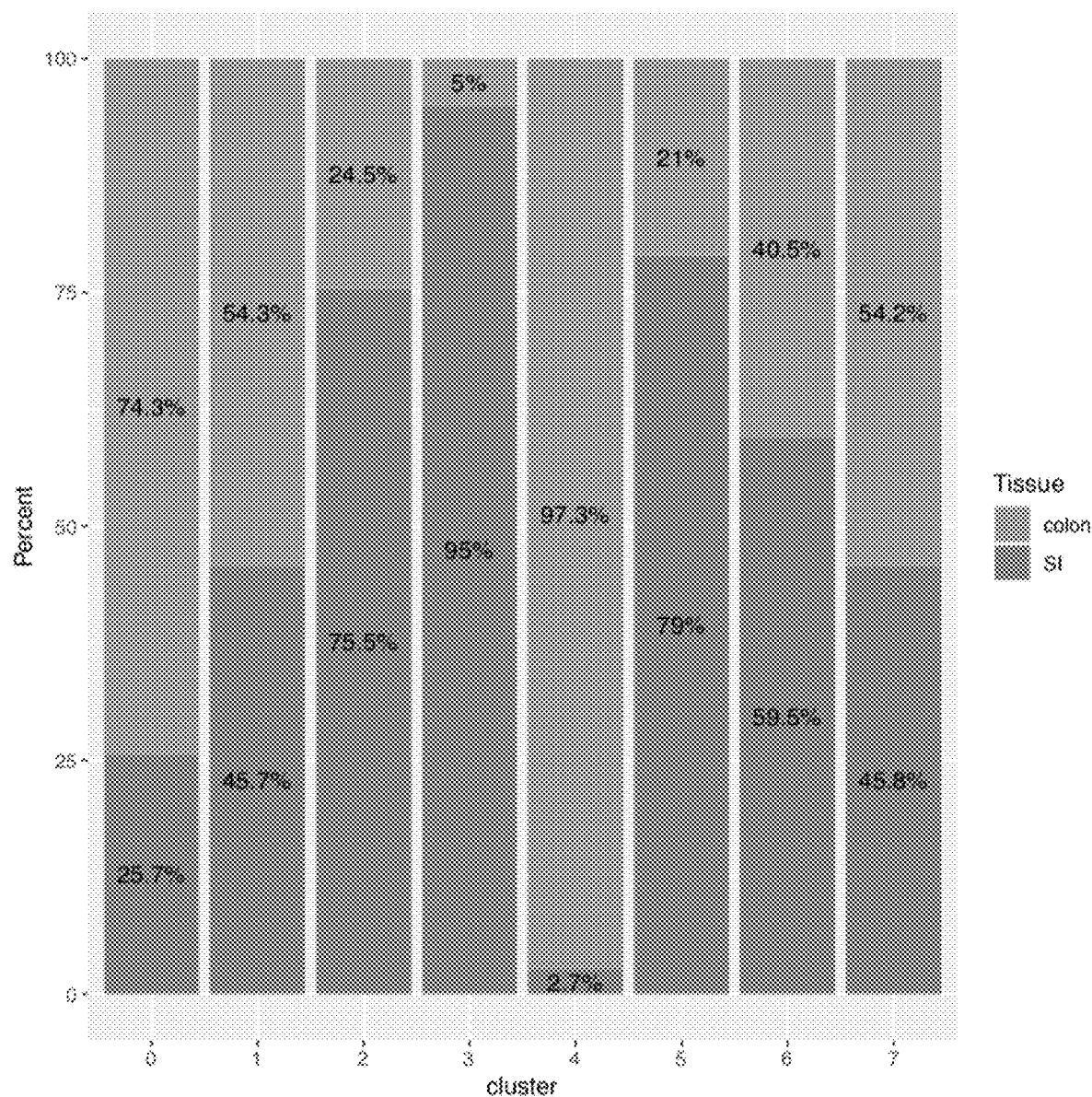

In some embodiments, the CRISPR-Cas system that can be used to modify a polynucleotide of the present invention described herein can be a Class 1 CRISPR-Cas system. Class 1 CRISPR-Cas systems are divided into Types I, II, and IV. Makarova et al. 2020. Nat. Rev. 18: 67-83., particularly as described in FIG. 1. Type I CRISPR-Cas systems are divided into 9 subtypes (I-A, I-B, I-C, I-D, I-E, I-F1, I-F2, I-F3, and IG). Makarova et al., 2020. Class 1, Type I CRISPR-Cas systems can contain a Cas3 protein that can have helicase activity. Type III CRISPR-Cas systems are divided into 6 subtypes (III-A, III-B, III-C, III-D, III-E, and III-F). Type III CRISPR-Cas systems can contain a Cas10 that can include an RNA recognition motif called Palm and a cyclase domain that can cleave polynucleotides. Makarova et al., 2020. Type IV CRISPR-Cas systems are divided into 3 subtypes. (IV-A, IV-B, and IV-C). Makarova et al., 2020. Class 1 systems also include CRISPR-Cas variants, including Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems. Peters et al., PNAS 114 (35) (2017); DOI: 10.1073/pnas.1709035114; see also, Makarova et al. 2018. The CRISPR Journal, v. 1, n5, FIG. 5.

The Class 1 systems typically use a multi-protein effector complex, which can, in some embodiments, include ancillary proteins, such as one or more proteins in a complex referred to as a CRISPR-associated complex for antiviral defense (Cascade), one or more adaptation proteins (e.g., Cas1, Cas2, RNA nuclease), and/or one or more accessory proteins (e.g., Cas 4, DNA nuclease), CRISPR associated Rossman fold (CARF) domain containing proteins, and/or RNA transcriptase.

The backbone of the Class 1 CRISPR-Cas system effector complexes can be formed by RNA recognition motif domain-containing protein(s) of the repeat-associated mysterious proteins (RAMPs) family subunits (e.g., Cas 5, Cas6, and/or Cas7). RAMP proteins are characterized by having one or more RNA recognition motif domains. In some embodiments, multiple copies of RAMPs can be present. In some embodiments, the Class I CRISPR-Cas system can include 1, 2, 3, 4, 5, 6, 7, 8, 9, 10, 11, 12 or more Cas5, Cas6, and/or Cas 7 proteins. In some embodiments, the Cas6 protein is an RNAse, which can be responsible for pre-crRNA processing. When present in a Class 1 CRISPR-Cas system, Cas6 can be optionally physically associated with the effector complex.

Figure 2A:
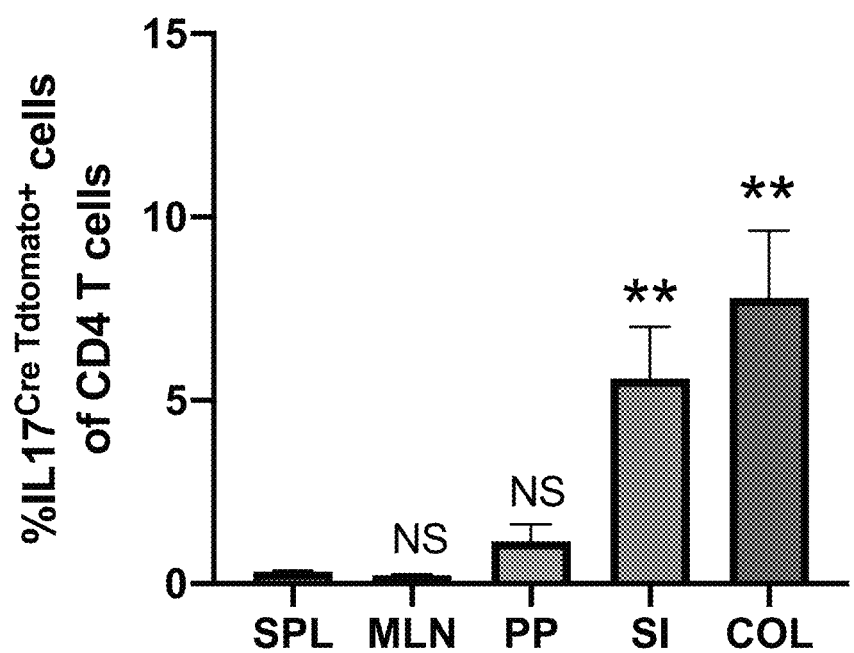
FIGS. 2A-2B— FIG. 2A. Graph showing the percentage of CD4 T cells that are TdTomato positive in each tissue.
Figure 2B:
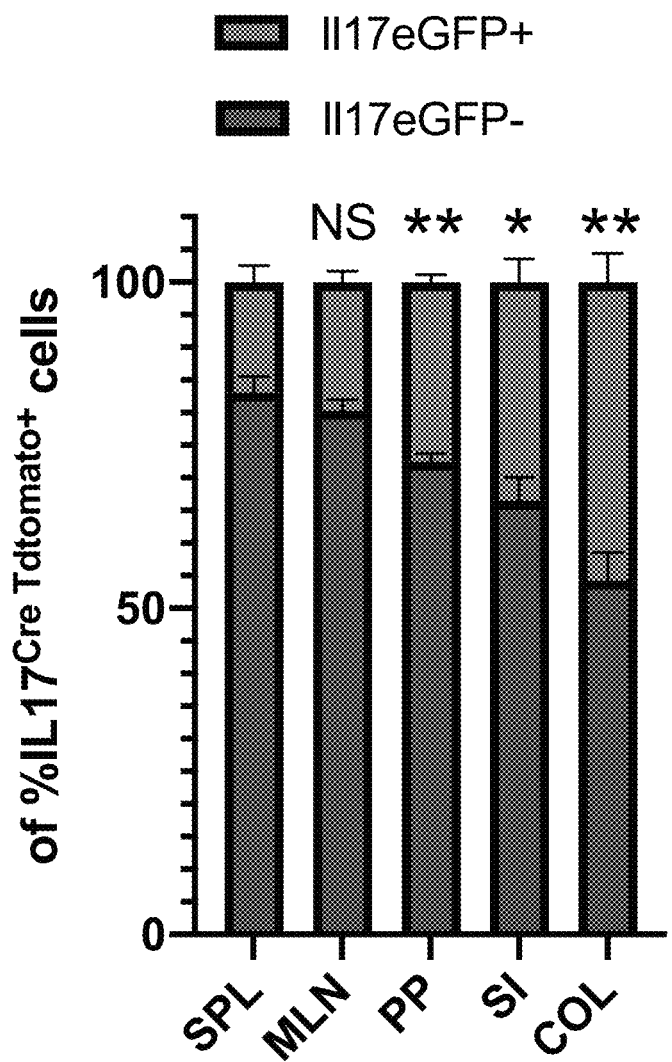

Class 1 CRISPR-Cas system effector complexes can, in some embodiments, also include a large subunit. The large subunit can be composed of or include a Cas8 and/or Cas10 protein. See, e.g., FIGS. 1 and 2. Koonin E V, Makarova K S. 2019. Phil. Trans. R. Soc. B 374: 20180087, DOI: 10.1098/rstb.2018.0087 and Makarova et al. 2020.

Class 1 CRISPR-Cas system effector complexes can, in some embodiments, include a small subunit (for example, Cas11). See, e.g., FIGS. 1 and 2. Koonin E V, Makarova K S. 2019 Origins and Evolution of CRISPR-Cas systems. Phil. Trans. R. Soc. B 374: 20180087, DOI: 10.1098/rstb.2018.0087.

In some embodiments, the Class 1 CRISPR-Cas system can be a Type I CRISPR-Cas system. In some embodiments, the Type I CRISPR-Cas system can be a subtype I-A CRISPR-Cas system. In some embodiments, the Type I CRISPR-Cas system can be a subtype I-B CRISPR-Cas system. In some embodiments, the Type I CRISPR-Cas system can be a subtype I-C CRISPR-Cas system. In some embodiments, the Type I CRISPR-Cas system can be a subtype I-D CRISPR-Cas system. In some embodiments, the Type I CRISPR-Cas system can be a subtype I-E CRISPR-Cas system. In some embodiments, the Type I CRISPR-Cas system can be a subtype I-F1 CRISPR-Cas system. In some embodiments, the Type I CRISPR-Cas system can be a subtype I-F2 CRISPR-Cas system. In some embodiments, the Type I CRISPR-Cas system can be a subtype I-F3 CRISPR-Cas system. In some embodiments, the Type I CRISPR-Cas system can be a subtype I-G CRISPR-Cas system. In some embodiments, the Type I CRISPR-Cas system can be a CRISPR-Cas variant, such as a Type I-A, I-B, I-E, I-F and I-U variants, which can include variants carried by transposons and plasmids, including versions of subtype I-F encoded by a large family of Tn7-like transposon and smaller groups of Tn7-like transposons that encode similarly degraded subtype I-B systems as previously described.

In some embodiments, the Class 1 CRISPR-Cas system can be a Type III CRISPR-Cas system. In some embodiments, the Type III CRISPR-Cas system can be a subtype III-A CRISPR-Cas system. In some embodiments, the Type III CRISPR-Cas system can be a subtype III-B CRISPR-Cas system. In some embodiments, the Type III CRISPR-Cas system can be a subtype III-C CRISPR-Cas system. In some embodiments, the Type III CRISPR-Cas system can be a subtype III-D CRISPR-Cas system. In some embodiments, the Type III CRISPR-Cas system can be a subtype III-E CRISPR-Cas system. In some embodiments, the Type III CRISPR-Cas system can be a subtype III-F CRISPR-Cas system.

In some embodiments, the Class 1 CRISPR-Cas system can be a Type IV CRISPR-Cas-system. In some embodiments, the Type IV CRISPR-Cas system can be a subtype IV-A CRISPR-Cas system. In some embodiments, the Type IV CRISPR-Cas system can be a subtype IV-B CRISPR-Cas system. In some embodiments, the Type IV CRISPR-Cas system can be a subtype IV-C CRISPR-Cas system.

The effector complex of a Class 1 CRISPR-Cas system can, in some embodiments, include a Cas3 protein that is optionally fused to a Cas2 protein, a Cas4, a Cas5, a Cas6, a Cas7, a Cas8, a Cas10, a Cas11, or a combination thereof. In some embodiments, the effector complex of a Class 1 CRISPR-Cas system can have multiple copies, such as 1, 2, 3, 4, 5, 6, 7, 8, 9, 10, 11, 12, 13, or 14, of any one or more Cas proteins.

Class 2 CRISPR-Cas Systems

The compositions, systems, and methods described in greater detail elsewhere herein can be designed and adapted for use with Class 2 CRISPR-Cas systems. Thus, in some embodiments, the CRISPR-Cas system is a Class 2 CRISPR-Cas system. Class 2 systems are distinguished from Class 1 systems in that they have a single, large, multi-domain effector protein. In certain example embodiments, the Class 2 system can be a Type II, Type V, or Type VI system, which are described in Makarova et al. "Evolutionary classification of CRISPR-Cas systems: a burst of class 2 and derived variants" Nature Reviews Microbiology, 18:67-81 (February 2020), incorporated herein by reference. Each type of Class 2 system is further divided into subtypes. See Markova et al. 2020, particularly at Figure. 2. Class 2, Type II systems can be divided into 4 subtypes: II-A, II-B, II-C1, and II-C2. Class 2, Type V systems can be divided into 17 subtypes: V-A, V-B1, V-B2, V-C, V-D, V-E, V-F1, V-F1(V-U3), V-F2, V-F3, V-G, V-H, V-I, V-K (V-U5), V-U1, V-U2, and V-U4. Class 2, Type IV systems can be divided into 5 subtypes: VI-A, VI-B1, VI-B2, VI-C, and VI-D.

The distinguishing feature of these types is that their effector complexes consist of a single, large, multi-domain protein. Type V systems differ from Type II effectors (e.g., Cas9), which contain two nuclear domains that are each responsible for the cleavage of one strand of the target DNA, with the HNH nuclease inserted inside the Ruv-C like nuclease domain sequence. The Type V systems (e.g., Cas12) only contain a RuvC-like nuclease domain that cleaves both strands. Type VI (Cas13) are unrelated to the effectors of Type II and V systems and contain two HEPN domains and target RNA. Cas13 proteins also display collateral activity that is triggered by target recognition. Some Type V systems have also been found to possess this collateral activity with two single-stranded DNA in in vitro contexts.

In some embodiments, the Class 2 system is a Type II system. In some embodiments, the Type II CRISPR-Cas system is a II-A CRISPR-Cas system. In some embodiments, the Type II CRISPR-Cas system is a II-B CRISPR-Cas system. In some embodiments, the Type II CRISPR-Cas system is a II-C1 CRISPR-Cas system. In some embodiments, the Type II CRISPR-Cas system is a II-C2 CRISPR-Cas system. In some embodiments, the Type II system is a Cas9 system. In some embodiments, the Type II system includes a Cas9.

In some embodiments, the Class 2 system is a Type V system. In some embodiments, the Type V CRISPR-Cas system is a V-A CRISPR-Cas system. In some embodiments, the Type V CRISPR-Cas system is a V-B1 CRISPR-Cas system. In some embodiments, the Type V CRISPR-Cas system is a V-B2 CRISPR-Cas system. In some embodiments, the Type V CRISPR-Cas system is a V-C CRISPR-Cas system. In some embodiments, the Type V CRISPR-Cas system is a V-D CRISPR-Cas system. In some embodiments, the Type V CRISPR-Cas system is a V-E CRISPR-Cas system. In some embodiments, the Type V CRISPR-Cas system is a V-F1 CRISPR-Cas system. In some embodiments, the Type V CRISPR-Cas system is a V-F1 (V-U3) CRISPR-Cas system. In some embodiments, the Type V CRISPR-Cas system is a V-F2 CRISPR-Cas system. In some embodiments, the Type V CRISPR-Cas system is a V-F3 CRISPR-Cas system. In some embodiments, the Type V CRISPR-Cas system is a V-G CRISPR-Cas system. In some embodiments, the Type V CRISPR-Cas system is a V-H CRISPR-Cas system. In some embodiments, the Type V CRISPR-Cas system is a V-I CRISPR-Cas system. In some embodiments, the Type V CRISPR-Cas system is a V-K (V-U5) CRISPR-Cas system. In some embodiments, the Type V CRISPR-Cas system is a V-U1 CRISPR-Cas system. In some embodiments, the Type V CRISPR-Cas system is a V-U2 CRISPR-Cas system. In some embodiments, the Type V CRISPR-Cas system is a V-U4 CRISPR-Cas system. In some embodiments, the Type V CRISPR-Cas system includes a Cas12a (Cpf1), Cas12b (C2c1), Cas12c (C2c3), CasX, and/or Cas14.

In some embodiments the Class 2 system is a Type VI system. In some embodiments, the Type VI CRISPR-Cas system is a VI-A CRISPR-Cas system. In some embodiments, the Type VI CRISPR-Cas system is a VI-B1 CRISPR-Cas system. In some embodiments, the Type VI CRISPR-Cas system is a VI-B2 CRISPR-Cas system. In some embodiments, the Type VI CRISPR-Cas system is a VI-C CRISPR-Cas system. In some embodiments, the Type VI CRISPR-Cas system is a VI-D CRISPR-Cas system. In some embodiments, the Type VI CRISPR-Cas system includes a Cas13a (C2c2), Cas13b (Group 29/30), Cas13c, and/or Cas13d.

Specialized Cas-Based Systems

In some embodiments, the system is a Cas-based system that is capable of performing a specialized function or activity. For example, the Cas protein may be fused, operably coupled to, or otherwise associated with one or more functionals domains. In certain example embodiments, the Cas protein may be a catalytically dead Cas protein ("dCas") and/or have nickase activity. A nickase is a Cas protein that cuts only one strand of a double stranded target. In such embodiments, the dCas or nickase provide a sequence specific targeting functionality that delivers the functional domain to or proximate a target sequence. Example functional domains that may be fused to, operably coupled to, or otherwise associated with a Cas protein can be or include, but are not limited to a nuclear localization signal (NLS) domain, a nuclear export signal (NES) domain, a translational activation domain, a transcriptional activation domain (e.g. VP64, p65, MyoD1, HSF1, RTA, and SET7/9), a translation initiation domain, a transcriptional repression domain (e.g., a KRAB domain, NuE domain, NcoR domain, and a SID domain such as a SID4X domain), a nuclease domain (e.g., FokI), a histone modification domain (e.g., a histone acetyltransferase), a light inducible/controllable domain, a chemically inducible/controllable domain, a transposase domain, a homologous recombination machinery domain, a recombinase domain, an integrase domain, and combinations thereof. Methods for generating catalytically dead Cas9 or a nickase Cas9 (WO 2014/204725, Ran et al. Cell. 2013 Sep. 12; 154(6):1380-1389), Cas12 (Liu et al. Nature Communications, 8, 2095 (2017), and Cas13 (WO 2019/005884, WO2019/060746) are known in the art and incorporated herein by reference.

In some embodiments, the functional domains can have one or more of the following activities: methylase activity, demethylase activity, translation activation activity, translation initiation activity, translation repression activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, molecular switch activity, chemical inducibility, light inducibility, and nucleic acid binding activity. In some embodiments, the one or more functional domains may comprise epitope tags or reporters. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporters include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and auto-fluorescent proteins including blue fluorescent protein (BFP).

The one or more functional domain(s) may be positioned at, near, and/or in proximity to a terminus of the effector protein (e.g., a Cas protein). In embodiments having two or more functional domains, each of the two can be positioned at or near or in proximity to a terminus of the effector protein (e.g., a Cas protein). In some embodiments, such as those where the functional domain is operably coupled to the effector protein, the one or more functional domains can be tethered or linked via a suitable linker (including, but not limited to, GlySer linkers) to the effector protein (e.g., a Cas protein). When there is more than one functional domain, the functional domains can be same or different. In some embodiments, all the functional domains are the same. In some embodiments, all of the functional domains are different from each other. In some embodiments, at least two of the functional domains are different from each other. In some embodiments, at least two of the functional domains are the same as each other.

Other suitable functional domains can be found, for example, in International Patent Publication No. WO 2019/018423.

Split CRISPR-Cas Systems

In some embodiments, the CRISPR-Cas system is a split CRISPR-Cas system. See e.g., Zetche et al., 2015. Nat. Biotechnol. 33(2): 139-142 and WO 2019/018423, the compositions and techniques of which can be used in and/or adapted for use with the present invention. Split CRISPR-Cas proteins are set forth herein and in documents incorporated herein by reference in further detail herein. In certain embodiments, each part of a split CRISPR protein are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In some embodiments, CRISPR proteins may preferably split between domains, leaving domains intact. In particular embodiments, said Cas split domains (e.g., RuvC and HNH domains in the case of Cas9) can be simultaneously or sequentially introduced into the cell such that said split Cas domain(s) process the target nucleic acid sequence in the algae cell. The reduced size of the split Cas compared to the wild type Cas allows other methods of delivery of the systems to the cells, such as the use of cell penetrating peptides as described herein.

DNA and RNA Base Editing

In some embodiments, a polynucleotide of the present invention described elsewhere herein can be modified using a base editing system. In some embodiments, a Cas protein is connected or fused to a nucleotide deaminase. Thus, in some embodiments the Cas-based system can be a base editing system. As used herein "base editing" refers generally to the process of polynucleotide modification via a CRISPR-Cas-based or Cas-based system that does not include excising nucleotides to make the modification. Base editing can convert base pairs at precise locations without generating excess undesired editing byproducts that can be made using traditional CRISPR-Cas systems.

In certain example embodiments, the nucleotide deaminase may be a DNA base editor used in combination with a DNA binding Cas protein such as, but not limited to, Class 2 Type II and Type V systems. Two classes of DNA base editors are generally known: cytosine base editors (CBEs) and adenine base editors (ABEs). CBEs convert a C·G base pair into a T·A base pair (Komor et al. 2016. Nature. 533:420-424; Nishida et al. 2016. Science. 353; and Li et al. Nat. Biotech. 36:324-327) and ABEs convert an A·T base pair to a G·C base pair. Collectively, CBEs and ABEs can mediate all four possible transition mutations (C to T, A to G, T to C, and G to A). Rees and Liu. 2018. Nat. Rev. Genet. 19(12): 770-788, particularly at FIGS. 1b, 2a-2c, 3a-3f, and Table 1. In some embodiments, the base editing system includes a CBE and/or an ABE. In some embodiments, a polynucleotide of the present invention described elsewhere herein can be modified using a base editing system. Rees and Liu. 2018. Nat. Rev. Gent. 19(12):770-788. Base editors also generally do not need a DNA donor template and/or rely on homology-directed repair. Komor et al. 2016. Nature. 533: 420-424; Nishida et al. 2016. Science. 353; and Gaudeli et al. 2017. Nature. 551:464-471. Upon binding to a target locus in the DNA, base pairing between the guide RNA of the system and the target DNA strand leads to displacement of a small segment of ssDNA in an "R-loop". Nishimasu et al. Cell. 156:935-949. DNA bases within the ssDNA bubble are modified by the enzyme component, such as a deaminase. In some systems, the catalytically disabled Cas protein can be a variant or modified Cas can have nickase functionality and can generate a nick in the non-edited DNA strand to induce cells to repair the non-edited strand using the edited strand as a template. Komor et al. 2016. Nature. 533:420-424; Nishida et al. 2016. Science. 353; and Gaudeli et al. 2017. Nature. 551:464-471. Base editors may be further engineered to optimize conversion of nucleotides (e.g. A:T to G:C). Richter et al. 2020. Nature Biotechnology. doi.org/10.1038/s41587-020-0453-z.

Other Example Type V base editing systems are described in WO 2018/213708, WO 2018/213726, PCT/US2018/067207, PCT/US2018/067225, and PCT/US2018/067307 which are incorporated by referenced herein.

In certain example embodiments, the base editing system may be a RNA base editing system. As with DNA base editors, a nucleotide deaminase capable of converting nucleotide bases may be fused to a Cas protein. However, in these embodiments, the Cas protein will need to be capable of binding RNA. Example RNA binding Cas proteins include, but are not limited to, RNA-binding Cas9s such as *Francisella novicida* Cas9 ("FnCas9"), and Class 2 Type VI Cas systems. The nucleotide deaminase may be a cytidine deaminase or an adenosine deaminase, or an adenosine deaminase engineered to have cytidine deaminase activity. In certain example embodiments, the RNA based editor may be used to delete or introduce a post-translation modification site in the expressed mRNA. In contrast to DNA base editors, whose edits are permanent in the modified cell, RNA base editors can provide edits where finer temporal control may be needed, for example in modulating a particular immune response. Example Type VI RNA-base editing systems are described in Cox et al. 2017. Science 358: 1019-1027, WO 2019/005884, WO 2019/005886, WO 2019/071048, PCT/US20018/05179, PCT/US2018/067207, which are incorporated herein by reference. An example FnCas9 system that may be adapted for RNA base editing purposes is described in WO 2016/106236, which is incorporated herein by reference.

An example method for delivery of base-editing systems, including use of a split-intein approach to divide CBE and ABE into reconstitutable halves, is described in Levy et al.

Nature Biomedical Engineering doi.org/10.1038/s41441-019-0505-5 (2019), which is incorporated herein by reference.

Prime Editors

In some embodiments, a polynucleotide of the present invention described elsewhere herein can be modified using a prime editing system (See e.g. Anzalone et al. 2019. Nature. 576: 149-157). Like base editing systems, prime editing systems can be capable of targeted modification of a polynucleotide without generating double stranded breaks and does not require donor templates. Further prime editing systems can be capable of all 12 possible combination swaps. Prime editing can operate via a "search-and-replace" methodology and can mediate targeted insertions, deletions, all 12 possible base-to-base conversion, and combinations thereof. Generally, a prime editing system, as exemplified by PE1, PE2, and PE3 (Id.), can include a reverse transcriptase fused or otherwise coupled or associated with an RNA-programmable nickase, and a prime-editing extended guide RNA (pegRNA) to facility direct copying of genetic information from the extension on the pegRNA into the target polynucleotide. Embodiments that can be used with the present invention include these and variants thereof. Prime editing can have the advantage of lower off-target activity than traditional CRISPR-Cas systems along with few byproducts and greater or similar efficiency as compared to traditional CRISPR-Cas systems.

In some embodiments, the prime editing guide molecule can specify both the target polynucleotide information (e.g. sequence) and contain a new polynucleotide cargo that replaces target polynucleotides. To initiate transfer from the guide molecule to the target polynucleotide, the PE system can nick the target polynucleotide at a target side to expose a 3'hydroxyl group, which can prime reverse transcription of an edit-encoding extension region of the guide molecule (e.g. a prime editing guide molecule or peg guide molecule) directly into the target site in the target polynucleotide. See e.g. Anzalone et al. 2019. Nature. 576: 149-157, particularly at FIGS. 1b, 1c, related discussion, and Supplementary discussion.

In some embodiments, a prime editing system can be composed of a Cas polypeptide having nickase activity, a reverse transcriptase, and a guide molecule. The Cas polypeptide can lack nuclease activity. The guide molecule can include a target binding sequence as well as a primer binding sequence and a template containing the edited polynucleotide sequence. The guide molecule, Cas polypeptide, and/or reverse transcriptase can be coupled together or otherwise associate with each other to form an effector complex and edit a target sequence. In some embodiments, the Cas polypeptide is a Class 2, Type V Cas polypeptide. In some embodiments, the Cas polypeptide is a Cas9 polypeptide (e.g. is a Cas9 nickase). In some embodiments, the Cas polypeptide is fused to the reverse transcriptase. In some embodiments, the Cas polypeptide is linked to the reverse transcriptase.

In some embodiments, the prime editing system can be a PE1 system or variant thereof, a PE2 system or variant thereof, or a PE3 (e.g. PE3, PE3b) system. See e.g., Anzalone et al. 2019. Nature. 576: 149-157, particularly at pgs. 2-3, FIGS. 2a, 3a-3f, 4a-4b, Extended data FIGS. 3a-3b, 4, The peg guide molecule can be about 10 to about 200 or more nucleotides in length, such as 10 to/or 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length. Optimization of the peg guide molecule can be accomplished as described in Anzalone et al. 2019. Nature. 576: 149-157, particularly at pg. 3, FIG. 2a-2b, and Extended Data FIGS. 5a-c.

CRISPR Associated Transposase (CAST) Systems

In some embodiments, a polynucleotide of the present invention described elsewhere herein can be modified using a CRISPR Associated Transposase ("CAST") system. CAST system can include a Cas protein that is catalytically inactive, or engineered to be catalytically active, and further comprises a transposase (or subunits thereof) that catalyze RNA-guided DNA transposition. Such systems are able to insert DNA sequences at a target site in a DNA molecule without relying on host cell repair machinery. CAST systems can be Class1 or Class 2 CAST systems. An example Class 1 system is described in Klompe et al. Nature, doi: 10.1038/s41586-019-1323, which is in incorporated herein by reference. An example Class 2 system is described in Strecker et al. Science. 10/1126/science. aax9181 (2019), and PCT/US2019/066835 which are incorporated herein by reference.

Guide Molecules

The CRISPR-Cas or Cas-Based system described herein can, in some embodiments, include one or more guide molecules. The terms guide molecule, guide sequence and guide polynucleotide, refer to polynucleotides capable of guiding Cas to a target genomic locus and are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. The guide molecule can be a polynucleotide.

The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay (Qui et al. 2004. BioTechniques. 36(4)702-707). Similarly, cleavage of a target nucleic acid sequence may be evaluated in a test tube by providing the target nucleic acid sequence, components of a nucleic acid-targeting complex, including the guide sequence to be tested and a control guide sequence different from the test guide sequence, and comparing binding or rate of cleavage at the target sequence between the test and control guide sequence reactions. Other assays are possible and will occur to those skilled in the art.

In some embodiments, the guide molecule is an RNA. The guide molecule(s) (also referred to interchangeably herein as guide polynucleotide and guide sequence) that are included in the CRISPR-Cas or Cas based system can be any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, can be about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.com), and Maq (available at maq.sourceforge.net).

A guide sequence, and hence a nucleic acid-targeting guide, may be selected to target any target nucleic acid sequence. The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

In some embodiments, a nucleic acid-targeting guide is selected to reduce the degree secondary structure within the nucleic acid-targeting guide. In some embodiments, about or less than about 75%, 50%, 40%, 30%, 25%, 20%, 15%, 10%, 5%, 1%, or fewer of the nucleotides of the nucleic acid-targeting guide participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and PA Carr and GM Church, 2009, Nature Biotechnology 27(12): 1151-62).

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27 to 30 nt, e.g., 27, 28, 29, or 30 nt, from 30 to 35 nt, e.g., 30, 31, 32, 33, 34, or 35 nt, or 35 nt or longer.

The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and crRNA sequence are contained within a single transcript, such that hybridization between the two produces a transcript having a secondary structure, such as a hairpin.

In general, degree of complementarity is with reference to the optimal alignment of the sca sequence and tracr sequence, along the length of the shorter of the two sequences. Optimal alignment may be determined by any suitable alignment algorithm and may further account for secondary structures, such as self-complementarity within either the sca sequence or tracr sequence. In some embodiments, the degree of complementarity between the tracr sequence and sca sequence along the length of the shorter of the two when optimally aligned is about or more than about 25%, 30%, 40%, 50%, 60%, 70%, 80%, 90%, 95%, 97.5%, 99%, or higher.

In some embodiments, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and tracr RNA can be 30 or 50 nucleotides in length. In some embodiments, the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In some embodiments according to the invention, the guide RNA (capable of guiding Cas to a target locus) may comprise (1) a guide sequence capable of hybridizing to a genomic target locus in the eukaryotic cell; (2) a tracr sequence; and (3) a tracr mate sequence. All (1) to (3) may reside in a single RNA, i.e., an sgRNA (arranged in a 5' to 3' orientation), or the tracr RNA may be a different RNA than the RNA containing the guide and tracr sequence. The tracr hybridizes to the tracr mate sequence and directs the CRISPR/Cas complex to the target sequence. Where the tracr RNA is on a different RNA than the RNA containing the guide and tracr sequence, the length of each RNA may be optimized to be shortened from their respective native lengths, and each may be independently chemically modified to protect from degradation by cellular RNase or otherwise increase stability.

Many modifications to guide sequences are known in the art and are further contemplated within the context of this invention. Various modifications may be used to increase the specificity of binding to the target sequence and/or increase the activity of the Cas protein and/or reduce off-target effects. Example guide sequence modifications are described in PCT US2019/045582, specifically paragraphs [0178]-[0333] which is incorporated herein by reference.

Target Sequences, PAMs, and PFSs
Target Sequences

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to an RNA polynucleotide being or comprising the target sequence. In other words, the target polynucleotide can be a polynucleotide or a part of a polynucleotide to which a part of the guide sequence is designed to have complementarity with and to which the effector function mediated by the complex comprising the CRISPR effector protein and a guide molecule is to be directed. In some embodiments, a target sequence is located in the nucleus or cytoplasm of a cell.

The guide sequence can specifically bind a target sequence in a target polynucleotide. The target polynucleotide may be DNA. The target polynucleotide may be RNA. The target polynucleotide can have one or more (e.g., 1, 2, 3, 4, 5, 6, 7, 8, 9, 10, etc. or more) target sequences. The target polynucleotide can be on a vector. The target polynucleotide can be genomic DNA. The target polynucleotide can be episomal. Other forms of the target polynucleotide are described elsewhere herein.

The target sequence may be DNA. The target sequence may be any RNA sequence. In some embodiments, the target sequence may be a sequence within an RNA molecule selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nucleolar RNA (snoRNA), double stranded RNA (dsRNA), non-coding RNA (ncRNA), long non-coding RNA (lncRNA), and small cytoplasmatic RNA (scRNA). In some preferred embodiments, the target sequence (also referred to herein as a target polynucleotide) may be a sequence within an RNA molecule selected from the group consisting of mRNA, pre-mRNA, and rRNA. In some preferred embodiments, the target sequence may be a sequence within an RNA molecule selected from the group consisting of ncRNA, and lncRNA. In some more preferred embodiments, the target sequence may be a sequence within an mRNA molecule or a pre-mRNA molecule.

PAM and PFS Elements

PAM elements are sequences that can be recognized and bound by Cas proteins. Cas proteins/effector complexes can then unwind the dsDNA at a position adjacent to the PAM element. It will be appreciated that Cas proteins and systems that include them that target RNA do not require PAM sequences (Marraffini et al. 2010. Nature. 463:568-571). Instead, many rely on PFSs, which are discussed elsewhere herein. In certain embodiments, the target sequence should be associated with a PAM (protospacer adjacent motif) or PFS (protospacer flanking sequence or site), that is, a short sequence recognized by the CRISPR complex. Depending on the nature of the CRISPR-Cas protein, the target sequence should be selected, such that its complementary sequence in the DNA duplex (also referred to herein as the non-target sequence) is upstream or downstream of the PAM. In the embodiments, the complementary sequence of the target sequence is downstream or 3' of the PAM or upstream or 5' of the PAM. The precise sequence and length requirements for the PAM differ depending on the Cas protein used, but PAMs are typically 2-5 base pair sequences adjacent the protospacer (that is, the target sequence). Examples of the natural PAM sequences for different Cas proteins are provided herein below and the skilled person will be able to identify further PAM sequences for use with a given Cas protein.

The ability to recognize different PAM sequences depends on the Cas polypeptide(s) included in the system. See e.g., Gleditzsch et al. 2019. RNA Biology. 16(4):504-517. Table A below shows several Cas polypeptides and the PAM sequence they recognize.

TABLE A

| Example PAM Sequences | |
|---|---|
| Cas Protein | PAM Sequence |
| SpCas9 | NGG/NRG |
| SaCas9 | NGRRT or NGRRN |
| NmeCas9 | NNNNGATT |
| CjCas9 | NNNNRYAC |
| StCas9 | NNAGAAW |
| Cast2a (Cpf1) (including LbCpf1 and AsCpf1) | TTTV |
| Cas12b (C2c1) | TTT, TTA, and TTC |
| Cas12c (C2c3) | TA |
| Cas12d (CasY) | TA |
| Cas12e (CasX) | 5'-TTCN-3' |

In a preferred embodiment, the CRISPR effector protein may recognize a 3' PAM. In certain embodiments, the CRISPR effector protein may recognize a 3' PAM which is 5'H, wherein His A, C or U.

Further, engineering of the PAM Interacting (PI) domain on the Cas protein may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523(7561):481-5. doi: 10.1038/nature 14592. As further detailed herein, the skilled person will understand that Cas13 proteins may be modified analogously. Gao et al, "Engineered Cpf1 Enzymes with Altered PAM Specificities," bioRxiv 091611; doi: dx.doi.org/10.1101/091611 (Dec. 4, 2016). Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

PAM sequences can be identified in a polynucleotide using an appropriate design tool, which are commercially available as well as online. Such freely available tools include, but are not limited to, CRISPRFinder and CRISPRTarget. Mojica et al. 2009. Microbiol. 155 (Pt. 3):733-740; Atschul et al. 1990. J. Mol. Biol. 215:403-410; Biswass et al. 2013 RNA Biol. 10:817-827; and Grissa et al. 2007. Nucleic Acid Res. 35:W52-57. Experimental approaches to PAM identification can include, but are not limited to, plasmid depletion assays (Jiang et al. 2013. Nat. Biotechnol. 31:233-239; Esvelt et al. 2013. Nat. Methods. 10:1116-1121; Kleinstiver et al. 2015. Nature. 523:481-485), screened by a high-throughput in vivo model called PAM-SCNAR (Pattanayak et al. 2013. Nat. Biotechnol. 31:839-843 and Leenay et al. 2016. Mol. Cell. 16:253), and negative screening (Zetsche et al. 2015. Cell. 163:759-771).

As previously mentioned, CRISPR-Cas systems that target RNA do not typically rely on PAM sequences. Instead such systems typically recognize protospacer flanking sites (PFSs) instead of PAMs Thus, Type VI CRISPR-Cas systems typically recognize protospacer flanking sites (PFSs) instead of PAMs. PFSs represents an analogue to PAMs for RNA targets. Type VI CRISPR-Cas systems employ a Cas13. Some Cas13 proteins analyzed to date, such as Cas13a (C2c2) identified from Leptotrichia shahii (LShCAs13a) have a specific discrimination against G at the 3' end of the target RNA. The presence of a C at the corresponding crRNA repeat site can indicate that nucleotide pairing at this position is rejected. However, some Cas13 proteins (e.g., LwaCAs13a and PspCas13b) do not seem to have a PFS preference. See e.g., Gleditzsch et al. 2019. RNA Biology. 16(4):504-517.

Some Type VI proteins, such as subtype B, have 5'-recognition of D (G, T, A) and a 3'-motif requirement of NAN or NNA. One example is the Cas13b protein identified in Bergeyella zoohelcum (BzCas13b). See e.g., Gleditzsch et al. 2019. RNA Biology. 16(4):504-517.

Overall Type VI CRISPR-Cas systems appear to have less restrictive rules for substrate (e.g., target sequence) recognition than those that target DNA (e.g., Type V and type II).

Zinc Finger Nucleases

In some embodiments, the polynucleotide is modified using a Zinc Finger nuclease or system thereof. One type of programmable DNA-binding domain is provided by artificial zinc-finger (ZF) technology, which involves arrays of ZF modules to target new DNA-binding sites in the genome. Each finger module in a ZF array targets three DNA bases. A customized array of individual zinc finger domains is assembled into a ZF protein (ZFP).

ZFPs can comprise a functional domain. The first synthetic zinc finger nucleases (ZFNs) were developed by fusing a ZF protein to the catalytic domain of the Type 11S restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference.

TALE Nucleases

In some embodiments, a TALE nuclease or TALE nuclease system can be used to modify a polynucleotide. In some embodiments, the methods provided herein use isolated, non-naturally occurring, recombinant or engineered DNA binding proteins that comprise TALE monomers or TALE monomers or half monomers as a part of their organizational structure that enable the targeting of nucleic acid sequences with improved efficiency and expanded specificity.

Naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", "TALE monomers" or "monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-$(X_{12}X_{13})$-$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such monomers, the RVD consists of a single amino acid. In such cases the RVD may be alternatively represented as X*, where X represents $X_{12}$ and (*) indicates that $X_{13}$ is absent. The DNA binding domain comprises several repeats of TALE monomers and this may be represented as $(X_{1-11}$-$(X_{12}X_{13})$-$X_{14-33}$ or 34 or 35$)_z$, where in an advantageous embodiment, z is at least 5 to 40. In a further advantageous embodiment, z is at least 10 to 26.

The TALE monomers can have a nucleotide binding affinity that is determined by the identity of the amino acids in its RVD. For example, polypeptide monomers with an RVD of NI can preferentially bind to adenine (A), monomers with an RVD of NG can preferentially bind to thymine (T), monomers with an RVD of HD can preferentially bind to cytosine (C) and monomers with an RVD of NN can preferentially bind to both adenine (A) and guanine (G). In some embodiments, monomers with an RVD of IG can preferentially bind to T. Thus, the number and order of the polypeptide monomer repeats in the nucleic acid binding domain of a TALE determines its nucleic acid target specificity. In some embodiments, monomers with an RVD of NS can recognize all four base pairs and can bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011).

The polypeptides used in methods of the invention can be isolated, non-naturally occurring, recombinant or engineered nucleic acid binding proteins that have nucleic acid or DNA binding regions containing polypeptide monomer repeats that are designed to target specific nucleic acid sequences.

As described herein, polypeptide monomers having an RVD of HN or NH preferentially bind to guanine and thereby allow the generation of TALE polypeptides with high binding specificity for guanine containing target nucleic acid sequences. In some embodiments, polypeptide monomers having RVDs RN, NN, NK, SN, NH, KN, HN, NQ, HH, RG, KH, RH and SS can preferentially bind to guanine. In some embodiments, polypeptide monomers having RVDs RN, NK, NQ, HH, KH, RH, SS and SN can preferentially bind to guanine and can thus allow the generation of TALE polypeptides with high binding specificity for guanine containing target nucleic acid sequences. In some embodiments, polypeptide monomers having RVDs HH, KH, NH, NK, NQ, RH, RN and SS can preferentially bind to guanine and thereby allow the generation of TALE polypeptides with high binding specificity for guanine containing target nucleic acid sequences. In some embodiments, the RVDs that have high binding specificity for guanine are RN, NH RH and KH. Furthermore, polypeptide monomers having an RVD of NV can preferentially bind to adenine and guanine. In some embodiments, monomers having RVDs of H*, HA, KA, N*, NA, NC, NS, RA, and S* bind to adenine, guanine, cytosine and thymine with comparable affinity.

The predetermined N-terminal to C-terminal order of the one or more polypeptide monomers of the nucleic acid or DNA binding domain determines the corresponding predetermined target nucleic acid sequence to which the polypeptides of the invention will bind. As used herein the monomers and at least one or more half monomers are "specifically ordered to target" the genomic locus or gene of interest. In plant genomes, the natural TALE-binding sites always begin with a thymine (T), which may be specified by a cryptic signal within the non-repetitive N-terminus of the TALE polypeptide; in some cases, this region may be referred to as repeat 0. In animal genomes, TALE binding sites do not necessarily have to begin with a thymine (T) and polypeptides of the invention may target DNA sequences that begin with T, A, G or C. The tandem repeat of TALE monomers always ends with a half-length repeat or a stretch of sequence that may share identity with only the first 20 amino acids of a repetitive full-length TALE monomer and this half repeat may be referred to as a half-monomer. Therefore, it follows that the length of the nucleic acid or DNA being targeted is equal to the number of full monomers plus two.

As described in Zhang et al., Nature Biotechnology 29:149-153 (2011), TALE polypeptide binding efficiency may be increased by including amino acid sequences from the "capping regions" that are directly N-terminal or C-terminal of the DNA binding region of naturally occurring TALEs into the engineered TALEs at positions N-terminal or C-terminal of the engineered TALE DNA binding region. Thus, in certain embodiments, the TALE polypeptides described herein further comprise an N-terminal capping region and/or a C-terminal capping region.

An exemplary amino acid sequence of a N-terminal capping region is:

(SEQ ID NO: 1)
M D P I R S R T P S P A R E L L S G P Q P D G V Q
P T A D R G V S P P A G G P L D G L P A R R T M S
R T R L P S P P A P S P A F S A D S F S D L L R Q
F D P S L F N T S L F D S L P P F G A H H T E A A
T G E W D E V Q S G L R A A D A P P P T M R V A V
T A A R P P R A K P A P R R R A A Q P S D A S P A
A Q V D L R T L G Y S Q Q Q Q E K I K P K V R S T
V A Q H H E A L V G H G F T H A H I V A L S Q H P
A A L G T V A V K Y Q D M I A A L P E A T H E A I
V G V G K Q W S G A R A L E A L L T V A G E L R G
P P L Q L D T G Q L L K I A K R G G V T A V E A V
H A W R N A L T G A P L N

An exemplary amino acid sequence of a C-terminal capping region is:

(SEQ ID NO: 2)
R P A L E S I V A Q L S R P D P A L A A L T N D H
L V A L A C L G G R P A L D A V K K G L P H A P A
L I K R T N R R I P E R T S H R V A D H A Q V V R
V L G F F Q C H S H P A Q A F D D A M T Q F G M S
R H G L L Q L F R R V G V T E L E A R S G T L P P
A S Q R W D R I L Q A S G M K R A K P S P T S T Q
T P D Q A S L H A F A D S L E R D L D A P S P M H
E G D Q T R A S

As used herein the predetermined "N-terminus" to "C terminus" orientation of the N-terminal capping region, the DNA binding domain comprising the repeat TALE monomers and the C-terminal capping region provide structural basis for the organization of different domains in the d-TALEs or polypeptides of the invention.

The entire N-terminal and/or C-terminal capping regions are not necessary to enhance the binding activity of the DNA binding region. Therefore, in certain embodiments, fragments of the N-terminal and/or C-terminal capping regions are included in the TALE polypeptides described herein.

In certain embodiments, the TALE polypeptides described herein contain a N-terminal capping region fragment that included at least 10, 20, 30, 40, 50, 54, 60, 70, 80, 87, 90, 94, 100, 102, 110, 117, 120, 130, 140, 147, 150, 160, 170, 180, 190, 200, 210, 220, 230, 240, 250, 260 or 270 amino acids of an N-terminal capping region. In certain embodiments, the N-terminal capping region fragment amino acids are of the C-terminus (the DNA-binding region proximal end) of an N-terminal capping region. As described in Zhang et al., *Nature Biotechnology* 29:149-153 (2011), N-terminal capping region fragments that include the C-terminal 240 amino acids enhance binding activity equal to the full length capping region, while fragments that include the C-terminal 147 amino acids retain greater than 80% of the efficacy of the full length capping region, and fragments that include the C-terminal 117 amino acids retain greater than 50% of the activity of the full-length capping region.

In some embodiments, the TALE polypeptides described herein contain a C-terminal capping region fragment that included at least 6, 10, 20, 30, 37, 40, 50, 60, 68, 70, 80, 90, 100, 110, 120, 127, 130, 140, 150, 155, 160, 170, 180 amino acids of a C-terminal capping region. In certain embodiments, the C-terminal capping region fragment amino acids are of the N-terminus (the DNA-binding region proximal end) of a C-terminal capping region. As described in Zhang et al., Nature Biotechnology 29:149-153 (2011), C-terminal capping region fragments that include the C-terminal 68 amino acids enhance binding activity equal to the full-length capping region, while fragments that include the C-terminal 20 amino acids retain greater than 50% of the efficacy of the full-length capping region.

In certain embodiments, the capping regions of the TALE polypeptides described herein do not need to have identical sequences to the capping region sequences provided herein. Thus, in some embodiments, the capping region of the TALE polypeptides described herein have sequences that are at least 50%, 60%, 70%, 80%, 85%, 90%, 91%, 92%, 93%, 94%, 95%, 96%, 97%, 98% or 99% identical or share identity to the capping region amino acid sequences provided herein. Sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the TALE polypeptides described herein have sequences that are at least 95% identical or share identity to the capping region amino acid sequences provided herein.

Sequence homologies can be generated by any of a number of computer programs known in the art, which include but are not limited to BLAST or FASTA. Suitable computer programs for carrying out alignments like the GCG Wisconsin Bestfit package may also be used. Once the software has produced an optimal alignment, it is possible to calculate % homology, preferably % sequence identity. The software typically does this as part of the sequence comparison and generates a numerical result.

In some embodiments described herein, the TALE polypeptides of the invention include a nucleic acid binding domain linked to the one or more effector domains. The terms "effector domain" or "regulatory and functional domain" refer to a polypeptide sequence that has an activity other than binding to the nucleic acid sequence recognized by the nucleic acid binding domain. By combining a nucleic acid binding domain with one or more effector domains, the polypeptides of the invention may be used to target the one or more functions or activities mediated by the effector domain to a particular target DNA sequence to which the nucleic acid binding domain specifically binds.

In some embodiments of the TALE polypeptides described herein, the activity mediated by the effector domain is a biological activity. For example, in some embodiments the effector domain is a transcriptional inhibitor (i.e., a repressor domain), such as an mSin interaction domain (SID). SID4X domain or a Kruppel-associated box (KRAB) or fragments of the KRAB domain. In some embodiments the effector domain is an enhancer of transcription (i.e. an activation domain), such as the VP16, VP64 or p65 activation domain. In some embodiments, the nucleic acid binding is linked, for example, with an effector domain that includes but is not limited to a transposase, integrase, recombinase, resolvase, invertase, protease, DNA methyltransferase, DNA demethylase, histone acetylase, histone deacetylase, nuclease, transcriptional repressor, transcriptional activator, transcription factor recruiting, protein nuclear-localization signal or cellular uptake signal.

In some embodiments, the effector domain is a protein domain which exhibits activities which include but are not limited to transposase activity, integrase activity, recombinase activity, resolvase activity, invertase activity, protease activity, DNA methyltransferase activity, DNA demethylase activity, histone acetylase activity, histone deacetylase activity, nuclease activity, nuclear-localization signaling activity, transcriptional repressor activity, transcriptional activator activity, transcription factor recruiting activity, or cellular uptake signaling activity. Other preferred embodiments of the invention may include any combination of the activities described herein.

Meganucleases

In some embodiments, a meganuclease or system thereof can be used to modify a polynucleotide. Meganucleases, which are endodeoxyribonucleases characterized by a large recognition site (double-stranded DNA sequences of 12 to 40 base pairs). Exemplary methods for using meganucleases can be found in U.S. Pat. Nos. 8,163,514, 8,133,697, 8,021,867, 8,119,361, 8,119,381, 8,124,369, and 8,129,134, which are specifically incorporated by reference.

Sequences Related to Nucleus Targeting and Transportation

In some embodiments, one or more components (e.g., the Cas protein and/or deaminase, Zn Finger protein, TALE, or meganuclease) in the composition for engineering cells may comprise one or more sequences related to nucleus targeting and transportation. Such sequence may facilitate the one or more components in the composition for targeting a sequence within a cell. In order to improve targeting of the CRISPR-Cas protein and/or the nucleotide deaminase protein or catalytic domain thereof used in the methods of the present disclosure to the nucleus, it may be advantageous to provide one or both of these components with one or more nuclear localization sequences (NLSs).

In some embodiments, the NLSs used in the context of the present disclosure are heterologous to the proteins. Non-limiting examples of NLSs include an NLS sequence derived from: the NLS of the SV40 virus large T-antigen, having the amino acid sequence PKKKRKV (SEQ ID NO: 3) or PKKKRKVEAS (SEQ ID NO: 4); the NLS from nucleoplasmin (e.g., the nucleoplasmin bipartite NLS with the sequence KRPAATKKAGQAKKKK (SEQ ID NO: 5)); the c-myc NLS having the amino acid sequence PAAKRVKLD (SEQ ID NO: 6) or RQRRNELKRSP (SEQ ID NO: 7); the hRNPA1 M9 NLS having the sequence NQSSNFGPMKGGNFGGRSSGPYGGGGQYFAK-PRNQGGY (SEQ ID NO: 8); the sequence RMRIZFKNKGKDTAELRRRRVEVSVELRKAKKD-EQILKRRNV (SEQ ID NO: 9) of the IBB domain from importin-alpha; the sequences VSRKRPRP (SEQ ID NO: 10) and PPKKARED (SEQ ID NO: 11) of the myoma T protein; the sequence PQPKKKPL (SEQ ID NO: 12) of human p53; the sequence SALIKKKKKMAP (SEQ ID NO: 13) of mouse c-abl IV; the sequences DRLRR (SEQ ID NO: 14) and PKQKKRK (SEQ ID NO: 15) of the influenza virus NS1; the sequence RKLKKKIKKL (SEQ ID NO: 16) of the Hepatitis virus delta antigen; the sequence REKKKFLKRR (SEQ ID NO: 17) of the mouse Mx1 protein; the sequence KRKGDEVDGVDEVAKKKSKK (SEQ ID NO: 18) of the human poly(ADP-ribose) polymerase; and the sequence RKCLQAGMNLEARKTKK (SEQ ID NO: 19) of the steroid hormone receptors (human) glucocorticoid. In general, the one or more NLSs are of sufficient strength to drive accumulation of the DNA-targeting Cas protein in a detectable amount in the nucleus of a eukaryotic cell. In general, strength of nuclear localization activity may derive from the number of NLSs in the CRISPR-Cas protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of nucleic acid-targeting complex formation (e.g., assay for deaminase activity) at the target sequence, or assay for altered gene expression activity affected by DNA-targeting complex formation and/or DNA-targeting), as compared to a control not exposed to the CRISPR-Cas protein and deaminase protein, or exposed to a CRISPR-Cas and/or deaminase protein lacking the one or more NLSs.

The CRISPR-Cas and/or nucleotide deaminase proteins may be provided with 1 or more, such as with, 2, 3, 4, 5, 6, 7, 8, 9, 10, or more heterologous NLSs. In some embodiments, the proteins comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. In preferred embodiments of the CRISPR-Cas proteins, an NLS attached to the C-terminal of the protein.

In certain embodiments, the CRISPR-Cas protein and the deaminase protein are delivered to the cell or expressed within the cell as separate proteins. In these embodiments, each of the CRISPR-Cas and deaminase protein can be provided with one or more NLSs as described herein. In certain embodiments, the CRISPR-Cas and deaminase proteins are delivered to the cell or expressed with the cell as a fusion protein. In these embodiments one or both of the CRISPR-Cas and deaminase protein is provided with one or more NLSs. Where the nucleotide deaminase is fused to an adaptor protein (such as MS2) as described above, the one or more NLS can be provided on the adaptor protein, provided that this does not interfere with aptamer binding. In particular embodiments, the one or more NLS sequences may also function as linker sequences between the nucleotide deaminase and the CRISPR-Cas protein.

In certain embodiments, guides of the disclosure comprise specific binding sites (e.g. aptamers) for adapter proteins, which may be linked to or fused to an nucleotide deaminase or catalytic domain thereof. When such a guide forms a CRISPR complex (e.g., CRISPR-Cas protein binding to guide and target) the adapter proteins bind and, the nucleotide deaminase or catalytic domain thereof associated with the adapter protein is positioned in a spatial orientation which is advantageous for the attributed function to be effective.

The skilled person will understand that modifications to the guide which allow for binding of the adapter+ nucleotide deaminase, but not proper positioning of the adapter+ nucleotide deaminase (e.g. due to steric hindrance within the three dimensional structure of the CRISPR complex) are modifications which are not intended. The one or more modified guide may be modified at the tetra loop, the stem loop 1, stem loop 2, or stem loop 3, as described herein, preferably at either the tetra loop or stem loop 2, and in some cases at both the tetra loop and stem loop 2.

In some embodiments, a component (e.g., the dead Cas protein, the nucleotide deaminase protein or catalytic domain thereof, or a combination thereof) in the systems may comprise one or more nuclear export signals (NES), one or more nuclear localization signals (NLS), or any combinations thereof. In some cases, the NES may be an HIV Rev NES. In certain cases, the NES may be MAPK NES. When the component is a protein, the NES or NLS may be at the C terminus of component. Alternatively or additionally, the NES or NLS may be at the N terminus of component. In some examples, the Cas protein and optionally said nucleotide deaminase protein or catalytic domain thereof comprise one or more heterologous nuclear export signal(s) (NES(s)) or nuclear localization signal(s) (NLS(s)), preferably an HIV Rev NES or MAPK NES, preferably C-terminal.

Templates

In some embodiments, the composition for engineering cells comprise a template, e.g., a recombination template. A template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cas protein mediated cleavage event. In an embodiment, the template nucleic acid may include sequence that corresponds to both, a first site on the target sequence that is cleaved in a first Cas protein mediated event, and a second site on the target sequence that is cleaved in a second Cas protein mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, 150+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50,100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50,100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the disclosure can be constructed using recombinant techniques (see, for example, Sambrook et al., 2001 and Ausubel et al., 1996).

In certain embodiments, a template nucleic acid for correcting a mutation may be designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

In certain embodiments, a template nucleic acid for correcting a mutation may be designed for use with a homology-independent targeted integration system. Suzuki et al. describe in vivo genome editing via CRISPR/Cas9 mediated homology-independent targeted integration (2016, Nature 540:144-149). Schmid-Burgk, et al. describe use of the CRISPR-Cas9 system to introduce a double-strand break (DSB) at a user-defined genomic location and insertion of a universal donor DNA (Nat Commun. 2016 Jul. 28; 7:12338). Gao, et al. describe "Plug-and-Play Protein Modification Using Homology-Independent Universal Genome Engineering" (Neuron. 2019 Aug. 21; 103(4):583-597).

RNAi

In some embodiments, the genetic modulating agents may be interfering RNAs. In certain embodiments, diseases caused by a dominant mutation in a gene is targeted by silencing the mutated gene using RNAi. In some cases, the nucleotide sequence may comprise coding sequence for one or more interfering RNAs. In certain examples, the nucleotide sequence may be interfering RNA (RNAi). As used herein, the term "RNAi" refers to any type of interfering RNA, including but not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

The term "RNAi" can include both gene silencing RNAi molecules, and also RNAi effector molecules which activate the expression of a gene.

In certain embodiments, a modulating agent may comprise silencing one or more endogenous genes. As used herein, "gene silencing" or "gene silenced" in reference to an activity of an RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, a "siRNA" refers to a nucleic acid that forms a double stranded RNA, which double stranded RNA has the ability to reduce or inhibit expression of a gene or target gene when the siRNA is present or expressed in the same cell as the target gene. The double stranded RNA siRNA can be formed by the complementary strands. In one embodiment, a siRNA refers to a nucleic acid that can form a double stranded siRNA. The sequence of the siRNA can correspond to the full-length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length).

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

The terms "microRNA" or "miRNA", used interchangeably herein, are endogenous RNAs, some of which are known to regulate the expression of protein-coding genes at the posttranscriptional level. Endogenous microRNAs are small RNAs naturally present in the genome that are capable of modulating the productive utilization of mRNA. The term artificial microRNA includes any type of RNA sequence, other than endogenous microRNA, which is capable of modulating the productive utilization of mRNA. MicroRNA sequences have been described in publications such as Lim, et al., Genes & Development, 17, p. 991-1008 (2003), Lim et al Science 299, 1540 (2003), Lee and Ambros Science, 294, 862 (2001), Lau et al., Science 294, 858-861 (2001), Lagos-Quintana et al, Current Biology, 12, 735-739 (2002), Lagos Quintana et al, Science 294, 853-857 (2001), and Lagos-Quintana et al, RNA, 9, 175-179 (2003), which are incorporated by reference. Multiple microRNAs can also be incorporated into a precursor molecule. Furthermore, miRNA-like stem-loops can be expressed in cells as a vehicle to deliver artificial miRNAs and short interfering RNAs (siRNAs) for the purpose of modulating the expression of endogenous genes through the miRNA and/or RNAi pathways.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al. 2004. Cell 1 16:281-297), comprises a dsRNA molecule.

Antibodies

In certain embodiments, the one or more agents is an antibody. The term "antibody" is used interchangeably with the term "immunoglobulin" herein, and includes intact antibodies, fragments of antibodies, e.g., Fab, F(ab')2 fragments, and intact antibodies and fragments that have been mutated either in their constant and/or variable region (e.g., mutations to produce chimeric, partially humanized, or fully humanized antibodies, as well as to produce antibodies with a desired trait, e.g., enhanced binding and/or reduced FcR binding). The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fabc, Fd, dAb, $V_{HH}$ and scFv and/or Fv fragments.

As used herein, a preparation of antibody protein having less than about 50% of non-antibody protein (also referred to herein as a "contaminating protein"), or of chemical precursors, is considered to be "substantially free." 40%, 30%, 20%, 10% and more preferably 5% (by dry weight), of non-antibody protein, or of chemical precursors is considered to be substantially free. When the antibody protein or biologically active portion thereof is recombinantly produced, it is also preferably substantially free of culture medium, i.e., culture medium represents less than about 30%, preferably less than about 20%, more preferably less than about 10%, and most preferably less than about 5% of the volume or mass of the protein preparation.

The term "antigen-binding fragment" refers to a polypeptide fragment of an immunoglobulin or antibody that binds antigen or competes with intact antibody (i.e., with the intact antibody from which they were derived) for antigen binding (i.e., specific binding). As such these antibodies or fragments thereof are included in the scope of the invention, provided that the antibody or fragment binds specifically to a target molecule.

It is intended that the term "antibody" encompass any Ig class or any Ig subclass (e.g. the IgG1, IgG2, IgG3, and IgG4 subclasses of IgG) obtained from any source (e.g., humans and non-human primates, and in rodents, lagomorphs, caprines, bovines, equines, ovines, etc.).

The term "Ig class" or "immunoglobulin class", as used herein, refers to the five classes of immunoglobulin that have been identified in humans and higher mammals, IgG, IgM, IgA, IgD, and IgE. The term "Ig subclass" refers to the two subclasses of IgM (H and L), three subclasses of IgA (IgA1, IgA2, and secretory IgA), and four subclasses of IgG (IgG1, IgG2, IgG3, and IgG4) that have been identified in humans and higher mammals. The antibodies can exist in monomeric or polymeric form; for example, IgM antibodies exist in pentameric form, and IgA antibodies exist in monomeric, dimeric or multimeric form.

The term "IgG subclass" refers to the four subclasses of immunoglobulin class IgG-IgG1, IgG2, IgG3, and IgG4 that have been identified in humans and higher mammals by the heavy chains of the immunoglobulins, VI-γ4, respectively. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by p pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of an antibody light chain are referred to interchangeably as "light chain constant regions", "light chain constant domains", "CL" regions or "CL" domains. The "constant" domains of an antibody heavy chain are referred to interchangeably as "heavy chain constant regions", "heavy chain constant domains", "CH" regions or "CH" domains). The "variable" domains of an antibody light chain are referred to interchangeably as "light chain variable regions", "light chain variable domains", "VL" regions or "VL" domains). The "variable" domains of an antibody heavy chain are referred to interchangeably as "heavy chain constant regions", "heavy chain constant domains", "VH" regions or "VH" domains).

The term "region" can also refer to a part or portion of an antibody chain or antibody chain domain (e.g., a part or portion of a heavy or light chain or a part or portion of a constant or variable domain, as defined herein), as well as more discrete parts or portions of said chains or domains. For example, light and heavy chains or light and heavy chain variable domains include "complementarity determining regions" or "CDRs" interspersed among "framework regions" or "FRs", as defined herein.

The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof.

The term "antibody-like protein scaffolds" or "engineered protein scaffolds" broadly encompasses proteinaceous non-immunoglobulin specific-binding agents, typically obtained by combinatorial engineering (such as site-directed random mutagenesis in combination with phage display or other molecular selection techniques). Usually, such scaffolds are derived from robust and small soluble monomeric proteins (such as Kunitz inhibitors or lipocalins) or from a stably folded extra-membrane domain of a cell surface receptor (such as protein A, fibronectin or the ankyrin repeat).

Such scaffolds have been extensively reviewed in Binz et al. (Engineering novel binding proteins from nonimmunoglobulin domains. Nat Biotechnol 2005, 23:1257-1268), Gebauer and Skerra (Engineered protein scaffolds as next-generation antibody therapeutics. Curr Opin Chem Biol. 2009, 13:245-55), Gill and Damle (Biopharmaceutical drug discovery using novel protein scaffolds. Curr Opin Biotechnol 2006, 17:653-658), Skerra (Engineered protein scaffolds for molecular recognition. J Mol Recognit 2000, 13:167-187), and Skerra (Alternative non-antibody scaffolds for molecular recognition. Curr Opin Biotechnol 2007, 18:295-304), and include without limitation affibodies, based on the Z-domain of staphylococcal protein A, a three-helix bundle of 58 residues providing an interface on two of its alpha-helices (Nygren, Alternative binding proteins: Affibody binding proteins developed from a small three-helix bundle scaffold. FEBS J 2008, 275:2668-2676); engineered Kunitz domains based on a small (ca. 58 residues) and robust, disulphide-crosslinked serine protease inhibitor, typically of human origin (e.g. LACI-D1), which can be engineered for different protease specificities (Nixon and Wood, Engineered protein inhibitors of proteases. Curr Opin Drug Discov Dev 2006, 9:261-268); monobodies or adnectins based on the 10th extracellular domain of human fibronectin III (10Fn3), which adopts an Ig-like beta-sandwich fold (94 residues) with 2-3 exposed loops, but lacks the central disulphide bridge (Koide and Koide, Monobodies: antibody mimics based on the scaffold of the fibronectin type III domain. Methods Mol Biol 2007, 352:95-109); anticalins derived from the lipocalins, a diverse family of eight-stranded beta-barrel proteins (ca. 180 residues) that naturally form binding sites for small ligands by means of four structurally variable loops at the open end, which are abundant in humans, insects, and many other organisms (Skerra, Alternative binding proteins: Anticalins harnessing the structural plasticity of the lipocalin ligand pocket to engineer novel binding activities. FEBS J 2008, 275:2677-2683); DARPins, designed ankyrin repeat domains (166 residues), which provide a rigid interface arising from typically three repeated beta-turns (Stumpp et al., DARPins: a new generation of protein therapeutics. Drug Discov Today 2008, 13:695-701); avimers (multimerized LDLR-A module) (Silverman et al., Multivalent avimer proteins evolved by exon shuffling of a family of human receptor domains. Nat Biotechnol 2005, 23:1556-1561); and cysteine-rich knottin peptides (Kolmar, Alternative binding proteins: biological activity and therapeutic potential of cystine-knot miniproteins. FEBS J 2008, 275:2684-2690).

"Specific binding" of an antibody means that the antibody exhibits appreciable affinity for a particular antigen or epitope and, generally, does not exhibit significant cross reactivity. "Appreciable" binding includes binding with an affinity of at least 25 µM. Antibodies with affinities greater than $1\times10^7$ $M^{-1}$ (or a dissociation coefficient of 1 µM or less or a dissociation coefficient of 1 nm or less) typically bind with correspondingly greater specificity. Values intermediate of those set forth herein are also intended to be within the scope of the present invention and antibodies of the invention bind with a range of affinities, for example, 100 nM or less, 75 nM or less, 50 nM or less, 25 nM or less, for example 10 nM or less, 5 nM or less, 1 nM or less, or in embodiments 500 pM or less, 100 pM or less, 50 pM or less or 25 pM or less. An antibody that "does not exhibit significant crossreactivity" is one that will not appreciably bind to an entity other than its target (e.g., a different epitope or a different molecule). For example, an antibody that specifically binds to a target molecule will appreciably bind the target molecule but will not significantly react with non-target molecules or peptides. An antibody specific for a particular epitope will, for example, not significantly cross-react with remote epitopes on the same protein or peptide. Specific binding can be determined according to any art-recognized means for determining such binding. Preferably, specific binding is determined according to Scatchard analysis and/or competitive binding assays.

As used herein, the term "affinity" refers to the strength of the binding of a single antigen-combining site with an antigenic determinant. Affinity depends on the closeness of stereochemical fit between antibody combining sites and antigen determinants, on the size of the area of contact between them, on the distribution of charged and hydrophobic groups, etc. Antibody affinity can be measured by equilibrium dialysis or by the kinetic BIACORE™ method. The dissociation constant, Kd, and the association constant, Ka, are quantitative measures of affinity.

As used herein, the term "monoclonal antibody" refers to an antibody derived from a clonal population of antibody-producing cells (e.g., B lymphocytes or B cells) which is homogeneous in structure and antigen specificity. The term "polyclonal antibody" refers to a plurality of antibodies originating from different clonal populations of antibody-producing cells which are heterogeneous in their structure and epitope specificity but which recognize a common antigen. Monoclonal and polyclonal antibodies may exist within bodily fluids, as crude preparations, or may be purified, as described herein.

The term "binding portion" of an antibody (or "antibody portion") includes one or more complete domains, e.g., a pair of complete domains, as well as fragments of an antibody that retain the ability to specifically bind to a target molecule. It has been shown that the binding function of an antibody can be performed by fragments of a full-length antibody. Binding fragments are produced by recombinant DNA techniques, or by enzymatic or chemical cleavage of intact immunoglobulins. Binding fragments include Fab, Fab', F(ab')2, Fabc, Fd, dAb, Fv, single chains, single-chain antibodies, e.g., scFv, and single domain antibodies.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, FR residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Examples of portions of antibodies or epitope-binding proteins encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CHI domain; (v) the Fv fragment having the $V_L$ and $V_H$ domains of a single arm of an antibody; (vi) the dAb fragment (Ward et al., 341 Nature 544 (1989)) which consists of a $V_H$ domain or a $V_L$ domain that binds antigen; (vii) isolated CDR regions or isolated CDR regions presented in a functional framework; (viii) F(ab')$_2$ fragments which are bivalent fragments including two Fab' fragments linked by a disulphide bridge at the hinge region; (ix) single chain antibody molecules (e.g., single chain Fv; scFv) (Bird et al., 242 Science 423 (1988); and Huston et al., 85 PNAS 5879 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; Hollinger et al., 90 PNAS 6444 (1993)); (xi) "linear antibodies" comprising a pair of tandem Fd segments ($V_H$—$C_h1$-$V_H$-$C_h1$) which, together with complementary light chain polypeptides, form a pair of antigen binding regions (Zapata et al., Protein Eng. 8(10): 1057-62 (1995); and U.S. Pat. No. 5,641,870).

As used herein, a "blocking" antibody or an antibody "antagonist" is one which inhibits or reduces biological activity of the antigen(s) it binds. In certain embodiments, the blocking antibodies or antagonist antibodies or portions thereof described herein completely inhibit the biological activity of the antigen(s).

Antibodies may act as agonists or antagonists of the recognized polypeptides. For example, the present invention includes antibodies which disrupt receptor/ligand interactions either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or of one of its down-stream substrates by immunoprecipitation followed by western blot analysis. In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex. Likewise, encompassed by the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides disclosed herein. The antibody agonists and antagonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16): 3668-3678 (1998); Harrop et al., J. Immunol. 161(4):1786-1794 (1998); Zhu et al., Cancer Res. 58(15):3209-3214 (1998); Yoon et al., J. Immunol. 160(7):3170-3179 (1998); Prat et al., J. Cell. Sci. III (Pt2):237-247 (1998); Pitard et al., J. Immunol. Methods 205(2):177-190 (1997); Liautard et al., Cytokine 9(4):233-241 (1997); Carlson et al., J. Biol. Chem. 272(17):11295-11301 (1997); Taryman et al., Neuron 14(4): 755-762 (1995); Muller et al., Structure 6(9):1153-1167 (1998); Bartunek et al., Cytokine 8(1):14-20 (1996).

The antibodies as defined for the present invention include derivatives that are modified, i.e., by the covalent attachment of any type of molecule to the antibody, such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

Simple binding assays can be used to screen for or detect agents that bind to a target protein, or disrupt the interaction between proteins (e.g., a receptor and a ligand). Because certain targets of the present invention are transmembrane proteins, assays that use the soluble forms of these proteins rather than full-length protein can be used, in some embodiments. Soluble forms include, for example, those lacking the transmembrane domain and/or those comprising the IgV domain or fragments thereof which retain their ability to bind their cognate binding partners. Further, agents that inhibit or enhance protein interactions for use in the compositions and methods described herein, can include recombinant peptido-mimetics.

Detection methods useful in screening assays include antibody-based methods, detection of a reporter moiety, detection of cytokines as described herein, and detection of a gene signature as described herein.

Another variation of assays to determine binding of a receptor protein to a ligand protein is through the use of affinity biosensor methods. Such methods may be based on the piezoelectric effect, electrochemistry, or optical methods, such as ellipsometry, optical wave guidance, and surface plasmon resonance (SPR).

Bi-Specific Antibodies

In certain embodiments, the one or more therapeutic agents can be bi-specific antigen-binding constructs, e.g., bi-specific antibodies (bsAb) or BiTEs, that bind two antigens (see, e.g., Suurs et al., A review of bispecific antibodies and antibody constructs in oncology and clinical challenges. Pharmacol Ther. 2019 September; 201:103-119; and Huehls, et al., Bispecific T cell engagers for cancer immunotherapy. Immunol Cell Biol. 2015 March; 93(3): 290-296). The bi-specific antigen-binding construct includes two antigen-binding polypeptide constructs, e.g., antigen binding domains, wherein at least one polypeptide construct specifically binds to a surface protein. In some embodiments, the antigen-binding construct is derived from known antibodies or antigen-binding constructs. In some embodiments, the antigen-binding polypeptide constructs comprise two antigen binding domains that comprise antibody fragments. In some embodiments, the first antigen binding domain and second antigen binding domain each independently comprises an antibody fragment selected from the group of: an scFv, a Fab, and an Fc domain. The antibody fragments may be the same format or different formats from each other. For example, in some embodiments, the antigen-binding polypeptide constructs comprise a first antigen binding domain comprising an scFv and a second antigen binding domain comprising a Fab. In some embodiments, the antigen-binding polypeptide constructs comprise a first antigen binding domain and a second antigen binding domain, wherein both antigen binding domains comprise an scFv. In some embodiments, the first and second antigen binding domains each comprise a Fab. In some embodiments, the first and second antigen binding domains each comprise an Fc domain. Any combination of antibody formats is suitable for the bi-specific antibody constructs disclosed herein.

In certain embodiments, immune cells can be engaged to other immune cells. In certain embodiments, immune cells are targeted with a bsAb having affinity for both the immune cell and a payload. In certain embodiments, two targets are disrupted on an immune cell by the bsAb (e.g., CXCR6 and another surface marker). By means of an example, an agent, such as a bi-specific antibody, specifically binds to a gene product expressed on the cell surface of the immune cells.

Aptamers

In certain embodiments, the one or more agents is an aptamer. Nucleic acid aptamers are nucleic acid species that have been engineered through repeated rounds of in vitro selection or equivalently, SELEX (systematic evolution of ligands by exponential enrichment) to bind to various molecular targets such as small molecules, proteins, nucleic acids, cells, tissues and organisms. Nucleic acid aptamers have specific binding affinity to molecules through interactions other than classic Watson-Crick base pairing. Aptamers are useful in biotechnological and therapeutic applications as they offer molecular recognition properties similar to antibodies. In addition to their discriminate recognition, aptamers offer advantages over antibodies as they can be engineered completely in a test tube, are readily produced by chemical synthesis, possess desirable storage properties, and elicit little or no immunogenicity in therapeutic applications. In certain embodiments, RNA aptamers may be expressed from a DNA construct. In other embodiments, a nucleic acid aptamer may be linked to another polynucleotide sequence. The polynucleotide sequence may be a double stranded DNA polynucleotide sequence. The aptamer may be covalently linked to one strand of the polynucleotide sequence. The aptamer may be ligated to the polynucleotide sequence. The polynucleotide sequence may be configured, such that the polynucleotide sequence may be linked to a solid support or ligated to another polynucleotide sequence.

Aptamers, like peptides generated by phage display or monoclonal antibodies ("mAbs"), are capable of specifically binding to selected targets and modulating the target's activity, e.g., through binding, aptamers may block their target's ability to function. A typical aptamer is 10-15 kDa in size (30-45 nucleotides), binds its target with sub-nanomolar affinity, and discriminates against closely related targets (e.g., aptamers will typically not bind other proteins from the same gene family). Structural studies have shown that aptamers are capable of using the same types of binding interactions (e.g., hydrogen bonding, electrostatic complementarity, hydrophobic contacts, steric exclusion) that drives affinity and specificity in antibody-antigen complexes.

Aptamers have a number of desirable characteristics for use in research and as therapeutics and diagnostics including high specificity and affinity, biological efficacy, and excellent pharmacokinetic properties. In addition, they offer specific competitive advantages over antibodies and other protein biologics. Aptamers are chemically synthesized and are readily scaled as needed to meet production demand for research, diagnostic or therapeutic applications. Aptamers are chemically robust. They are intrinsically adapted to regain activity following exposure to factors such as heat and denaturants and can be stored for extended periods (>1 yr) at room temperature as lyophilized powders. Not being bound by a theory, aptamers bound to a solid support or beads may be stored for extended periods.

Oligonucleotides in their phosphodiester form may be quickly degraded by intracellular and extracellular enzymes such as endonucleases and exonucleases. Aptamers can include modified nucleotides conferring improved characteristics on the ligand, such as improved in vivo stability or improved delivery characteristics. Examples of such modifications include chemical substitutions at the ribose and/or phosphate and/or base positions. SELEX identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-O-methyl (2'-OMe) substituents. Modifications of aptamers may also include, modifications at exocyclic amines, substitution of 4-thiouridine, substitution of 5-bromo or 5-iodo-uracil; backbone modifications, phosphorothioate or allyl phosphate modifications, methylations, and unusual base-pairing combinations such as the isobases isocytidine and isoguanosine. Modifications can also include 3' and 5' modifications such as capping. As used herein, the term phosphorothioate encompasses one or more non-bridging oxygen atoms in a phosphodiester bond replaced by one or more sulfur atoms. In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, 0-allyl, S-alkyl, S-allyl, or halo group. Methods of synthesis of 2'-modified sugars are described, e.g., in Sproat, et al., Nucl. Acid Res. 19:733-738 (1991); Cotten, et al, Nucl. Acid Res. 19:2629-2635 (1991); and Hobbs, et al, Biochemistry 12:5138-5145 (1973). Other modifications are known to one of ordinary skill in the art. In certain embodiments, aptamers include aptamers with improved off-rates as described in International Patent Publication No. WO 2009012418, "Method for generating aptamers with improved off-rates," incorporated herein by reference in its entirety. In certain embodiments aptamers are chosen from a library of aptamers. Such libraries include, but are not limited to those described in Rohloff et al., "Nucleic Acid Ligands With Protein-like Side Chains: Modified Aptamers and Their Use as Diagnostic and Therapeutic Agents," Molecular Therapy Nucleic Acids (2014) 3, e201. Aptamers are also commercially available (see, e.g., SomaLogic, Inc., Boulder, Colorado). In certain embodiments, the present invention may utilize any aptamer containing any modification as described herein.

Inflammatory and Autoimmune Diseases

In certain embodiments, modulation of T cell balance may be used to treat inflammatory diseases, disorders or aberrant autoimmune responses. Specific autoimmune responses resulting from an immunotherapy is described further herein. As used throughout the present specification, the terms "autoimmune disease" or "autoimmune disorder" used interchangeably refer to a diseases or disorders caused by an immune response against a self-tissue or tissue component (self-antigen) and include a self-antibody response and/or cell-mediated response. The terms encompass organ-specific autoimmune diseases, in which an autoimmune response is directed against a single tissue, as well as non-organ specific autoimmune diseases, in which an autoimmune response is directed against a component present in two or more, several or many organs throughout the body. Examples of autoimmune diseases include but are not limited to acute disseminated encephalomyelitis (ADEM); Addison's disease; ankylosing spondylitis; antiphospholipid antibody syndrome (APS); aplastic anemia; autoimmune gastritis; autoimmune hepatitis; autoimmune thrombocytopenia; Behget's disease; coeliac disease; dermatomyositis; diabetes mellitus type I; Goodpasture's syndrome; Graves' disease; Guillain-Barre syndrome (GBS); Hashimoto's disease; idiopathic thrombocytopenic purpura; inflammatory bowel disease (IBD) including Crohn's disease and ulcerative colitis; mixed connective tissue disease; multiple sclerosis (MS); myasthenia gravis; opsoclonus myoclonus syndrome (OMS); optic neuritis; Ord's thyroiditis; pemphigus; pernicious anaemia; polyarteritis nodosa; polymyositis; primary biliary cirrhosis; primary myxedema; psoriasis; rheumatic fever; rheumatoid arthritis; Reiter's syndrome; scleroderma; Sjögren's syndrome; systemic lupus erythematosus; Takayasu's arteritis; temporal arteritis; vitiligo; warm autoimmune hemolytic anemia; or Wegener's granulomatosis.

Examples of inflammatory diseases or disorders include, but are not limited to, asthma, allergy, allergic rhinitis, allergic airway inflammation, atopic dermatitis (AD), chronic obstructive pulmonary disease (COPD), inflammatory bowel disease (IBD), Irritable bowel syndrome (IBS), multiple sclerosis, arthritis, psoriasis, eosinophilic esophagitis, eosinophilic pneumonia, eosinophilic psoriasis, hypereosinophilic syndrome, graft-versus-host disease, uveitis, cardiovascular disease, pain, multiple sclerosis, lupus, vasculitis, chronic idiopathic urticaria and Eosinophilic Granulomatosis with Polyangiitis (Churg-Strauss Syndrome).

The asthma may be allergic asthma, non-allergic asthma, severe refractory asthma, asthma exacerbations, viral-induced asthma or viral-induced asthma exacerbations, steroid resistant asthma, steroid sensitive asthma, eosinophilic asthma or non-eosinophilic asthma and other related disorders characterized by airway inflammation or airway hyperresponsiveness (AHR).

The COPD may be a disease or disorder associated in part with, or caused by, cigarette smoke, air pollution, occupational chemicals, allergy or airway hyperresponsiveness.

The allergy may be associated with foods, pollen, mold, dust mites, animals, or animal dander.

The IBD may be ulcerative colitis (UC), Crohn's Disease, collagenous colitis, lymphocytic colitis, ischemic colitis, diversion colitis, Behcet's syndrome, infective colitis, indeterminate colitis, and other disorders characterized by inflammation of the mucosal layer of the large intestine or colon.

The arthritis may be selected from the group consisting of osteoarthritis, rheumatoid arthritis and psoriatic arthritis.

Checkpoint Blockade Therapy

In certain embodiments, Th17 subpopulations may be modulated in combination with an immunotherapy, such that the immunotherapy provides an intended anti-tumor response, but does not cause adverse Th17 autoimmunity. Immunotherapy can include checkpoint blockers (CBP), chimeric antigen receptors (CARs), and adoptive T cell therapy. Antibodies that block the activity of checkpoint receptors, including CTLA-4, PD-1, Tim-3, Lag-3, and TIGIT, either alone or in combination, have been associated with improved effector $CD8^+$ T cell responses in multiple pre-clinical cancer models (Johnston et al., 2014. The immunoreceptor TIGIT regulates anti-tumor and antiviral CD8(+) T cell effector function. Cancer cell 26, 923-937; Ngiow et al., 2011. Anti-TIM3 antibody promotes T cell IFN-gamma-mediated antitumor immunity and suppresses established tumors. Cancer research 71, 3540-3551; Sakuishi et al., 2010. Targeting Tim-3 and PD-I pathways to reverse T cell exhaustion and restore anti-tumor immunity. The Journal of experimental medicine 207, 2187-2194; and Woo et al., 2012. Immune inhibitory molecules LAG-3 and PD-1 synergistically regulate T-cell function to promote tumoral immune escape. Cancer research 72, 917-927). Similarly, blockade of CTLA-4 and PD-1 in patients (Brahmer et al., 2012. Safety and activity of anti-PD-L1 antibody in patients with advanced cancer. The New England journal of medicine 366, 2455-2465; Hodi et al., 2010. Improved survival with ipilimumab in patients with metastatic melanoma. The New England journal of medicine 363, 711-723; Schadendorf et al., 2015. Pooled Analysis of Long-Term Survival Data From Phase II and Phase III Trials of Ipilimumab in Unresectable or Metastatic Melanoma. Journal of clinical oncology. official journal of the American Society of Clinical Oncology 33, 1889-1894; Topalian et al., 2012. Safety, activity, and immune correlates of anti-PD-1 antibody in cancer. The New England journal of medicine 366, 2443-2454; and Wolchok et al., 2017. Overall Survival with Combined Nivolumab and Ipilimumab in Advanced Melanoma. The New England journal of medicine 377, 1345-1356) has shown increased frequencies of proliferating T cells, often with specificity for tumor antigens, as well as increased $CD8^+$ T cell effector function (Ayers et al., 2017. IFN-gamma-related mRNA profile predicts clinical response to PD-1 blockade. The Journal of clinical investigation 127, 2930-2940; Das et al., 2015. Combination therapy with anti-CTLA-4 and anti-PD-1 leads to distinct immunologic changes in vivo. Journal of immunology 194, 950-959; Gubin et al., 2014. Checkpoint blockade cancer immunotherapy targets tumour-specific mutant antigens. Nature 515, 577-581; Huang et al., 2017. T-cell invigoration to tumour burden ratio associated with anti-PD-1 response. Nature 545, 60-65; Kamphorst et al., 2017. Proliferation of $PD-1^+$ CD8 T cells in peripheral blood after PD-1-targeted therapy in lung cancer patients. Proceedings of the National Academy of Sciences of the United States of America 114, 4993-4998; Kvistborg et al., 2014. Anti-CTLA-4 therapy broadens the melanoma-reactive $CD8^+$ T cell response. Science translational medicine 6, 254rai28; van Rooij et al., 2013. Tumor exome analysis reveals neoantigen-specific T-cell reactivity in an ipilimumab-responsive melanoma. Journal of clinical oncology. official journal of the American Society of Clinical Oncology 31, e439-442; and Yuan et al., 2008. CTLA-4 blockade enhances polyfunctional NY-ESO-1 specific T cell responses in metastatic melanoma patients with clinical benefit. Proceedings of the National Academy of Sciences of the United States of America 105, 20410-20415). Accordingly, the success of checkpoint receptor blockade has been attributed to the binding of blocking antibodies to checkpoint receptors expressed on dysfunctional $CD8^+$ T cells and restoring effector function in these cells. The check point blockade therapy may be an inhibitor of any check point protein described herein. The checkpoint blockade therapy may comprise anti-TIM3, anti-CTLA4, anti-PD-L1, anti-PD1, anti-TIGIT, anti-LAG3, or combinations thereof. Anti-PD1 antibodies are disclosed in U.S. Pat. No. 8,735,553. Antibodies to LAG-3 are disclosed in U.S. Pat. No. 9,132,281. Anti-CTLA4 antibodies are disclosed in U.S. Pat. Nos. 9,327,014; 9,320,811; and 9,062,111. Specific check point inhibitors include, but are not limited to anti-CTLA4 antibodies (e.g., Ipilimumab and tremelimumab), anti-PD-1 antibodies (e.g., Nivolumab, Pembrolizumab), and anti-PD-L1 antibodies (e.g., Atezolizumab).

In certain embodiments, immunotherapy leads to immune-related adverse events (irAEs) (see, e.g., Byun et al., (2017) Cancer immunotherapy-immune checkpoint blockade and associated endocrinopathies. Nat Rev Endocrinol. 2017 April; 13(4): 195-207; Abdel-Wahab et al., (2016) Adverse Events Associated with Immune Checkpoint Blockade in Patients with Cancer: A Systematic Review of Case Reports. PLoS ONE 11 (7): e0160221. doi:10.1371/journal.pone.0160221; and Gelao et al., Immune Checkpoint Blockade in Cancer Treatment: A Double-Edged Sword Cross-Targeting the Host as an "Innocent Bystander", Toxins 2014, 6, 914-933; doi:10.3390/toxins6030914). Thus, patients receiving immunotherapy are at risk for adverse autoimmune responses.

In certain embodiments, irAEs are related to Th17 pathogenicity. In one study, patients treated with ipilimumab had fluctuations in serum IL-17 levels, such that serum IL-17 levels in patients with colitis versus no irAEs demonstrated significantly higher serum IL-17 levels in the patients with colitis (Callahan et al., (2011) Evaluation of serum IL-17 levels during ipilimumab therapy: Correlation with colitis. Journal of Clinical Oncology 29, no. 15_suppl 2505-2505).

Adoptive Cell Transfer

In certain embodiments, T cells of a specific subtype are used in adoptive cell transfer. In certain embodiments, T cells modified to decrease expression of one or more signature genes is used in adoptive cell transfer. In certain embodiments, cells with reduced or abolished CXCR6 are used in adoptive cell transfer. In certain embodiments, reduced CXCR6 generates T cells having less pathogenicity. In certain embodiments, T cells differentiated according to the present invention are used in adoptive cell transfer to treat an aberrant inflammatory response (e.g., autoimmune response). In certain embodiments, a modulating agent according to the present invention is used in combination with ACT to prevent an aberrant immune response.

As used herein, "ACT", "adoptive cell therapy" and "adoptive cell transfer" may be used interchangeably. In certain embodiments, Adoptive cell therapy (ACT) can refer to the transfer of cells to a patient with the goal of transferring the functionality and characteristics into the new host by engraftment of the cells (see, e.g., Mettananda et al., Editing an a-globin enhancer in primary human hematopoietic stem cells as a treatment for β-thalassemia, Nat Commun. 2017 Sep. 4; 8(1):424). As used herein, the term "engraft" or "engraftment" refers to the process of cell incorporation into a tissue of interest in vivo through contact with existing cells of the tissue. Adoptive cell therapy (ACT) can refer to the transfer of cells, most commonly immune-derived cells, back into the same patient or into a new recipient host with the goal of transferring the immunologic functionality and characteristics into the new host. If possible, use of autologous cells helps the recipient by minimizing GVHD issues. The adoptive transfer of autologous tumor infiltrating lymphocytes (TIL) (Zacharakis et al., (2018) Nat Med. 2018 June; 24(6):724-730; Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57.) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma, metastatic breast cancer and colorectal carcinoma, as well as patients with CD19-expressing hematologic malignancies (Kalos et al., (2011) Science Translational Medicine 3 (95): 95ra73). In certain embodiments, allogenic cells immune cells are transferred (see, e.g., Ren et al., (2017) Clin Cancer Res 23 (9) 2255-2266). As described further herein, allogenic cells can be edited to reduce alloreactivity and prevent graft-versus-host disease. Thus, use of allogenic cells allows for cells to be obtained from healthy donors and prepared for use in patients as opposed to preparing autologous cells from a patient after diagnosis.

Aspects of the invention involve the adoptive transfer of immune system cells, such as T cells, specific for selected antigens, such as tumor associated antigens or tumor specific neoantigens (see, e.g., Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144; and Rajasagi et al., 2014, Systematic identification of personal tumor-specific neoantigens in chronic lymphocytic leukemia. Blood. 2014 Jul. 17; 124(3):453-62).

In certain embodiments, an antigen (such as a tumor antigen) to be targeted in adoptive cell therapy (such as particularly CAR or TCR T cell therapy) of a disease (such as particularly of tumor or cancer) may be selected from a group consisting of B cell maturation antigen (BCMA) (see, e.g., Friedman et al., Effective Targeting of Multiple BCMA-Expressing Hematological Malignancies by Anti-BCMA CAR T Cells, Hum Gene Ther. 2018 Mar. 8; Berdeja J G, et al. Durable clinical responses in heavily pretreated patients with relapsed/refractory multiple myeloma: updated results from a multicenter study of bb2121 anti-Bcma CAR T cell therapy. Blood. 2017; 130:740; and Mouhieddine and Ghobrial, Immunotherapy in Multiple Myeloma: The Era of CAR T Cell Therapy, Hematologist, May-June 2018, Volume 15, issue 3); PSA (prostate-specific antigen); prostate-specific membrane antigen (PSMA); PSCA (Prostate stem cell antigen); Tyrosine-protein kinase transmembrane receptor ROR1; fibroblast activation protein (FAP); Tumor-associated glycoprotein 72 (TAG72); Carcinoembryonic antigen (CEA); Epithelial cell adhesion molecule (EPCAM); Mesothelin; Human Epidermal growth factor Receptor 2 (ERBB2 (Her2/neu)); Prostase; Prostatic acid phosphatase (PAP); elongation factor 2 mutant (ELF2M); Insulin-like growth factor 1 receptor (IGF-1R); gplOO; BCR-ABL (breakpoint cluster region-Abelson); tyrosinase; New York esophageal squamous cell carcinoma 1 (NY-ESO-1); x-light chain, LAGE (L antigen); MAGE (melanoma antigen); Melanoma-associated antigen 1 (MAGE-A1); MAGE A3; MAGE A6; legumain; Human papillomavirus (HPV) E6; HPV E7; prostein; survivin; PCTA1 (Galectin 8); Melan-A/MART-1; Ras mutant; TRP-1 (tyrosinase related protein 1, or gp75); Tyrosinase-related Protein 2 (TRP2); TRP-2/INT2 (TRP-2/intron 2); RAGE (renal antigen); receptor for advanced glycation end products 1 (RAGEl); Renal ubiquitous 1, 2 (RU1, RU2); intestinal carboxyl esterase (iCE); Heat shock protein 70-2 (HSP70-2) mutant; thyroid stimulating hormone receptor (TSHR); CD123; CD171; CD19; CD20; CD22; CD26; CD30; CD33; CD44v7/8 (cluster of differentiation 44, exons 7/8); CD53; CD92; CD100; CD148; CD150; CD200; CD261; CD262; CD362; CS-1 (CD2 subset 1, CRACC, SLAMF7, CD319, and 19A24); C-type lectin-like molecule-1 (CLL-1); ganglioside GD3 (aNeu5Ac(2-8)aNeu5Ac(2-3)bDGalp(1-4)bDGlcp(1-1)Cer); Tn antigen (Tn Ag); Fms-Like Tyrosine Kinase 3 (FLT3); CD38; CD138; CD44v6; B7H3 (CD276); KIT (CD117); Interleukin-13 receptor subunit alpha-2 (IL-13Ra2); Interleukin 11 receptor alpha (IL-11Ra); prostate stem cell antigen (PSCA); Protease Serine 21 (PRSS21); vascular endothelial growth factor receptor 2 (VEGFR2); Lewis(Y) antigen; CD24; Platelet-derived growth factor receptor beta (PDGFR-beta); stage-specific embryonic antigen-4 (SSEA-4); Mucin 1, cell surface associated (MUC1); mucin 16 (MUC16); epidermal growth factor receptor (EGFR); epidermal growth factor receptor variant III (EGFRvIII); neural cell adhesion molecule (NCAM); carbonic anhydrase IX (CAIX); Proteasome (Prosome, Macropain) Subunit, Beta Type, 9 (LMP2); ephrin type-A receptor 2 (EphA2); Ephrin B2; Fucosyl GMl; sialyl Lewis adhesion molecule (sLe); ganglioside GM3 (aNeu5Ac(2-3)bDGalp(1-4)bDGlcp(1-1) Cer); TGS5; high molecular weight-melanoma-associated antigen (HMWMAA); o-acetyl-GD2 ganglioside (OAcGD2); Folate receptor alpha; Folate receptor beta; tumor endothelial marker 1 (TEM1/CD248); tumor endothelial marker 7-related (TEM7R); claudin 6 (CLDN6); G protein-coupled receptor class C group 5, member D (GPRC5D); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (OR51E2); TCR Gamma Alternate Reading Frame Protein (TARP); Wilms tumor protein (WT1); ETS translocation-variant gene 6, located on chromosome 12p (ETV6-AML); sperm protein 17 (SPA17); X Antigen Family, Member 1A (XAGEl); angiopoietin-binding cell surface receptor 2 (Tie 2); CT (cancer/testis (antigen)); melanoma cancer testis antigen-1 (MAD-CT-1); melanoma cancer testis antigen-2 (MAD-CT-2); Fos-related antigen 1; $p5^3$; $p^{53}$ mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor; Cyclin B1; Cyclin D1; v-myc avian myelocytomatosis viral oncogene neuroblastoma derived homolog (MYCN); Ras Homolog Family Member C (RhoC); Cytochrome P450 1B1 (CYP1B1); CCCTC-Binding Factor (Zinc Finger Protein)-Like (BORIS); Squamous Cell Carcinoma Antigen Recognized By T Cells-1 or 3 (SART1, SART3); Paired box protein Pax-5 (PAX5); proacrosin binding protein sp32 (OY-TES1); lymphocyte-specific protein tyrosine kinase (LCK); A kinase anchor protein 4 (AKAP-4); synovial sarcoma, X breakpoint-1, -2, -3 or -4 (SSX1, SSX2, SSX3, SSX4); CD79a; CD79b; CD72; Leukocyte-associated immunoglobulin-like receptor 1 (LAIR1); Fc fragment of IgA receptor (FCAR); Leukocyte immunoglobulin-like receptor subfamily A member 2 (LILRA2); CD300 molecule-like family member f (CD300LF); C-type lectin domain family 12 member A (CLECi2A); bone marrow stromal cell antigen 2 (BST2); EGF-like module-containing mucin-like hormone receptor-like 2 (EMR2); lymphocyte antigen 75 (LY75); Glypican-3 (GPC3); Fc receptor-like 5 (FCRL5); mouse double minute 2 homolog (MDM2); livin; alphafetoprotein (AFP); transmembrane activator and CAML Interactor (TACI); B-cell activating factor receptor (BAFF-R); V-Ki-ras2 Kirsten rat sarcoma viral oncogene homolog (KRAS); immunoglobulin lambda-like polypeptide 1 (IGLL1); 707-AP (707 alanine proline); ART-4 (adenocarcinoma antigen recognized by T4 cells); BAGE (B antigen; b-catenin/m, b-catenin/mutated);

CAMEL (CTL-recognized antigen on melanoma); CAP1 (carcinoembryonic antigen peptide 1); CASP-8 (caspase-8); CDC27m (cell-division cycle 27 mutated); CDK4/m (cycline-dependent kinase 4 mutated); Cyp-B (cyclophilin B); DAM (differentiation antigen melanoma); EGP-2 (epithelial glycoprotein 2); EGP-40 (epithelial glycoprotein 40); Erbb2, 3, 4 (erythroblastic leukemia viral oncogene homolog-2, -3, 4); FBP (folate binding protein); fAchR (Fetal acetylcholine receptor); G250 (glycoprotein 250); GAGE (G antigen); GnT-V (N-acetylglucosaminyltransferase V); HAGE (helicase antigen); ULA-A (human leukocyte antigen-A); HST2 (human signet ring tumor 2); KIAA0205; KDR (kinase insert domain receptor); LDLR/FUT (low density lipid receptor/GDP L-fucose: b-D-galactosidase 2-a-L fucosyltransferase); L1CAM (L1 cell adhesion molecule); MC1R (melanocortin 1 receptor); Myosin/m (myosin mutated); MUM-1, -2, -3 (melanoma ubiquitous mutated 1, 2, 3); NA88-A (NA cDNA clone of patient M88); KG2D (Natural killer group 2, member D) ligands; oncofetal antigen (h5T4); p190 minor bcr-abl (protein of 190KD bcr-abl); Pml/RARa (promyelocytic leukaemia/retinoic acid receptor a); PRAME (preferentially expressed antigen of melanoma); SAGE (sarcoma antigen); TEL/AML 1 (translocation Etsfamily leukemia/acute myeloid leukemia 1); TPI/m (triose-phosphate isomerase mutated); CD70; and any combination thereof.

In certain embodiments, an antigen to be targeted in adoptive cell therapy (such as particularly CAR or TCR T cell therapy) of a disease (such as particularly of tumor or cancer) is a tumor-specific antigen (TSA).

In certain embodiments, an antigen to be targeted in adoptive cell therapy (such as particularly CAR or TCR T cell therapy) of a disease (such as particularly of tumor or cancer) is a neoantigen.

In certain embodiments, an antigen to be targeted in adoptive cell therapy (such as particularly CAR or TCR T cell therapy) of a disease (such as particularly of tumor or cancer) is a tumor-associated antigen (TAA).

In certain embodiments, an antigen to be targeted in adoptive cell therapy (such as particularly CAR or TCR T cell therapy) of a disease (such as particularly of tumor or cancer) is a universal tumor antigen. In certain preferred embodiments, the universal tumor antigen is selected from the group consisting of a human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (Dl), and any combinations thereof.

In certain embodiments, an antigen (such as a tumor antigen) to be targeted in adoptive cell therapy (such as particularly CAR or TCR T cell therapy) of a disease (such as particularly of tumor or cancer) may be selected from a group consisting of: CD19, BCMA, CD70, CLL-1, MAGE A3, MAGE A6, HPV E6, HPV E7, WT1, CD22, CD171, ROR1, MUC16, and SSX2. In certain preferred embodiments, the antigen may be CD19. For example, CD19 may be targeted in hematologic malignancies, such as in lymphomas, more particularly in B-cell lymphomas, such as without limitation in diffuse large B-cell lymphoma, primary mediastinal b-cell lymphoma, transformed follicular lymphoma, marginal zone lymphoma, mantle cell lymphoma, acute lymphoblastic leukemia including adult and pediatric ALL, non-Hodgkin lymphoma, indolent non-Hodgkin lymphoma, or chronic lymphocytic leukemia. For example, BCMA may be targeted in multiple myeloma or plasma cell leukemia (see, e.g., 2018 American Association for Cancer Research (AACR) Annual meeting Poster: Allogeneic Chimeric Antigen Receptor T Cells Targeting B Cell Maturation Antigen). For example, CLL1 may be targeted in acute myeloid leukemia. For example, MAGE A3, MAGE A6, SSX2, and/or KRAS may be targeted in solid tumors. For example, HPV E6 and/or HPV E7 may be targeted in cervical cancer or head and neck cancer. For example, WT1 may be targeted in acute myeloid leukemia (AML), myelodysplastic syndromes (MDS), chronic myeloid leukemia (CML), non-small cell lung cancer, breast, pancreatic, ovarian or colorectal cancers, or mesothelioma. For example, CD22 may be targeted in B cell malignancies, including non-Hodgkin lymphoma, diffuse large B-cell lymphoma, or acute lymphoblastic leukemia. For example, CD171 may be targeted in neuroblastoma, glioblastoma, or lung, pancreatic, or ovarian cancers. For example, ROR1 may be targeted in ROR1+ malignancies, including non-small cell lung cancer, triple negative breast cancer, pancreatic cancer, prostate cancer, ALL, chronic lymphocytic leukemia, or mantle cell lymphoma. For example, MUC16 may be targeted in MUC16ecto+ epithelial ovarian, fallopian tube or primary peritoneal cancer. For example, CD70 may be targeted in both hematologic malignancies as well as in solid cancers such as renal cell carcinoma (RCC), gliomas (e.g., GBM), and head and neck cancers (HNSCC). CD70 is expressed in both hematologic malignancies as well as in solid cancers, while its expression in normal tissues is restricted to a subset of lymphoid cell types (see, e.g., 2018 American Association for Cancer Research (AACR) Annual meeting Poster: Allogeneic CRISPR Engineered Anti-CD70 CAR-T Cells Demonstrate Potent Preclinical Activity Against Both Solid and Hematological Cancer Cells).

Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088, 379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004, 811; 6,284,240; 6,392,013; 6,410,014; 6,753,162; 8,211, 422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. Preferably, a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ξ or FcRγ (scFv-CD3ξ or scFv-FcRγ; see U.S. Pat. Nos. 7,741,465; 5,912,172; U.S. Pat. No. 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ξ; see U.S. Pat. Nos. 8,911,993; 8,916,381; 8,975,071; 9,101,584; 9,102,760; 9,102,761). Third-generation CARs include a combination of costimulatory endodomains, such a CD3ξ-chain, CD97, GDI 1a-CD18, CD2, ICOS, CD27, CD154, CDS, OX40, 4-1BB, CD2, CD7, LIGHT, LFA-1, NKG2C, B7-H3, CD30, CD40, PD-1, or CD28 signaling domains (for example scFv-CD28-4-1BB-CD3ξ or scFv-CD28-OX40-CD3ξ; see U.S. Pat. Nos. 8,906,682; 8,399,645; 5,686,281; PCT Publication No. WO2014134165; PCT Publication No. WO2012079000). In certain embodiments, the primary signaling domain comprises a functional signaling domain of a protein selected from the group consisting of CD3 zeta, CD3 gamma, CD3 delta, CD3 epsilon, common FcR gamma (FCERIG), FcR beta (Fc Epsilon Rib), CD79a, CD79b, Fc gamma RIIa, DAP10, and DAP12. In certain preferred embodiments, the primary signaling domain comprises a functional signaling domain of CD3ξ or FcRγ. In certain embodiments, the one or more costimulatory signaling domains comprise a functional signaling domain of a protein selected, each independently, from the group consisting of: CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8 alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD1ib, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAMI, CRTAM, Ly9 (CD229), CD160 (BY55), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D. In certain embodiments, the one or more costimulatory signaling domains comprise a functional signaling domain of a protein selected, each independently, from the group consisting of: 4-1BB, CD27, and CD28. In certain embodiments, a chimeric antigen receptor may have the design as described in U.S. Pat. No. 7,446,190, comprising an intracellular domain of CD3ξ chain (such as amino acid residues 52-163 of the human CD3 zeta chain, as shown in SEQ ID NO: 14 of U.S. Pat. No. 7,446,190), a signaling region from CD28 and an antigen-binding element (or portion or domain; such as scFv). The CD28 portion, when between the zeta chain portion and the antigen-binding element, may suitably include the transmembrane and signaling domains of CD28 (such as amino acid residues 114-220 of SEQ ID NO: 10, full sequence shown in SEQ ID NO: 6 of U.S. Pat. No. 7,446,190); these can include the following portion of CD28 as set forth in Genbank identifier NM_006139 (sequence version 1, 2 or 3):

(SEQ ID NO: 20)
IEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAP

PRDFAAYRS.

Alternatively, when the zeta sequence lies between the CD28 sequence and the antigen-binding element, intracellular domain of CD28 can be used alone (such as amino sequence set forth in SEQ ID NO: 9 of U.S. Pat. No. 7,446,190). Hence, certain embodiments employ a CAR comprising (a) a zeta chain portion comprising the intracellular domain of human CD3ξ chain, (b) a costimulatory signaling region, and (c) an antigen-binding element (or portion or domain), wherein the costimulatory signaling region comprises the amino acid sequence encoded by SEQ ID NO: 6 of U.S. Pat. No. 7,446,190.

Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T cell attack and/or minimize side effects.

By means of an example and without limitation, Kochenderfer et al., (2009) J Immunother. 32 (7): 689-702 described anti-CD19 chimeric antigen receptors (CAR). FMC63-28Z CAR contained a single chain variable region moiety (scFv) recognizing CD19 derived from the FMC63 mouse hybridoma (described in Nicholson et al., (1997)

Molecular Immunology 34: 1157-1165), a portion of the human CD28 molecule, and the intracellular component of the human TCR-ξ molecule. FMC63-CD828BBZ CAR contained the FMC63 scFv, the hinge and transmembrane regions of the CD8 molecule, the cytoplasmic portions of CD28 and 4-1BB, and the cytoplasmic component of the TCR-ξ molecule. The exact sequence of the CD28 molecule included in the FMC63-28Z CAR corresponded to Genbank identifier NM_006139; the sequence included all amino acids starting with the amino acid sequence IEVMYPPPY (SEQ NO: 21) and continuing all the way to the carboxy-terminus of the protein. To encode the anti-CD19 scFv component of the vector, the authors designed a DNA sequence which was based on a portion of a previously published CAR (Cooper et al., (2003) Blood 101: 1637-1644). This sequence encoded the following components in frame from the 5' end to the 3' end: an XhoI site, the human granulocyte-macrophage colony-stimulating factor (GM-CSF) receptor α-chain signal sequence, the FMC63 light chain variable region (as in Nicholson et al., supra), a linker peptide (as in Cooper et al., supra), the FMC63 heavy chain variable region (as in Nicholson et al., supra), and a NotI site. A plasmid encoding this sequence was digested with XhoI and NotI. To form the MSGV-FMC63-28Z retroviral vector, the XhoI and NotI-digested fragment encoding the FMC63 scFv was ligated into a second XhoI and NotI-digested fragment that encoded the MSGV retroviral backbone (as in Hughes et al., (2005) Human Gene Therapy 16: 457-472) as well as part of the extracellular portion of human CD28, the entire transmembrane and cytoplasmic portion of human CD28, and the cytoplasmic portion of the human TCR-ξ molecule (as in Maher et al., 2002) Nature Biotechnology 20: 70-75). The FMC63-28Z CAR is included in the KTE-C19 (axicabtagene ciloleucel) anti-CD19 CAR-T therapy product in development by Kite Pharma, Inc. for the treatment of inter alia patients with relapsed/refractory aggressive B-cell non-Hodgkin lymphoma (NHL). Accordingly, in certain embodiments, cells intended for adoptive cell therapies, more particularly immunoresponsive cells such as T cells, may express the FMC63-28Z CAR as described by Kochenderfer et al. (supra). Hence, in certain embodiments, cells intended for adoptive cell therapies, more particularly immunoresponsive cells such as T cells, may comprise a CAR comprising an extracellular antigen-binding element (or portion or domain; such as scFv) that specifically binds to an antigen, an intracellular signaling domain comprising an intracellular domain of a CD3ξ chain, and a costimulatory signaling region comprising a signaling domain of CD28. Preferably, the CD28 amino acid sequence is as set forth in Genbank identifier NM_006139 (sequence version 1, 2 or 3) starting with the amino acid sequence IEVMYPPPY (SEQ ID NO: 21) and continuing all the way to the carboxy-terminus of the protein. The sequence is reproduced herein:

(SEQ ID NO: 20)
IEVMYPPPYLDNEKSNGTIIHVKGKHLCPSPLFPGPSKPFWVLVVVGGV

LACYSLLVTVAFIIFWVRSKRSRLLHSDYMNMTPRRPGPTRKHYQPYAP

PRDFAAYRS.

Preferably, the antigen is CD19, more preferably the antigen-binding element is an anti-CD19 scFv, even more preferably the anti-CD19 scFv as described by Kochenderfer et al. (supra).

Additional anti-CD19 CARs are further described in International Patent Publication No. WO2015187528. More particularly Example 1 and Table 1 of WO2015187528, incorporated by reference herein, demonstrate the generation of anti-CD19 CARs based on a fully human anti-CD19 monoclonal antibody (47G4, as described in US20100104509) and murine anti-CD19 monoclonal antibody (as described in Nicholson et al. and explained above). Various combinations of a signal sequence (human CD8-alpha or GM-CSF receptor), extracellular and transmembrane regions (human CD8-alpha) and intracellular T cell signaling domains (CD28-CD3ξ; 4-1BB-CD3ξ; CD27-CD3ξ; CD28-CD27-CD3ξ, 4-1BB-CD27-CD3ξ; CD27-4-1BB-CD3ξ; CD28-CD27-FcεRI gamma chain; or CD28-FcεRI gamma chain) were disclosed. Hence, in certain embodiments, cells intended for adoptive cell therapies, more particularly immunoresponsive cells such as T cells, may comprise a CAR comprising an extracellular antigen-binding element that specifically binds to an antigen, an extracellular and transmembrane region as set forth in Table 1 of WO2015187528 and an intracellular T cell signaling domain as set forth in Table 1 of WO2015187528. Preferably, the antigen is CD19, more preferably the antigen-binding element is an anti-CD19 scFv, even more preferably the mouse or human anti-CD19 scFv as described in Example 1 of WO2015187528. In certain embodiments, the CAR comprises, consists essentially of or consists of an amino acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 as set forth in Table 1 of WO2015187528.

By means of an example and without limitation, chimeric antigen receptor that recognizes the CD70 antigen is described in International Patent Publication WO2012058460A2 (see also, Park et al., CD70 as a target for chimeric antigen receptor T cells in head and neck squamous cell carcinoma, Oral Oncol. 2018 March; 78:145-150; and Jin et al., CD70, a novel target of CAR T cell therapy for gliomas, Neuro Oncol. 2018 Jan. 10; 20(1):55-65). CD70 is expressed by diffuse large B-cell and follicular lymphoma and also by the malignant cells of Hodgkin's lymphoma, Waldenstrom's macroglobulinemia and multiple myeloma, and by HTLV-1- and EBV-associated malignancies. (Agathanggelou et al. Am. J. Pathol. 1995; 147: 1152-1160; Hunter et al., Blood 2004; 104:4881. 26; Lens et al., J Immunol. 2005; 174:6212-6219; Baba et al., J Virol. 2008; 82:3843-3852.) In addition, CD70 is expressed by non-hematological malignancies such as renal cell carcinoma and glioblastoma. (Junker et al., J Urol. 2005; 173:2150-2153; Chahlavi et al., Cancer Res 2005; 65:5428-5438) Physiologically, CD70 expression is transient and restricted to a subset of highly activated T, B, and dendritic cells.

By means of an example and without limitation, chimeric antigen receptor that recognizes BCMA has been described (see, e.g., US20160046724A1; WO2016014789A2; WO2017211900A1; WO2015158671A1; US20180085444A1; WO2018028647A1; US20170283504A1; and WO2013154760A1).

In certain embodiments, the immune cell may, in addition to a CAR or exogenous TCR as described herein, further comprise a chimeric inhibitory receptor (inhibitory CAR) that specifically binds to a second target antigen and is capable of inducing an inhibitory or immunosuppressive or repressive signal to the cell upon recognition of the second target antigen. In certain embodiments, the chimeric inhibitory receptor comprises an extracellular antigen-binding element (or portion or domain) configured to specifically bind to a target antigen, a transmembrane domain, and an intracellular immunosuppressive or repressive signaling domain. In certain embodiments, the second target antigen is an antigen that is not expressed on the surface of a cancer cell or infected cell or the expression of which is downregulated on a cancer cell or an infected cell. In certain embodiments, the second target antigen is an MHC-class I molecule. In certain embodiments, the intracellular signaling domain comprises a functional signaling portion of an immune checkpoint molecule, such as for example PD-1 or CTLA4. Advantageously, the inclusion of such inhibitory CAR reduces the chance of the engineered immune cells attacking non-target (e.g., non-cancer) tissues.

Alternatively, T cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., U.S. Patent Publication Nos. US 2015/0368342, US 2016/0175359, US 2015/0368360) and/or an exogenous signal, such as a small molecule drug (U.S. Patent Publication No. US 2016/0166613, Yung et al., Science, 2015), in order to elicit a T cell response. Some CARs may also comprise a "suicide switch" to induce cell death of the CAR T cells following treatment (Buddee et al., PLoS One, 2013) or to downregulate expression of the CAR following binding to the target antigen (WO 2016/011210).

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ξ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with y-irradiated activating and propagating cells (AaPC), which co-express the cancer antigen and co-stimulatory molecules. The engineered CAR T cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

In certain embodiments, ACT includes co-transferring CD4+Th1 cells and CD8+ CTLs to induce a synergistic antitumour response (see, e.g., Li et al., Adoptive cell therapy with CD4+T helper 1 cells and CD8+ cytotoxic T cells enhances complete rejection of an established tumour, leading to generation of endogenous memory responses to non-targeted tumour epitopes. Clin Transl Immunology. 2017 October; 6(10): e160).

In certain embodiments, Th17 cells are transferred to a subject in need thereof. Th17 cells have been reported to directly eradicate melanoma tumors in mice to a greater extent than Th1 cells (Muranski P, et al., Tumor-specific Th17-polarized cells eradicate large established melanoma. Blood. 2008 Jul. 15; 112(2):362-73; and Martin-Orozco N, et al., T helper 17 cells promote cytotoxic T cell activation in tumor immunity. Immunity. 2009 Nov. 20; 31(5):787-98). Those studies involved an adoptive T cell transfer (ACT) therapy approach, which takes advantage of $CD4^+$ T cells that express a TCR recognizing tyrosinase tumor antigen. Exploitation of the TCR leads to rapid expansion of Th17 populations to large numbers ex vivo for reinfusion into the autologous tumor-bearing hosts.

In certain embodiments, ACT may include autologous iPSC-based vaccines, such as irradiated iPSCs in autologous anti-tumor vaccines (see e.g., Kooreman, Nigel G. et al., Autologous iPSC-Based Vaccines Elicit Anti-tumor Responses In Vivo, Cell Stem Cell 22, 1-13, 2018, doi.org/10.1016/j.stem.2018.01.016).

Unlike T cell receptors (TCRs) that are MHC restricted, CARs can potentially bind any cell surface-expressed antigen and can thus be more universally used to treat patients (see Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267). In certain embodiments, in the absence of endogenous T cell infiltrate (e.g., due to aberrant antigen processing and presentation), which precludes the use of TIL therapy and immune checkpoint blockade, the transfer of CAR T cells may be used to treat patients (see, e.g., Hinrichs C S, Rosenberg S A. Exploiting the curative potential of adoptive T-cell therapy for cancer. Immunol Rev (2014) 257(1):56-71. doi:10.1111/imr.12132).

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In certain embodiments, the treatment can be administered after lymphodepleting pretreatment in the form of chemotherapy (typically a combination of cyclophosphamide and fludarabine) or radiation therapy. Initial studies in ACT had short lived responses and the transferred cells did not persist in vivo for very long (Houot et al., T-cell-based immunotherapy: adoptive cell transfer and checkpoint inhibition. Cancer Immunol Res (2015) 3(10):1115-22; and Kamta et al., Advancing Cancer Therapy with Present and Emerging Immuno-Oncology Approaches. Front. Oncol. (2017) 7:64). Immune suppressor cells like Tregs and MDSCs may attenuate the activity of transferred cells by outcompeting them for the necessary cytokines. Not being bound by a theory lymphodepleting pretreatment may eliminate the suppressor cells allowing the TILs to persist.

In one embodiment, the treatment can be administered into patients undergoing an immunosuppressive treatment (e.g., glucocorticoid treatment). The cells or population of cells, may be made resistant to at least one immunosuppressive agent due to the inactivation of a gene encoding a receptor for such immunosuppressive agent. In certain embodiments, the immunosuppressive treatment provides for the selection and expansion of the immunoresponsive T cells within the patient.

In certain embodiments, the treatment can be administered before primary treatment (e.g., surgery or radiation therapy) to shrink a tumor before the primary treatment. In another embodiment, the treatment can be administered after primary treatment to remove any remaining cancer cells.

In certain embodiments, immunometabolic barriers can be targeted therapeutically prior to and/or during ACT to enhance responses to ACT or CAR T cell therapy and to support endogenous immunity (see, e.g., Irving et al., Engineering Chimeric Antigen Receptor T-Cells for Racing in Solid Tumors: Don't Forget the Fuel, Front. Immunol., 3 Apr. 2017, doi.org/10.3389/fimmu.2017.00267).

The administration of cells or population of cells, such as immune system cells or cell populations, such as more particularly immunoresponsive cells or cell populations, as disclosed herein may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administered in one or more doses. In another embodiment, the effective amount of cells is administrated as a single dose. In another embodiment, the effective amount of cells is administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells is administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853; Ren et al., 2017, Multiplex genome editing to generate universal CAR T cells resistant to PD1 inhibition, Clin Cancer Res. 2017 May 1; 23(9):2255-2266. doi: 10.1158/1078-0432.CCR-16-1300. Epub 2016 Nov. 4; Qasim et al., 2017, Molecular remission of infant B-ALL after infusion of universal TALEN gene-edited CAR T cells, Sci Transl Med. 2017 Jan. 25; 9(374); Legut, et al., 2018, CRISPR-mediated TCR replacement generates superior anticancer transgenic T cells. Blood, 131(3), 311-322; and Georgiadis et al., Long Terminal Repeat CRISPR-CAR-Coupled "Universal" T Cells Mediate Potent Anti-leukemic Effects, Molecular Therapy, In Press, Corrected Proof, Available online 6 Mar. 2018). Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed for example to insert or knock-in an exogenous gene, such as an exogenous gene encoding a CAR or a TCR, at a preselected locus in a cell (e.g. TRAC locus); to eliminate potential alloreactive T cell receptors (TCR) or to prevent inappropriate pairing between endogenous and exogenous TCR chains, such as to knock-out or knock-down expression of an endogenous TCR in a cell; to disrupt the target of a chemotherapeutic agent in a cell; to block an immune checkpoint, such as to knock-out or knock-down expression of an immune checkpoint protein or receptor in a cell; to knock-out or knock-down expression of other gene or genes in a cell, the reduced expression or lack of expression of which can enhance the efficacy of adoptive therapies using the cell; to knock-out or knock-down expression of an endogenous gene in a cell, said endogenous gene encoding an antigen targeted by an exogenous CAR or TCR; to knock-out or knock-down expression of one or more MHC constituent proteins in a cell; to activate a T cell; to modulate cells such that the cells are resistant to exhaustion or dysfunction; and/or increase the differentiation and/or proliferation of functionally exhausted or dysfunctional CD8+ T cells (see PCT Patent Publications: WO2013176915, WO2014059173, WO2014172606, WO2014184744, and WO2014191128).

In certain embodiments, editing may result in inactivation of a gene. By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art. In certain embodiments, homology directed repair (HDR) is used to concurrently inactivate a gene (e.g., TRAC) and insert an endogenous TCR or CAR into the inactivated locus.

Hence, in certain embodiments, editing of cells (such as by CRISPR/Cas), particularly cells intended for adoptive cell therapies, more particularly immunoresponsive cells such as T cells, may be performed to insert or knock-in an exogenous gene, such as an exogenous gene encoding a CAR or a TCR, at a preselected locus in a cell. Conventionally, nucleic acid molecules encoding CARs or TCRs are transfected or transduced to cells using randomly integrating vectors, which, depending on the site of integration, may lead to clonal expansion, oncogenic transformation, variegated transgene expression and/or transcriptional silencing of the transgene. Directing of transgene(s) to a specific locus in a cell can minimize or avoid such risks and advantageously provide for uniform expression of the transgene(s) by the cells. Without limitation, suitable 'safe harbor' loci for directed transgene integration include CCR5 or AAVS1. Homology-directed repair (HDR) strategies are known and described elsewhere in this specification allowing to insert transgenes into desired loci (e.g., TRAC locus).

Further suitable loci for insertion of transgenes, in particular CAR or exogenous TCR transgenes, include without limitation loci comprising genes coding for constituents of endogenous T cell receptor, such as T cell receptor alpha locus (TRA) or T cell receptor beta locus (TRB), for example T cell receptor alpha constant (TRAC) locus, T cell receptor beta constant 1 (TRBC1) locus or T cell receptor beta constant 2 (TRBC1) locus. Advantageously, insertion of a transgene into such locus can simultaneously achieve expression of the transgene, potentially controlled by the endogenous promoter, and knock-out expression of the endogenous TCR. This approach has been exemplified in Eyquem et al., (2017) Nature 543: 113-117, wherein the authors used CRISPR/Cas9 gene editing to knock-in a DNA molecule encoding a CD19-specific CAR into the TRAC locus downstream of the endogenous promoter; the CAR-T cells obtained by CRISPR were significantly superior in terms of reduced tonic CAR signaling and exhaustion.

T cell receptors (TCR) are cell surface receptors that participate in the activation of T cells in response to the presentation of antigen. The TCR is generally made from two chains, a and β, which assemble to form a heterodimer and associates with the CD3-transducing subunits to form the T cell receptor complex present on the cell surface. Each a and p chain of the TCR consists of an immunoglobulin-like N-terminal variable (V) and constant (C) region, a hydrophobic transmembrane domain, and a short cytoplasmic region. As for immunoglobulin molecules, the variable region of the a and p chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Hence, in certain embodiments, editing of cells (such as by CRISPR/Cas), particularly cells intended for adoptive cell therapies, more particularly immunoresponsive cells such as T cells, may be performed to knock-out or knock-down expression of an endogenous TCR in a cell. For example, NHEJ-based or HDR-based gene editing approaches can be employed to disrupt the endogenous TCR alpha and/or beta chain genes. For example, gene editing system or systems, such as CRISPR/Cas system or systems, can be designed to target a sequence found within the TCR beta chain conserved between the beta 1 and beta 2 constant region genes (TRBC1 and TRBC2) and/or to target the constant region of the TCR alpha chain (TRAC) gene.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

In certain embodiments, editing of cells (such as by CRISPR/Cas), particularly cells intended for adoptive cell therapies, more particularly immunoresponsive cells such as T cells, may be performed to block an immune checkpoint, such as to knock-out or knock-down expression of an immune checkpoint protein or receptor in a cell. Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

International Patent Publication No. WO2014172606 relates to the use of MT1 and/or MT2 inhibitors to increase proliferation and/or activity of exhausted CD8+ T cells and to decrease CD8+ T cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, ILIORB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, TIM-3, CEACAM-1, CEACAM-3, or CEACAM-5. In preferred embodiments, the gene locus involved in the expression of PD-1 or CTLA-4 genes is targeted. In other preferred embodiments, combinations of genes are targeted, such as but not limited to PD-1 and TIGIT.

By means of an example and without limitation, International Patent Publication No WO2016196388 concerns an engineered T cell comprising (a) a genetically engineered antigen receptor that specifically binds to an antigen, which receptor may be a CAR; and (b) a disrupted gene encoding a PD-L1, an agent for disruption of a gene encoding a PD-L1, and/or disruption of a gene encoding PD-L1, wherein the disruption of the gene may be mediated by a gene editing nuclease, a zinc finger nuclease (ZFN), CRISPR/Cas9 and/or TALEN. WO2015142675 relates to immune effector cells comprising a CAR in combination with an agent (such as CRISPR, TALEN or ZFN) that increases the efficacy of the immune effector cells in the treatment of cancer, wherein the agent may inhibit an immune inhibitory molecule, such as PD1, PD-L1, CTLA-4, TIM-3, LAG-3, VISTA, BTLA, TIGIT, LAIR1, CD160, 2B4, TGFR beta, CEACAM-1, CEACAM-3, or CEACAM-5. Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In certain embodiments, cells may be engineered to express a CAR, wherein expression and/or function of methylcytosine dioxygenase genes (TET1, TET2 and/or TET3) in the cells has been reduced or eliminated, such as by CRISPR, ZNF or TALEN (for example, as described in International Patent Publication No WO201704916).

In certain embodiments, editing of cells (such as by CRISPR/Cas), particularly cells intended for adoptive cell therapies, more particularly immunoresponsive cells such as T cells, may be performed to knock-out or knock-down expression of an endogenous gene in a cell, said endogenous gene encoding an antigen targeted by an exogenous CAR or TCR, thereby reducing the likelihood of targeting of the engineered cells. In certain embodiments, the targeted antigen may be one or more antigen selected from the group consisting of CD38, CD138, CS-1, CD33, CD26, CD30, CD53, CD92, CD100, CD148, CD150, CD200, CD261, CD262, CD362, human telomerase reverse transcriptase (hTERT), survivin, mouse double minute 2 homolog (MDM2), cytochrome P450 1B1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53, cyclin (D1), B cell maturation antigen (BCMA), transmembrane activator and CAML Interactor (TACI), and B-cell activating factor receptor (BAFF-R) (for example, as described in WO2016011210 and WO2017011804).

In certain embodiments, editing of cells (such as by CRISPR/Cas), particularly cells intended for adoptive cell therapies, more particularly immunoresponsive cells such as T cells, may be performed to knock-out or knock-down expression of one or more MHC constituent proteins, such as one or more HLA proteins and/or beta-2 microglobulin (B2M), in a cell, whereby rejection of non-autologous (e.g., allogeneic) cells by the recipient's immune system can be reduced or avoided. In preferred embodiments, one or more HLA class I proteins, such as HLA-A, B and/or C, and/or B2M may be knocked-out or knocked-down. Preferably, B2M may be knocked-out or knocked-down. By means of an example, Ren et al., (2017) Clin Cancer Res 23 (9) 2255-2266 performed lentiviral delivery of CAR and electro-transfer of Cas9 mRNA and gRNAs targeting endogenous TCR, 3-2 microglobulin (B2M) and PD1 simultaneously, to generate gene-disrupted allogeneic CAR T cells deficient of TCR, HLA class I molecule and PD1.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ, B2M and TCRα, B2M and TCRβ.

In certain embodiments, a cell may be multiply edited (multiplex genome editing) as taught herein to (1) knock-out or knock-down expression of an endogenous TCR (for example, TRBC1, TRBC2 and/or TRAC), (2) knock-out or knock-down expression of an immune checkpoint protein or receptor (for example PD1, PD-L1 and/or CTLA4); and (3) knock-out or knock-down expression of one or more MHC constituent proteins (for example, HLA-A, B and/or C, and/or B2M, preferably B2M).

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment, allogenic T cells may be obtained from healthy subjects. In one embodiment, T cells that have infiltrated a tumor are isolated. T cells may be removed during surgery. T cells may be isolated after removal of tumor tissue by biopsy. T cells may be isolated by any means known in the art. In one embodiment, T cells are obtained by apheresis. In one embodiment, the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Lagomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells (PBMC), bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily appreciate, a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+, CD4+, CDC, CD45RA+, and CD45RO+ T cells, can be further isolated by positive or negative selection techniques. For example, in one preferred embodiment, T cells are isolated by incubation with anti-CD3/anti-CD28 (i.e., 3×28)-conjugated beads, such as DYNABEADS® M-450 CD3/CD28 T, or XCYTE DYNA-BEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments, the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media. The cells then are frozen to $-80°$ C. at a rate of 1° per minute and stored in the vapor phase of a liquid nitrogen storage tank. Other methods of controlled freezing may be used as well as uncontrolled freezing immediately at $-20°$ C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment, neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation and Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment, the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/02m/peptide heterotrimeric complexes (see Parker et al., J. Immunol. 152:163, 1994).

In one embodiment, cells are directly labeled with an epitope-specific reagent for isolation by flow cytometry followed by characterization of phenotype and TCRs. In one embodiment, T cells are isolated by contacting with T cell specific antibodies. Sorting of antigen-specific T cells, or generally any cells of the present invention, can be carried out using any of a variety of commercially available cell sorters, including, but not limited to, MoFlo sorter (Dako-Cytomation, Fort Collins, Colo.), FACSAria™, FACSArray™, FACSVantage™, BD™ LSR II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment, both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

In certain embodiments, T cells comprising a CAR or an exogenous TCR may be manufactured as described in WO2015120096, by a method comprising enriching a population of lymphocytes obtained from a donor subject; stimulating the population of lymphocytes with one or more T cell stimulating agents to produce a population of activated T cells, wherein the stimulation is performed in a closed system using serum-free culture medium; transducing the population of activated T cells with a viral vector comprising a nucleic acid molecule which encodes the CAR or TCR, using a single cycle transduction to produce a population of transduced T cells, wherein the transduction is performed in a closed system using serum-free culture medium; and expanding the population of transduced T cells for a predetermined time to produce a population of engineered T cells, wherein the expansion is performed in a closed system using serum-free culture medium. In certain embodiments, T cells comprising a CAR or an exogenous TCR, may be manufactured as described in WO2015120096, by a method comprising obtaining a population of lymphocytes; stimulating the population of lymphocytes with one or more stimulating agents to produce a population of activated T cells, wherein the stimulation is performed in a closed system using serum-free culture medium; transducing the population of activated T cells with a viral vector comprising a nucleic acid molecule which encodes the CAR or TCR, using at least one cycle transduction to produce a population of transduced T cells, wherein the transduction is performed in a closed system using serum-free culture medium; and expanding the population of transduced T cells to produce a population of engineered T cells, wherein the expansion is performed in a closed system using serum-free culture medium. The predetermined time for expanding the population of transduced T cells may be 3 days. The time from enriching the population of lymphocytes to producing the engineered T cells may be 6 days. The closed system may be a closed bag system. Further provided is population of T cells comprising a CAR or an exogenous TCR obtainable or obtained by said method, and a pharmaceutical composition comprising such cells.

In certain embodiments, T cell maturation or differentiation in vitro may be delayed or inhibited by the method as described in WO2017070395, comprising contacting one or more T cells from a subject in need of a T cell therapy with an AKT inhibitor (such as, e.g., one or a combination of two or more AKT inhibitors disclosed in claim 8 of WO2017070395) and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function (such as, e.g., increased T cell proliferation; increased cytokine production; and/or increased cytolytic activity) relative to a T cell function of a T cell cultured in the absence of an AKT inhibitor.

In certain embodiments, a patient in need of a T cell therapy may be conditioned by a method as described in International Patent Publication No. WO2016191756 comprising administering to the patient a dose of cyclophosphamide between 200 mg/m2/day and 2000 mg/m2/day and a dose of fludarabine between 20 mg/m2/day and 900 mg/m$^2$/day.

Administration of Pharmaceutical Compositions

A "pharmaceutical composition" refers to a composition that usually contains an excipient, such as a pharmaceutically acceptable carrier that is conventional in the art and that is suitable for administration to cells or to a subject.

The pharmaceutical composition according to the present invention can, in one alternative, include a prodrug. When a pharmaceutical composition according to the present invention includes a prodrug, prodrugs and active metabolites of a compound may be identified using routine techniques known in the art. (See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992)).

The term "pharmaceutically acceptable" as used throughout this specification is consistent with the art and means compatible with the other ingredients of a pharmaceutical composition and not deleterious to the recipient thereof.

As used herein, "carrier" or "excipient" includes any and all solvents, diluents, buffers (such as, e.g., neutral buffered saline or phosphate buffered saline), solubilizers, colloids, dispersion media, vehicles, fillers, chelating agents (such as, e.g., EDTA or glutathione), amino acids (such as, e.g., glycine), proteins, disintegrants, binders, lubricants, wetting agents, emulsifiers, sweeteners, colorants, flavorings, aromatizers, thickeners, agents for achieving a depot effect, coatings, antifungal agents, preservatives, stabilizers, antioxidants, tonicity controlling agents, absorption delaying agents, and the like. The use of such media and agents for pharmaceutical active components is well known in the art. Such materials should be non-toxic and should not interfere with the activity of the cells or active components.

The precise nature of the carrier or excipient or other material will depend on the route of administration. For example, the composition may be in the form of a parenterally acceptable aqueous solution, which is pyrogen-free and has suitable pH, isotonicity and stability. For general principles in medicinal formulation, the reader is referred to Cell Therapy: Stem Cell Transplantation, Gene Therapy, and Cellular Immunotherapy, by G. Morstyn & W. Sheridan eds., Cambridge University Press, 1996; and Hematopoietic Stem Cell Therapy, E. D. Ball, J. Lister & P. Law, Churchill Livingstone, 2000.

The pharmaceutical composition can be applied parenterally, rectally, orally or topically. Preferably, the pharmaceutical composition may be used for intravenous, intramuscular, subcutaneous, peritoneal, peridural, rectal, nasal, pulmonary, mucosal, or oral application. In a preferred embodiment, the pharmaceutical composition according to the invention is intended to be used as an infusion. The skilled person will understand that compositions which are to be administered orally or topically will usually not comprise cells, although it may be envisioned for oral compositions to also comprise cells, for example when gastro-intestinal tract indications are treated. Each of the cells or active components (e.g., immunomodulants) as discussed herein may be administered by the same route or may be administered by a different route. By means of example, and without limitation, cells may be administered parenterally and other active components may be administered orally.

Liquid pharmaceutical compositions may generally include a liquid carrier such as water or a pharmaceutically acceptable aqueous solution. For example, physiological saline solution, tissue or cell culture media, dextrose or other saccharide solution or glycols such as ethylene glycol, propylene glycol or polyethylene glycol may be included.

The composition may include one or more cell protective molecules, cell regenerative molecules, growth factors, anti-apoptotic factors or factors that regulate gene expression in the cells. Such substances may render the cells independent of their environment.

Such pharmaceutical compositions may contain further components ensuring the viability of the cells therein. For example, the compositions may comprise a suitable buffer system (e.g., phosphate or carbonate buffer system) to achieve desirable pH, more usually near neutral pH, and may comprise sufficient salt to ensure isoosmotic conditions for the cells to prevent osmotic stress. For example, suitable solution for these purposes may be phosphate-buffered saline (PBS), sodium chloride solution, Ringer's Injection or Lactated Ringer's Injection, as known in the art. Further, the composition may comprise a carrier protein, e.g., albumin (e.g., bovine or human albumin), which may increase the viability of the cells.

Further suitably pharmaceutically acceptable carriers or additives are well known to those skilled in the art and for instance may be selected from proteins such as collagen or gelatine, carbohydrates such as starch, polysaccharides, sugars (dextrose, glucose and sucrose), cellulose derivatives like sodium or calcium carboxymethylcellulose, hydroxypropyl cellulose or hydroxypropylmethyl cellulose, pregelatinized starches, pectin agar, carrageenan, clays, hydrophilic gums (acacia gum, guar gum, arabic gum and xanthan gum), alginic acid, alginates, hyaluronic acid, polyglycolic and polylactic acid, dextran, pectins, synthetic polymers such as water-soluble acrylic polymer or polyvinylpyrrolidone, proteoglycans, calcium phosphate and the like.

In certain embodiments, a pharmaceutical cell preparation as taught herein may be administered in a form of liquid composition. In embodiments, the cells or pharmaceutical composition comprising such can be administered systemically, topically, within an organ or at a site of organ dysfunction or lesion.

Preferably, the pharmaceutical compositions may comprise a therapeutically effective amount of the specified immune cells and/or other active components (e.g., immunomodulants). The term "therapeutically effective amount" refers to an amount which can elicit a biological or medicinal response in a tissue, system, animal or human that is being sought by a researcher, veterinarian, medical doctor or other clinician, and in particular can prevent or alleviate one or more of the local or systemic symptoms or features of a disease or condition being treated.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

The medicaments of the invention are prepared in a manner known to those skilled in the art, for example, by means of conventional dissolving, lyophilizing, mixing, granulating or confectioning processes. Methods well known in the art for making formulations are found, for example, in Remington: The Science and Practice of Pharmacy, 20th ed., ed. A. R. Gennaro, 2000, Lippincott Williams & Wilkins, Philadelphia, and Encyclopedia of Pharmaceutical Technology, eds. J. Swarbrick and J. C. Boylan, 1988-1999, Marcel Dekker, New York.

Administration of medicaments of the invention may be by any suitable means that results in a compound concentration that is effective for treating or inhibiting (e.g., by delaying) the development of a disease. The compound is admixed with a suitable carrier substance, e.g., a pharmaceutically acceptable excipient that preserves the therapeutic properties of the compound with which it is administered. One exemplary pharmaceutically acceptable excipient is physiological saline. The suitable carrier substance is generally present in an amount of 1-95% by weight of the total weight of the medicament. The medicament may be provided in a dosage form that is suitable for administration. Thus, the medicament may be in form of, e.g., tablets, capsules, pills, powders, granulates, suspensions, emulsions, solutions, gels including hydrogels, pastes, ointments, creams, plasters, drenches, delivery devices, injectables, implants, sprays, or aerosols.

Administration can be systemic or local. In addition, it may be advantageous to administer the composition into the central nervous system by any suitable route, including intraventricular and intrathecal injection. Pulmonary administration may also be employed by use of an inhaler or nebulizer, and formulation with an aerosolizing agent. It may also be desirable to administer the agent locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the pharmacological compositions including, but not limited to, encapsulation in liposomes, microparticles, microcapsules; minicells; polymers; capsules; tablets; and the like. In one embodiment, the agent may be delivered in a vesicle, in particular a liposome. In a liposome, the agent is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,837,028 and 4,737,323. In yet another embodiment, the pharmacological compositions can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (e.g., a tumor), thus requiring only a fraction of the systemic dose. See, for example, Goodson, In: Medical Applications of Controlled Release, 1984. (CRC Press, Boca Raton, Fla.).

The amount of the agents which will be effective in the treatment of a particular disorder or condition will depend on the nature of the disorder or condition and may be determined by standard clinical techniques by those of skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the agent with which to treat each individual patient. In certain embodiments, the attending physician will administer low doses of the agent and observe the patient's response. Larger doses of the agent may be administered until the optimal therapeutic effect is obtained for the patient, and at that point the dosage is not increased further. Effective doses may be extrapolated from dose-response curves derived from in vitro or animal model test systems. Ultimately the attending physician will decide on the appropriate duration of therapy using compositions of the present invention. Dosage will also vary according to the age, weight and response of the individual patient.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection.

Diagnostic Methods

The invention provides biomarkers for the identification, diagnosis, prognosis and manipulation of disease phenotypes (e.g., immune state), for use in a variety of diagnostic and/or therapeutic indications. Biomarkers in the context of the present invention encompasses, without limitation nucleic acids, proteins, reaction products, and metabolites, together with their polymorphisms, mutations, variants, modifications, subunits, fragments, and other analytes or sample-derived measures. In certain embodiments, biomarkers include the signature genes or signature gene products, and/or cells as described herein (e.g., CXCR6 and SLAMF6). Antibodies against the genes described herein for detection are known in the art.

In certain embodiments, the invention provides uses of the biomarkers for predicting risk for a certain phenotype. In certain embodiments, the invention provides uses of the biomarkers for selecting a treatment. In certain embodiments, a subject having a disease can be classified based on severity of the disease.

The terms "diagnosis" and "monitoring" are commonplace and well-understood in medical practice. By means of further explanation and without limitation the term "diagnosis" generally refers to the process or act of recognizing, deciding on or concluding on a disease or condition in a subject on the basis of symptoms and signs and/or from results of various diagnostic procedures (such as, for example, from knowing the presence, absence and/or quantity of one or more biomarkers characteristic of the diagnosed disease or condition).

The term "monitoring" generally refers to the follow-up of a disease or a condition in a subject for any changes which may occur over time.

The terms "prognosing" or "prognosis" generally refer to an anticipation on the progression of a disease or condition and the prospect (e.g., the probability, duration, and/or extent) of recovery. A good prognosis of the diseases or conditions taught herein may generally encompass anticipation of a satisfactory partial or complete recovery from the diseases or conditions, preferably within an acceptable time period. A good prognosis of such may more commonly encompass anticipation of not further worsening or aggravating of such, preferably within a given time period. A poor prognosis of the diseases or conditions as taught herein may generally encompass anticipation of a substandard recovery and/or unsatisfactorily slow recovery, or to substantially no recovery or even further worsening of such.

The terms also encompass prediction of a disease. The terms "predicting" or "prediction" generally refer to an advance declaration, indication or foretelling of a disease or condition in a subject not (yet) having said disease or condition. For example, a prediction of a disease or condition in a subject may indicate a probability, chance or risk that the subject will develop said disease or condition, for example within a certain time period or by a certain age. Said probability, chance or risk may be indicated inter alia as an absolute value, range or statistics, or may be indicated relative to a suitable control subject or subject population (such as, e.g., relative to a general, normal or healthy subject or subject population). Hence, the probability, chance or risk that a subject will develop a disease or condition may be advantageously indicated as increased or decreased, or as fold-increased or fold-decreased relative to a suitable control subject or subject population. As used herein, the term "prediction" of the conditions or diseases as taught herein in a subject may also particularly mean that the subject has a 'positive' prediction of such, i.e., that the subject is at risk of having such (e.g., the risk is significantly increased vis-à-vis a control subject or subject population). The term "prediction of no" diseases or conditions as taught herein as described herein in a subject may particularly mean that the subject has a 'negative' prediction of such, i.e., that the subject's risk of having such is not significantly increased vis-à-vis a control subject or subject population.

In certain example embodiments, one or more genes in Tables 1-4 may be used as markers to detect the presence of autoimmune disease, such as those disclosed therein. In certain example embodiments, the one or more genes or gene products may be detected by expression in Th17 cell residing in the central nervous system.

Biomarkers

The term "biomarker" is widespread in the art and commonly broadly denotes a biological molecule, more particularly an endogenous biological molecule, and/or a detectable portion thereof, whose qualitative and/or quantitative evaluation in a tested object (e.g., in or on a cell, cell population, tissue, organ, or organism, e.g., in a biological sample of a subject) is predictive or informative with respect to one or more aspects of the tested object's phenotype and/or genotype. The terms "marker" and "biomarker" may be used interchangeably throughout this specification. Biomarkers as intended herein may be nucleic acid-based or peptide-, polypeptide- and/or protein-based. For example, a marker may be comprised of peptide(s), polypeptide(s) and/or protein(s) encoded by a given gene, or of detectable portions thereof. Further, whereas the term "nucleic acid" generally encompasses DNA, RNA and DNA/RNA hybrid molecules, in the context of markers the term may typically refer to heterogeneous nuclear RNA (hnRNA), pre-mRNA, messenger RNA (mRNA), or complementary DNA (cDNA), or detectable portions thereof. Such nucleic acid species are particularly useful as markers, since they contain qualitative and/or quantitative information about the expression of the gene. Particularly preferably, a nucleic acid-based marker may encompass mRNA of a given gene, or cDNA made of the mRNA, or detectable portions thereof. Any such nucleic acid(s), peptide(s), polypeptide(s) and/or protein(s) encoded by or produced from a given gene are encompassed by the term "gene product(s)".

Preferably, markers as intended herein may be extracellular or cell surface markers, as methods to measure extracellular or cell surface marker(s) need not disturb the integrity of the cell membrane and may not require fixation/permeabilization of the cells.

Unless otherwise apparent from the context, reference herein to any marker, such as a peptide, polypeptide, protein, or nucleic acid, may generally also encompass modified forms of said marker, such as bearing post-expression modifications including, for example, phosphorylation, glycosylation, lipidation, methylation, cysteinylation, sulphonation, glutathionylation, acetylation, oxidation of methionine to methionine sulphoxide or methionine sulphone, and the like.

The term "peptide" as used throughout this specification preferably refers to a polypeptide as used herein consisting essentially of 50 amino acids or less, e.g., 45 amino acids or less, preferably 40 amino acids or less, e.g., 35 amino acids or less, more preferably 30 amino acids or less, e.g., 25 or less, 20 or less, 15 or less, 10 or less or 5 or less amino acids.

The term "polypeptide" as used throughout this specification generally encompasses polymeric chains of amino acid residues linked by peptide bonds. Hence, insofar a protein is only composed of a single polypeptide chain, the terms "protein" and "polypeptide" may be used interchangeably herein to denote such a protein. The term is not limited to any minimum length of the polypeptide chain. The term may encompass naturally, recombinantly, semi-synthetically or synthetically produced polypeptides. The term also encompasses polypeptides that carry one or more co- or post-expression-type modifications of the polypeptide chain, such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes polypeptide variants or mutants which carry amino acid sequence variations vis-à-vis a corresponding native polypeptide, such as, e.g., amino acid deletions, additions and/or substitutions. The term contemplates both full-length polypeptides and polypeptide parts or fragments, e.g., naturally-occurring polypeptide parts that ensue from processing of such full-length polypeptides.

The term "protein" as used throughout this specification generally encompasses macromolecules comprising one or more polypeptide chains, i.e., polymeric chains of amino acid residues linked by peptide bonds. The term may encompass naturally, recombinantly, semi-synthetically or synthetically produced proteins. The term also encompasses proteins that carry one or more co- or post-expression-type modifications of the polypeptide chain(s), such as, without limitation, glycosylation, acetylation, phosphorylation, sulfonation, methylation, ubiquitination, signal peptide removal, N-terminal Met removal, conversion of pro-enzymes or pre-hormones into active forms, etc. The term further also includes protein variants or mutants which carry amino acid sequence variations vis-à-vis a corresponding native protein, such as, e.g., amino acid deletions, additions and/or substitutions. The term contemplates both full-length proteins and protein parts or fragments, e.g., naturally-occurring protein parts that ensue from processing of such full-length proteins.

The reference to any marker, including any peptide, polypeptide, protein, or nucleic acid, corresponds to the marker commonly known under the respective designations in the art. The terms encompass such markers of any organism where found, and particularly of animals, preferably warm-blooded animals, more preferably vertebrates, yet more preferably mammals, including humans and non-human mammals, still more preferably of humans.

The terms particularly encompass such markers, including any peptides, polypeptides, proteins, or nucleic acids, with a native sequence, i.e., ones of which the primary sequence is the same as that of the markers found in or derived from nature. A skilled person understands that native sequences may differ between different species due to genetic divergence between such species. Moreover, native sequences may differ between or within different individuals of the same species due to normal genetic diversity (variation) within a given species. Also, native sequences may differ between or even within different individuals of the same species due to somatic mutations, or post-transcriptional or post-translational modifications. Any such variants or isoforms of markers are intended herein. Accordingly, all sequences of markers found in or derived from nature are considered "native". The terms encompass the markers when forming a part of a living organism, organ, tissue or cell, when forming a part of a biological sample, as well as when at least partly isolated from such sources. The terms also encompass markers when produced by recombinant or synthetic means.

In certain embodiments, markers, including any peptides, polypeptides, proteins, or nucleic acids, may be human, i.e., their primary sequence may be the same as a corresponding primary sequence of or present in a naturally occurring human markers. Hence, the qualifier "human" in this connection relates to the primary sequence of the respective markers, rather than to their origin or source. For example, such markers may be present in or isolated from samples of human subjects or may be obtained by other means (e.g., by recombinant expression, cell-free transcription or translation, or non-biological nucleic acid or peptide synthesis).

The reference herein to any marker, including any peptide, polypeptide, protein, or nucleic acid, also encompasses fragments thereof. Hence, the reference herein to measuring (or measuring the quantity of) any one marker may encompass measuring the marker and/or measuring one or more fragments thereof.

For example, any marker and/or one or more fragments thereof may be measured collectively, such that the measured quantity corresponds to the sum amounts of the collectively measured species. In another example, any marker and/or one or more fragments thereof may be measured each individually. The terms encompass fragments arising by any mechanism, in vivo and/or in vitro, such as, without limitation, by alternative transcription or translation, exo- and/or endo-proteolysis, exo- and/or endo-nucleolysis, or degradation of the peptide, polypeptide, protein, or nucleic acid, such as, for example, by physical, chemical and/or enzymatic proteolysis or nucleolysis.

The term "fragment" as used throughout this specification with reference to a peptide, polypeptide, or protein generally denotes a portion of the peptide, polypeptide, or protein, such as typically an N- and/or C-terminally truncated form of the peptide, polypeptide, or protein. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the amino acid sequence length of said peptide, polypeptide, or protein. For example, insofar not exceeding the length of the full-length peptide, polypeptide, or protein, a fragment may include a sequence of ≥5 consecutive amino acids, or ≥10 consecutive amino acids, or ≥20 consecutive amino acids, or ≥30 consecutive amino acids, e.g., ≥40 consecutive amino acids, such as for example≥50 consecutive amino acids, e.g., ≥60, ≥70, ≥80, ≥90, ≥100, ≥200, ≥300, ≥400, ≥500 or ≥600 consecutive amino acids of the corresponding full-length peptide, polypeptide, or protein.

The term "fragment" as used throughout this specification with reference to a nucleic acid (polynucleotide) generally denotes a 5'- and/or 3'-truncated form of a nucleic acid. Preferably, a fragment may comprise at least about 30%, e.g., at least about 50% or at least about 70%, preferably at least about 80%, e.g., at least about 85%, more preferably at least about 90%, and yet more preferably at least about 95% or even about 99% of the nucleic acid sequence length of said nucleic acid. For example, insofar not exceeding the length of the full-length nucleic acid, a fragment may include a sequence of ≥5 consecutive nucleotides, or ≥10 consecutive nucleotides, or ≥20 consecutive nucleotides, or ≥30 consecutive nucleotides, e.g., ≥40 consecutive nucleotides, such as for example≥50 consecutive nucleotides, e.g., ≥60, ≥70, ≥80, ≥90, ≥100, ≥200, ≥300, ≥400, ≥500 or ≥600 consecutive nucleotides of the corresponding full-length nucleic acid.

Cells such as immune cells as disclosed herein may in the context of the present specification be said to "comprise the expression" or conversely to "not express" one or more markers, such as one or more genes or gene products; or be described as "positive" or conversely as "negative" for one or more markers, such as one or more genes or gene products; or be said to "comprise" a defined "gene or gene product signature".

Such terms are commonplace and well-understood by the skilled person when characterizing cell phenotypes. By means of additional guidance, when a cell is said to be positive for or to express or comprise expression of a given marker, such as a given gene or gene product, a skilled person would conclude the presence or evidence of a distinct signal for the marker when carrying out a measurement capable of detecting or quantifying the marker in or on the cell. Suitably, the presence or evidence of the distinct signal for the marker would be concluded based on a comparison of the measurement result obtained for the cell to a result of the same measurement carried out for a negative control (for example, a cell known to not express the marker) and/or a positive control (for example, a cell known to express the marker). Where the measurement method allows for a quantitative assessment of the marker, a positive cell may generate a signal for the marker that is at least 1.5-fold higher than a signal generated for the marker by a negative control cell or than an average signal generated for the marker by a population of negative control cells, e.g., at least 2-fold, at least 4-fold, at least 10-fold, at least 20-fold, at least 30-fold, at least 40-fold, at least 50-fold higher or even higher. Further, a positive cell may generate a signal for the marker that is 3.0 or more standard deviations, e.g., 3.5 or more, 4.0 or more, 4.5 or more, or 5.0 or more standard deviations, higher than an average signal generated for the marker by a population of negative control cells.

A marker, for example a gene or gene product, for example a peptide, polypeptide, protein, or nucleic acid, or a group of two or more markers, is "detected" or "measured" in a tested object (e.g., in or on a cell, cell population, tissue, organ, or organism, e.g., in a biological sample of a subject) when the presence or absence and/or quantity of said marker or said group of markers is detected or determined in the tested object, preferably substantially to the exclusion of other molecules and analytes, e.g., other genes or gene products.

The terms "increased" or "increase" or "upregulated" or "upregulate" as used herein generally mean an increase by a statically significant amount. For avoidance of doubt, "increased" means a statistically significant increase of at least 10% as compared to a reference level, including an increase of at least 20%, at least 30%, at least 40%, at least 50%, at least 60%, at least 70%, at least 80%, at least 90%, at least 100% or more, including, for example at least 2-fold, at least 3-fold, at least 4-fold, at least 5-fold, at least 10-fold increase or greater as compared to a reference level, as that term is defined herein.

The term "reduced" or "reduce" or "decrease" or "decreased" or "downregulate" or "downregulated" as used herein generally means a decrease by a statistically significant amount relative to a reference. For avoidance of doubt, "reduced" means statistically significant decrease of at least 10% as compared to a reference level, for example a decrease by at least 20%, at least 30%, at least 40%, at least 50%, or at least 60%, or at least 70%, or at least 80%, at least 90% or more, up to and including a 100% decrease (i.e., absent level as compared to a reference sample), or any decrease between 10-100% as compared to a reference level, as that.

The terms "quantity", "amount" and "level" are synonymous and generally well-understood in the art. The terms as used throughout this specification may particularly refer to an absolute quantification of a marker in a tested object (e.g., in or on a cell, cell population, tissue, organ, or organism, e.g., in a biological sample of a subject), or to a relative quantification of a marker in a tested object, i.e., relative to another value such as relative to a reference value, or to a range of values indicating a base-line of the marker. Such values or ranges may be obtained as conventionally known.

An absolute quantity of a marker may be advantageously expressed as weight or as molar amount, or more commonly as a concentration, e.g., weight per volume or mol per volume. A relative quantity of a marker may be advantageously expressed as an increase or decrease or as a fold-increase or fold-decrease relative to said another value, such as relative to a reference value. Performing a relative comparison between first and second variables (e.g., first and second quantities) may but need not require determining first the absolute values of said first and second variables. For example, a measurement method may produce quantifiable readouts (such as, e.g., signal intensities) for said first and second variables, wherein said readouts are a function of the value of said variables, and wherein said readouts may be directly compared to produce a relative value for the first variable vs. the second variable, without the actual need to first convert the readouts to absolute values of the respective variables.

Reference values may be established according to known procedures previously employed for other cell populations, biomarkers and gene or gene product signatures. For example, a reference value may be established in an individual or a population of individuals characterized by a particular diagnosis, prediction and/or prognosis of said disease or condition (i.e., for whom said diagnosis, prediction and/or prognosis of the disease or condition holds true). Such population may comprise without limitation 2 or more, 10 or more, 100 or more, or even several hundred or more individuals.

A "deviation" of a first value from a second value may generally encompass any direction (e.g., increase: first value>second value; or decrease: first value<second value) and any extent of alteration.

For example, a deviation may encompass a decrease in a first value by, without limitation, at least about 10% (about 0.9-fold or less), or by at least about 20% (about 0.8-fold or less), or by at least about 30% (about 0.7-fold or less), or by at least about 40% (about 0.6-fold or less), or by at least about 50% (about 0.5-fold or less), or by at least about 60% (about 0.4-fold or less), or by at least about 70% (about 0.3-fold or less), or by at least about 80% (about 0.2-fold or less), or by at least about 90% (about 0.1-fold or less), relative to a second value with which a comparison is being made.

For example, a deviation may encompass an increase of a first value by, without limitation, at least about 10% (about 1.1-fold or more), or by at least about 20% (about 1.2-fold or more), or by at least about 30% (about 1.3-fold or more), or by at least about 40% (about 1.4-fold or more), or by at least about 50% (about 1.5-fold or more), or by at least about 60% (about 1.6-fold or more), or by at least about 70% (about 1.7-fold or more), or by at least about 80% (about 1.8-fold or more), or by at least about 90% (about 1.9-fold or more), or by at least about 100% (about 2-fold or more), or by at least about 150% (about 2.5-fold or more), or by at least about 200% (about 3-fold or more), or by at least about 500% (about 6-fold or more), or by at least about 700% (about 8-fold or more), or like, relative to a second value with which a comparison is being made.

Preferably, a deviation may refer to a statistically significant observed alteration. For example, a deviation may refer to an observed alteration which falls outside of error margins of reference values in a given population (as expressed, for example, by standard deviation or standard error, or by a predetermined multiple thereof, e.g., ±1xSD or ±2xSD or 3xSD, or ±1xSE or ±2xSE or ±3xSE). Deviation may also refer to a value falling outside of a reference range defined by values in a given population (for example, outside of a range which comprises 40%, 50%, ≥60%, ≥70%, ≥75% or 80% or 85% or ≥90% or ≥95% or even 100% of values in said population).

In a further embodiment, a deviation may be concluded if an observed alteration is beyond a given threshold or cut-off. Such threshold or cut-off may be selected as generally known in the art to provide for a chosen sensitivity and/or specificity of the prediction methods, e.g., sensitivity and/or specificity of at least 50%, or at least 60%, or at least 70%, or at least 80%, or at least 85%, or at least 90%, or at least 95%.

For example, receiver-operating characteristic (ROC) curve analysis can be used to select an optimal cut-off value of the quantity of a given immune cell population, biomarker or gene or gene product signatures, for clinical use of the present diagnostic tests, based on acceptable sensitivity and specificity, or related performance measures which are well-known per se, such as positive predictive value (PPV), negative predictive value (NPV), positive likelihood ratio (LR+), negative likelihood ratio (LR-), Youden index, or similar.

Detection of a biomarker may be by any means known in the art. Methods of detection include, but are not limited to enzymatic assays, flow cytometry, mass cytometry, fluorescence activated cell sorting (FACS), fluorescence microscopy, affinity separation, magnetic cell separation, microfluidic separation, RNA-seq (e.g., bulk or single cell), quantitative PCR, MERFISH (multiplex (in situ) RNA FISH), immunological assay methods by specific binding between a separable, detectable and/or quantifiable immunological binding agent (antibody) and the marker, mass spectrometry analysis methods, chromatography methods and combinations thereof. Immunological assay methods include without limitation immunohistochemistry, immunocytochemistry, flow cytometry, mass cytometry, fluorescence activated cell sorting (FACS), fluorescence microscopy, fluorescence based cell sorting using microfluidic systems, immunoaffinity adsorption based techniques such as affinity chromatography, magnetic particle separation, magnetic activated cell sorting or bead based cell sorting using microfluidic systems, enzyme-linked immunosorbent assay (ELISA) and ELISPOT based techniques, radioimmunoassay (RIA), Western blot, etc. While particulars of chromatography are well known in the art, for further guidance see, e.g., Meyer M., 1998, ISBN: 047198373X, and "Practical HPLC Methodology and Applications", Bidlingmeyer, B. A., John Wiley & Sons Inc., 1993. Exemplary types of chromatography include, without limitation, high-performance liquid chromatography (HPLC), normal phase HPLC (NP-HPLC), reversed phase HPLC (RP-HPLC), ion exchange chromatography (IEC), such as cation or anion exchange chromatography, hydrophilic interaction liquid chromatography (HILIC), hydrophobic interaction chromatography (MC), size exclusion chromatography (SEC) including gel filtration chromatography or gel permeation chromatography, chromatofocusing, affinity chromatography such as immunoaffinity, immobilized metal affinity chromatography, and the like.

Detection of Biomarkers

In one embodiment, the signature genes, biomarkers, and/or cells expressing biomarkers may be detected or isolated by immunofluorescence, immunohistochemistry (IHC), fluorescence activated cell sorting (FACS), mass spectrometry (MS), mass cytometry (CyTOF), sequencing, WGS (described herein), WES (described herein), RNA-seq, single-cell RNA-seq (described herein), quantitative RT-PCR, single-cell qPCR, FISH, RNA-FISH, MERFISH (multiplex (in situ) RNA FISH) and/or by in situ hybridization. Other methods including absorbance assays and colorimetric assays are known in the art and may be used herein. Detection may comprise primers and/or probes or fluorescently bar-coded oligonucleotide probes for hybridization to RNA (see e.g., Geiss G K, et al., Direct multiplexed measurement of gene expression with color-coded probe pairs. Nat Biotechnol. 2008 March; 26(3):317-25). In certain embodiments, cancer is diagnosed, prognosed, or monitored. For example, a tissue sample may be obtained and analyzed for specific cell markers (IHC) or specific transcripts (e.g., RNA-FISH). In one embodiment, tumor cells are stained for cell subtype specific signature genes. In one embodiment, the cells are fixed. In another embodiment, the cells are formalin fixed and paraffin embedded. Not being bound by a theory, the presence of the tumor subtypes indicate outcome and personalized treatments.

The present invention also may comprise a kit with a detection reagent that binds to one or more biomarkers or can be used to detect one or more biomarkers.

Sequencing

In certain embodiments, sequencing is used to identify expression of genes or transcriptomes in single cells. In certain embodiments, sequencing comprises high-throughput (formerly "next-generation") technologies to generate sequencing reads. Methods for constructing sequencing libraries are known in the art (see, e.g., Head et al., Library construction for next-generation sequencing: Overviews and challenges. Biotechniques. 2014; 56(2): 61-77). A "library" or "fragment library" may be a collection of nucleic acid molecules derived from one or more nucleic acid samples, in which fragments of nucleic acid have been modified, generally by incorporating terminal adapter sequences comprising one or more primer binding sites and identifiable sequence tags. In certain embodiments, the library members (e.g., cDNA) may include sequencing adaptors that are compatible with use in, e.g., Illumina's reversible terminator method, long read nanopore sequencing, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Schneider and Dekker (Nat Biotechnol. 2012 Apr. 10; 30(4):326-8); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

As used herein the term "transcriptome" refers to the set of transcript molecules. In some embodiments, transcript refers to RNA molecules, e.g., messenger RNA (mRNA) molecules, small interfering RNA (siRNA) molecules, transfer RNA (tRNA) molecules, ribosomal RNA (rRNA) molecules, and complimentary sequences, e.g., cDNA molecules. In some embodiments, a transcriptome refers to a set of mRNA molecules. In some embodiments, a transcriptome refers to a set of cDNA molecules. In some embodiments, a transcriptome refers to one or more of mRNA molecules, siRNA molecules, tRNA molecules, rRNA molecules, in a sample, for example, a single cell or a population of cells. In some embodiments, a transcriptome refers to cDNA generated from one or more of mRNA molecules, siRNA molecules, tRNA molecules, rRNA molecules, in a sample, for example, a single cell or a population of cells. In some embodiments, a transcriptome refers to 25%, 50%, 55, 60, 65, 70, 75, 80, 85, 90, 91, 92, 93, 94, 95, 96, 97, 98, 99, 99.9, or 100% of transcripts from a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

In certain embodiments, the invention involves single-cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p666-673, 2012).

In certain embodiments, the present invention involves single-cell RNA sequencing (scRNA-seq). In certain embodiments, the invention involves plate based single-cell RNA sequencing (see, e.g., Picelli, S. et al., 2014, "Full-length RNA-seq from single cells using Smart-seq2" Nature protocols 9, 171-181, doi:10.1038/nprot.2014.006).

In certain embodiments, the invention involves high-throughput single-cell RNA-seq where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. Jan; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Rosenberg et al., "Single-cell profiling of the developing mouse brain and spinal cord with split-pool barcoding" Science 15 Mar. 2018; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; Gierahn et al., "Seq-Well: portable, low-costRNA sequencing of single cells at high throughput" Nature Methods 14, 395-398 (2017); and Hughes, et al., "Highly Efficient, Massively-Parallel Single-Cell RNA-Seq Reveals Cellular States and Molecular Features of Human Skin Pathology" bioRxiv 689273; doi: doi.org/10.1101/689273, all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; International Patent Application No. PCT/US2016/059239, published as WO2017164936 on Sep. 28, 2017; International Patent Application No. PCT/US2018/060860, published as WO/2019/094984 on May 16, 2019; International Patent Application No. PCT/US2019/055894, published as WO/2020/077236 on Apr. 16, 2020; and Drokhlyansky, et al., "The enteric nervous system of the human and mouse colon at a single-cell resolution," bioRxiv 746743; doi: doi.org/10.1101/746743, which are herein incorporated by reference in their entirety.

In certain embodiments, dimension reduction is used to cluster single cells based on differentially expressed genes. In certain embodiments, the dimension reduction technique may be, but is not limited to, Uniform Manifold Approximation and Projection (UMAP) or t-SNE (see, e.g., Becht et al., Evaluation of UMAP as an alternative to t-SNE for single-cell data, bioRxiv 298430; doi.org/10.1101/298430; and Becht et al., 2019, Dimensionality reduction for visualizing single-cell data using UMAP, Nature Biotechnology volume 37, pages 38-44).

MS Methods

Biomarker detection may also be evaluated using mass spectrometry methods. A variety of configurations of mass spectrometers can be used to detect biomarker values. Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-column liquid chromatography source or can be a direct probe or stage such as used in matrix-assisted laser desorption. Common ion sources are, for example, electrospray, including nanospray and microspray or matrix-assisted laser desorption. Common mass analyzers include a quadrupole mass filter, ion trap mass analyzer and time-of-flight mass analyzer. Additional mass spectrometry methods are well known in the art (see Burlingame et al., Anal. Chem. 70:647 R-716R (1998); Kinter and Sherman, New York (2000)).

Protein biomarkers and biomarker values can be detected and measured by any of the following: electrospray ionization mass spectrometry (ESI-MS), ESI-MS/MS, ESI-MS/(MS)n, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), tandem time-of-flight (TOF/TOF) technology, called ultraflex III TOF/TOF, atmospheric pressure chemical ionization mass spectrometry (APCI-MS), APCI-MS/MS, APCI-(MS).sup.N, atmospheric pressure photoionization mass spectrometry (APPI-MS), APPI-MS/MS, and APPI-(MS).sup.N, quadrupole mass spectrometry, Fourier transform mass spectrometry (FTMS), quantitative mass spectrometry, and ion trap mass spectrometry.

Sample preparation strategies are used to label and enrich samples before mass spectroscopic characterization of protein biomarkers and determination biomarker values. Labeling methods include but are not limited to isobaric tag for relative and absolute quantitation (iTRAQ) and stable isotope labeling with amino acids in cell culture (SILAC). Capture reagents used to selectively enrich samples for candidate biomarker proteins prior to mass spectroscopic analysis include but are not limited to aptamers, antibodies, nucleic acid probes, chimeras, small molecules, an F(ab')$_2$ fragment, a single chain antibody fragment, an Fv fragment, a single chain Fv fragment, a nucleic acid, a lectin, a ligand-binding receptor, affibodies, nanobodies, ankyrins, domain antibodies, alternative antibody scaffolds (e.g. diabodies etc.) imprinted polymers, avimers, peptidomimetics, peptoids, peptide nucleic acids, threose nucleic acid, a hormone receptor, a cytokine receptor, and synthetic receptors, and modifications and fragments of these.

Immunoassays

Immunoassay methods are based on the reaction of an antibody to its corresponding target or analyte and can detect the analyte in a sample depending on the specific assay format. To improve specificity and sensitivity of an assay method based on immunoreactivity, monoclonal antibodies are often used because of their specific epitope recognition. Polyclonal antibodies have also been successfully used in various immunoassays because of their increased affinity for the target as compared to monoclonal antibodies Immunoassays have been designed for use with a wide range of biological sample matrices Immunoassay formats have been designed to provide qualitative, semi-quantitative, and quantitative results.

Quantitative results may be generated through the use of a standard curve created with known concentrations of the specific analyte to be detected. The response or signal from an unknown sample is plotted onto the standard curve, and a quantity or value corresponding to the target in the unknown sample is established.

Numerous immunoassay formats have been designed. ELISA or EIA can be quantitative for the detection of an analyte/biomarker. This method relies on attachment of a label to either the analyte or the antibody and the label component includes, either directly or indirectly, an enzyme. ELISA tests may be formatted for direct, indirect, competitive, or sandwich detection of the analyte. Other methods rely on labels such as, for example, radioisotopes ($I^{125}$) or fluorescence. Additional techniques include, for example, agglutination, nephelometry, turbidimetry, Western blot, immunoprecipitation, immunocytochemistry, immunohistochemistry, flow cytometry, Luminex assay, and others (see ImmunoAssay: A Practical Guide, edited by Brian Law, published by Taylor & Francis, Ltd., 2005 edition).

Exemplary assay formats include enzyme-linked immunosorbent assay (ELISA), radioimmunoassay, fluorescent, chemiluminescence, and fluorescence resonance energy transfer (FRET) or time resolved-FRET (TR-FRET) immunoassays. Examples of procedures for detecting biomarkers include biomarker immunoprecipitation followed by quantitative methods that allow size and peptide level discrimination, such as gel electrophoresis, capillary electrophoresis, planar electrochromatography, and the like.

Methods of detecting and/or quantifying a detectable label or signal generating material depend on the nature of the label. The products of reactions catalyzed by appropriate enzymes (where the detectable label is an enzyme; see above) can be, without limitation, fluorescent, luminescent, or radioactive or they may absorb visible or ultraviolet light. Examples of detectors suitable for detecting such detectable labels include, without limitation, x-ray film, radioactivity counters, scintillation counters, spectrophotometers, colorimeters, fluorometers, luminometers, and densitometers.

Any of the methods for detection can be performed in any format that allows for any suitable preparation, processing, and analysis of the reactions. This can be, for example, in multi-well assay plates (e.g., 96 wells or 384 wells) or using any suitable array or microarray. Stock solutions for various agents can be made manually or robotically, and all subsequent pipetting, diluting, mixing, distribution, washing, incubating, sample readout, data collection and analysis can be done robotically using commercially available analysis software, robotics, and detection instrumentation capable of detecting a detectable label.

Hybridization Assays

Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of a signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the expression profiles employed in the subject methods includes the technology described in U.S. Pat. Nos. 5,143,854; 5,288,644; 5,324, 633; 5,432,049; 5,470,710; 5,492,806; 5,503,980; 5,510, 270; 5,525,464; 5,547,839; 5,580,732; 5,661,028; 5,800, 992, the disclosures of which are herein incorporated by reference, as well as WO 95/21265; WO 96/31622; WO 97/10365; WO 97/27317; EP 373 203; and EP 785 280. In these methods, an array of "probe" nucleic acids that includes a probe for each of the biomarkers whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acids provides information regarding expression for each of the biomarkers that have been probed, where the expression information is in terms of whether or not the gene is expressed and, typically, at what level, where the expression data, i.e., expression profile, may be both qualitative and quantitative.

Optimal hybridization conditions will depend on the length (e.g., oligomer vs. polynucleotide greater than 200 bases) and type (e.g., RNA, DNA, PNA) of labeled probe and immobilized polynucleotide or oligonucleotide. General parameters for specific (i.e., stringent) hybridization conditions for nucleic acids are described in Sambrook et al., supra, and in Ausubel et al., "Current Protocols in Molecular Biology", Greene Publishing and Wiley-interscience, NY (1987), which is incorporated in its entirety for all purposes. When the cDNA microarrays are used, typical hybridization conditions are hybridization in 5×SSC plus 0.2% SDS at 65C for 4 hours followed by washes at 25° C. in low stringency wash buffer (1×SSC plus 0.2% SDS) followed by 10 minutes at 25° C. in high stringency wash buffer (0.1SSC plus 0.2% SDS) (see Shena et al., Proc. Natl. Acad. Sci. USA, Vol. 93, p. 10614 (1996)). Useful hybridization conditions are also provided in, e.g., Tijessen, Hybridization With Nucleic Acid Probes", Elsevier Science Publishers B.V. (1993) and Kricka, "Nonisotopic DNA Probe Techniques", Academic Press, San Diego, Calif. (1992).

In certain embodiments, a subject can be categorized based on signature genes or gene programs expressed by a tissue sample obtained from the subject. In certain embodiments, the tissue sample is analyzed by bulk sequencing. In certain embodiments, subtypes can be determined by determining the percentage of specific cell subtypes expressing the identified interacting genetic variants in the sample that contribute to the phenotype. In certain embodiments, gene expression associated with the cells are determined from bulk sequencing reads by deconvolution of the sample. For example, deconvoluting bulk gene expression data obtained from a tumor containing both malignant and non-malignant cells can include defining the relative frequency of a set of cell types in the tumor from the bulk gene expression data using cell type specific gene expression (e.g., cell types may be T cells, fibroblasts, macrophages, mast cells, B/plasma cells, endothelial cells, myocytes and dendritic cells); and defining a linear relationship between the frequency of the non-malignant cell types and the expression of a set of genes, wherein the set of genes comprises genes highly expressed by malignant cells and at most two non-malignant cell types, wherein the set of genes are derived from gene expression analysis of single cells in the tumor or the same tumor type, and wherein the residual of the linear relationship defines the malignant cell-specific (MCS) expression profile (see, e.g., WO 2018/191553; and Puram et al., Cell. 2017 Dec. 14; 171(7):1611-1624.e24).

Screening for T Cell Modulating Agents

In certain embodiments, the invention provides for screening of therapeutic agents capable of altering Th17 regulators. In certain embodiments, agents capable of blocking Th17 regulators on T cells are screened. In certain embodiments, the method comprises: a) applying a candidate agent to a cell population comprising Th17 T cells; b) detecting modulation of one or more phenotypic aspects of the cell population by the candidate agent, thereby identifying the agent. The phenotypic aspects of the cell population that is modulated may be a gene signature or biological program specific to a cell type or cell phenotype or phenotype specific to a population of cells (e.g., a pathogenic phenotype). In certain embodiments, steps can include administering candidate modulating agents to cells, detecting identified cell (sub)populations for changes in signatures, or identifying relative changes in cell (sub) populations which may comprise detecting relative abundance of particular gene signatures. The phenotype may be a change in secretion of cytokines associated with Th17 T cells. In certain embodiments, candidate agents are screened in in vivo models of autoimmunity or inflammation (e.g., mouse models). In certain embodiments, anti-tumor activity in a model is detected.

The term "agent" broadly encompasses any condition, substance or agent capable of modulating one or more phenotypic aspects of a cell or cell population as disclosed herein. Such conditions, substances or agents may be of physical, chemical, biochemical and/or biological nature. The term "candidate agent" refers to any condition, substance or agent that is being examined for the ability to modulate one or more phenotypic aspects of a cell or cell population as disclosed herein in a method comprising applying the candidate agent to the cell or cell population (e.g., exposing the cell or cell population to the candidate agent or contacting the cell or cell population with the candidate agent) and observing whether the desired modulation takes place.

Agents may include any potential class of biologically active conditions, substances or agents, such as for instance antibodies, proteins, peptides, nucleic acids, oligonucleotides, small molecules, or combinations thereof, as described herein.

The methods of phenotypic analysis can be utilized for evaluating environmental stress and/or state, for screening of chemical libraries, and to screen or identify structural, syntenic, genomic, and/or organism and species variations. For example, a culture of cells, can be exposed to an environmental stress, such as but not limited to heat shock, osmolarity, hypoxia, cold, oxidative stress, radiation, starvation, a chemical (for example a therapeutic agent or potential therapeutic agent) and the like. After the stress is applied, a representative sample can be subjected to analysis, for example at various time points, and compared to a control, such as a sample from an organism or cell, for example a cell from an organism, or a standard value. By exposing cells, or fractions thereof, tissues, or even whole animals, to different members of the chemical libraries, and performing the methods described herein, different members of a chemical library can be screened for their effect on immune phenotypes thereof simultaneously in a relatively short amount of time, for example using a high throughput method.

Aspects of the present disclosure relate to the correlation of an agent with the spatial proximity and/or epigenetic profile of the nucleic acids in a sample of cells. In some embodiments, the disclosed methods can be used to screen chemical libraries for agents that modulate chromatin architecture epigenetic profiles, and/or relationships thereof.

In some embodiments, screening of test agents involves testing a combinatorial library containing a large number of potential modulator compounds. A combinatorial chemical library may be a collection of diverse chemical compounds generated by either chemical synthesis or biological synthesis, by combining a number of chemical "building blocks" such as reagents. For example, a linear combinatorial chemical library, such as a polypeptide library, is formed by combining a set of chemical building blocks (amino acids) in every possible way for a given compound length (for example the number of amino acids in a polypeptide compound). Millions of chemical compounds can be synthesized through such combinatorial mixing of chemical building blocks.

In certain embodiments, the present invention provides for gene signature screening. The concept of signature screening was introduced by Stegmaier et al. (Gene expression-based high-throughput screening (GE-HTS) and application to leukemia differentiation. Nature Genet. 36, 257-263 (2004)), who realized that if a gene-expression signature was the proxy for a phenotype of interest, it could be used to find small molecules that effect that phenotype without knowledge of a validated drug target. The signatures or biological programs of the present invention may be used to screen for drugs that reduce the signature or biological program in cells as described herein. The signature or biological program may be used for GE-HTS. In certain embodiments, pharmacological screens may be used to identify drugs that are selectively toxic to cells having a signature.

The Connectivity Map (cmap) is a collection of genome-wide transcriptional expression data from cultured human cells treated with bioactive small molecules and simple pattern-matching algorithms that together enable the discovery of functional connections between drugs, genes and diseases through the transitory feature of common gene-expression changes (see, Lamb et al., The Connectivity Map: Using Gene-Expression Signatures to Connect Small Molecules, Genes, and Disease. Science 29 Sep. 2006: Vol. 313, Issue 5795, pp. 1929-1935, DOI: 10.1126/science.1132939; and Lamb, J., The Connectivity Map: a new tool for biomedical research. Nature Reviews Cancer January 2007: Vol. 7, pp. 54-60). In certain embodiments, Cmap can be used to screen for small molecules capable of modulating a signature or biological program of the present invention in silico.

Further embodiments are illustrated in the following Examples which are given for illustrative purposes only and are not intended to limit the scope of the invention.

EXAMPLES

Example 1—Tissue Specific Th17 Cells

Applicants used a fate tracking TdTomato and Il17-GFP mouse to study Th17 cells in tissues (FIG. 1). Cells that were ever Th17 (i.e, expressed Il-17A) express tomato (ex-Th17) and cells that are Th17 currently (i.e, express Il-17A) express GFP (current Th17). Applicants sorted cells obtained from different tissue samples to obtain ex-Th17 and current Th17 cells. CD4 T cells that are TdT+ GFP− and TdT+ GFP+ were selected by FACS. The cells sequenced were therefore either ex Th17 (red) or current Th17 cells (green) (FIG. 2). Applicants used hashing antibodies specific for cell surface markers to hash Th17 cells from each tissue (see, e.g., Stoeckius, et al. Cell Hashing with barcoded antibodies enables multiplexing and doublet detection for single cell genomics. Genome Biol 19, 224 (2018)). The Th17 cells were analyzed using single-cell RNA sequencing (scRNA-seq) in a single channel.

Single-cell RNA-sequencing identified tissue specific Th17 signatures (FIG. 3). Applicants identified Th17 specific cell programs (proliferating, Treg-like, effector-like, $T_{FH}$-like, Naïve-like and ISG-high (interferon stimulated genes) expression programs) (FIG. 4). Applicants used COMET to identify markers specific for the Th17 cells (see, e.g., Delaney et al., 2019, Combinatorial prediction of marker panels from single-cell transcriptomic data, Molecular Systems Biology 15: e9005, DOI 10.15252/msb.20199005). Applicants identified that PDL1 (CD274) is a marker of the novel ISG-high Th17 cluster (FIG. 5). Applicants provide evidence that indicates a Treg-origin of Tdt+ Foxp3+ cells using a Il17Cre$^{TdT}$xFoxp3$^{GFP}$ mouse (FIG. 6). Applicants used TCR clones to determine the origin of Treg-like Th17 cells. The Treg-like Th17 cells had less clonal TCR overlap indicating that they did not originate from ex-Th17 cells, but originated from Treg cells. Applicants also observed intestinal Th17 cell heterogeneity at single-cell resolution (FIG. 7).

Example 2—Tissue Specific Th17 Cells in EAE

Figure 8:
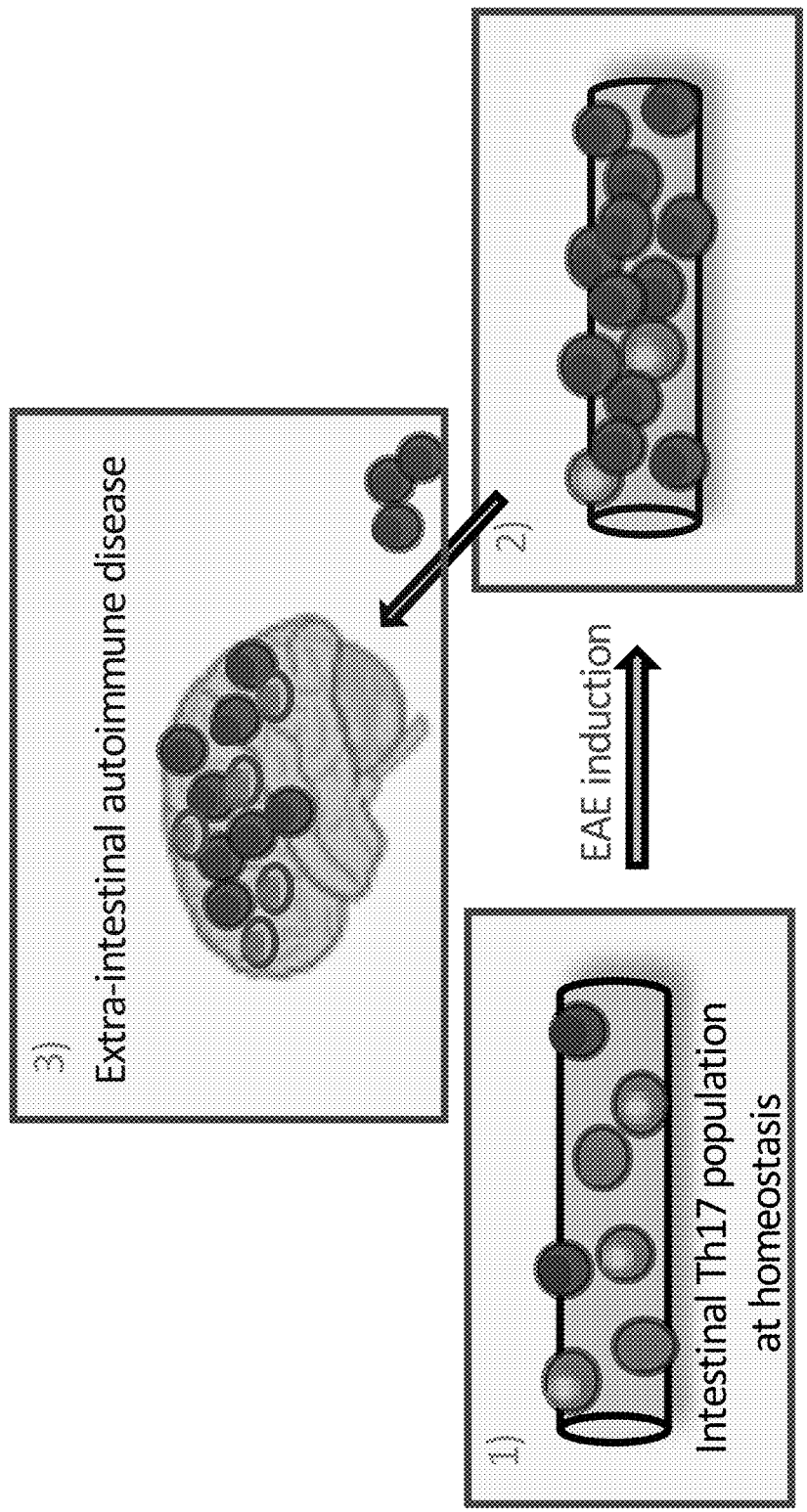
FIG. 8— Diagram showing EAE induction.
Figure 9:
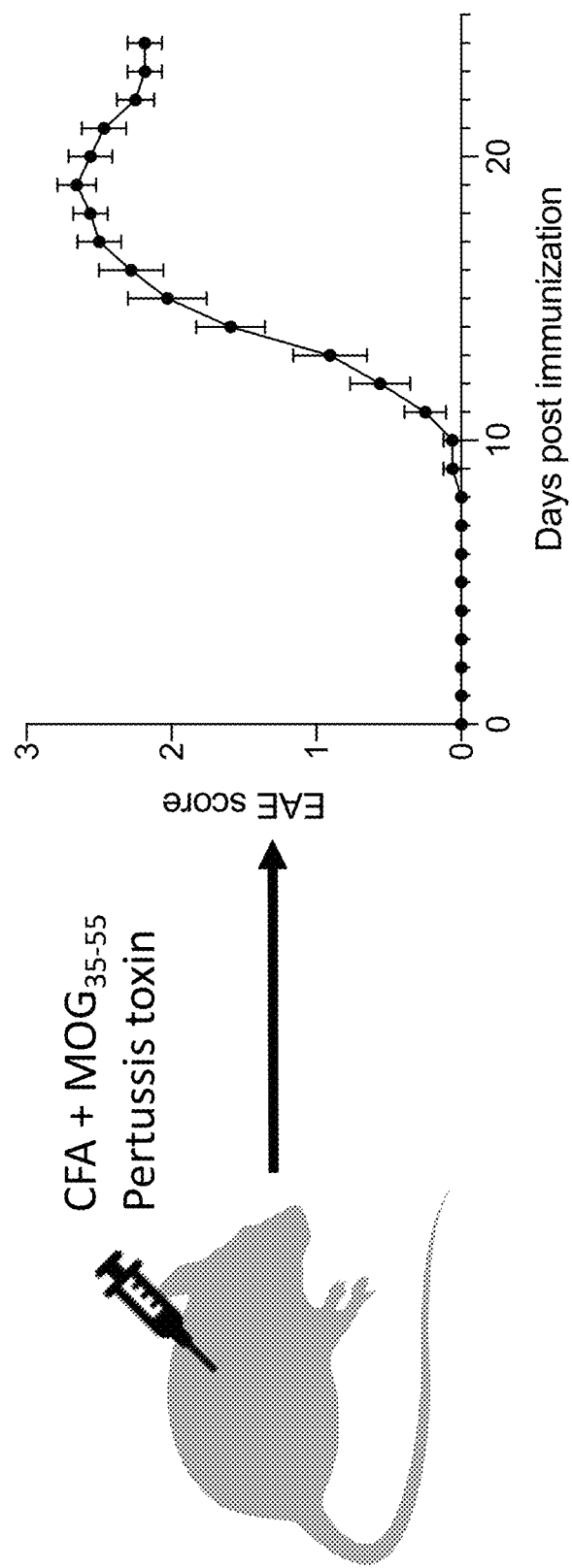
FIG. 9— Diagram and graph showing experimental autoimmune encephalomyelitis (EAE).
Figure 10A:
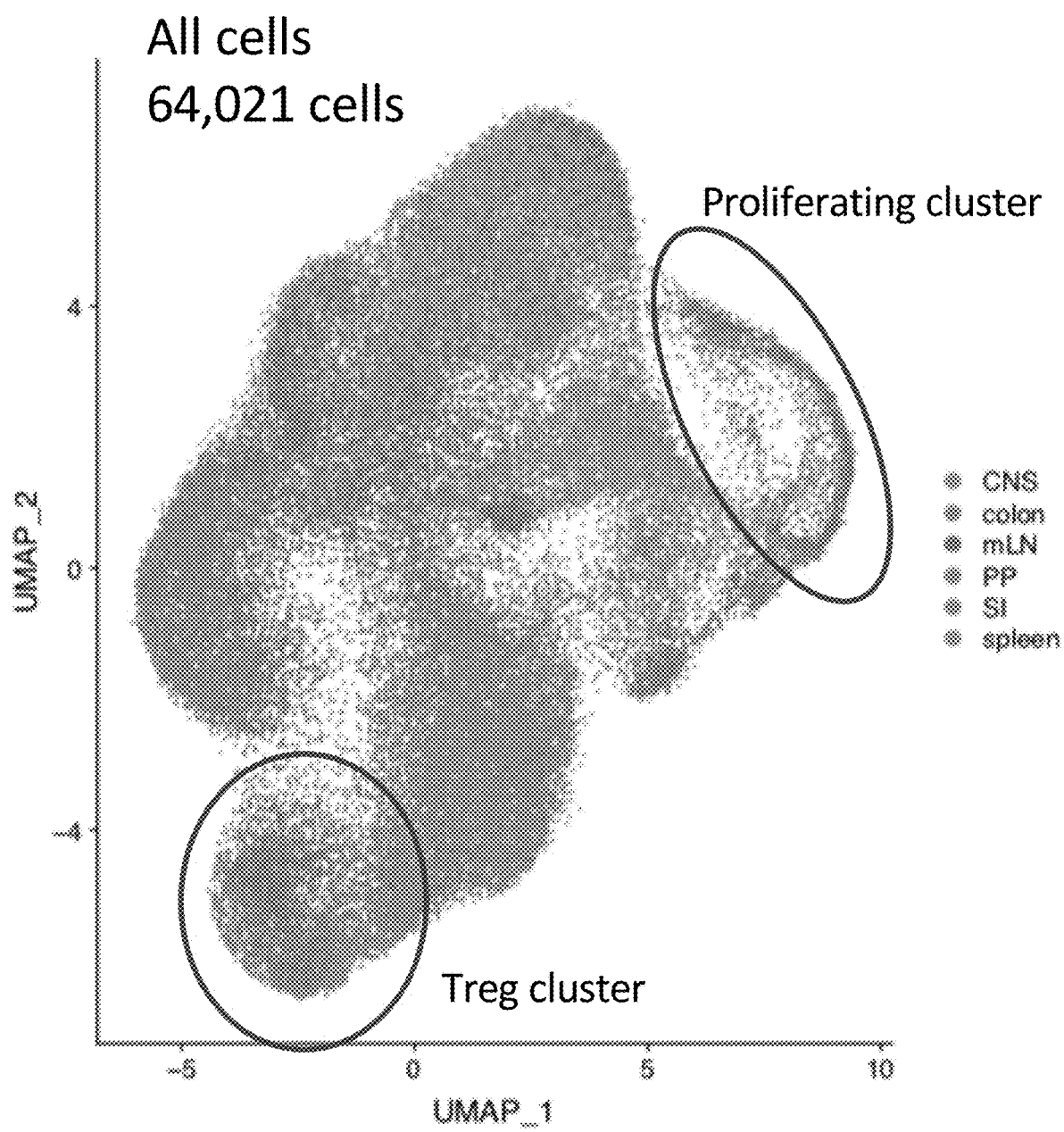
FIGS. 10A-10F— Tissue specific Th17 cells in treated EAE mice.
Figure 10B:
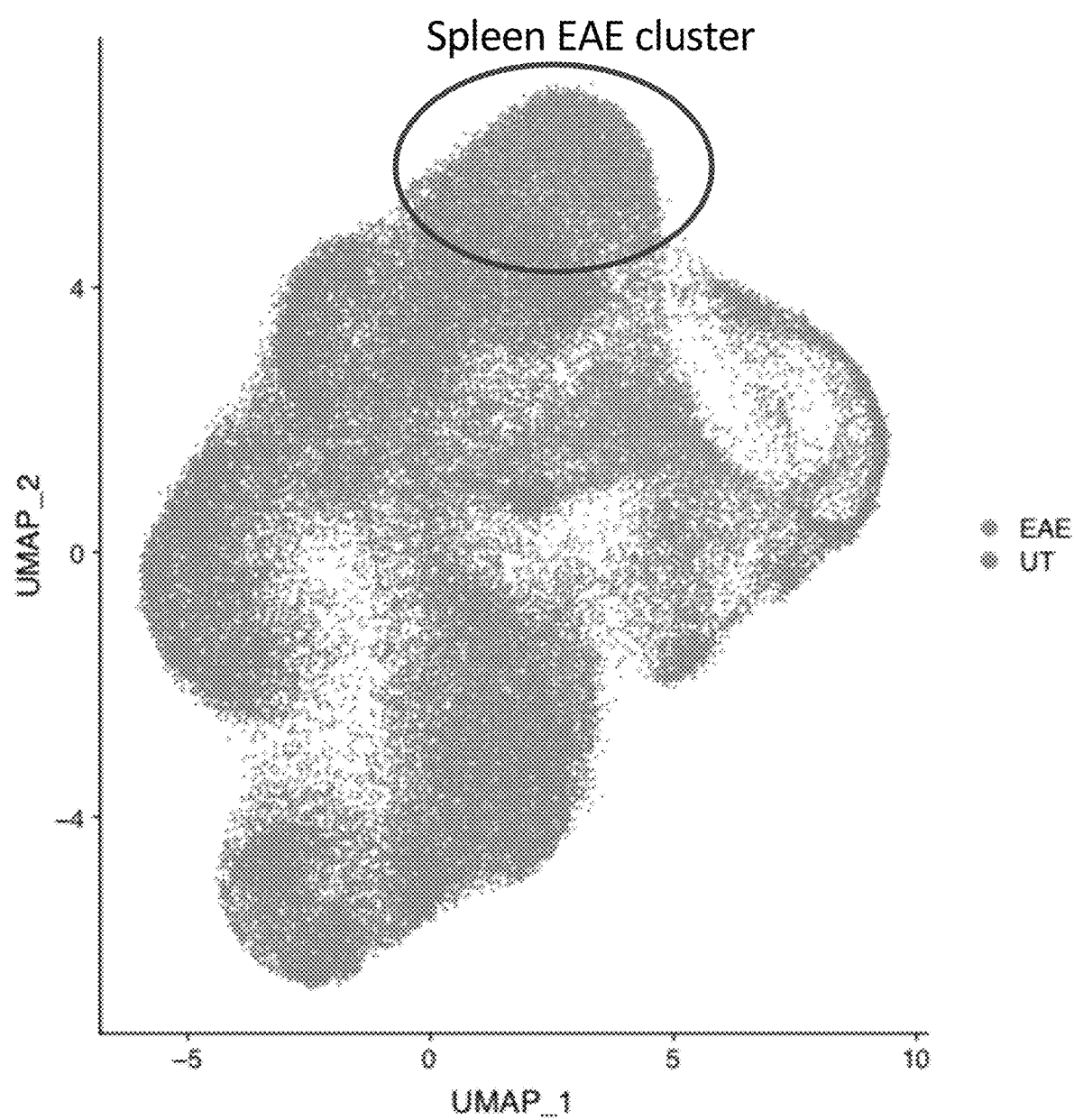
Figure 10C:
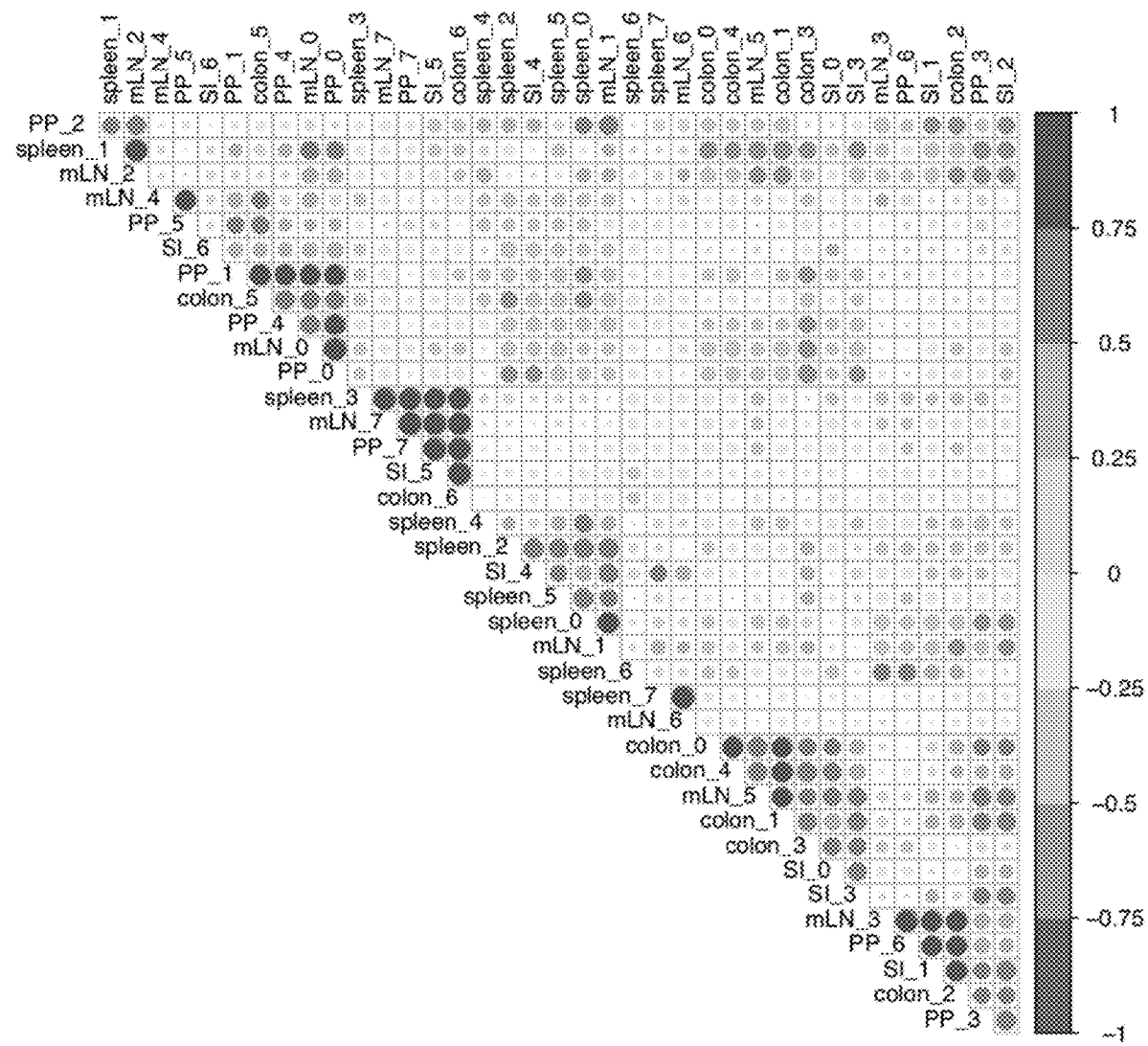
Figure 10D:
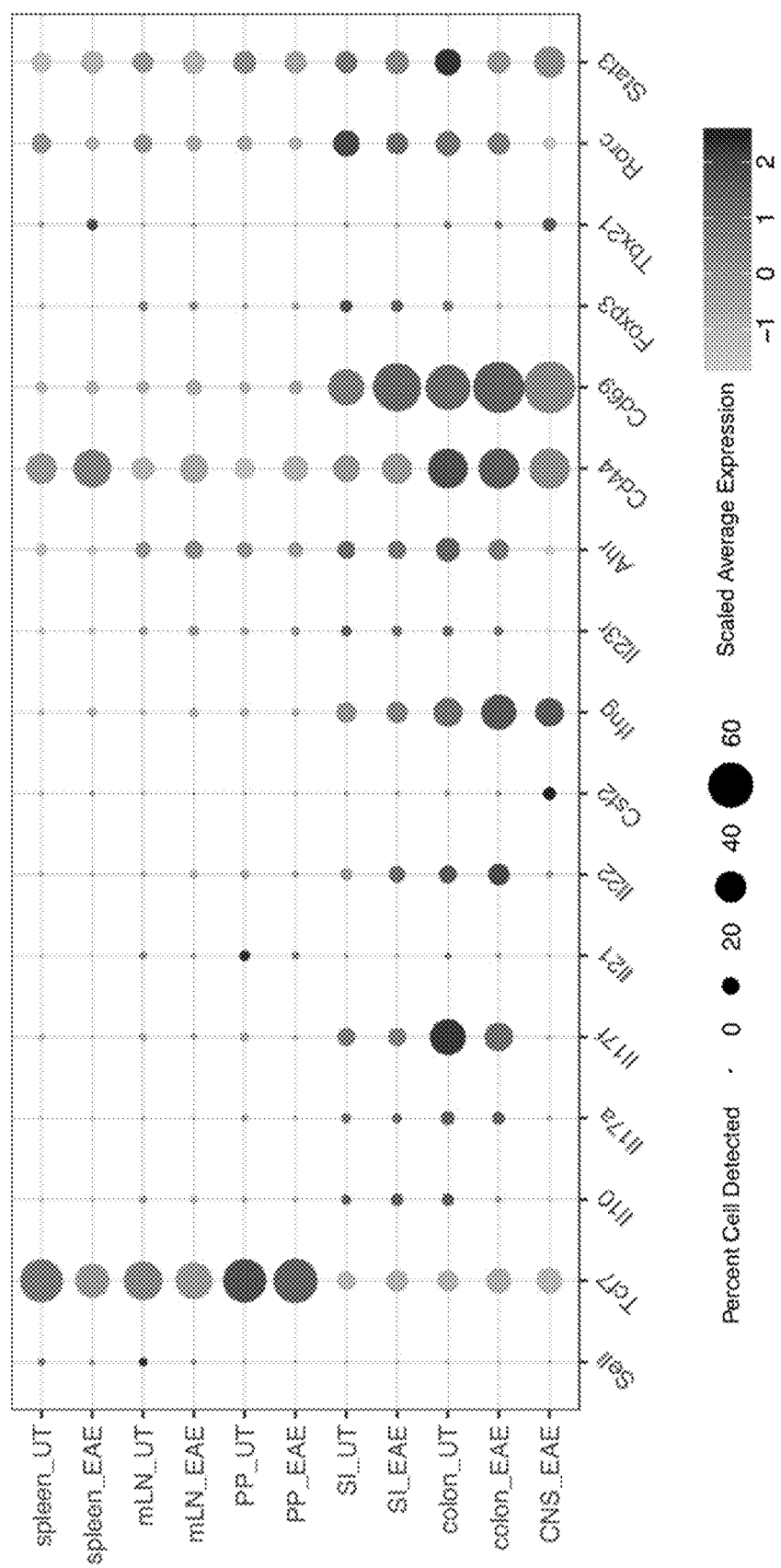
Figure 10E:
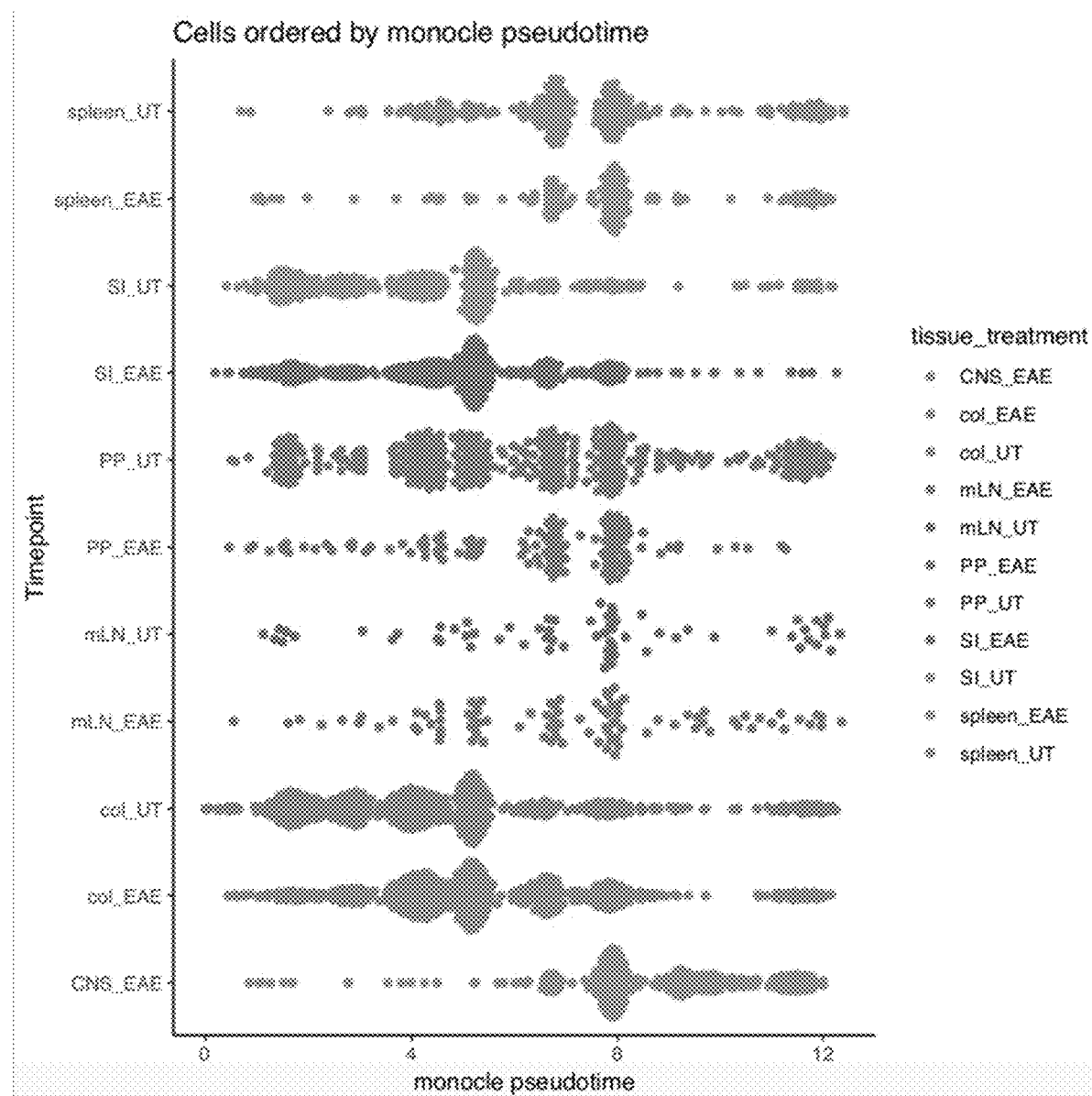
Figure 10F:
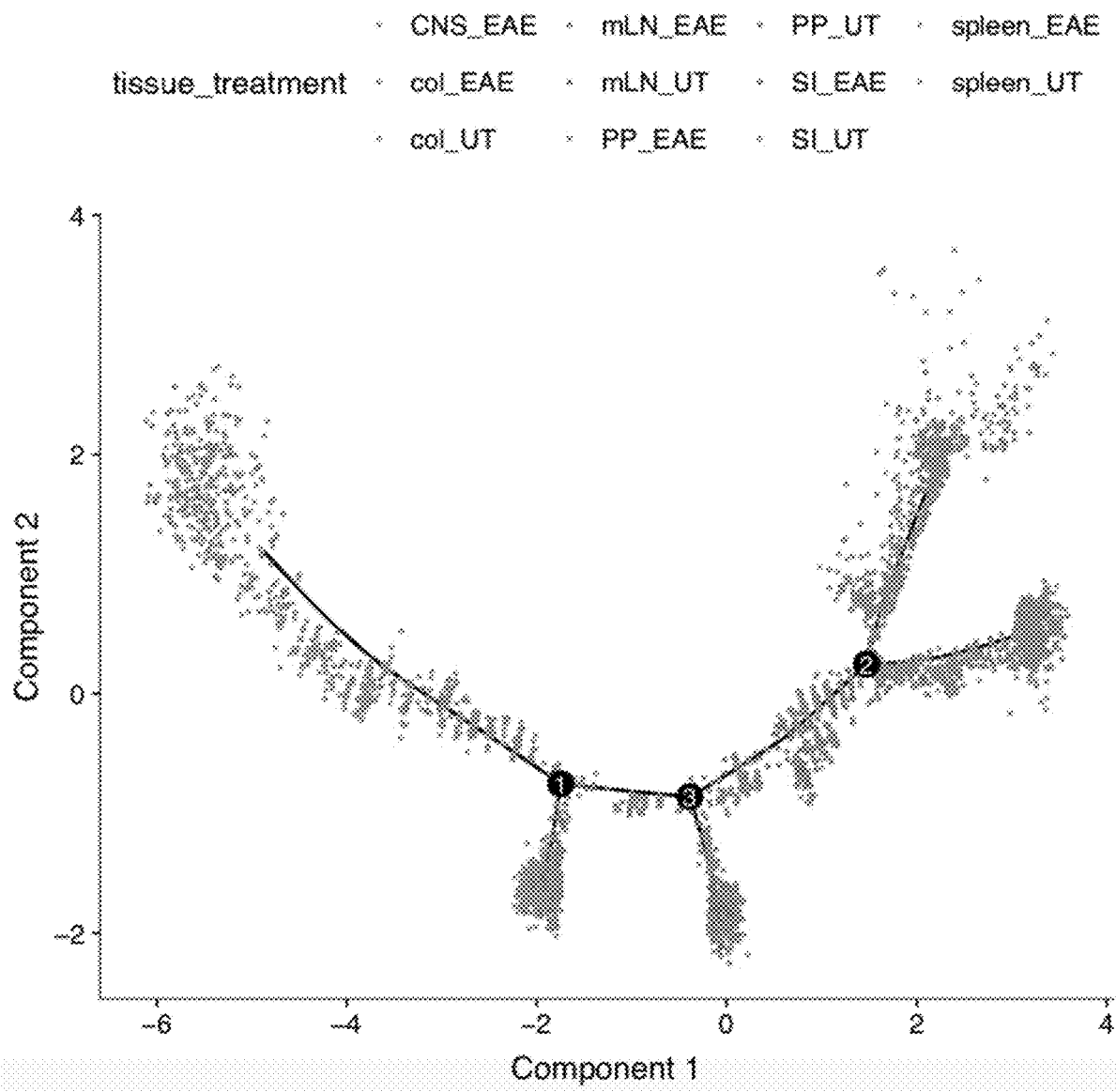
Figure 11:
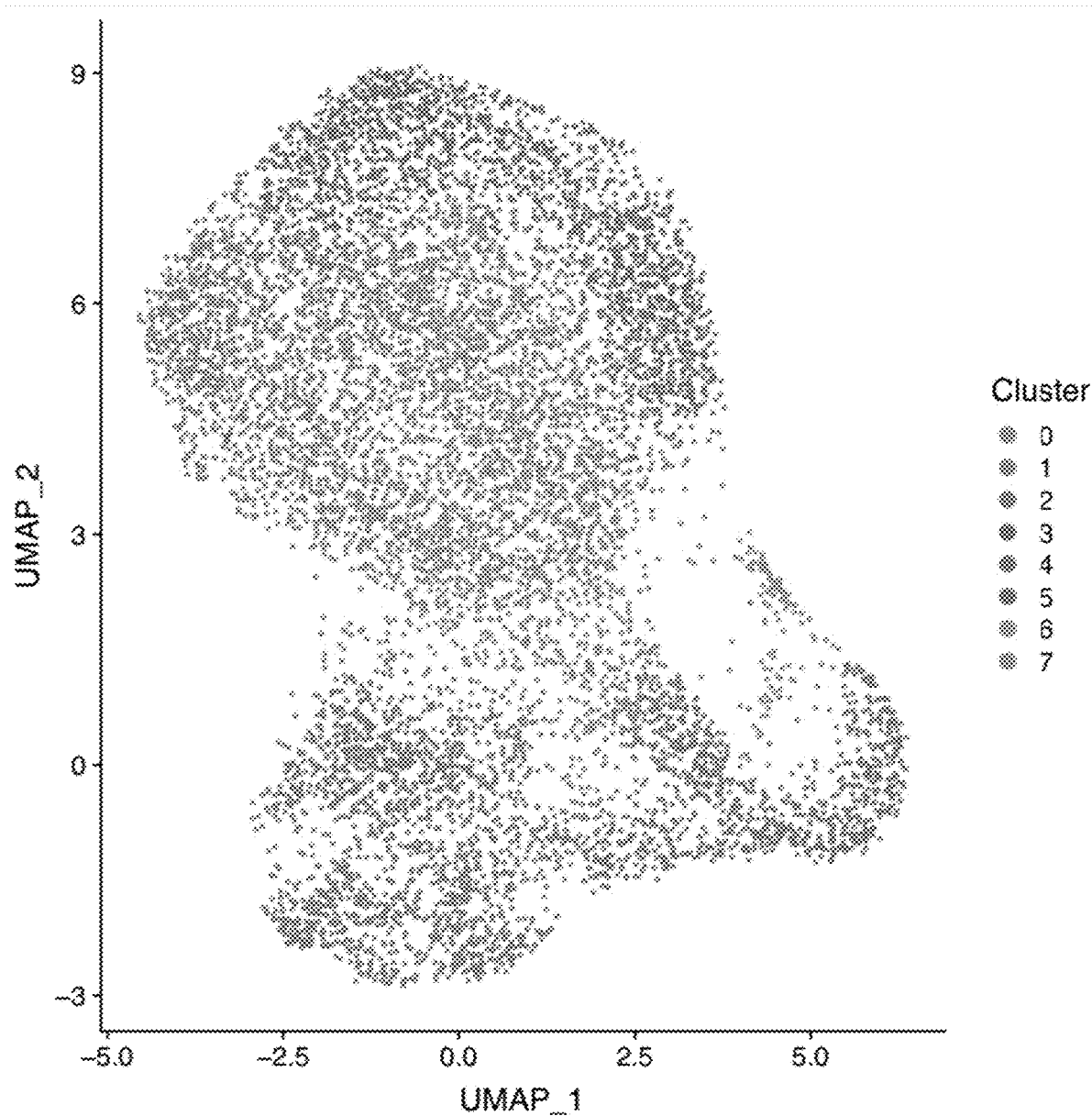
FIG. 11— UMAP labeled by cluster in EAE.
Figure 12A:
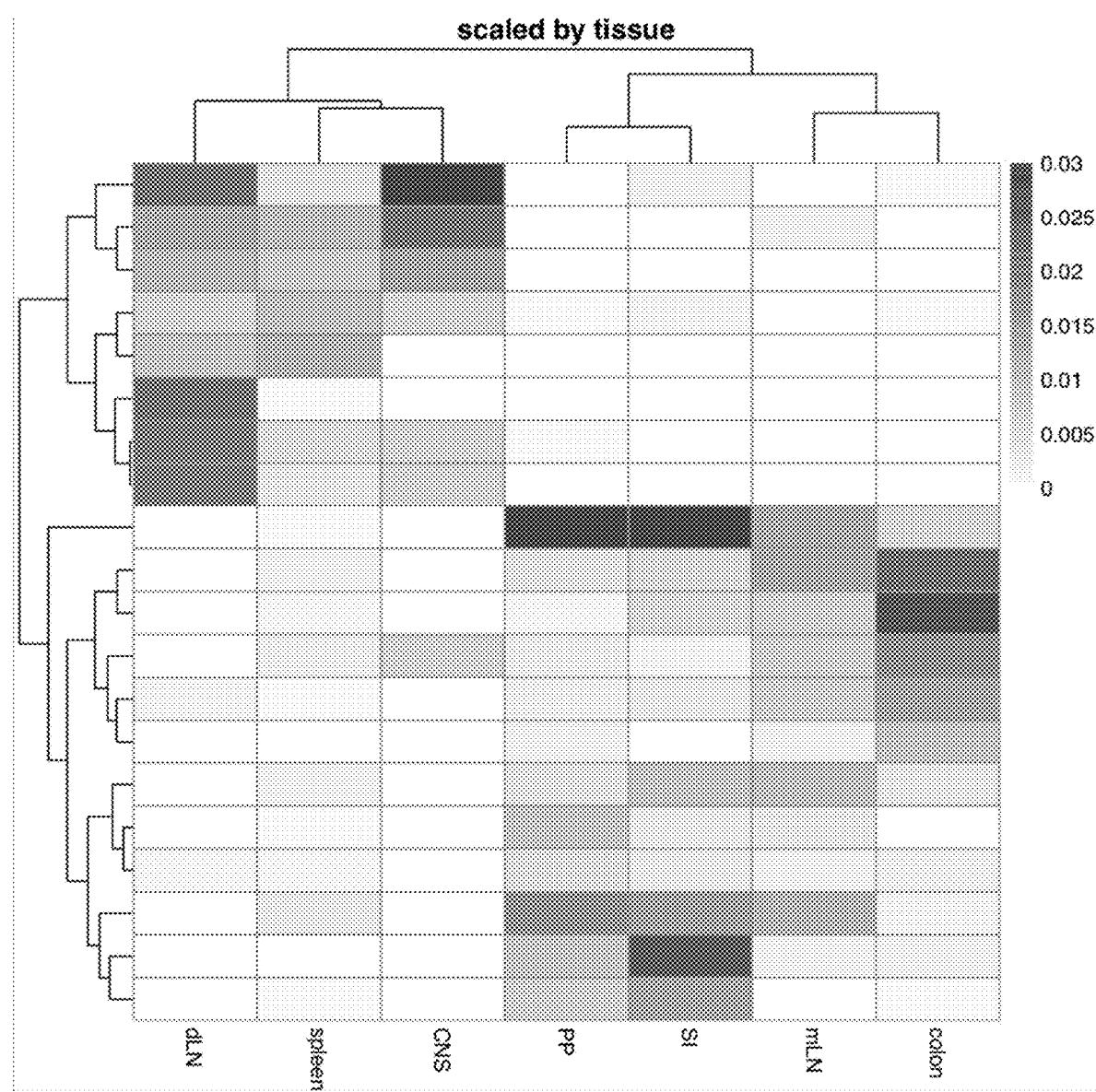
FIGS. 12A-12B— Th17 cells migrate from the spleen to CNS (central nervous system) and dLN (draining lymph nodes).
Figure 12A:
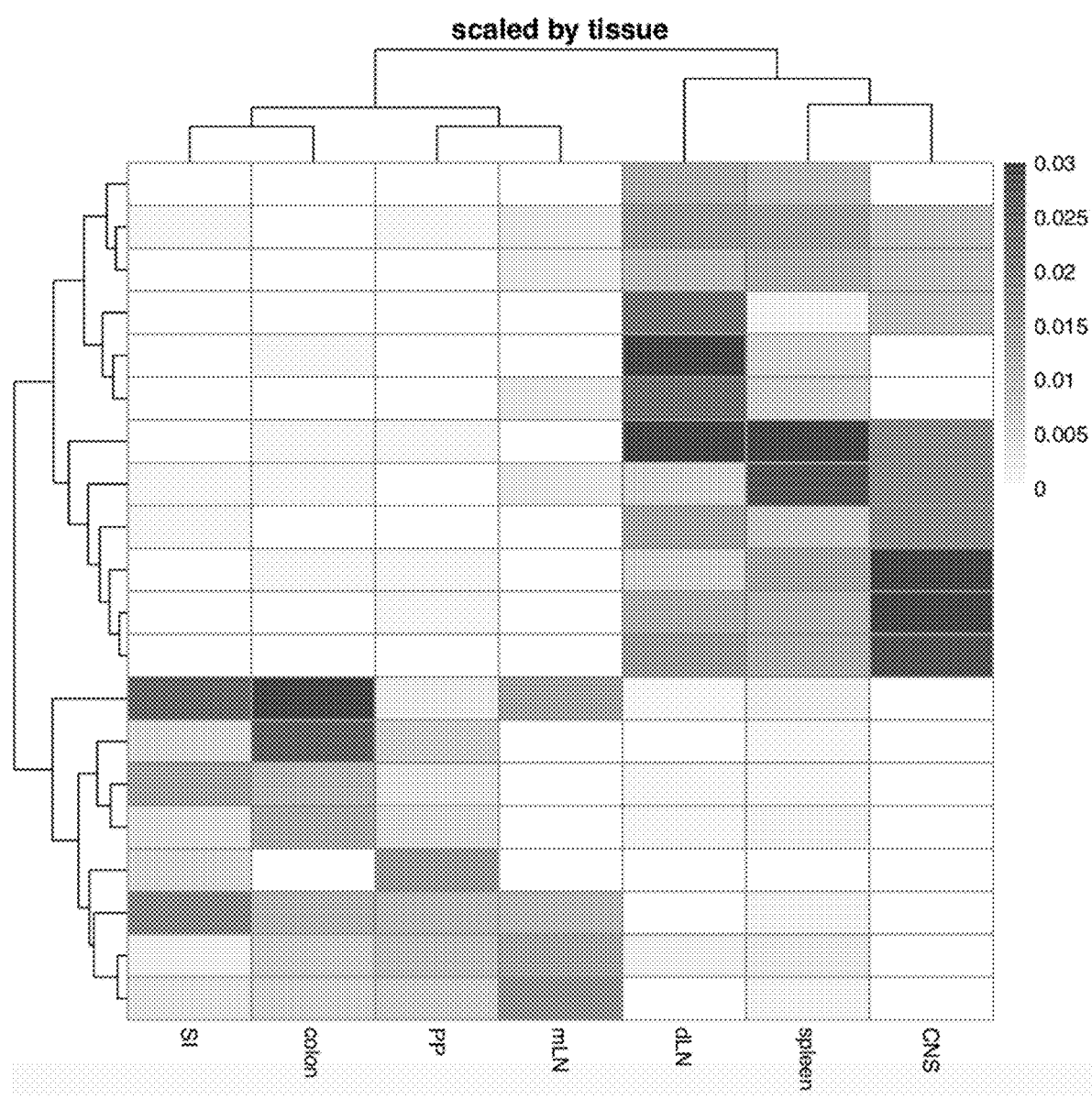
Figure 12B:
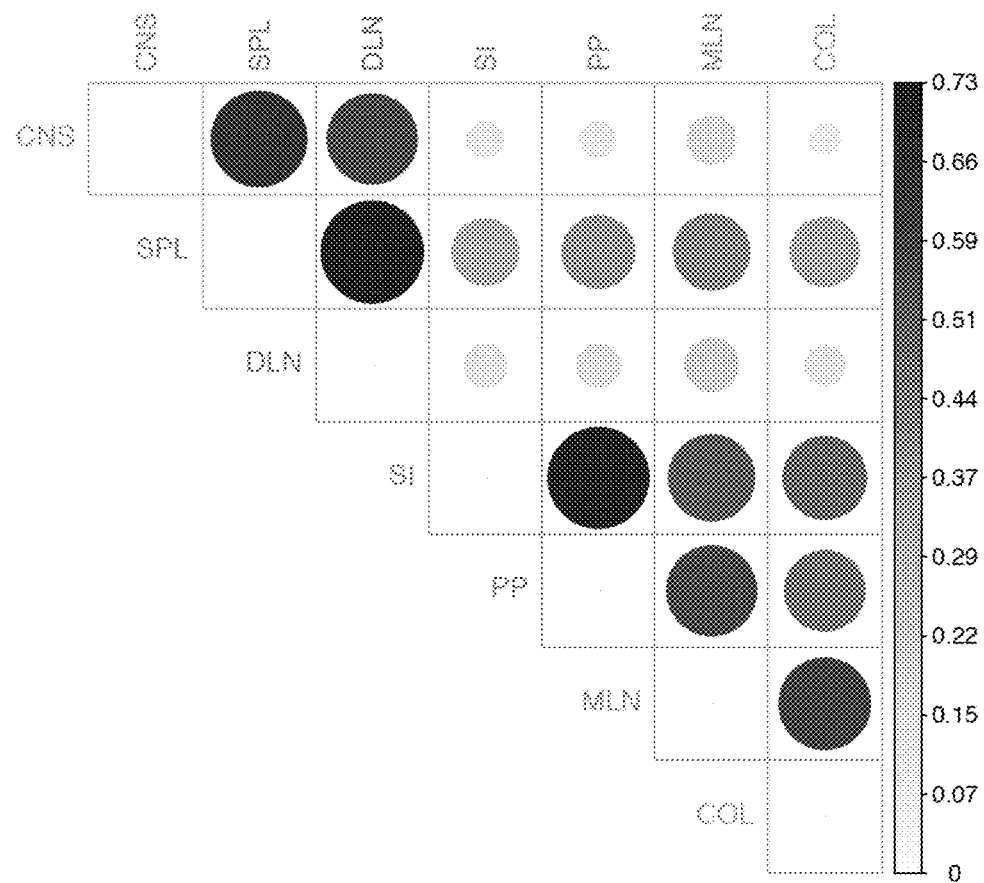
Figure 12B:
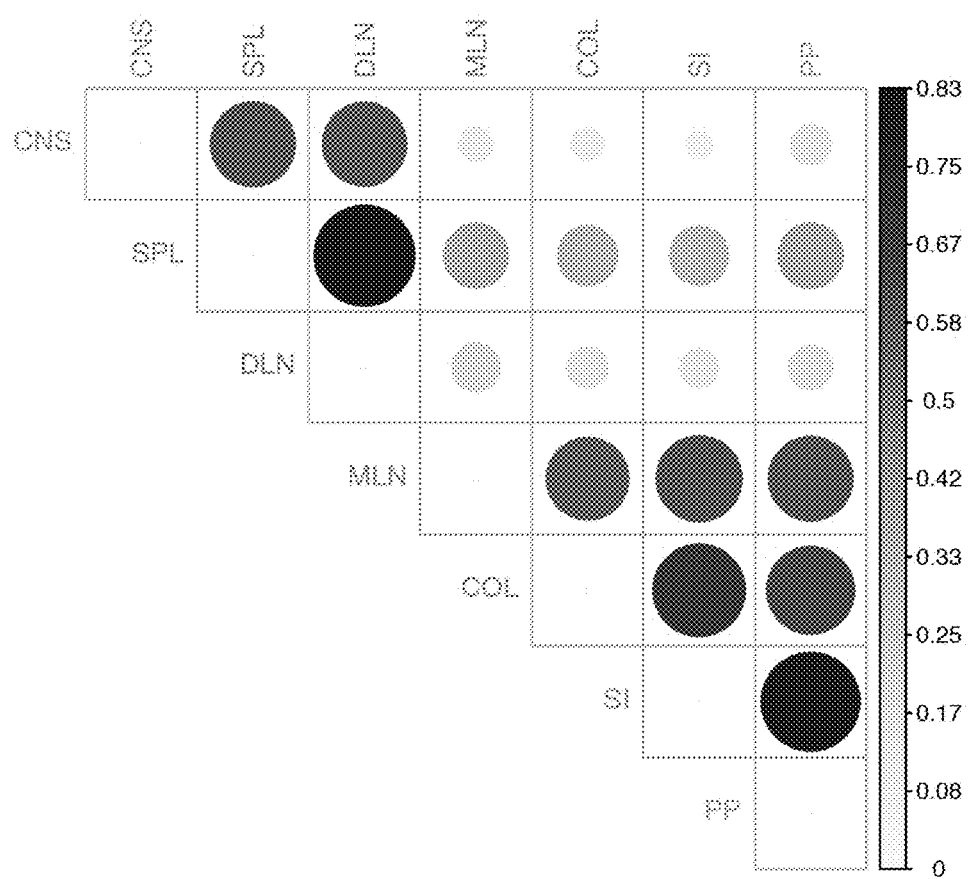
Figure 13A:
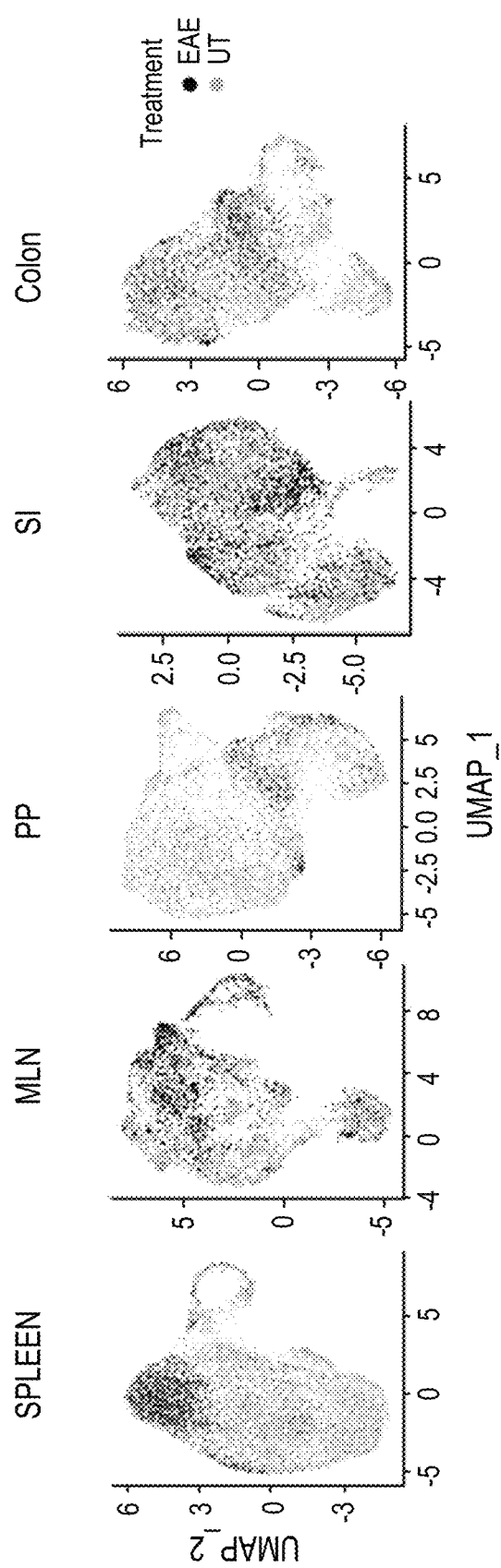
FIGS. 13A-13G— FIG. 13A. UMAP plots showing EAE and UT clusters in each tissue.
Figure 13B:
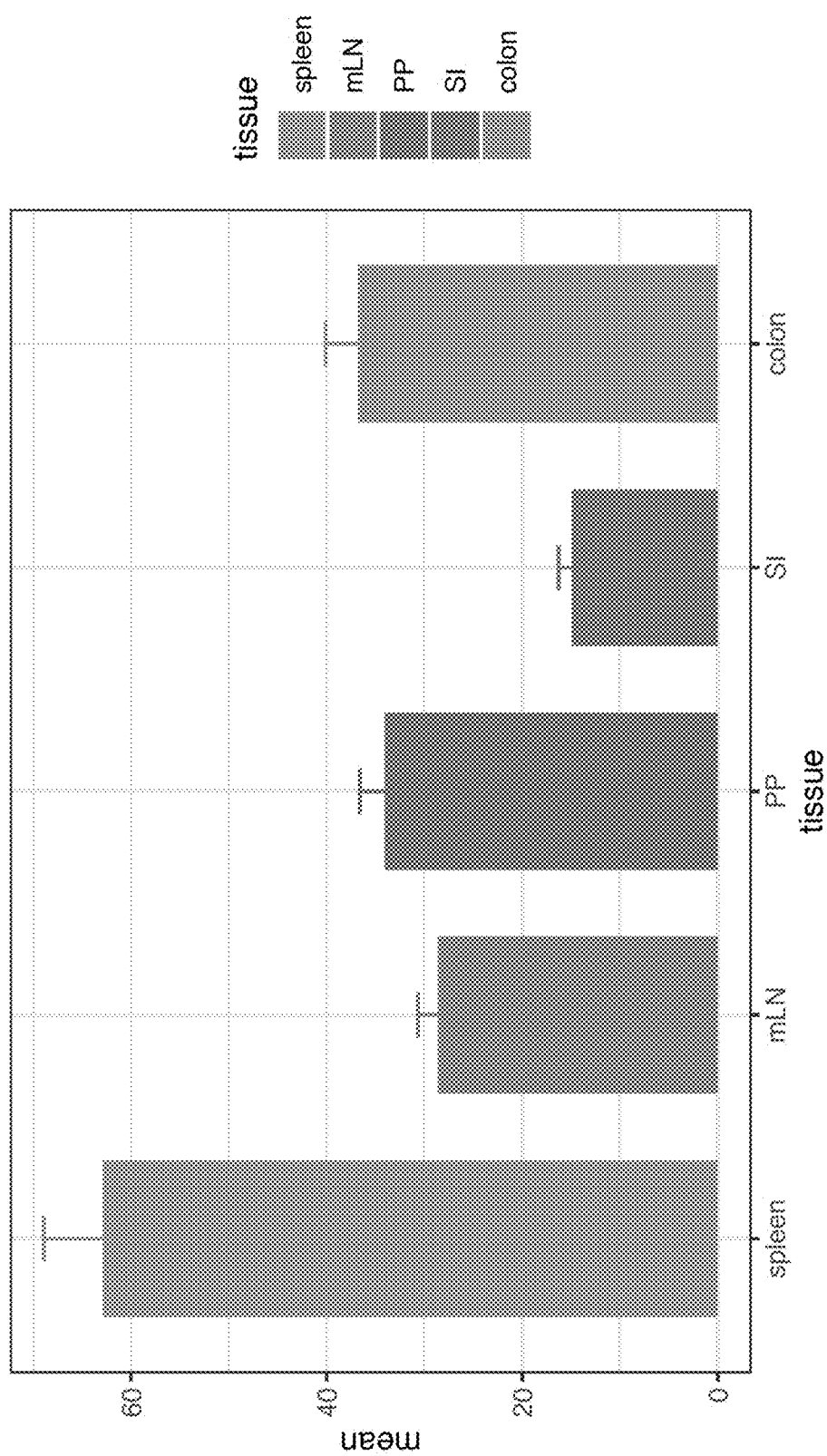
Figure 13C:
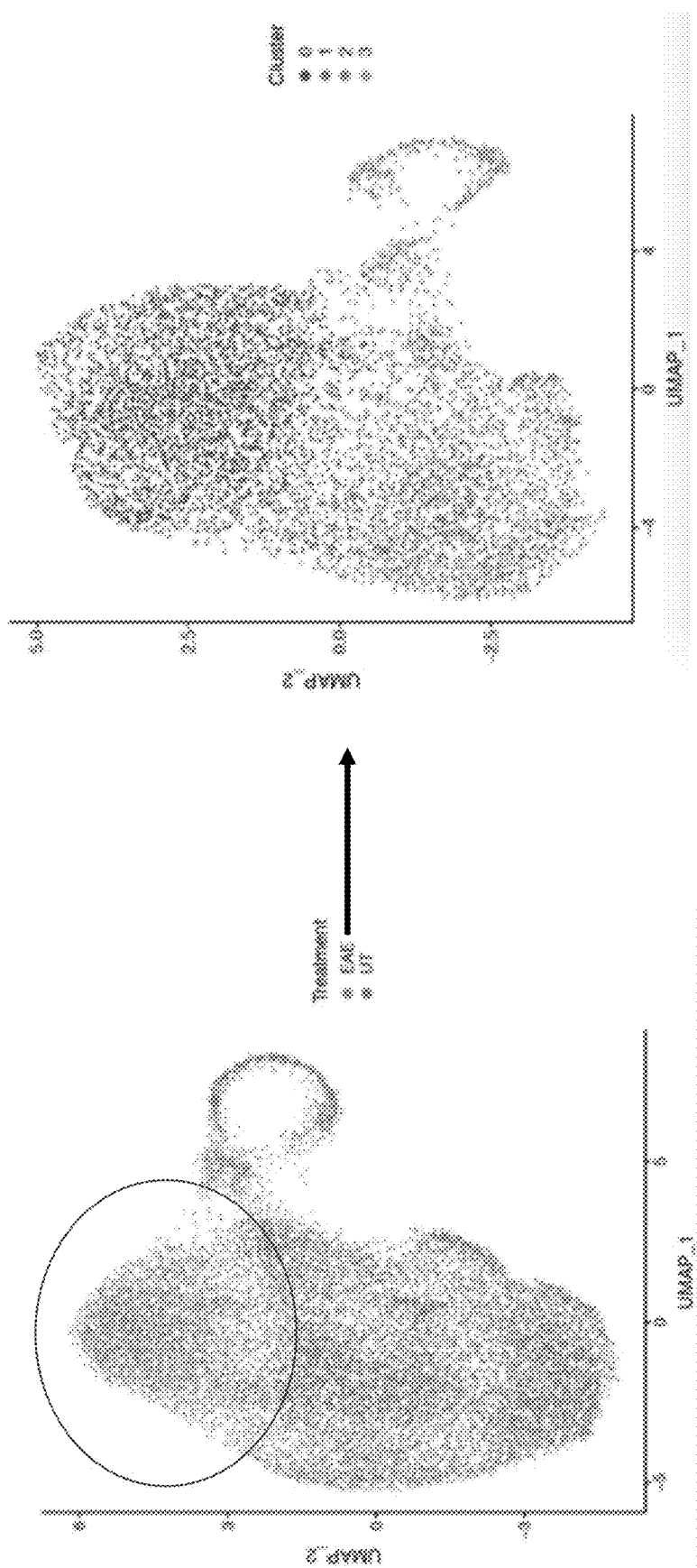
Figure 13D:
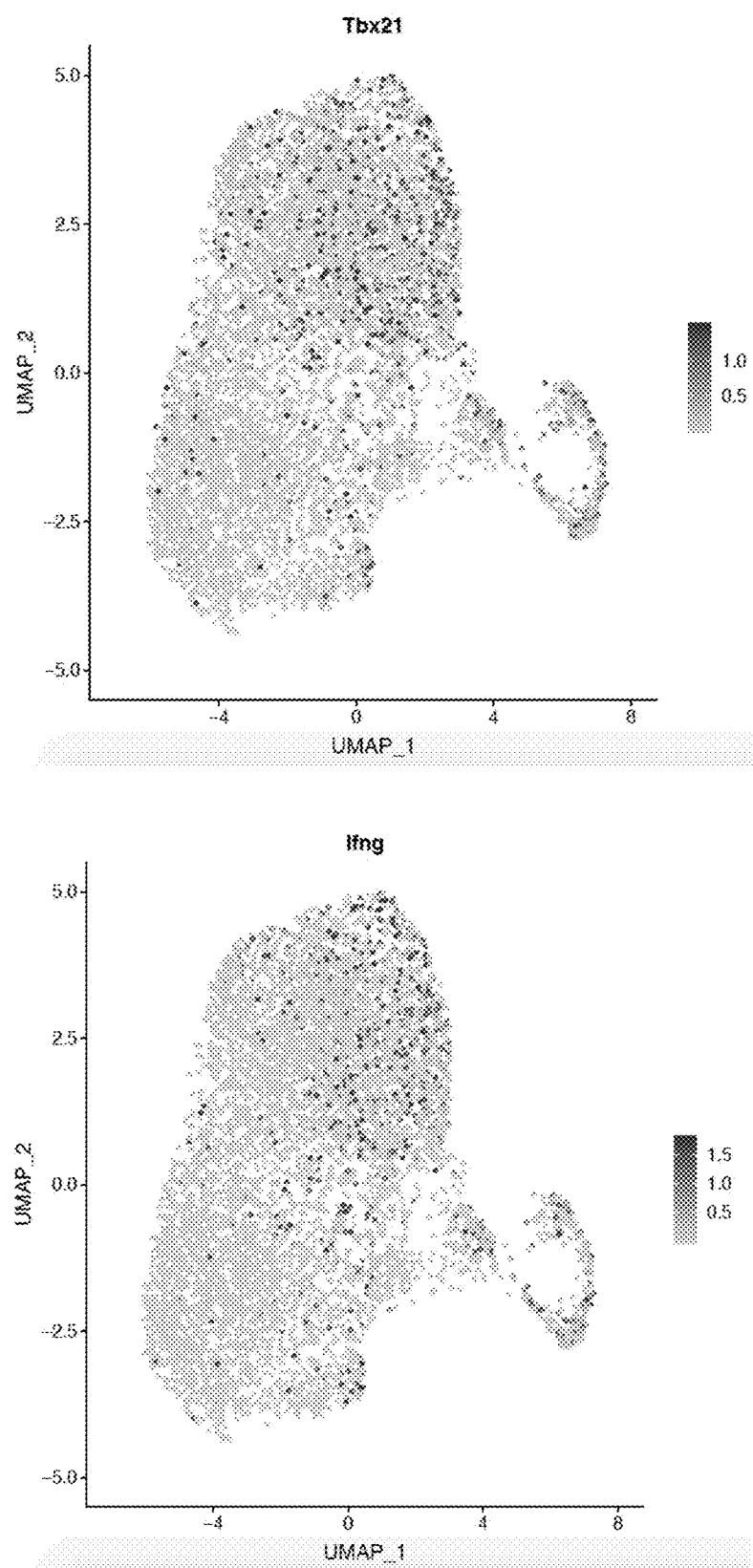
Figure 13D:
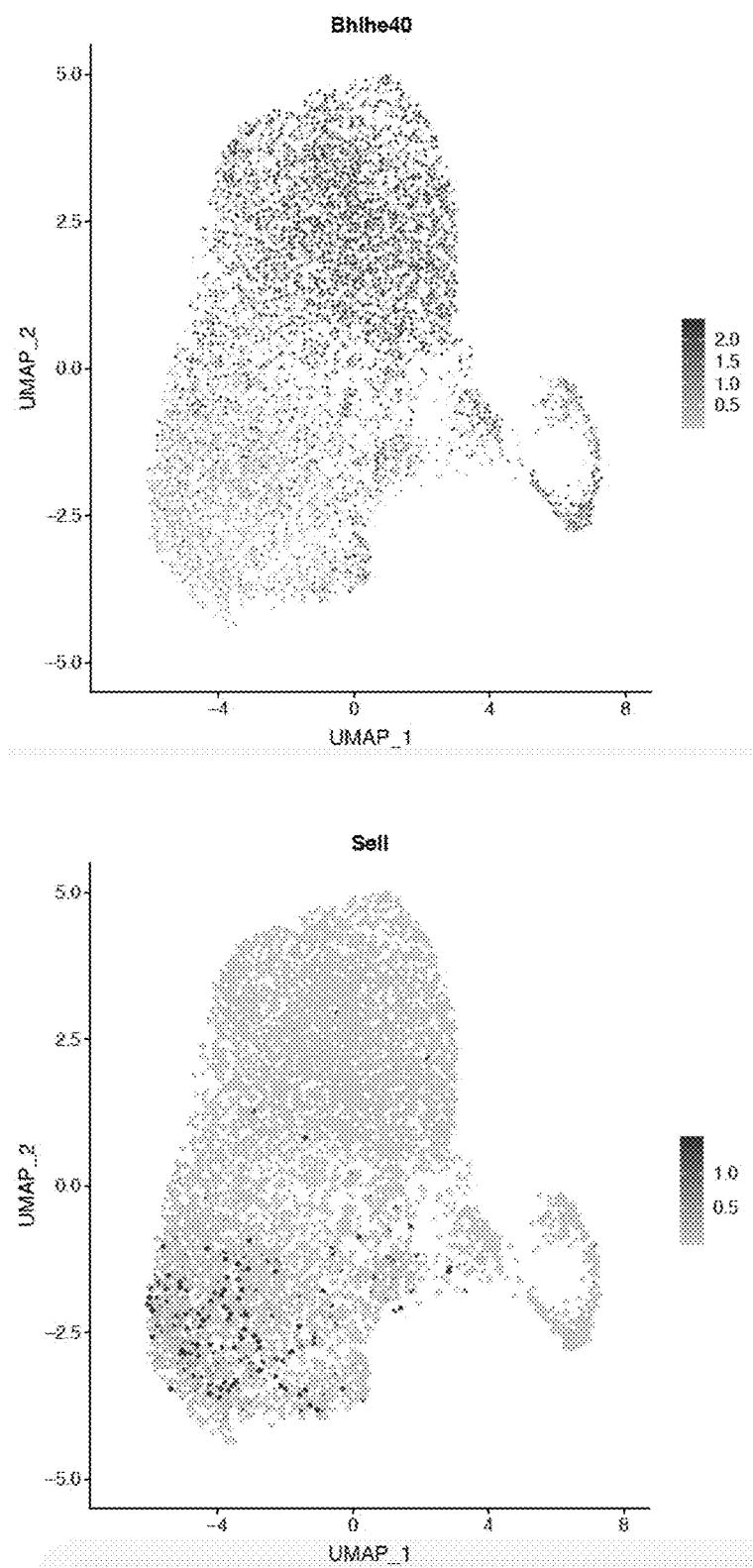
Figure 13D:
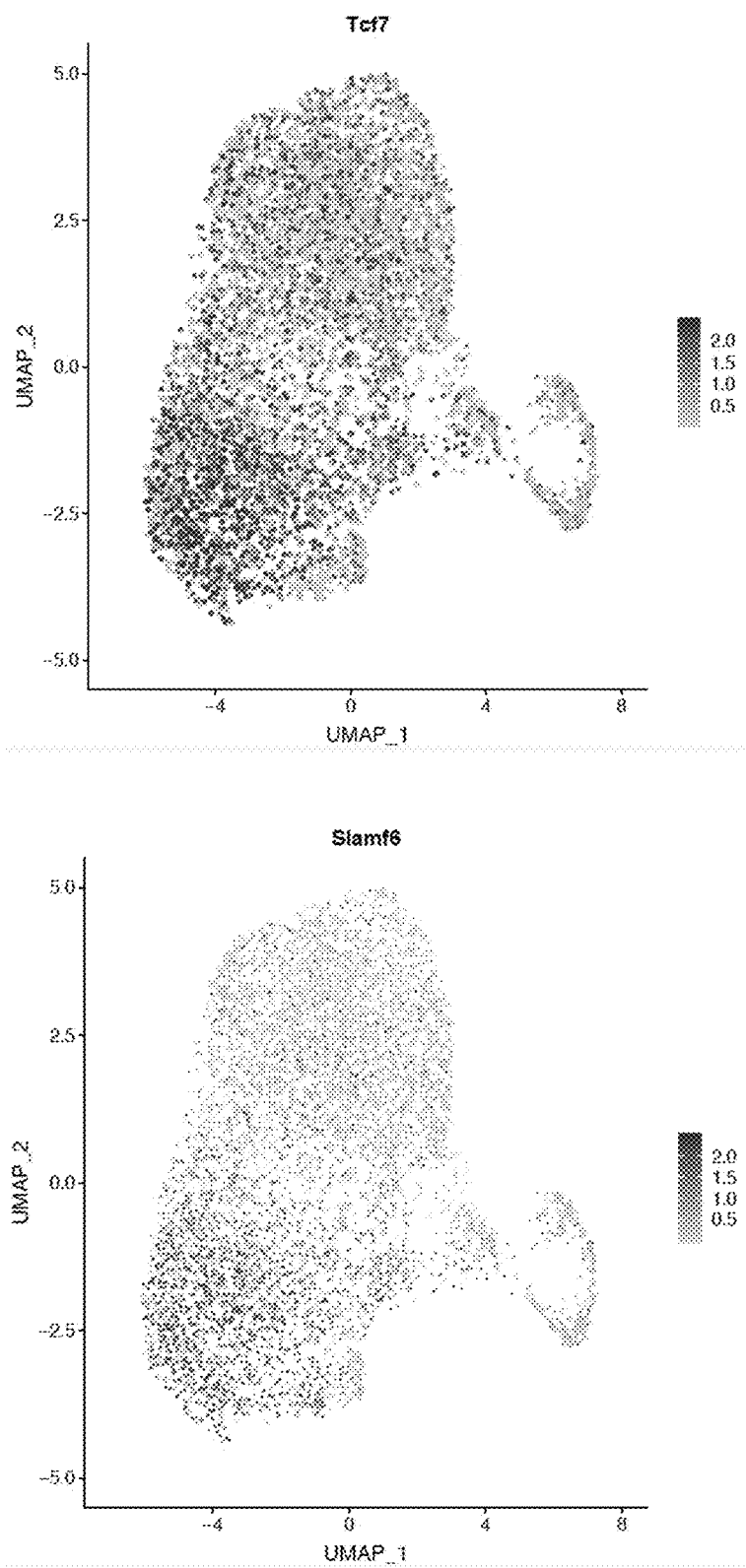
Figure 13E:
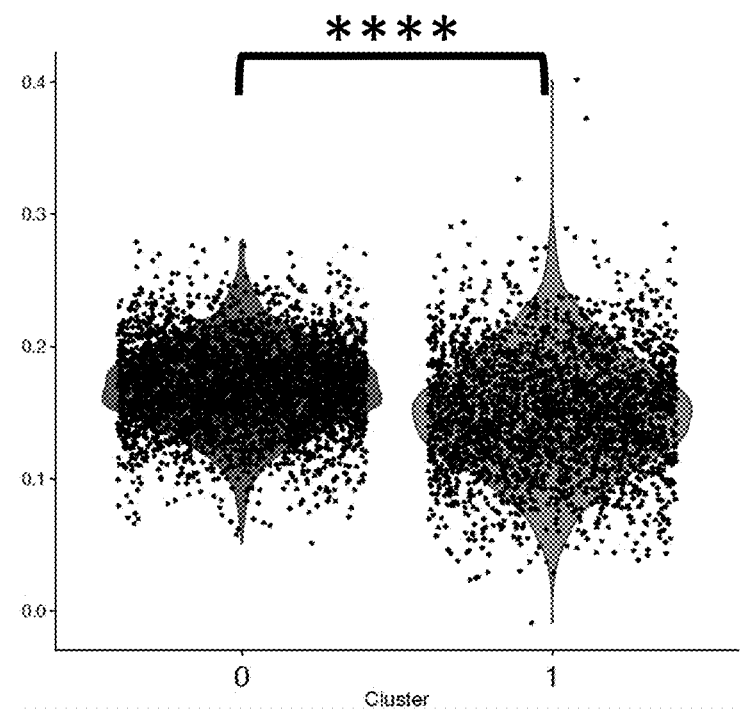
Figure 13E:
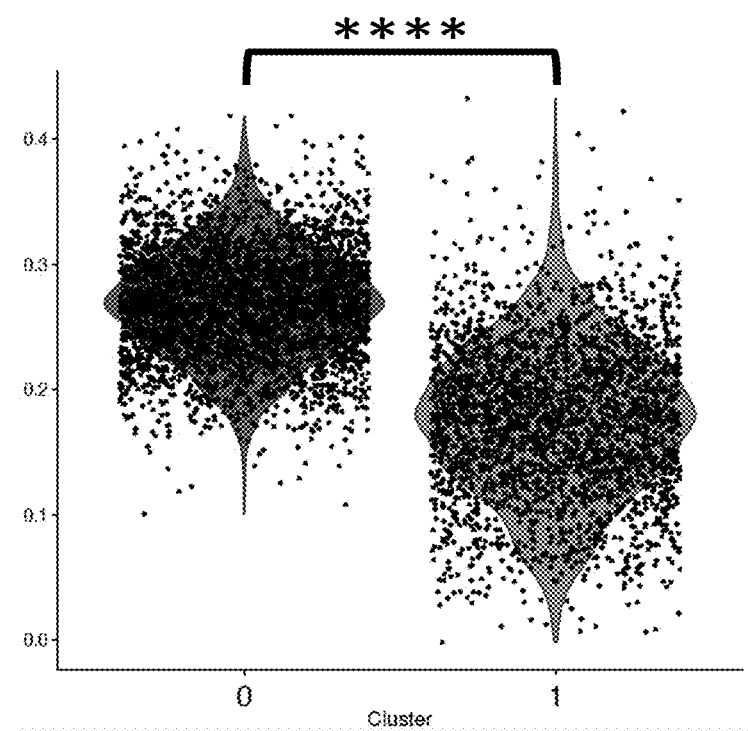
Figure 13E:
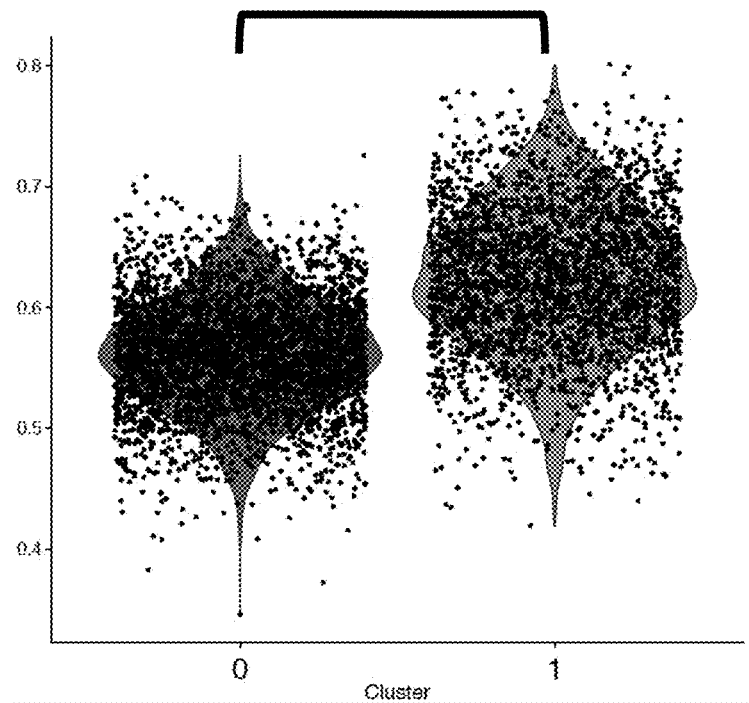
Figure 13E:
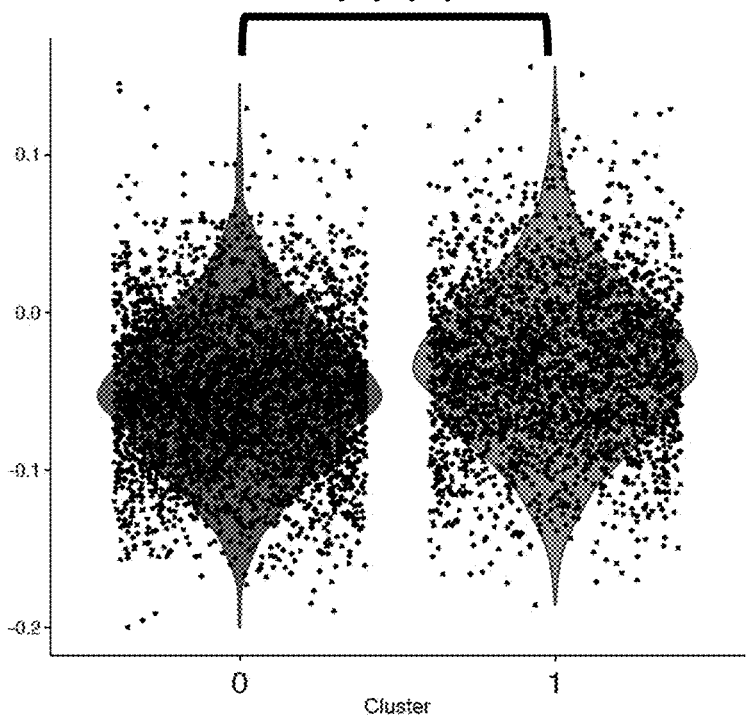
Figure 13F:
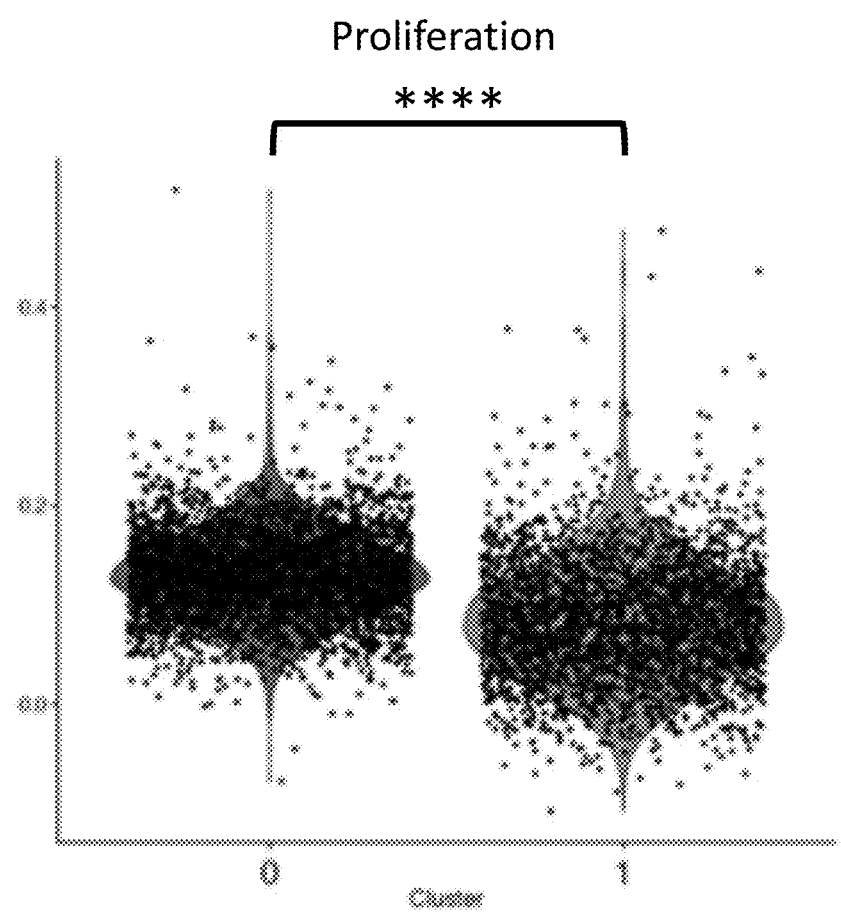
Figure 13G:
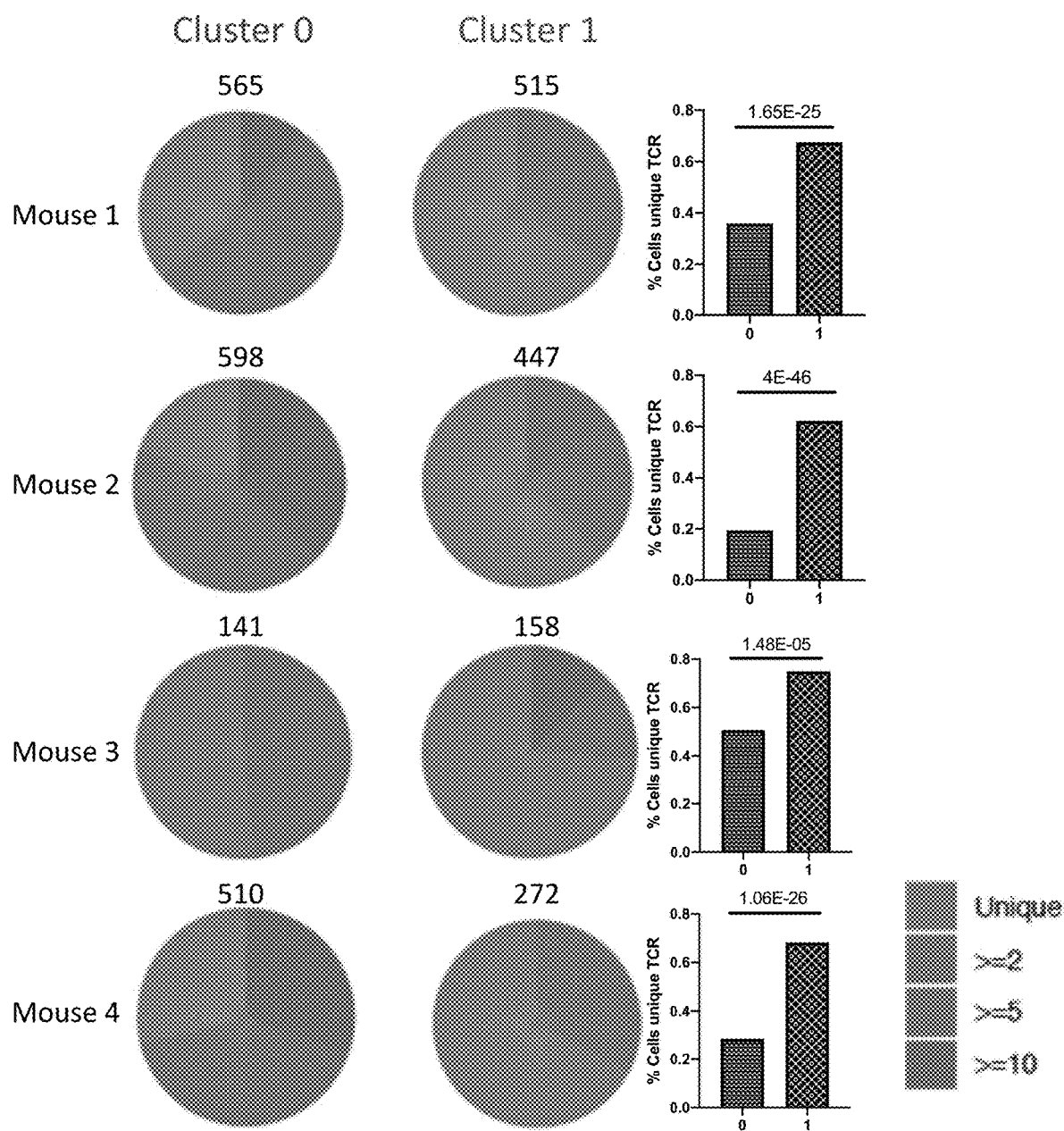
Figure 14A:
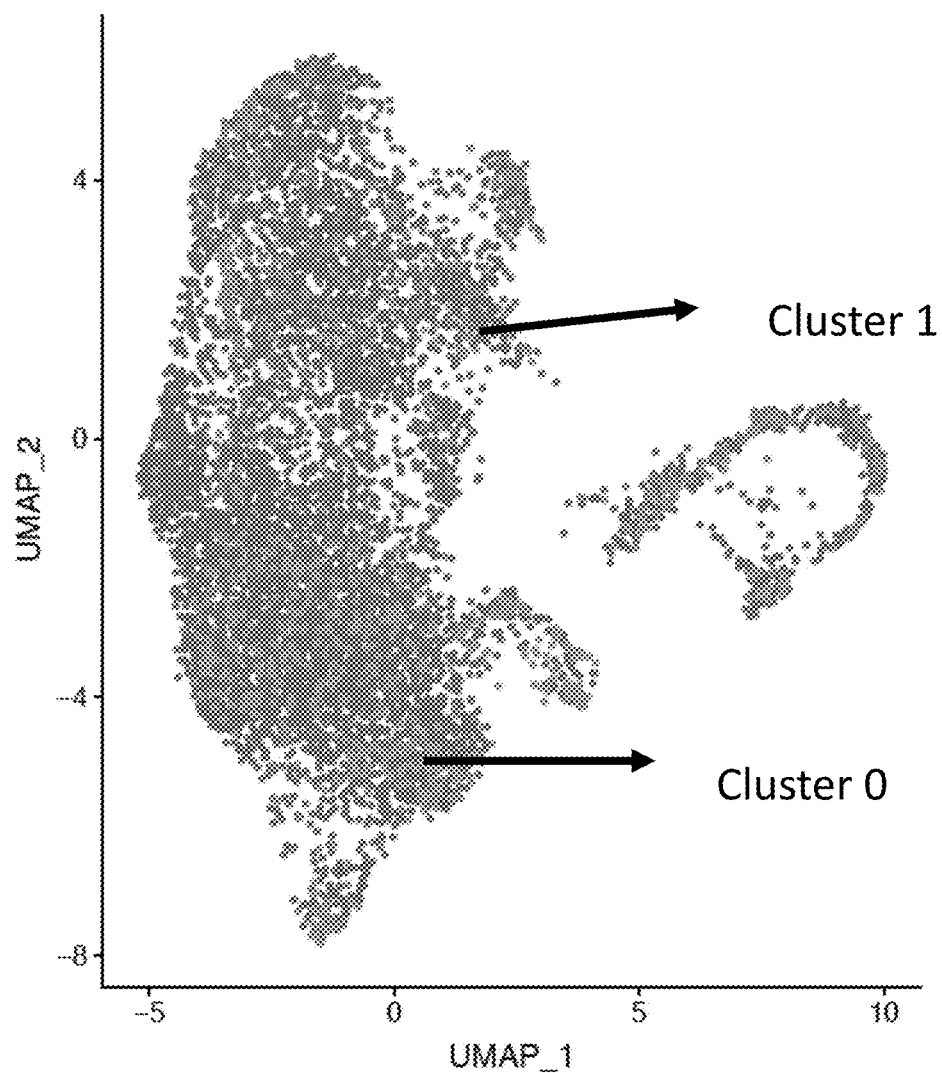
FIGS. 14A-14B— FIG. 14A. UMAP of Th17 cells in the CNS during EAE showing the number of cluster 0 and 1 Th17 cells.
Figure 14A:
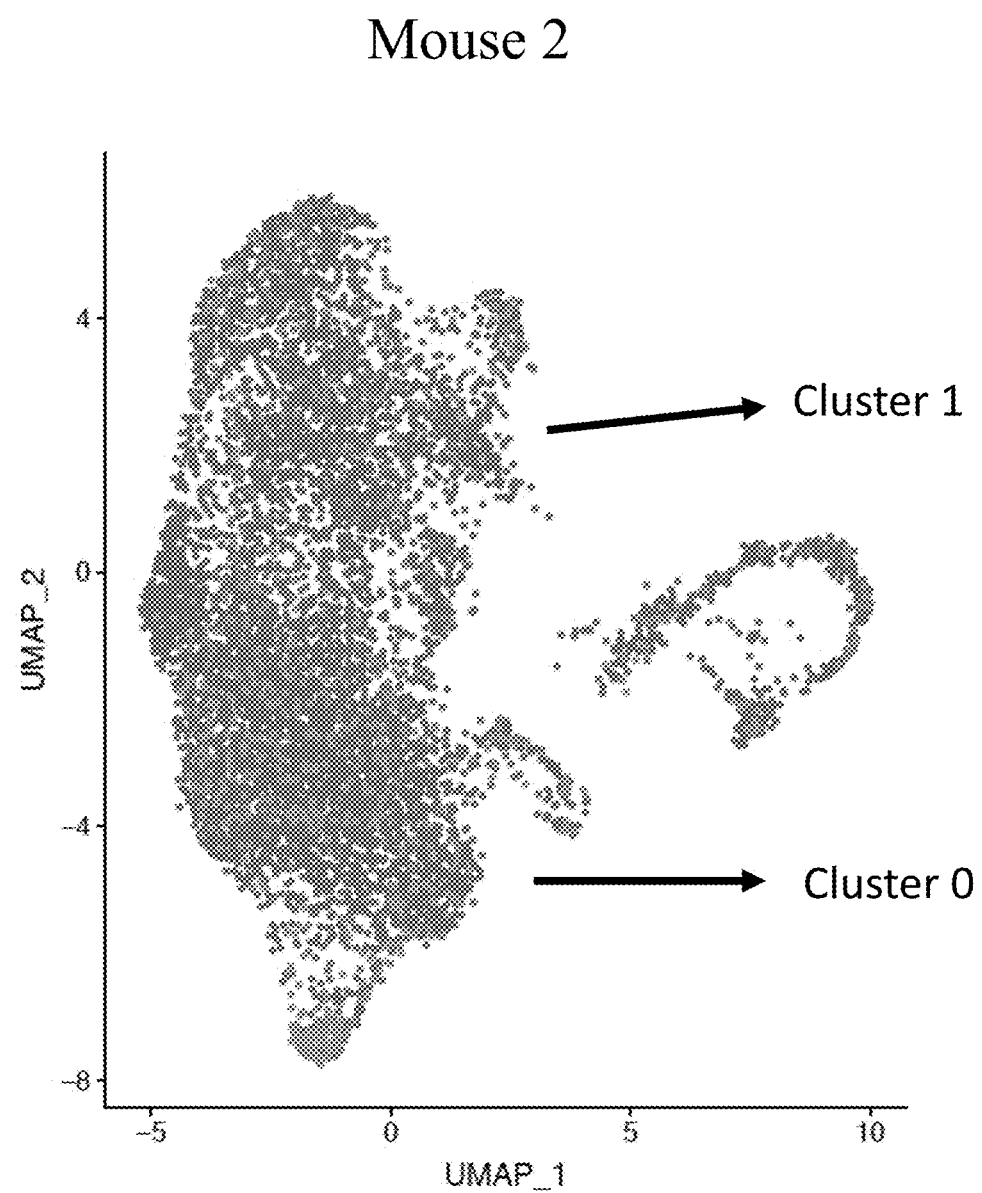
Figure 14B:
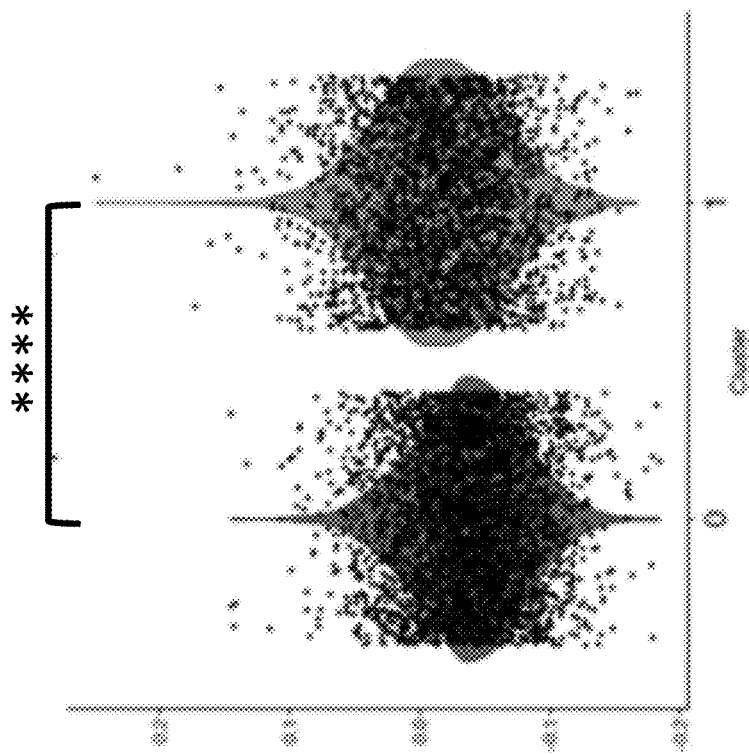
Figure 14B:
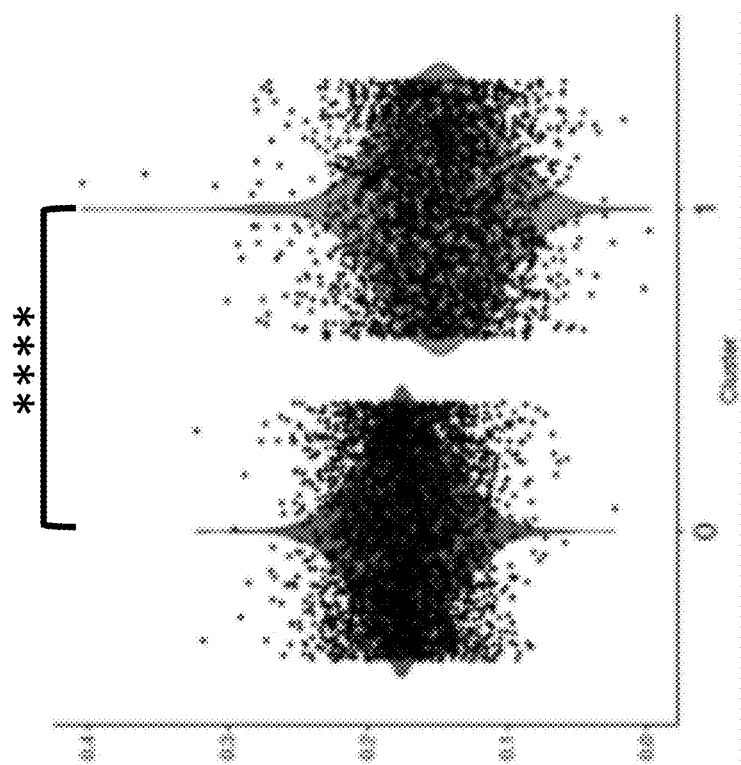
Figure 15A:
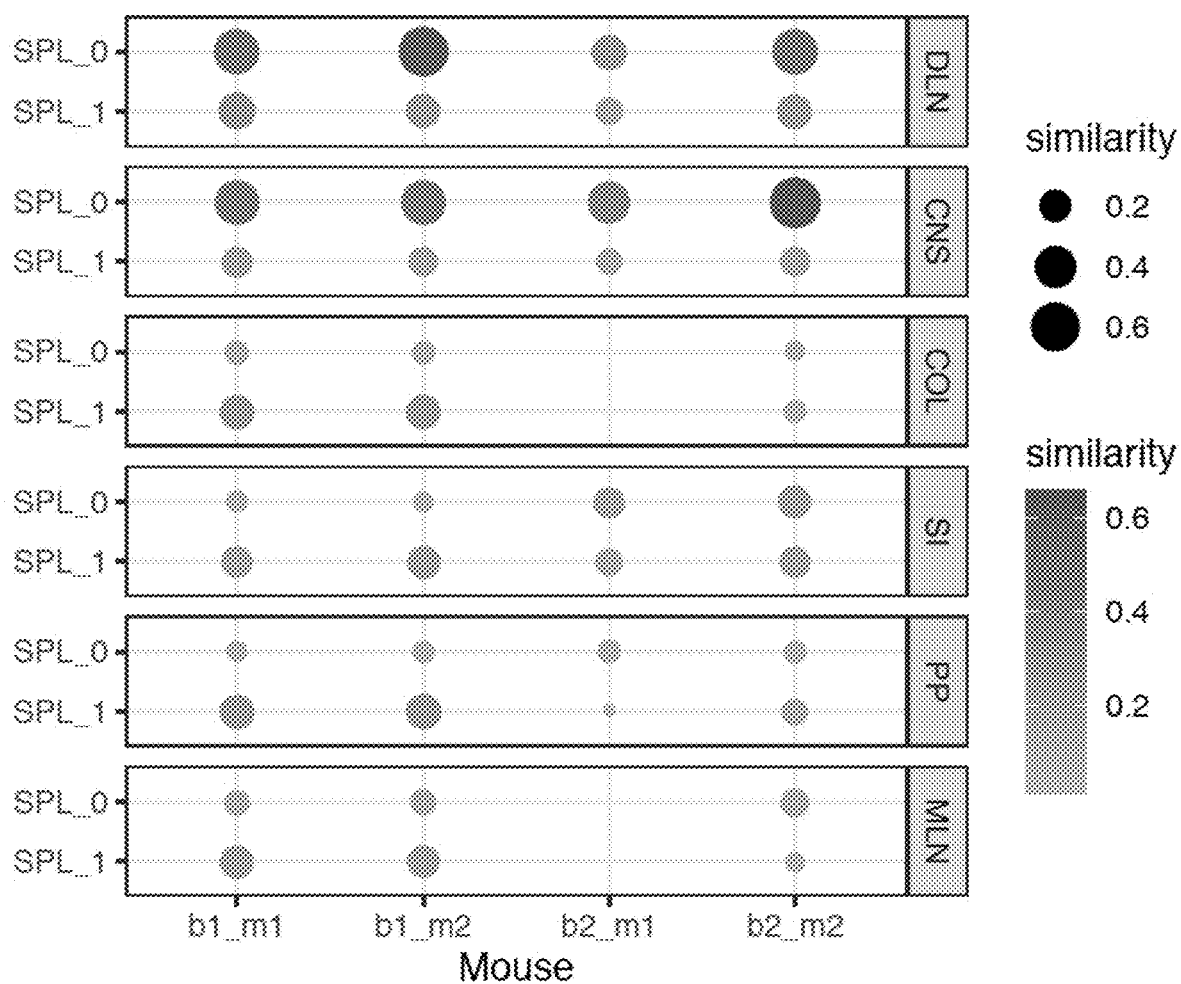
FIGS. 15A-15B— FIG. 15A. Graphs showing similarity between spleen cluster 0 and 1 as compared to Th17 cells in the CNS and dLN.
Figure 15B:
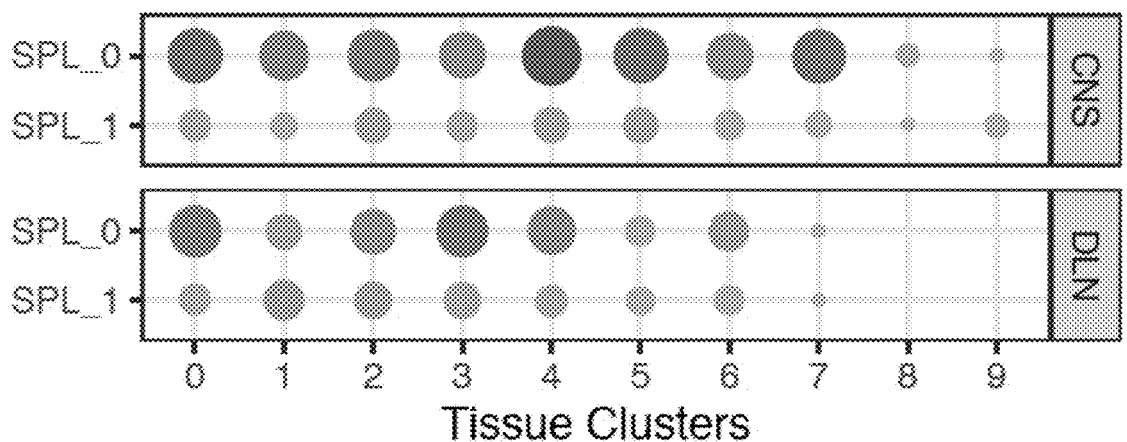
Figure 15B:
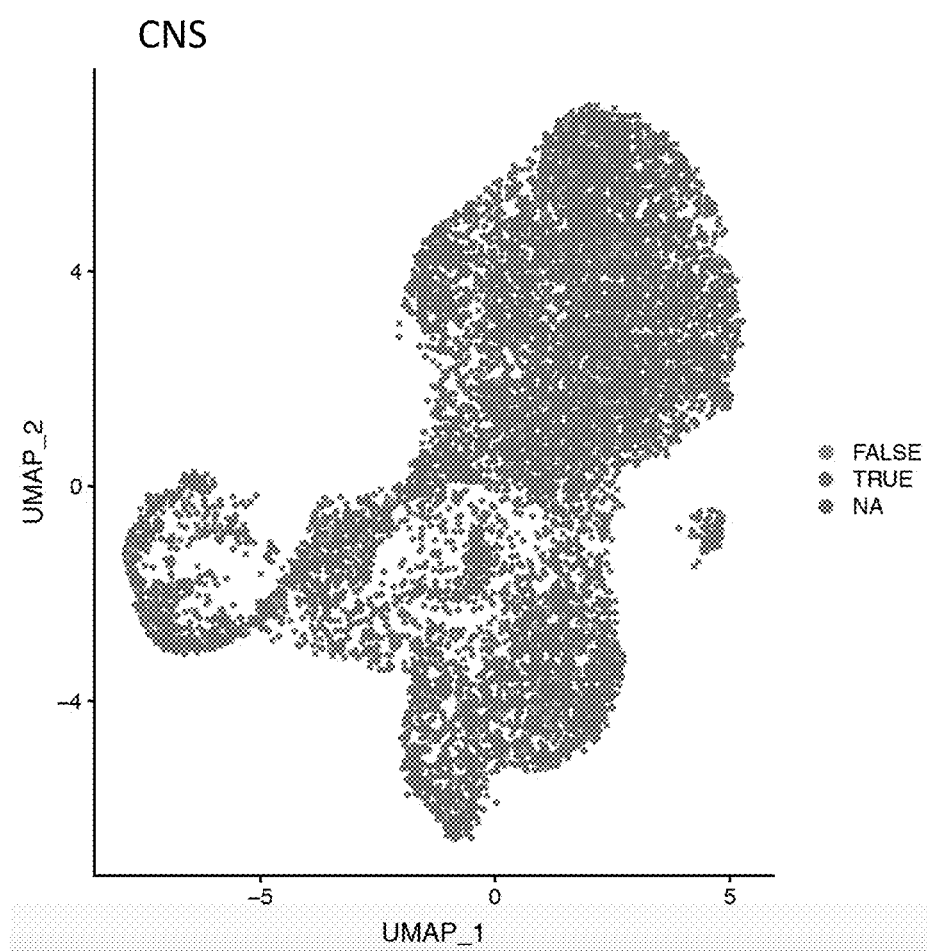
Figure 16A:
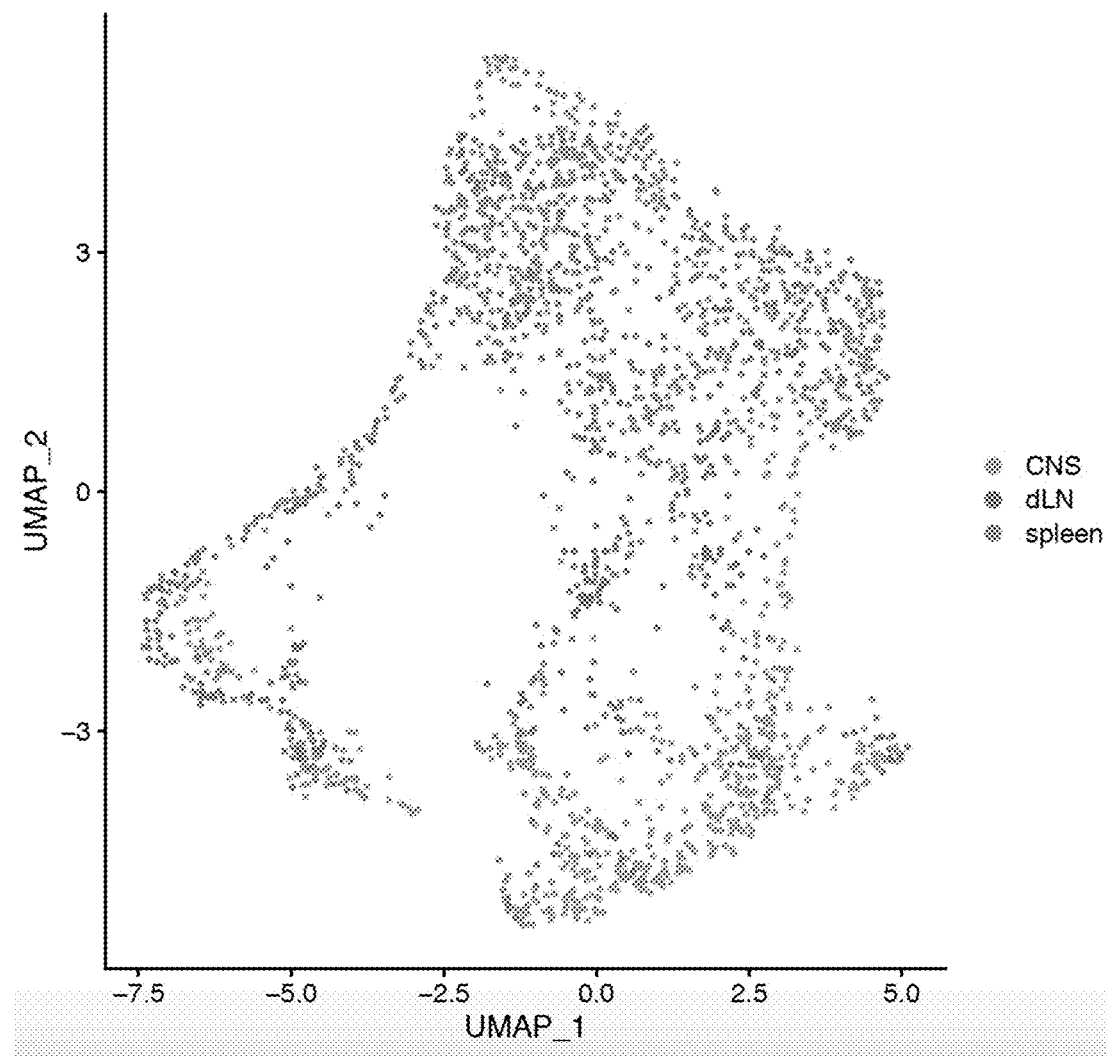
FIGS. 16A-16C— FIG. 16A. UMAP plot of spleen, CNS and dLN Th17 cells labeled by tissue.
Figure 16B:
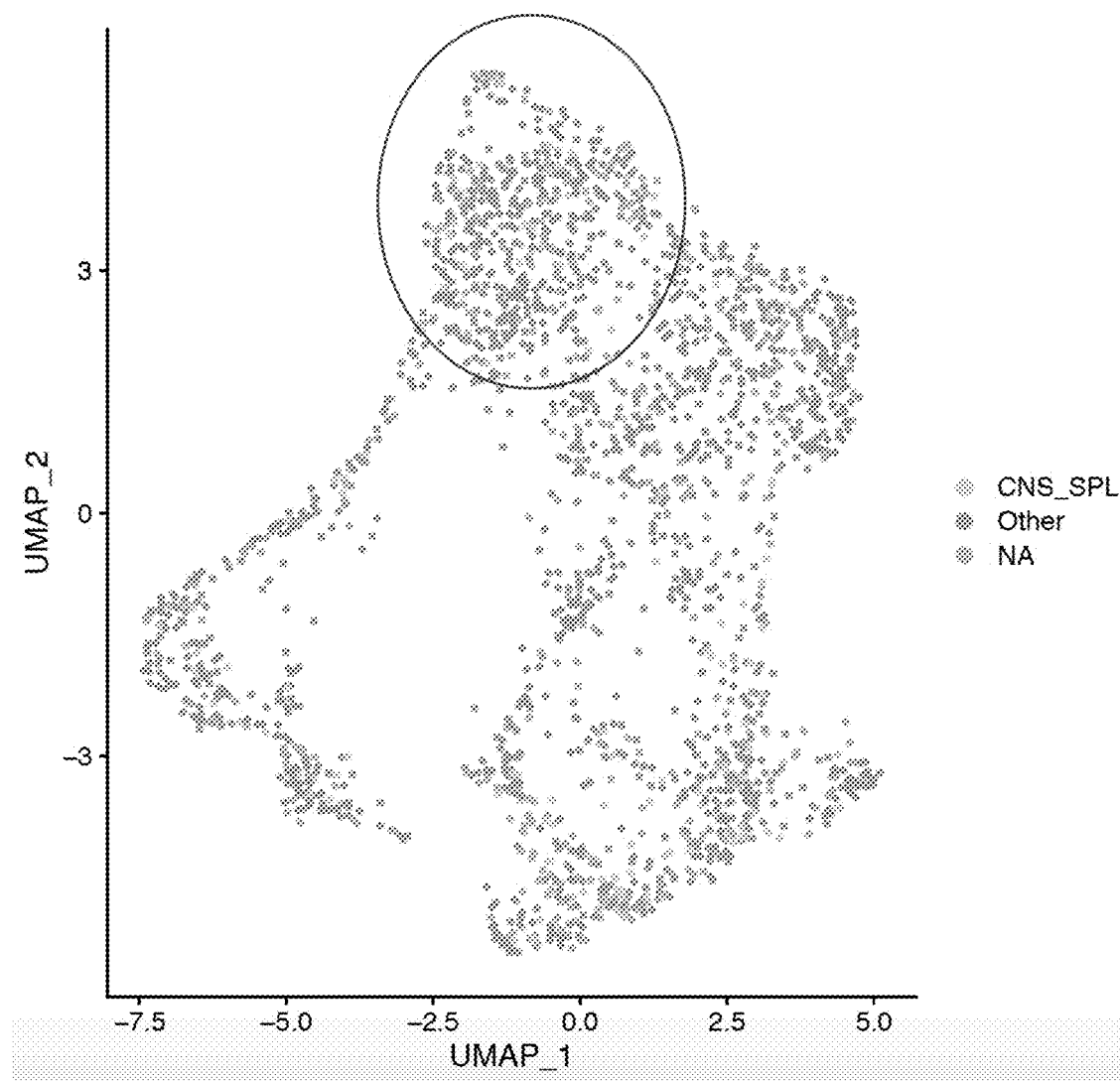
Figure 16C:
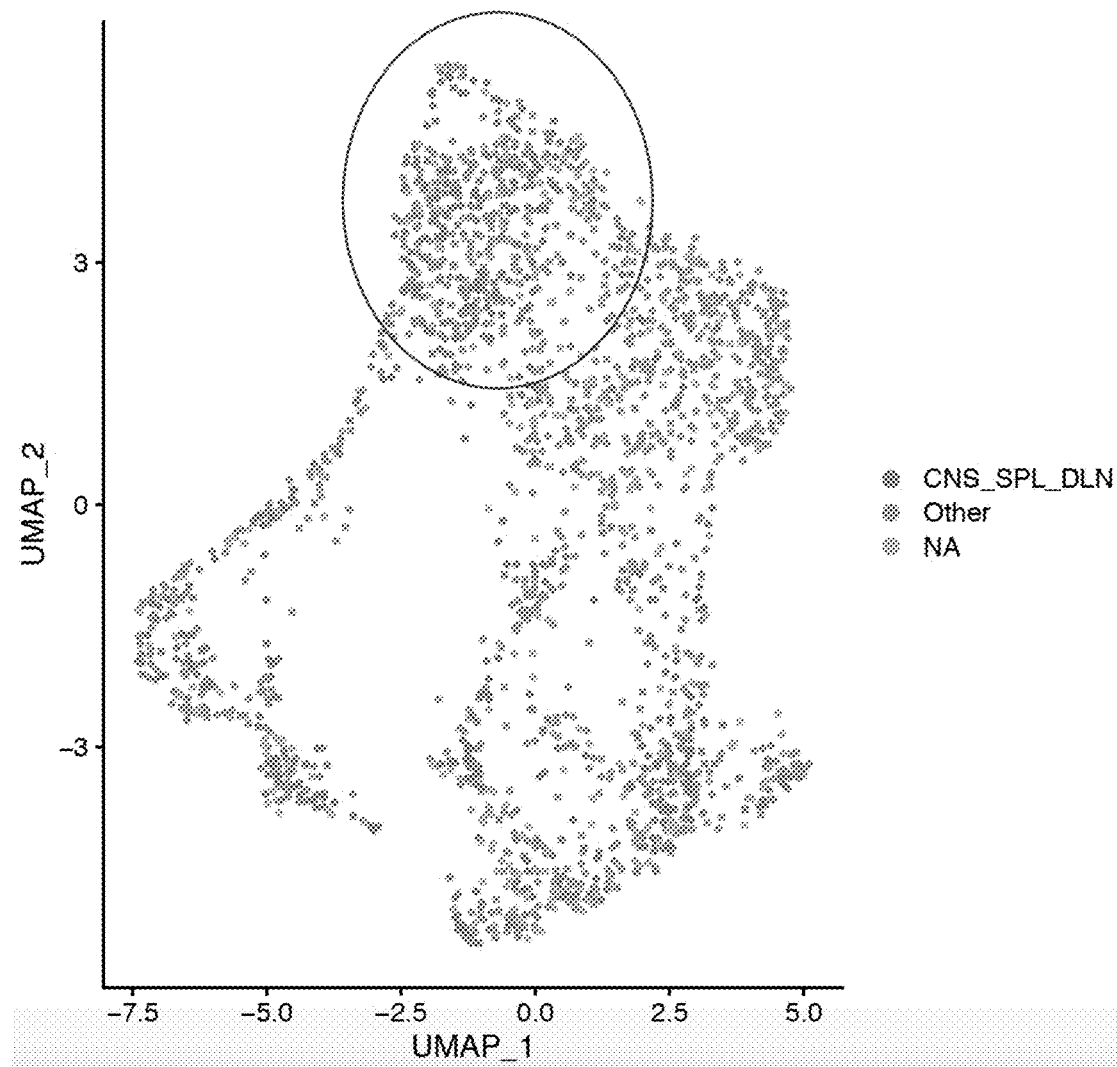
Figure 19:
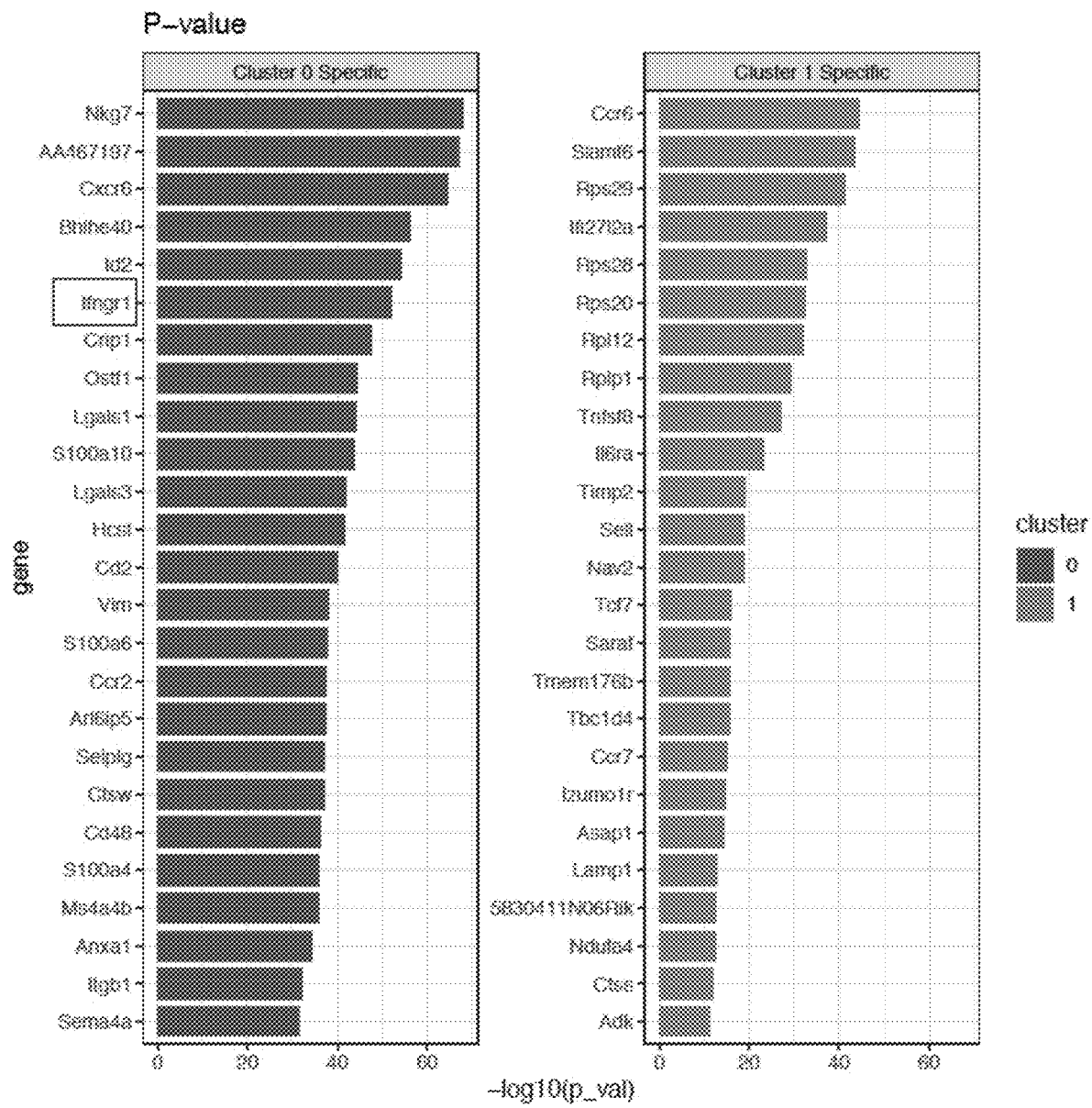
FIG. 19— Graphs showing differentially expressed genes between cluster 0 and 1. Ifngr1 is highlighted.
Figure 20:
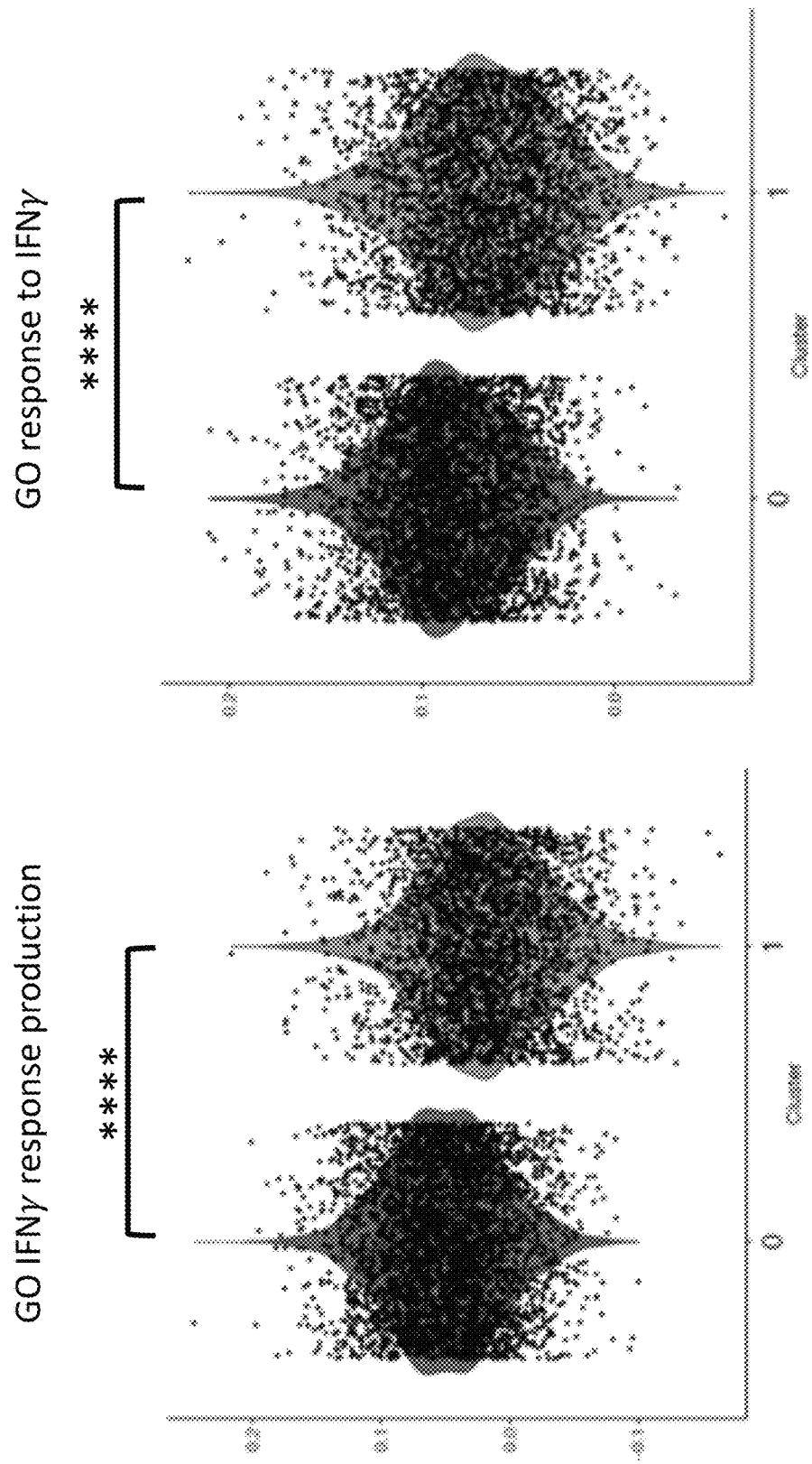
FIG. 20— Violin plots showing GO IFNγ-signaling for cluster 0 and 1 the pathogenic spleen.
Figure 21:
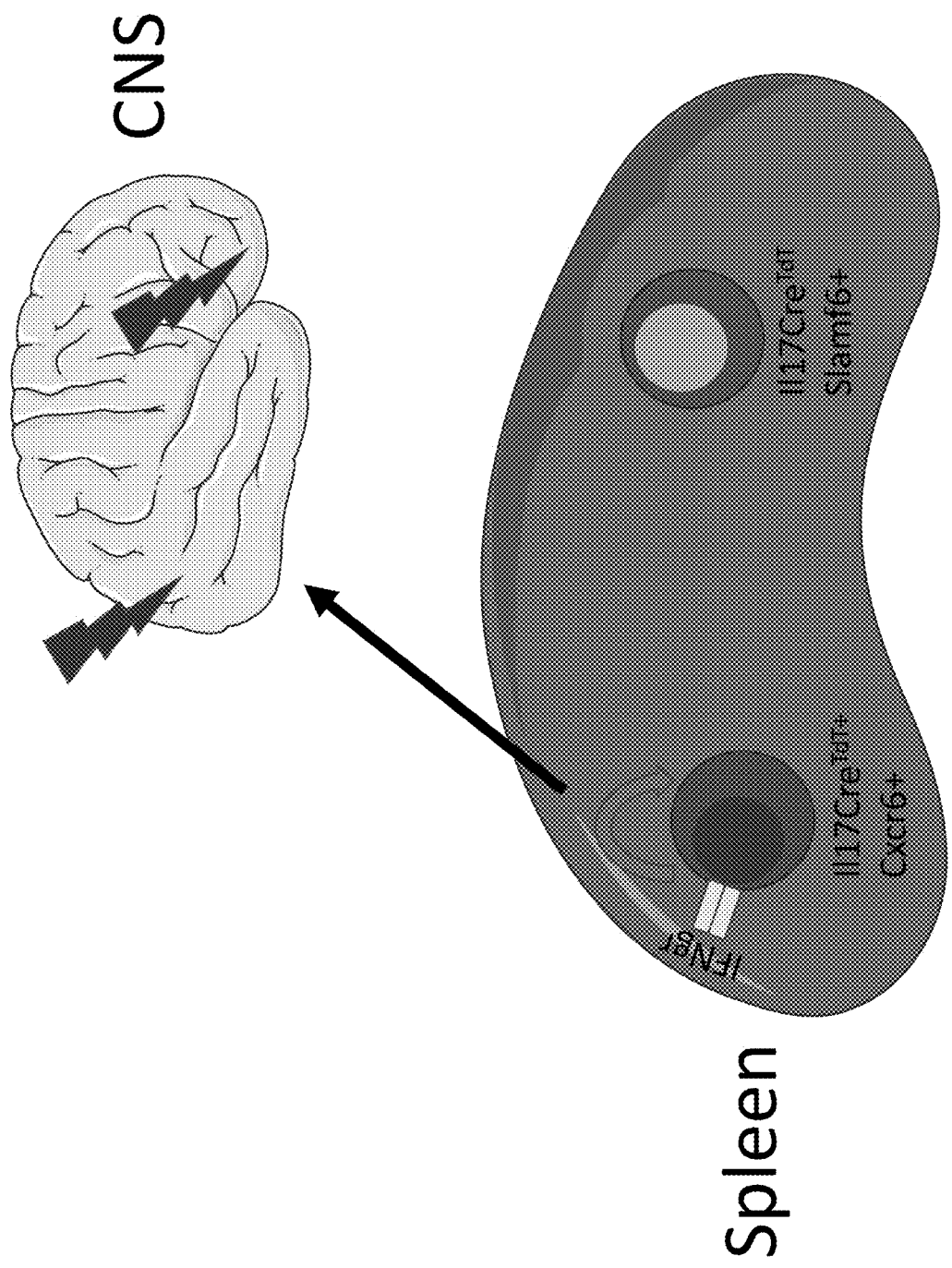
FIG. 21— Diagram showing a model of Th17 autoimmunity where Cluster 0 Th17 cells migrate from the spleen to the CNS.
Figure 22A:
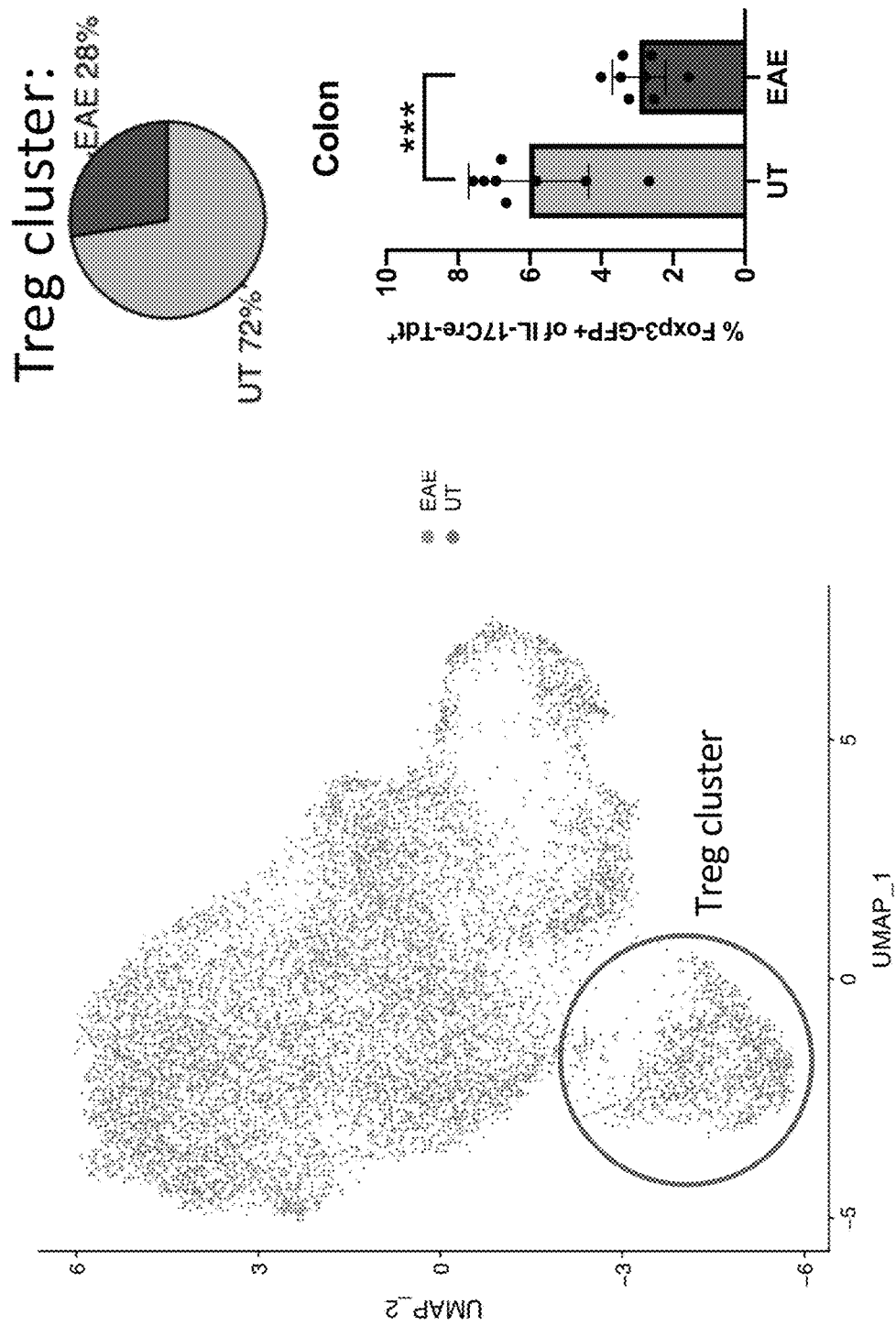
FIGS. 22A-22B— FIG. 22A. UMAP plot of Th17 cells in EAE and UT. Pie chart and graph showing the percentage of Treg-like Th17 cells in EAE and UT. Graphs showing the percentage of Treg cells (top) and Th17 cells in specific tissues for EAE and UT.
Figure 22A:
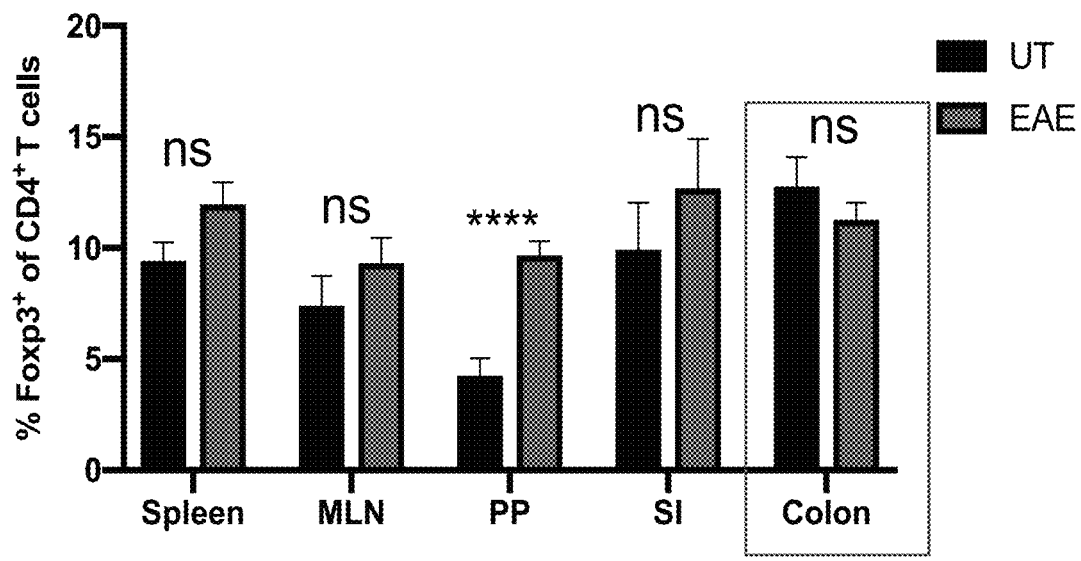
Figure 22A:
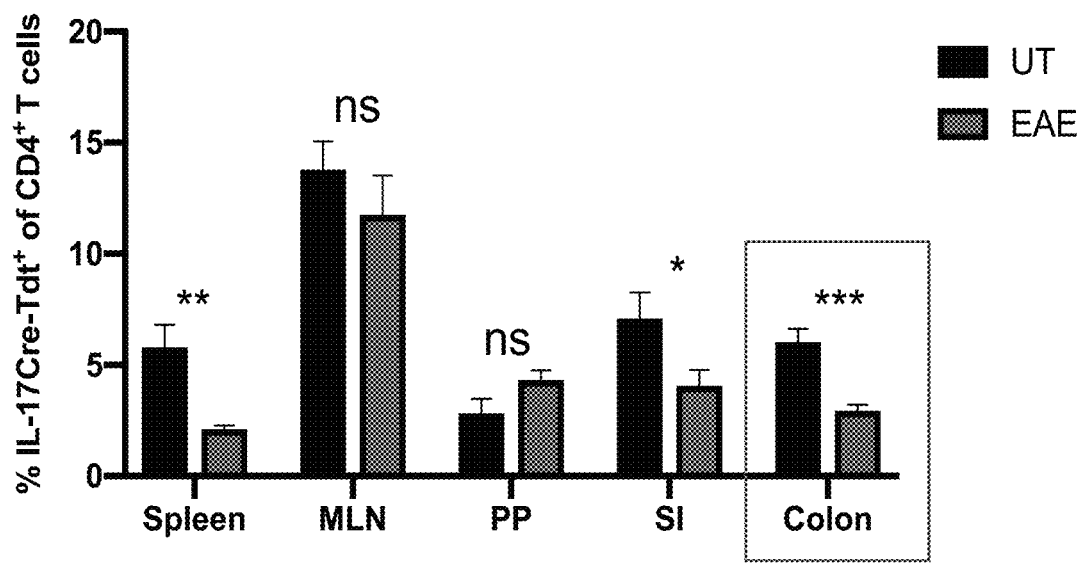
Figure 22B:
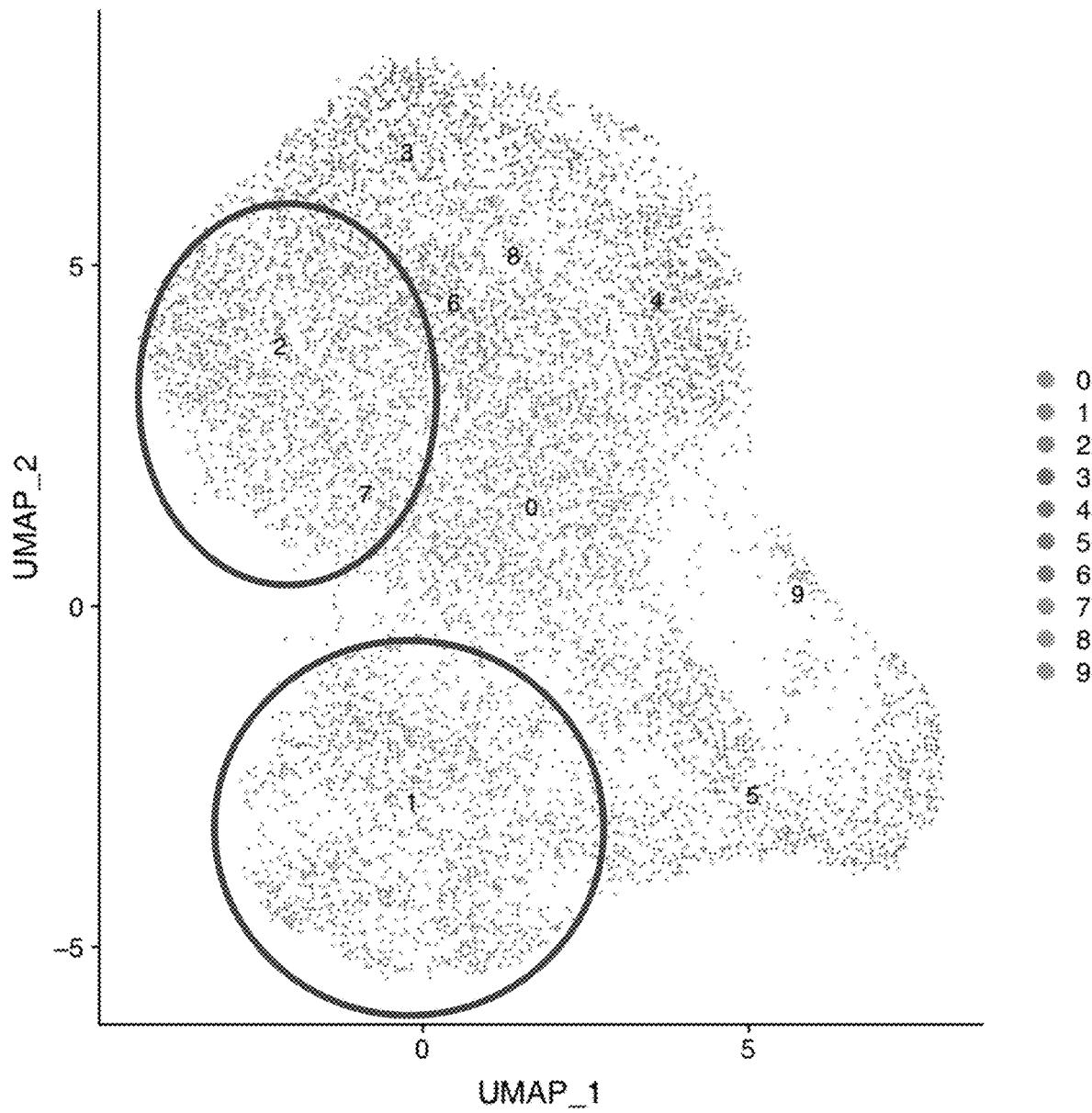
Figure 22B:
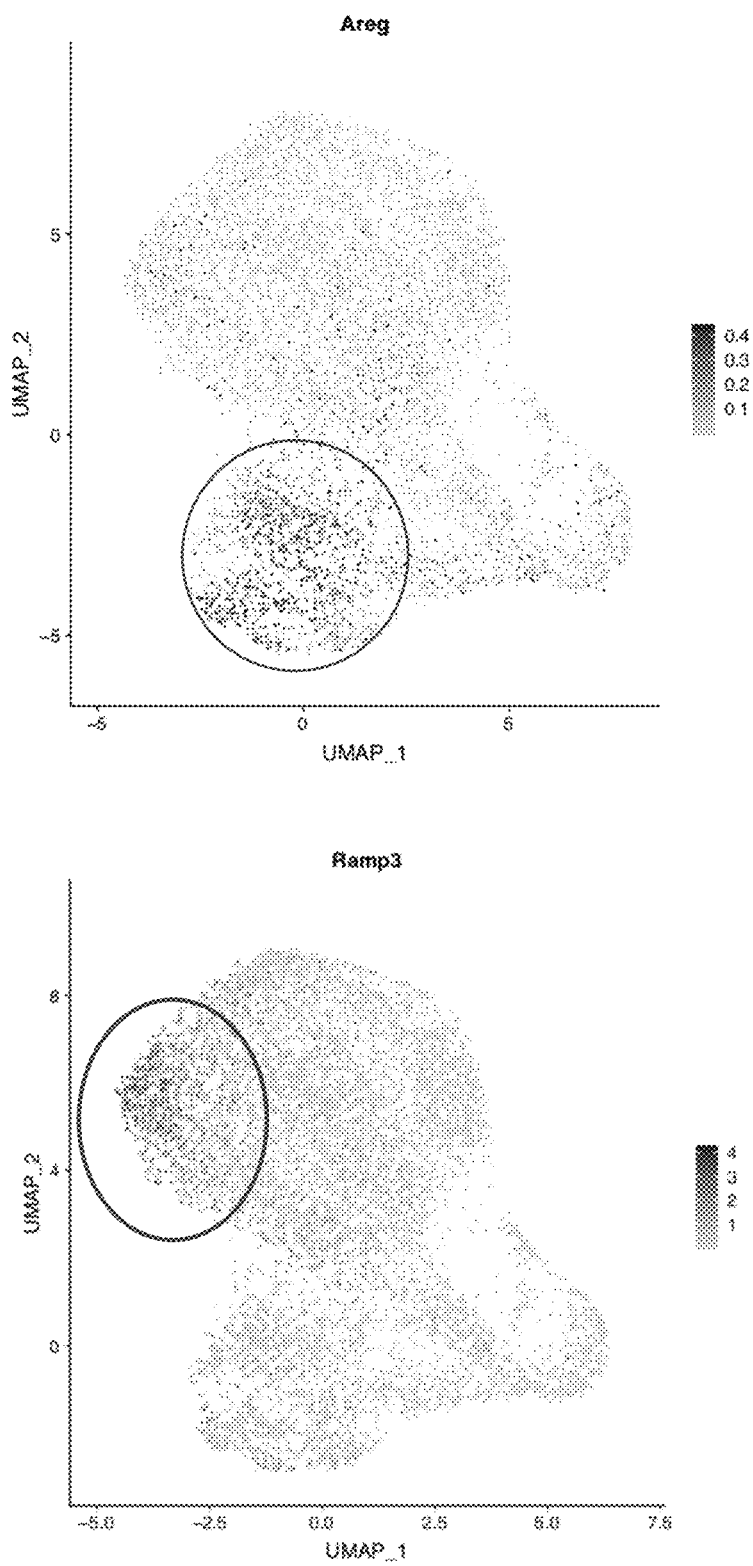
Figures 23A, 23B:
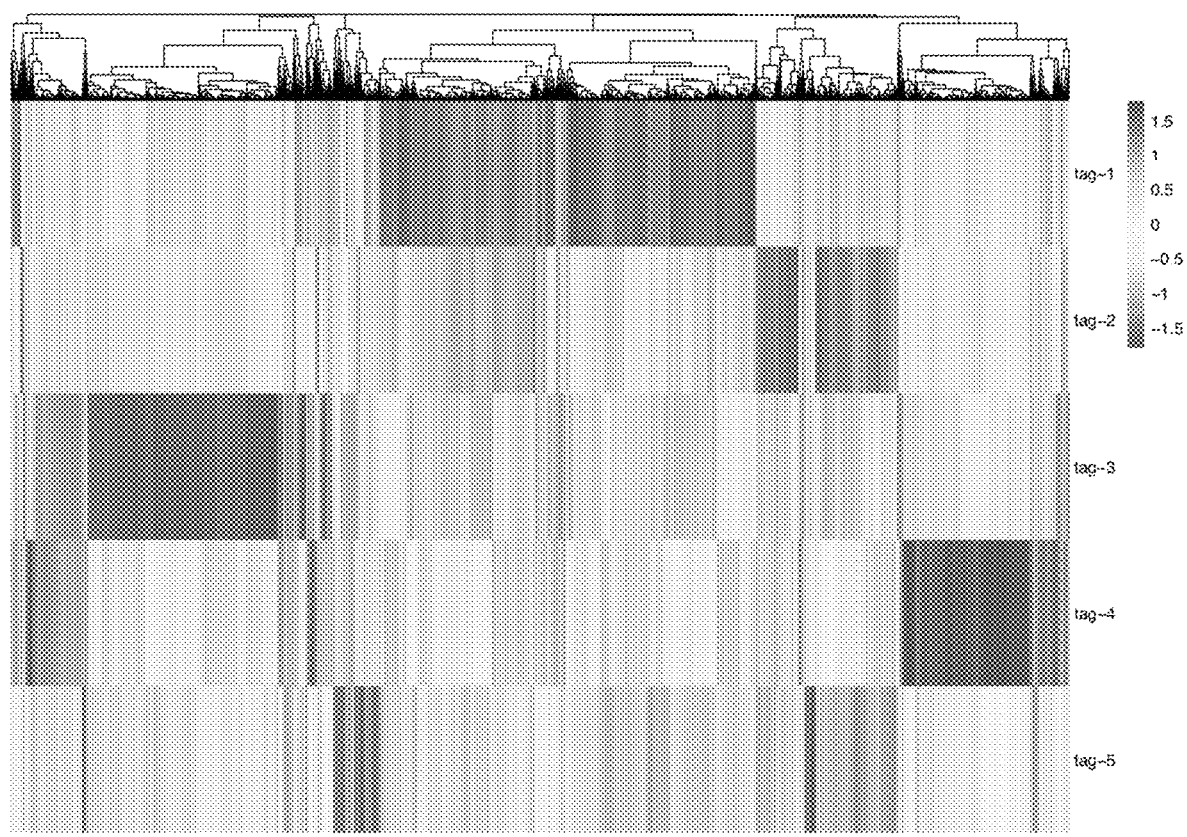
FIGS. 23A-23C— FIG. 23A. description of Hashing.
Figure 23C:
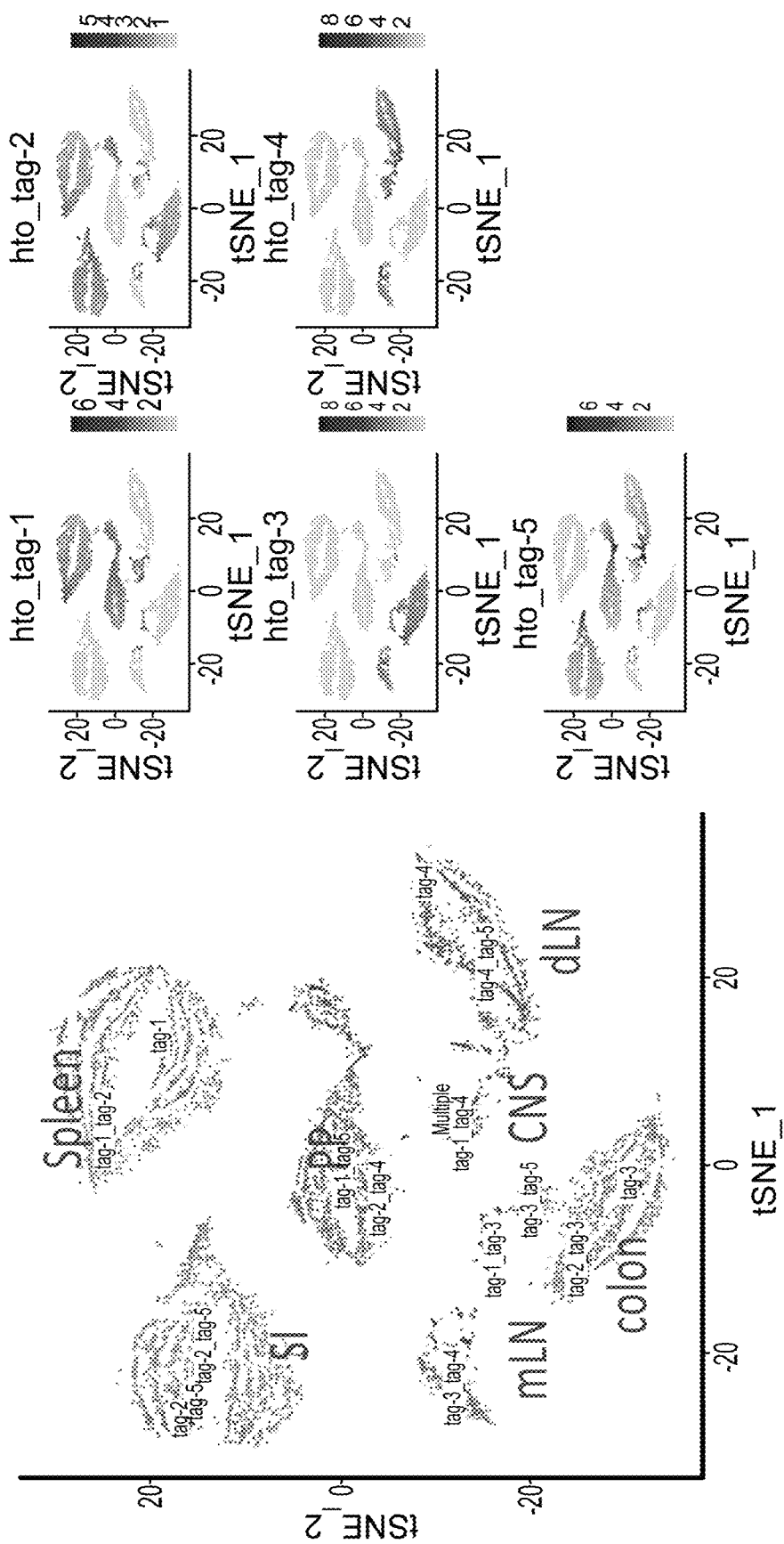
Figure 24A:
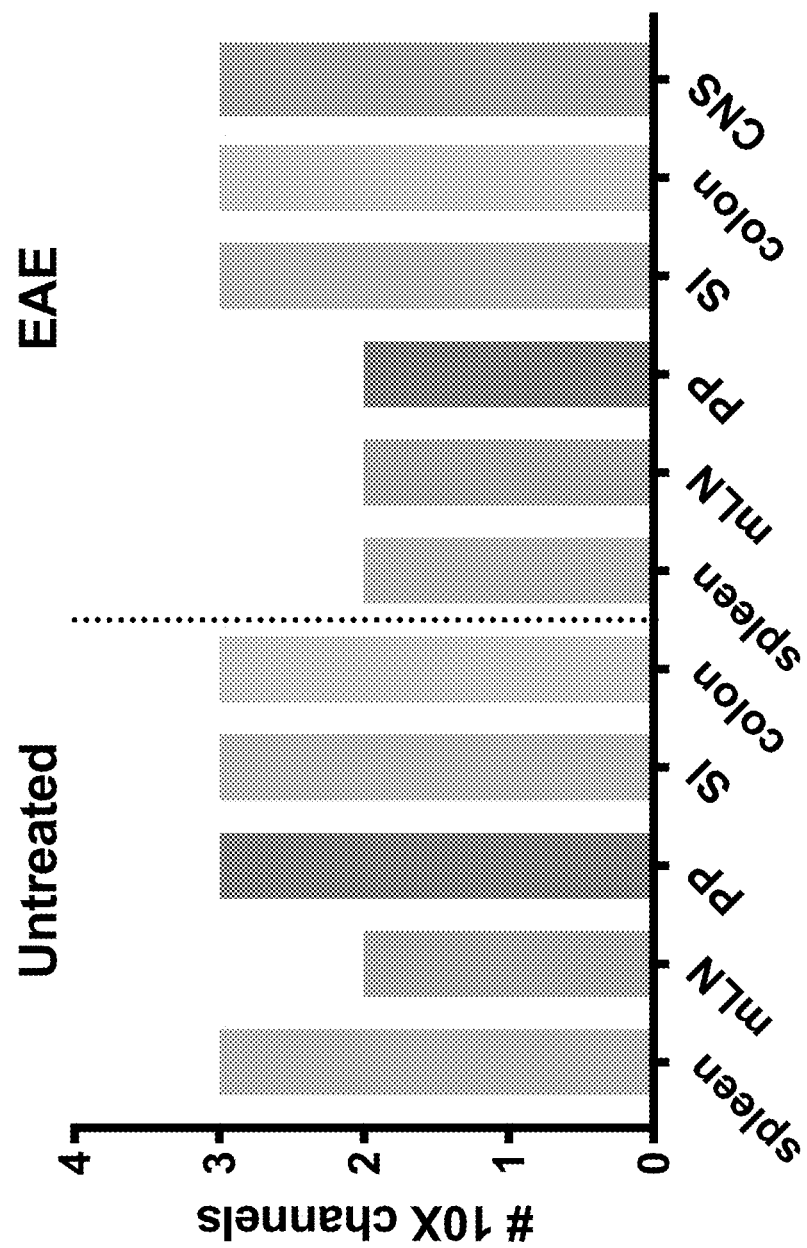
FIGS. 24A-24B— FIG. 24A. Graph showing 10× channels for the untreated and EAE Th17 cells.
Figure 24B:
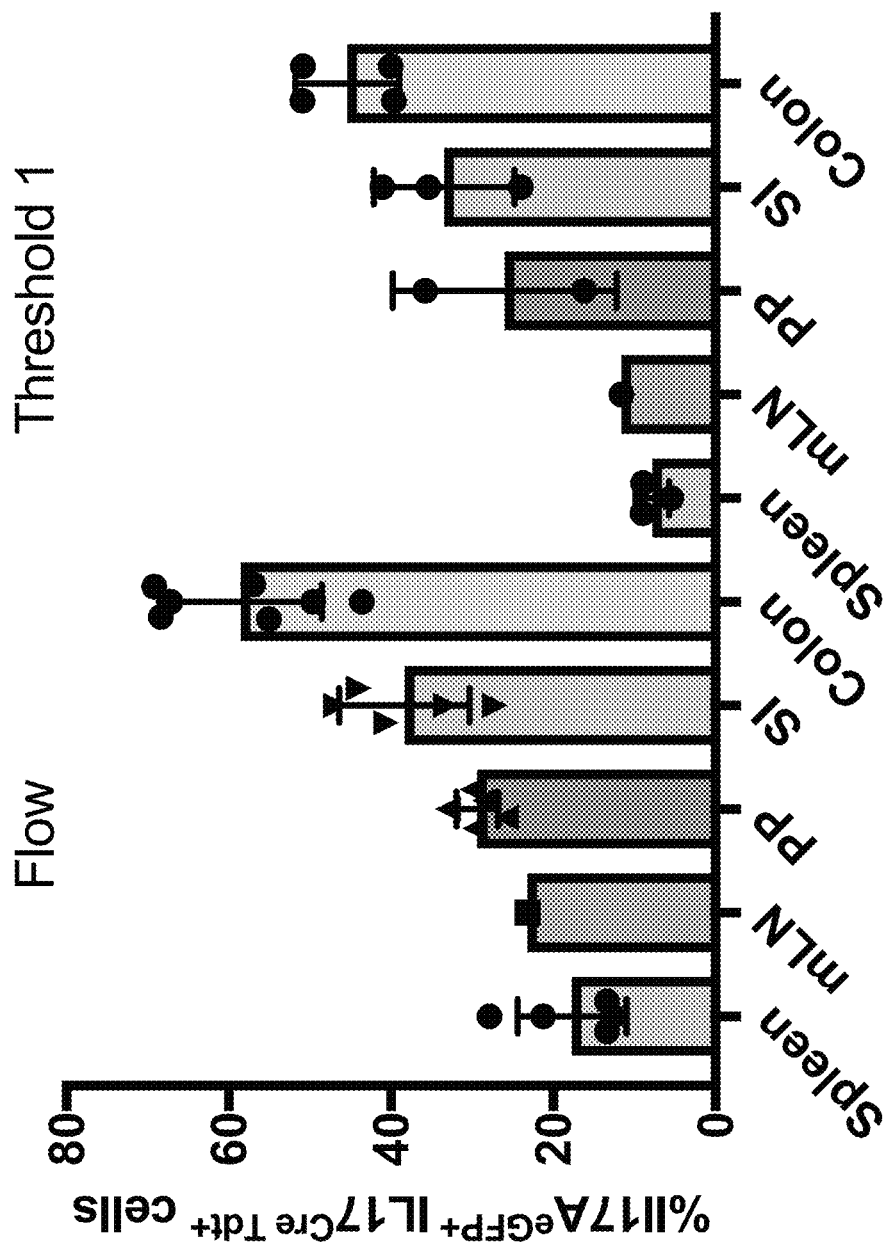

Applicants studied autoimmunity by using mice treated to induce experimental autoimmune encephalomyelitis (EAE) (FIGS. 8 and 9). Applicants discovered the dLN-Spleen-CNS axis in EAE (FIGS. 12, 15, 16). When comparing all of the tissues the most dramatic changes were observed in the spleen during EAE (FIGS. 10B, 13). Applicants discovered two clusters in the EAE spleen; a pathogenic (Cluster 0) and a stem-like (Cluster 1) population (FIG. 13). Cluster 0 may be the pathogenesis driving population and migrates to the CNS during EAE (FIG. 14). Cluster 0 has high clonal expansion and high proliferation. Cluster 0 is closely related to CNS and dLN Th17 populations and is transcriptionally similar to "pathogenic" Th17 cells. Applicants identified differentially expressed genes between Cluster 0 and cluster 1 (FIGS. 17, 18). Cluster 0 has high Cxcr6 and cluster 1 has high Slamf6. Table 4 shows that Slamf6 is downregulated in the spleen in EAE and Table 3 shows that Cxcr6 is upregulated in the spleen in EAE. Cluster 0 is increased in EAE. Slamf6 and Cxcr6 are surface markers that can be used to detect and quantitate each cluster (FIG. 18). Clusters may be identified by FACS, scRNA-seq or immunohistochemistry on samples obtained from a subject. Applicants also identified IFNγ-signaling for cluster 0 Th17 cells in the pathogenic spleen (FIGS. 19, 20).

Figure 25:
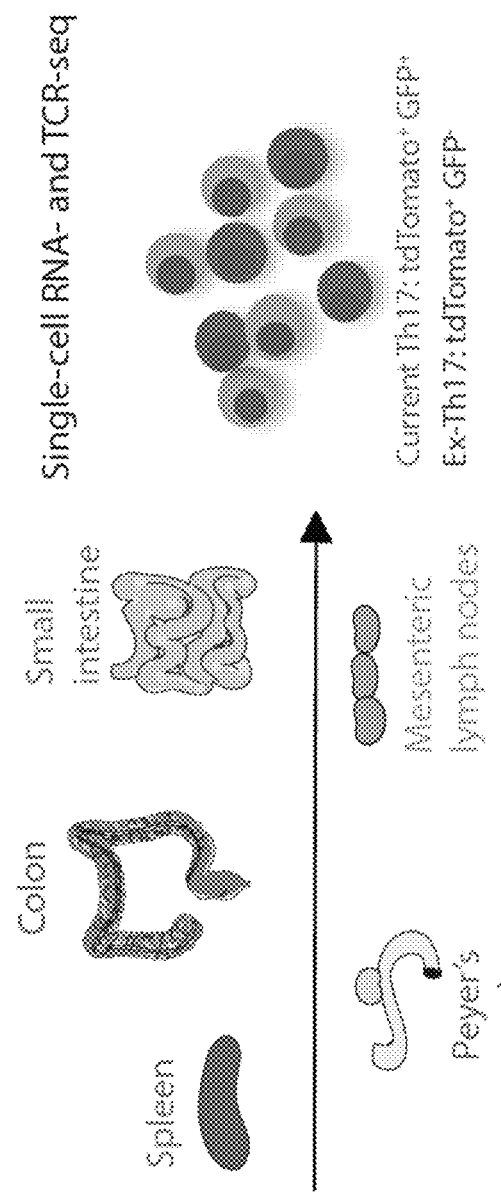
FIG. 25— Experimental set-up.
Figure 25:
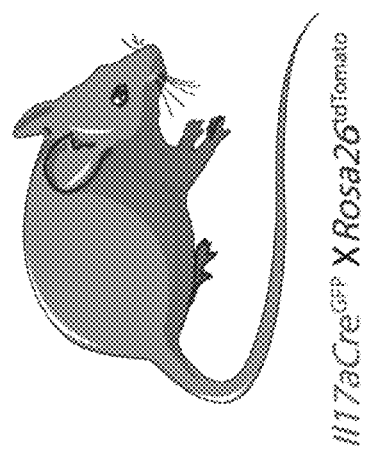
Figure 26:
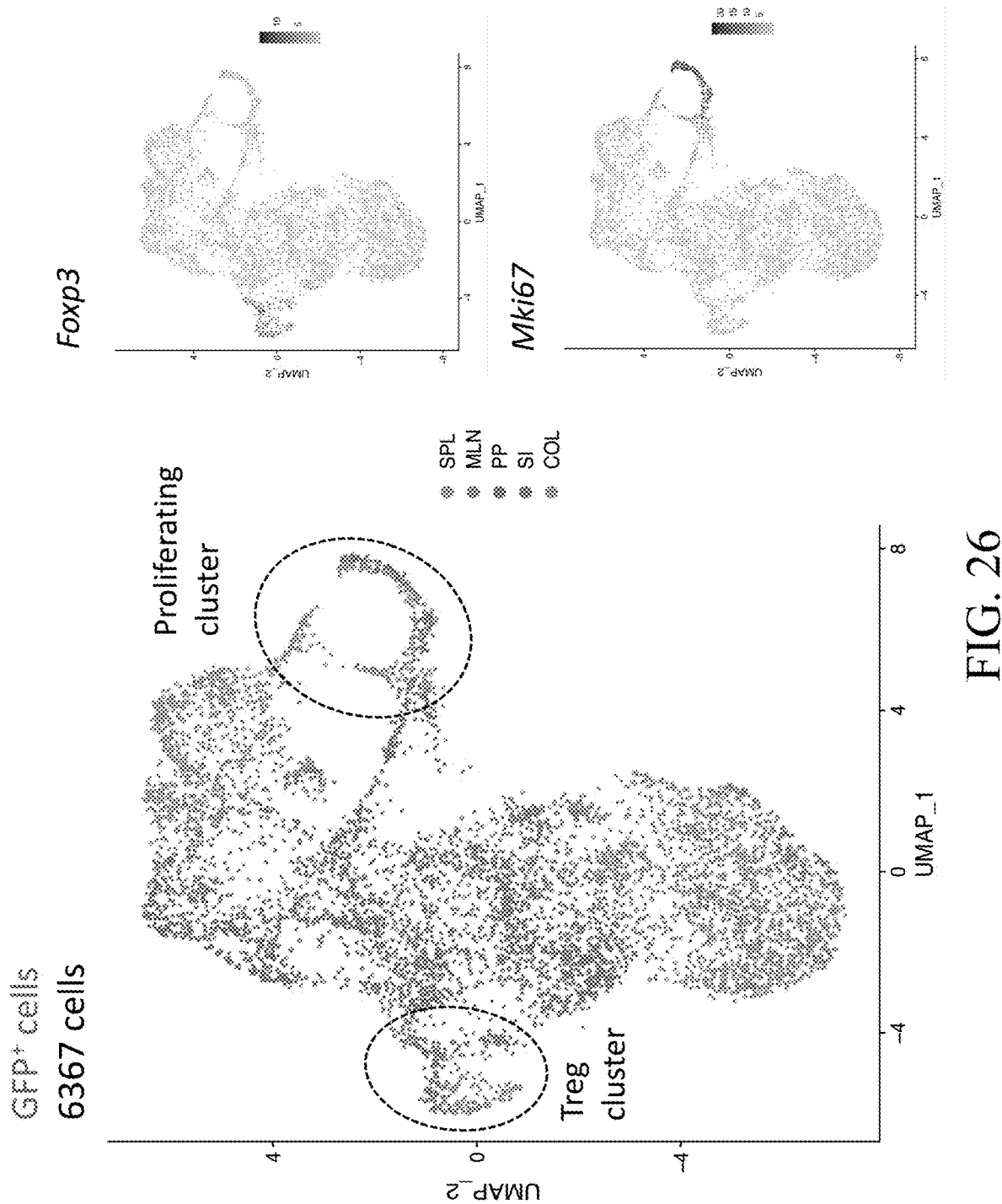
FIG. 26— Single-cell RNA sequencing identifies tissue-specific Th17 signatures.
Figure 27:
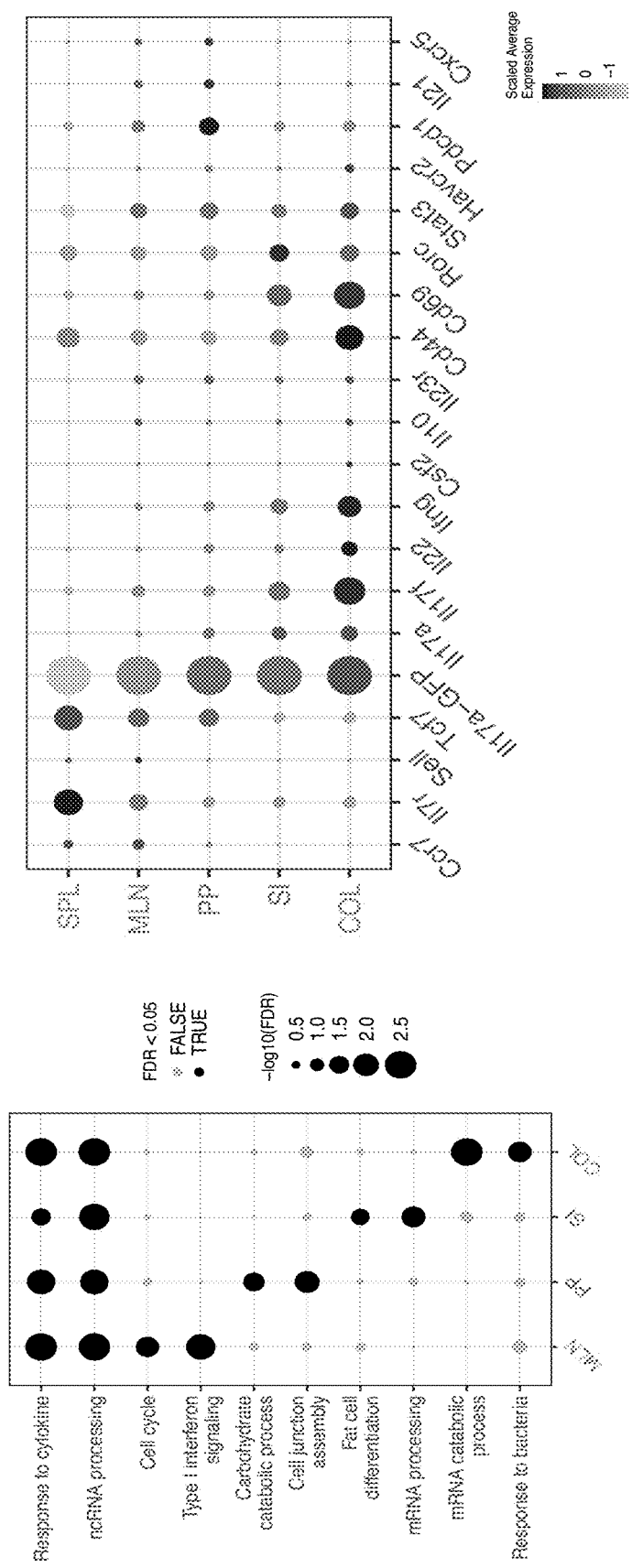
FIG. 27— Tissue specific Th17 signatures correspond to distinct functions.
Figure 28:
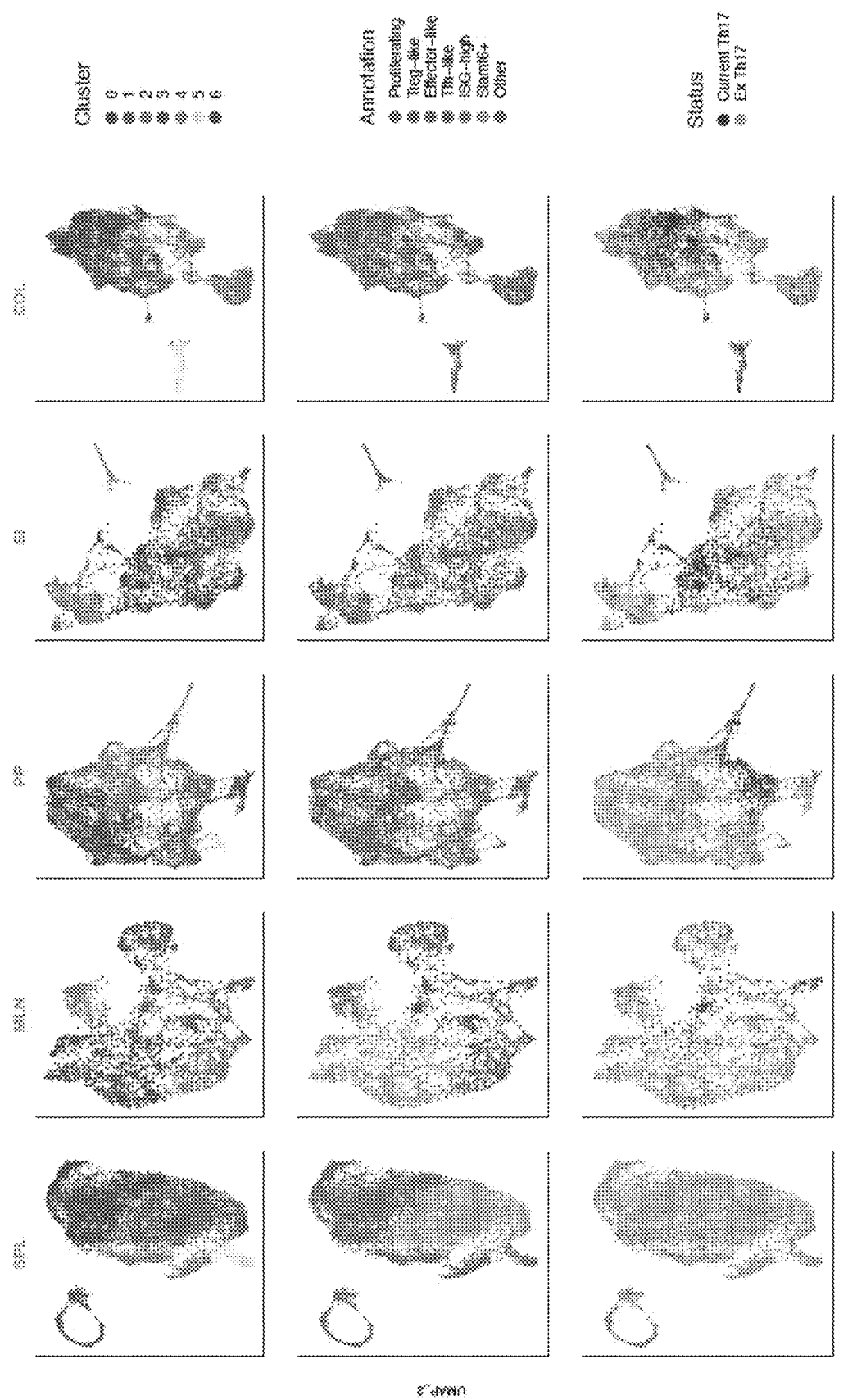
FIG. 28— Intra-tissue heterogeneity of tissue Th17 cells revealed with single-cell analysis.
Figure 29:
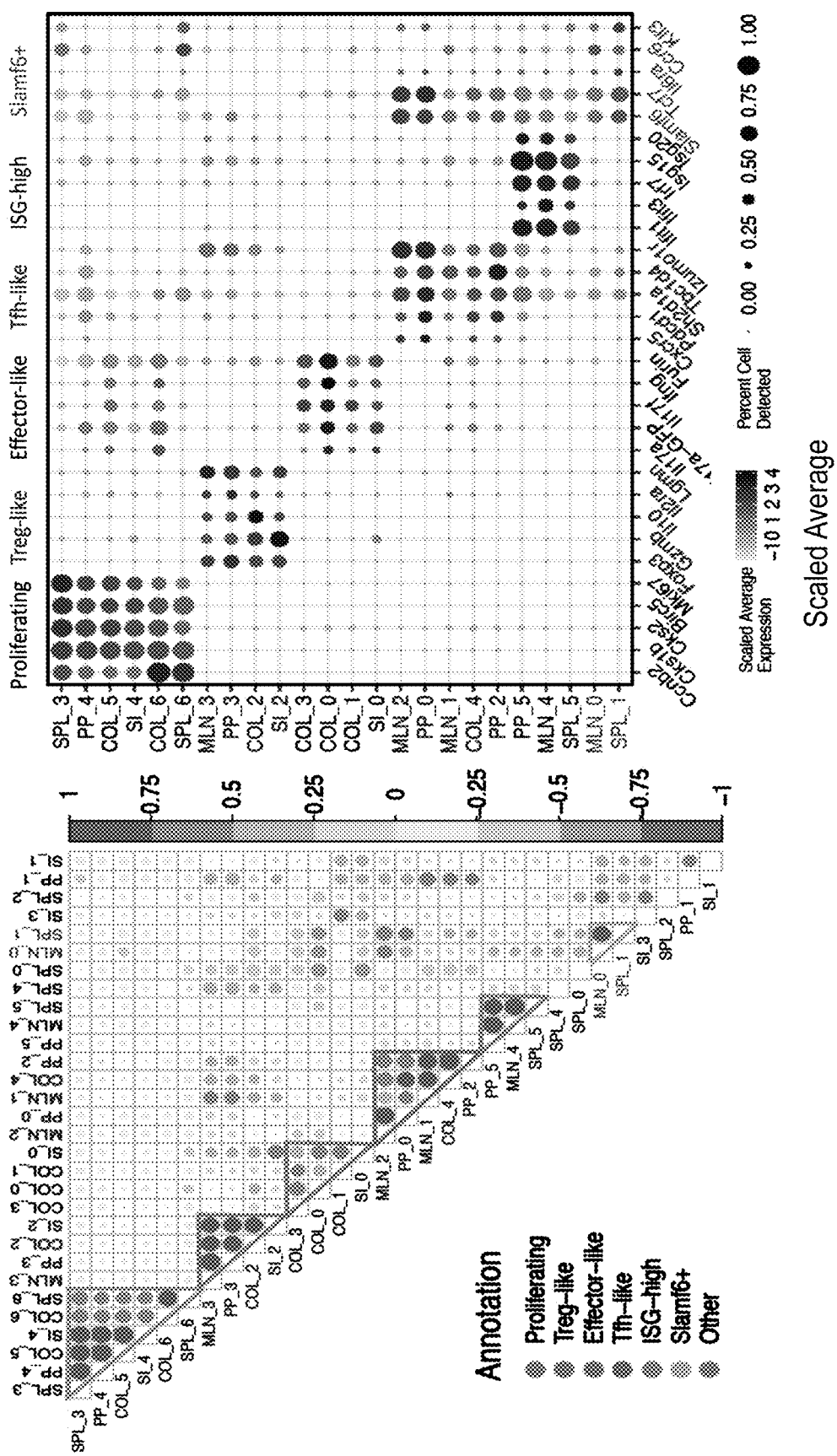
FIG. 29— Tissue Th17 cells acquire common heterogeneity in different tissues.
Figure 30A:
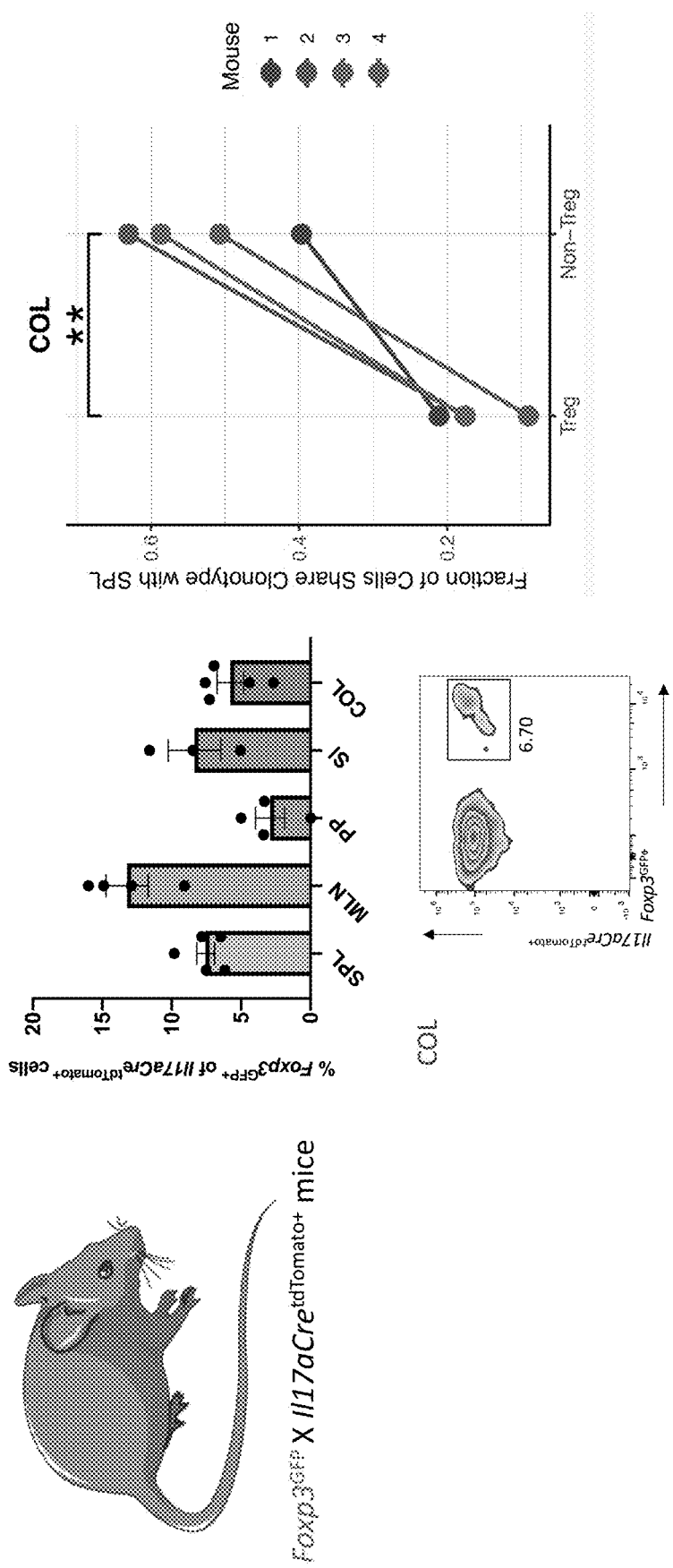
FIGS. 30A-30D— Low TCR similarity of IL7aCre$^{tdTomato+}$ Foxp3$^+$ Treg cells with tissue Th17 cells.
Figure 30B:
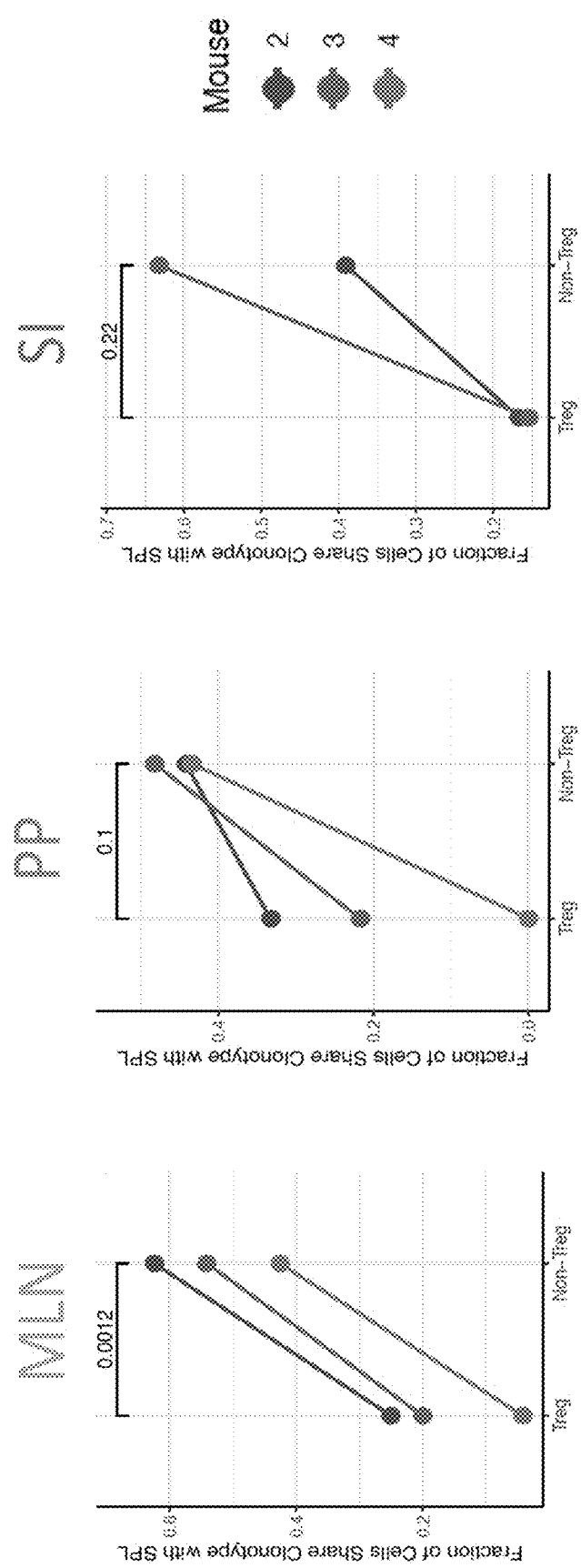
Figure 30C:
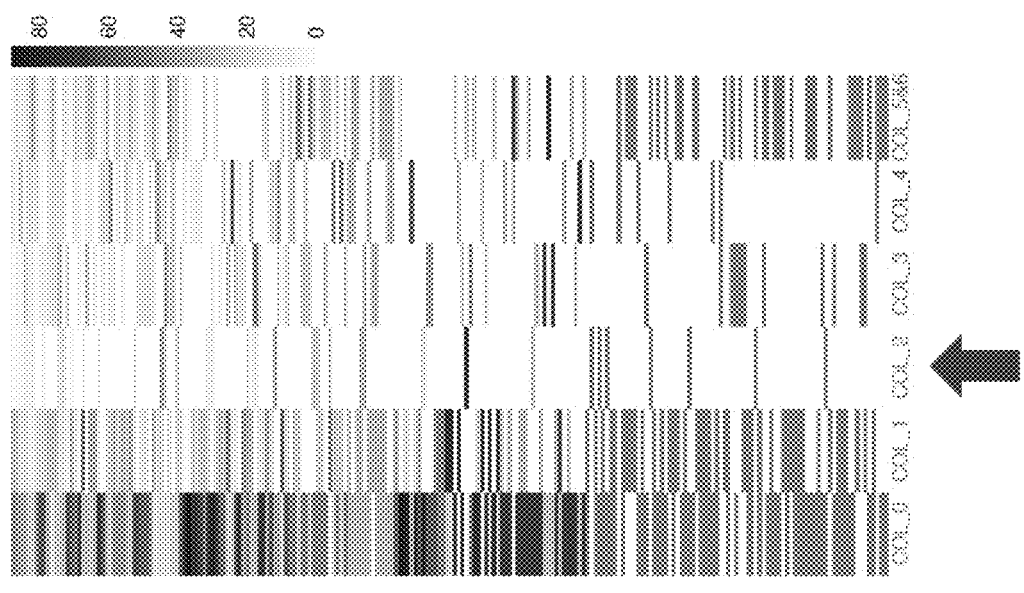
Figure 30C:
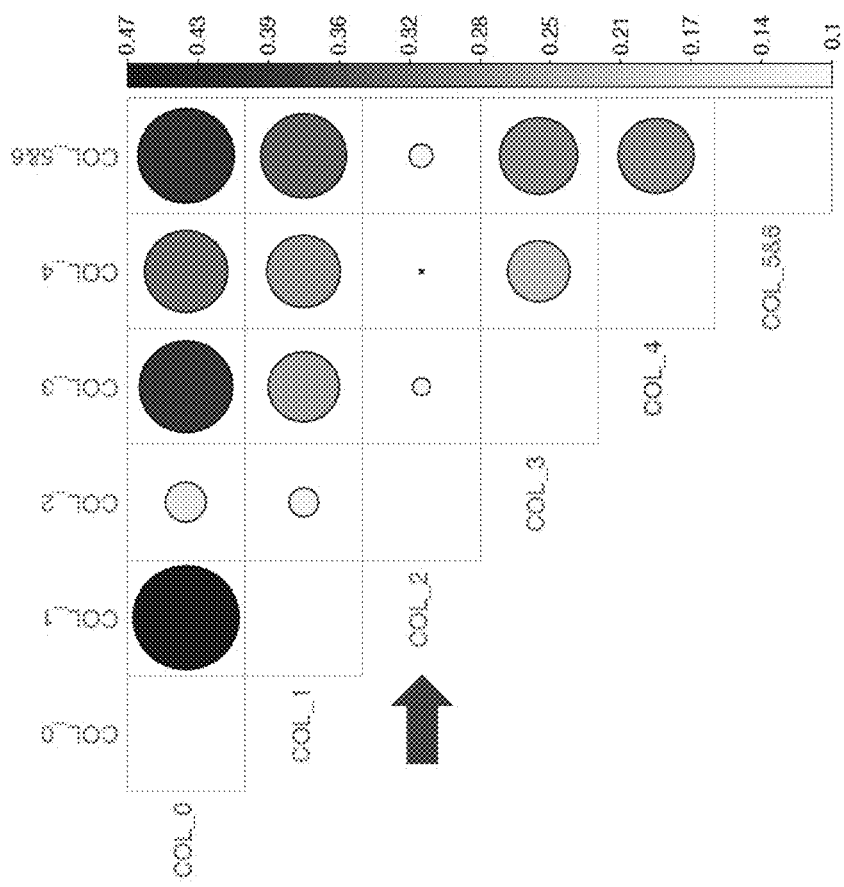
Figure 30D:
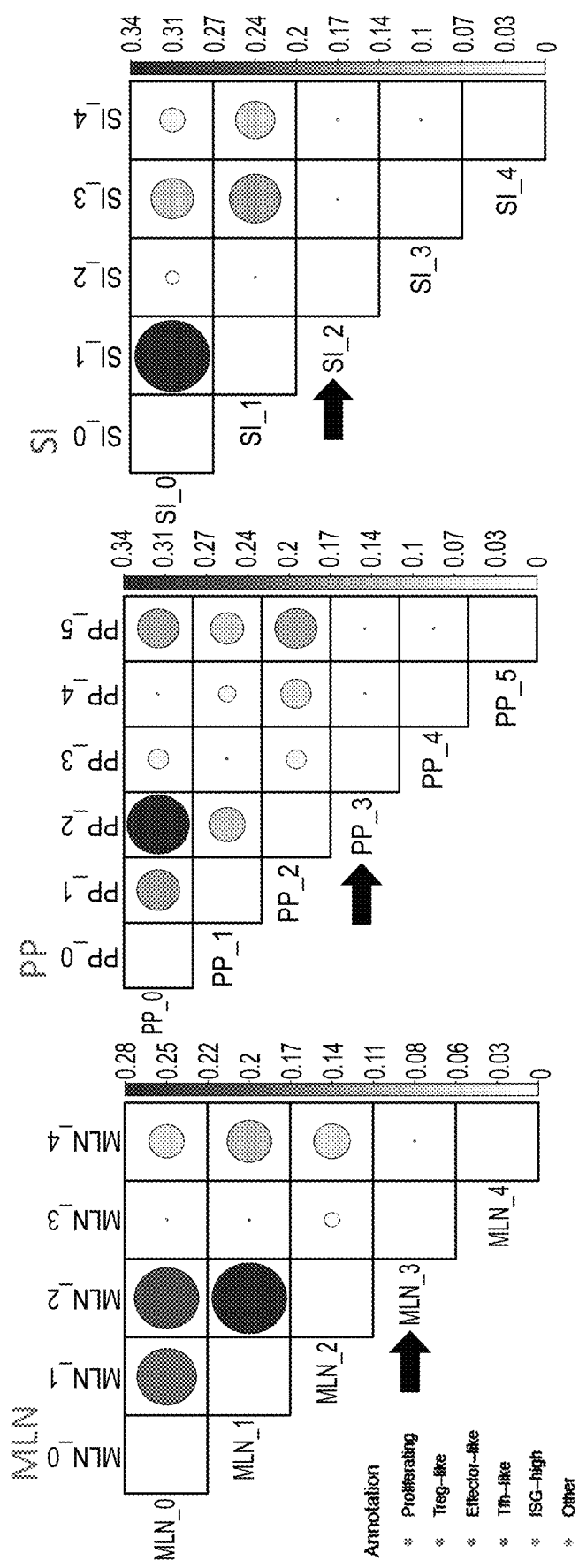
Figure 31:
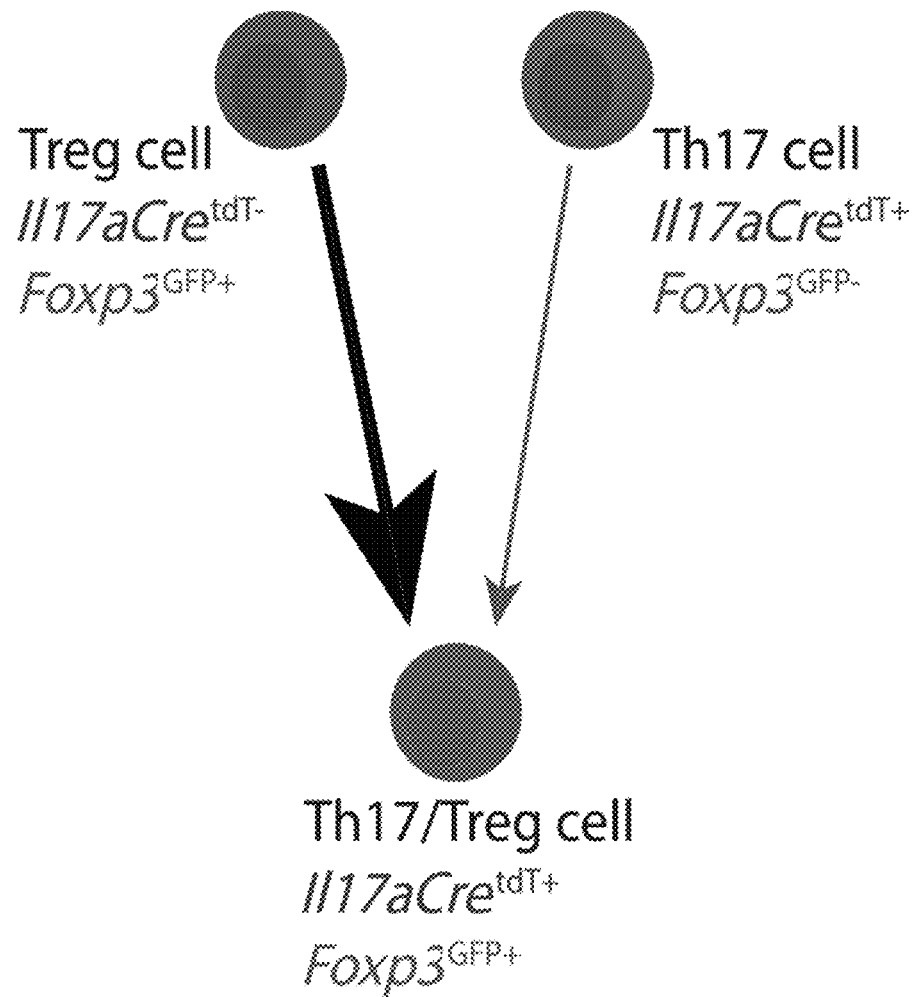
FIG. 31— TdTomato$^+$ tissue Treg cells are mostly derived from non-Th17 cells.

Example 3—Single-Cell Clonotype Tracing of Tissue Th17 Cells During CNS Autoimmunity Reveals Distinct Migration of Homeostatic and Pathogenic Subpopulations Applicants used a fate tracking TdTomato and Il17-GFP mouse to study single Th17 cells in tissues (FIG. 25). Single-cell RNA-sequencing identified tissue specific Th17 signatures (FIGS. 3 and 26-27). Applicants identified that tissue Th17 cells acquired common heterogeneity in different tissues (FIGS. 28-29). Applicants identified that TdTomato$^+$ tissue Treg cells are most likely derived from Treg cells but not from tissue Th17 cells (FIGS. 30-31).

Figure 32:
FIG. 32— Experimental autoimmune encephalomyelitis (EAE).
Figure 33A:
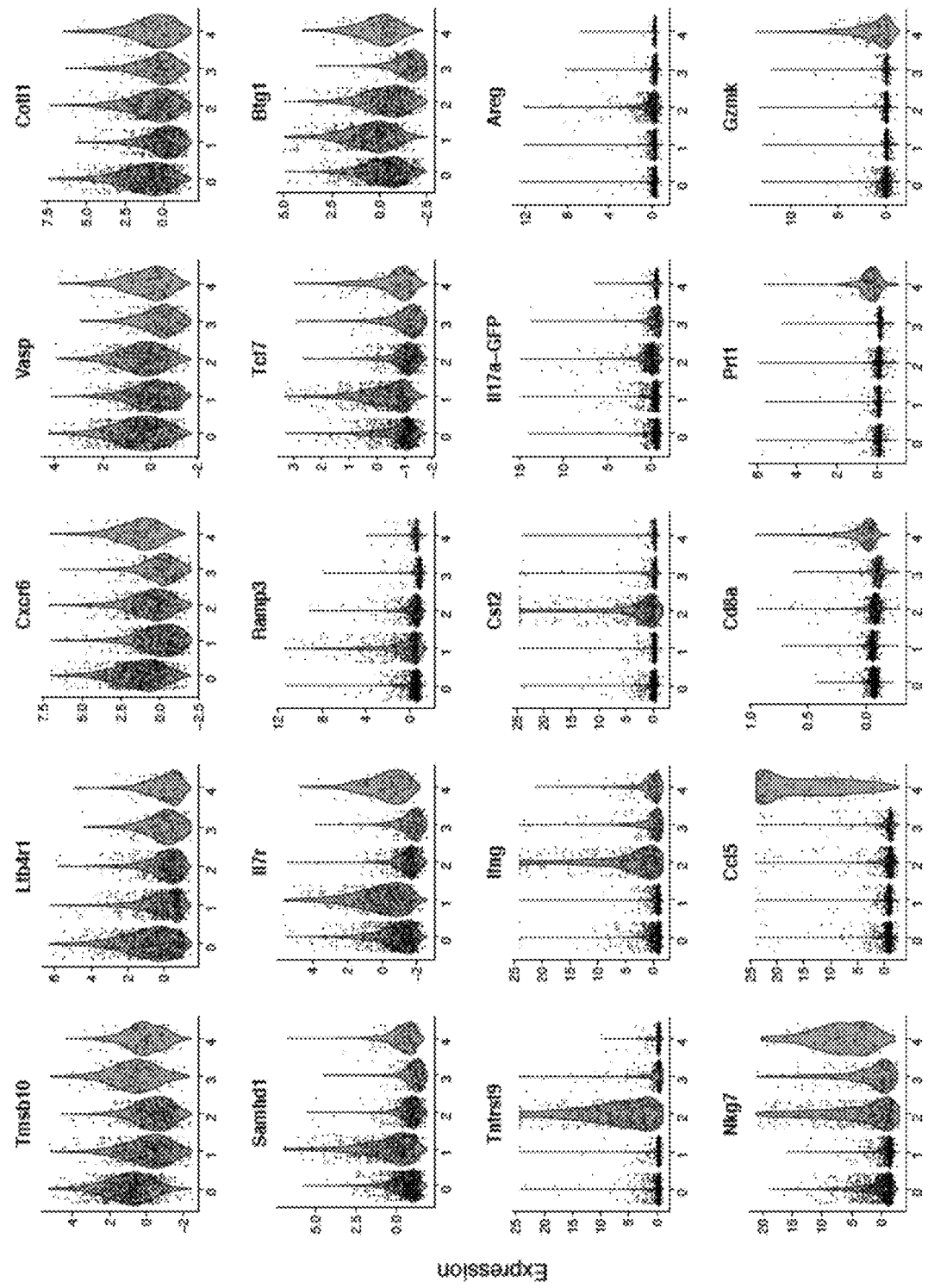
FIGS. 33A-33F— Identification of functionally distinct encephalitogenic Th17 cell subpopulations.
Figure 33B:
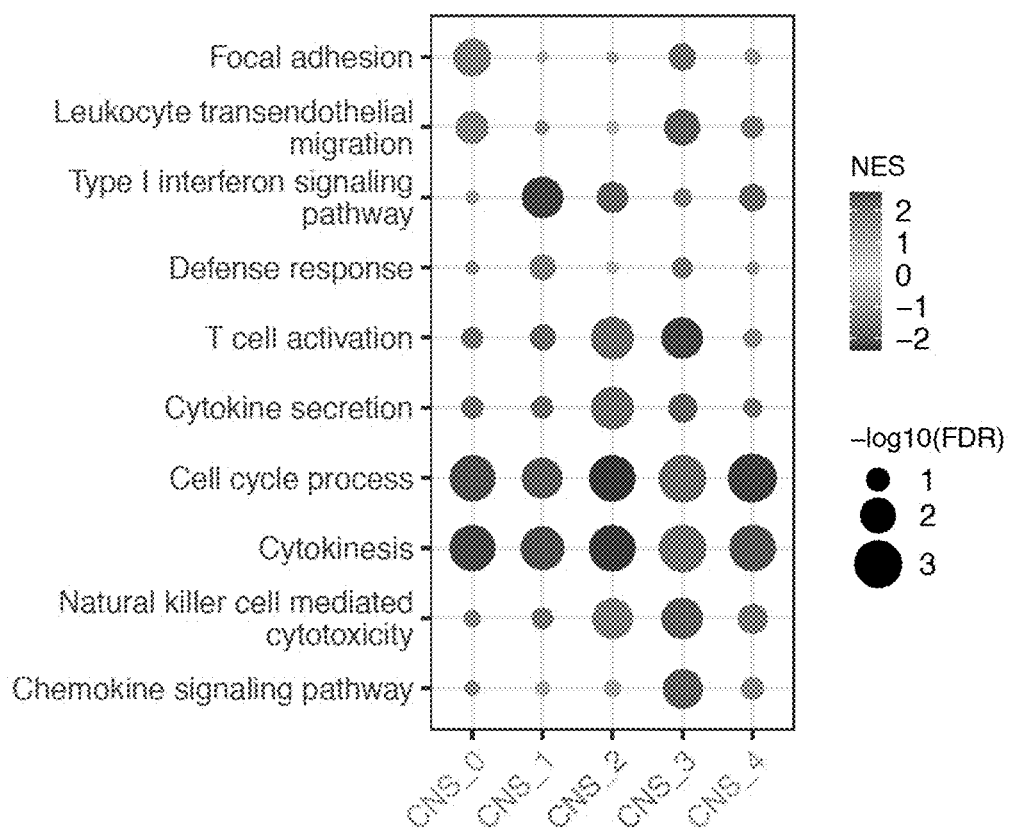
Figure 33C:
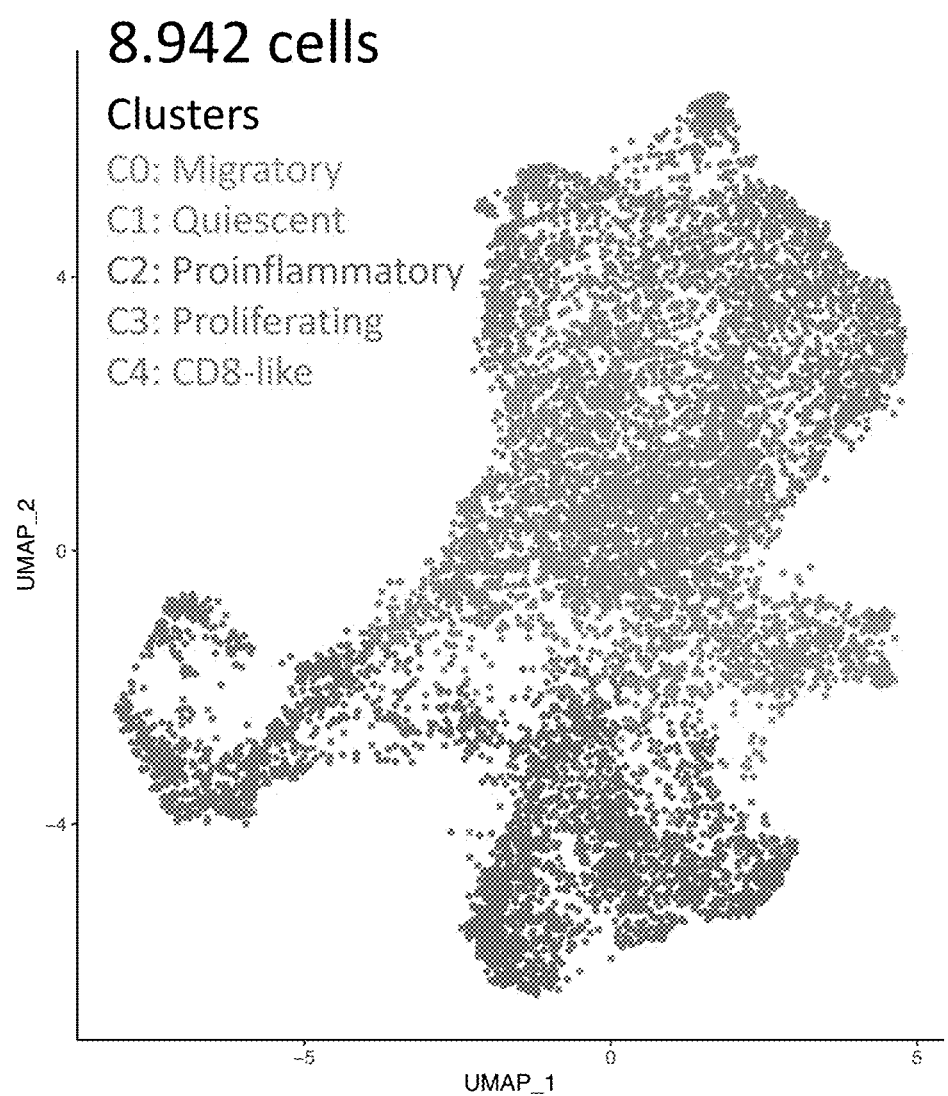
Figure 33D:
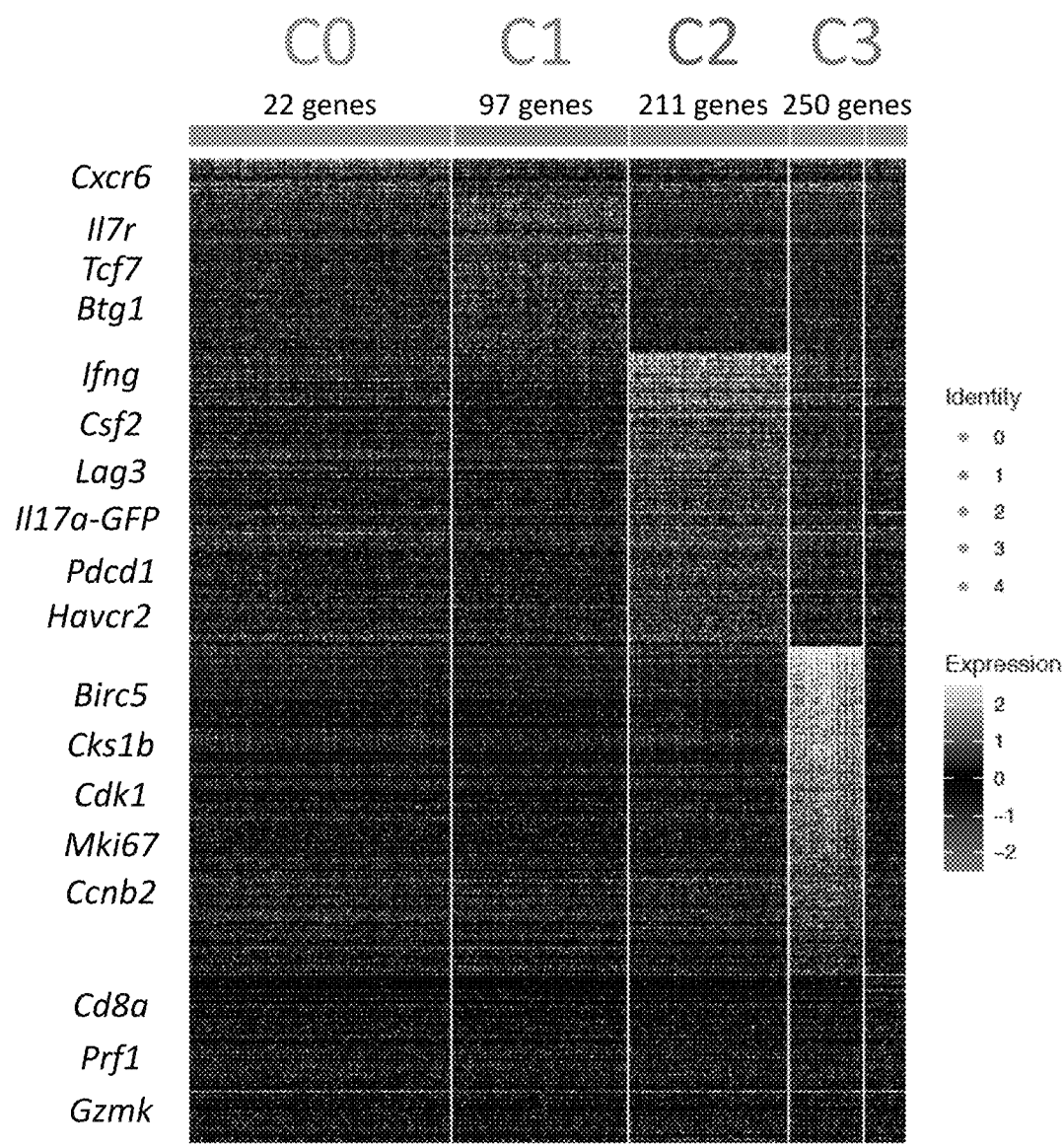
Figure 33E:
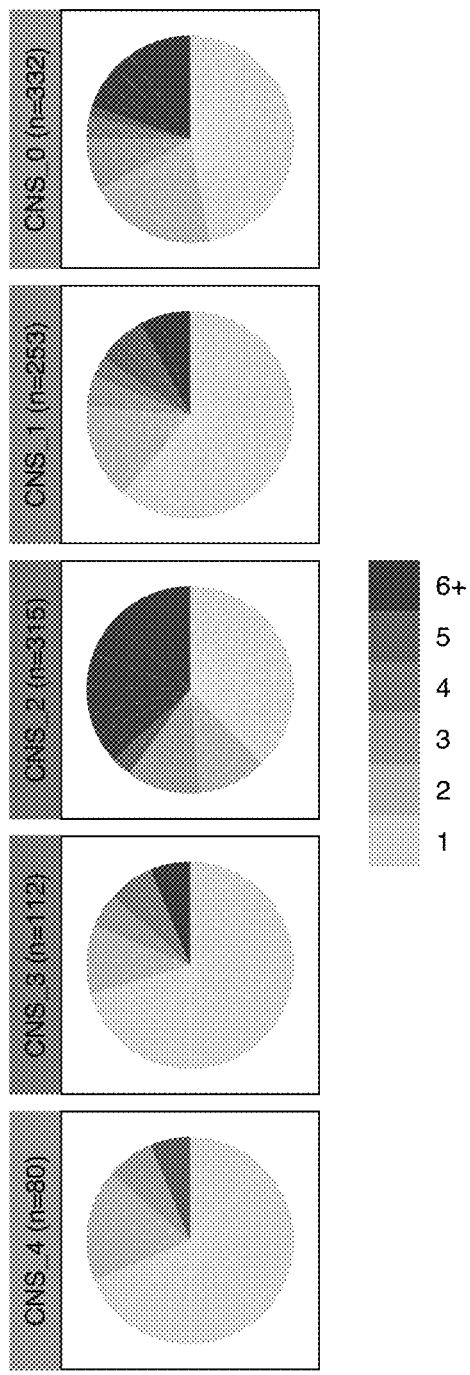
Figure 33F:
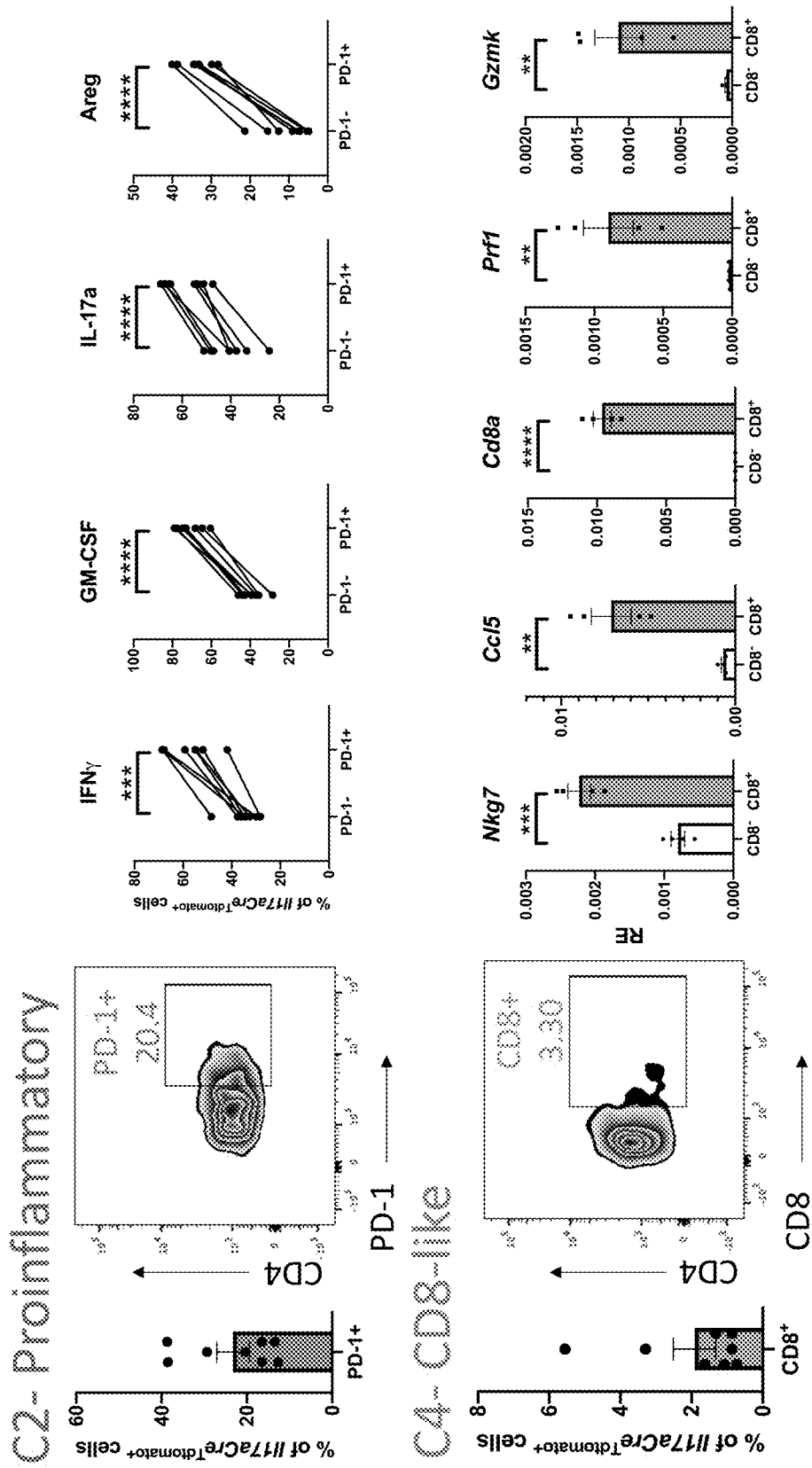
Figure 34:
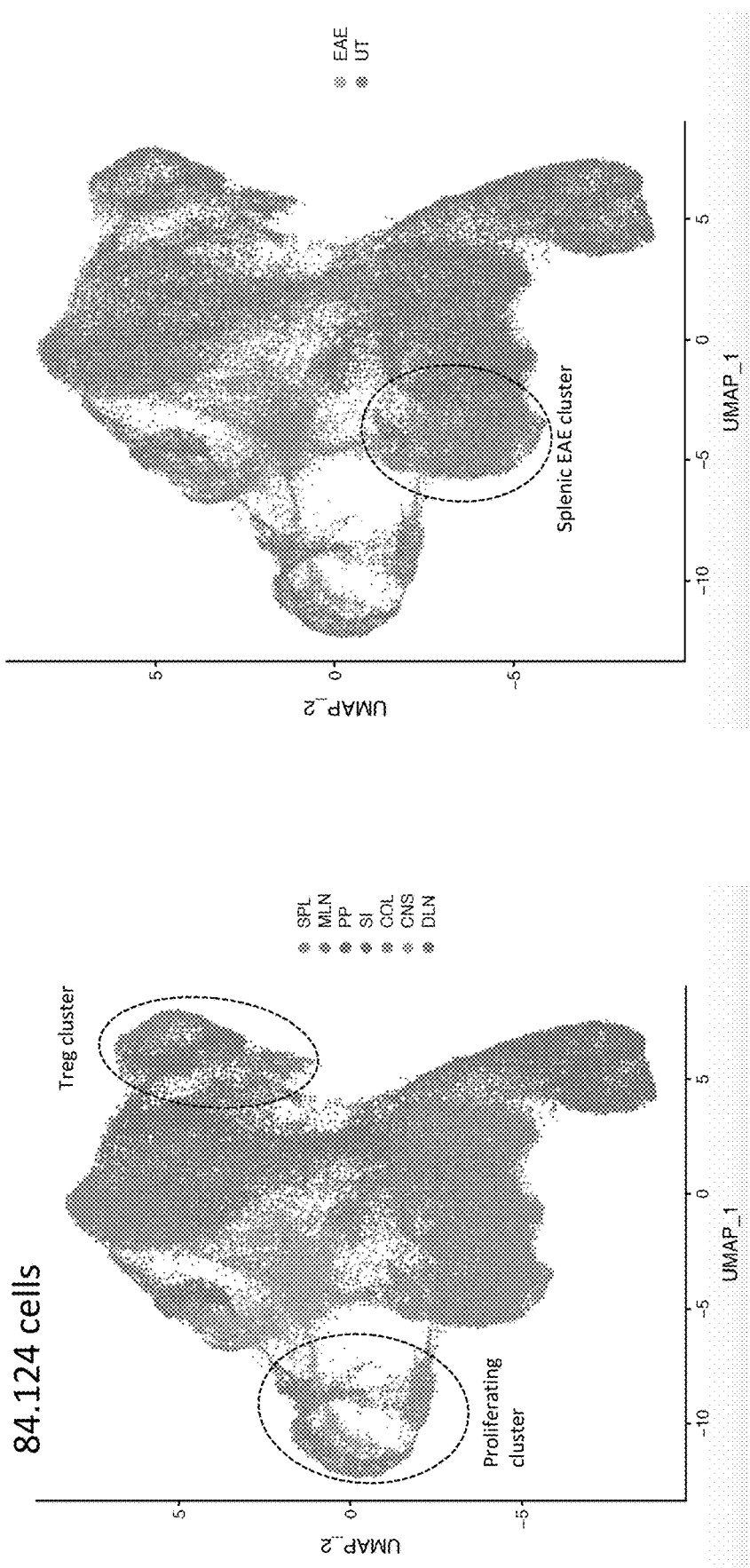
FIG. 34— Single-cell profiling of tissue Th17 cells during EAE (UT is Untreated).
Figure 35:
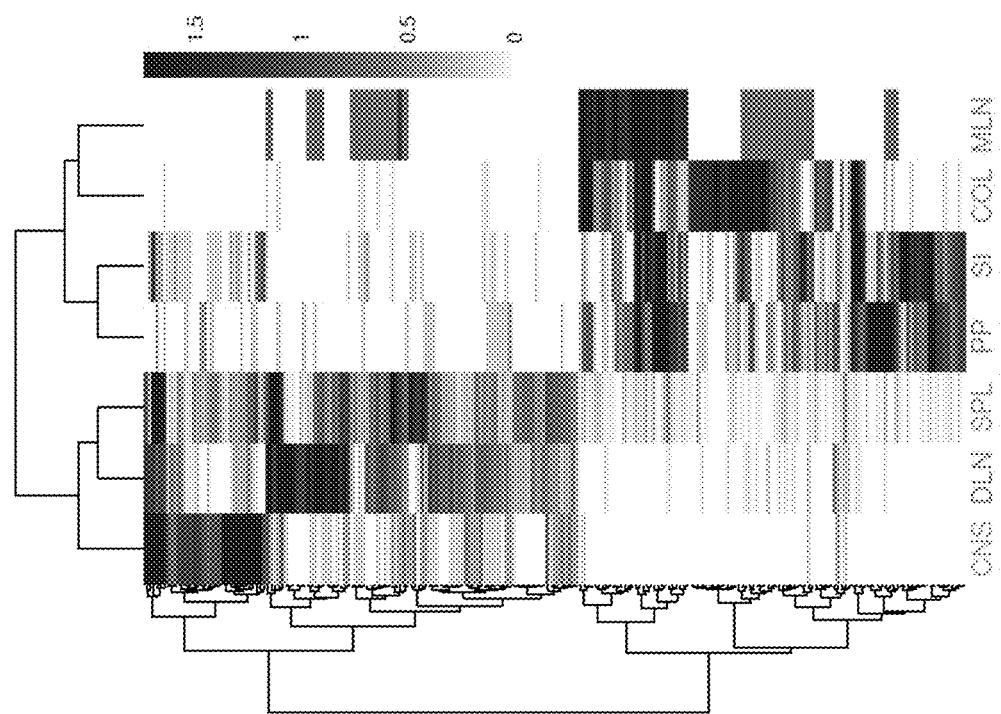
FIG. 35— Discovery of two ecosystems of Th17 cell migration during EAE.
Figure 35:
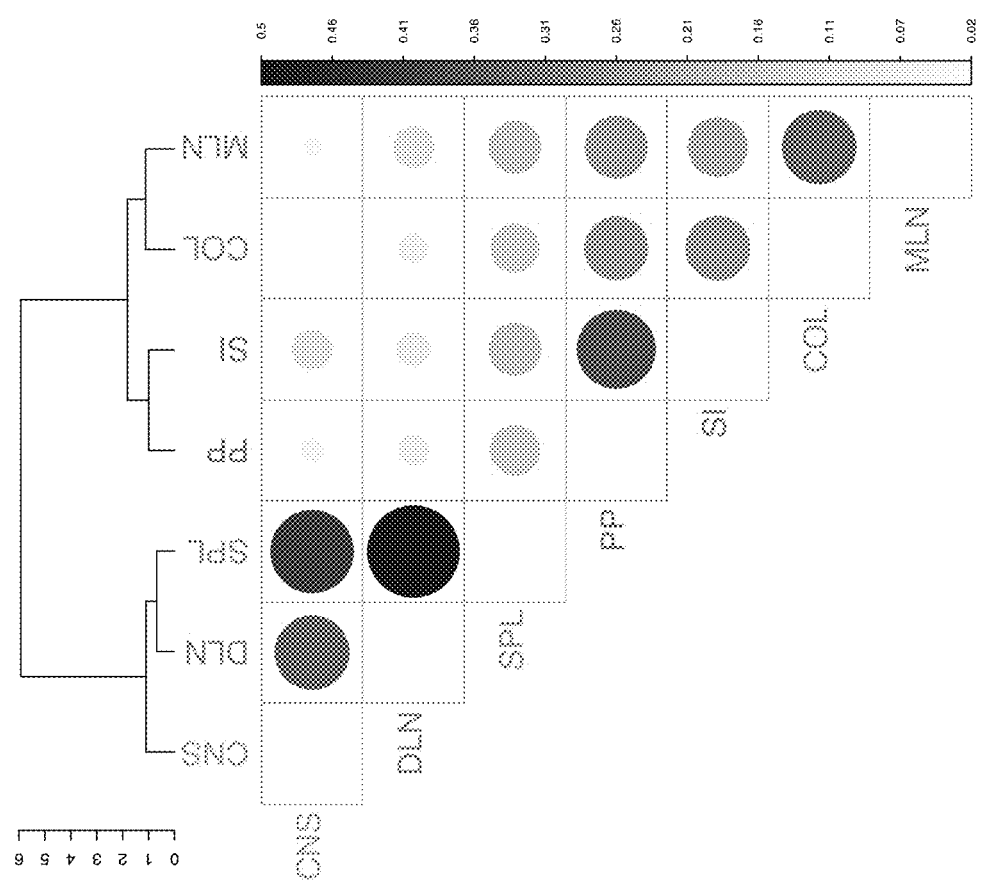
Figure 36:
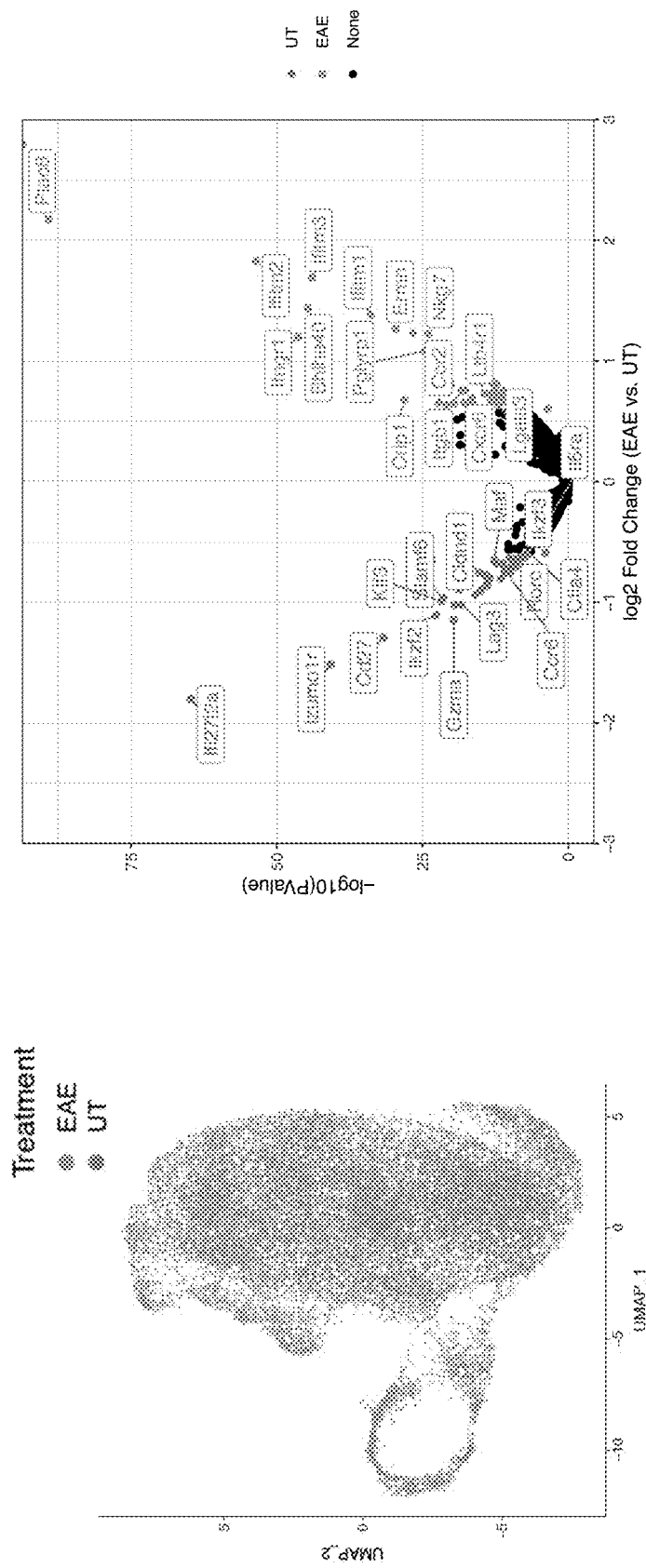
FIG. 36— Vast changes of the splenic Th17 population during EAE.
Figure 37A:
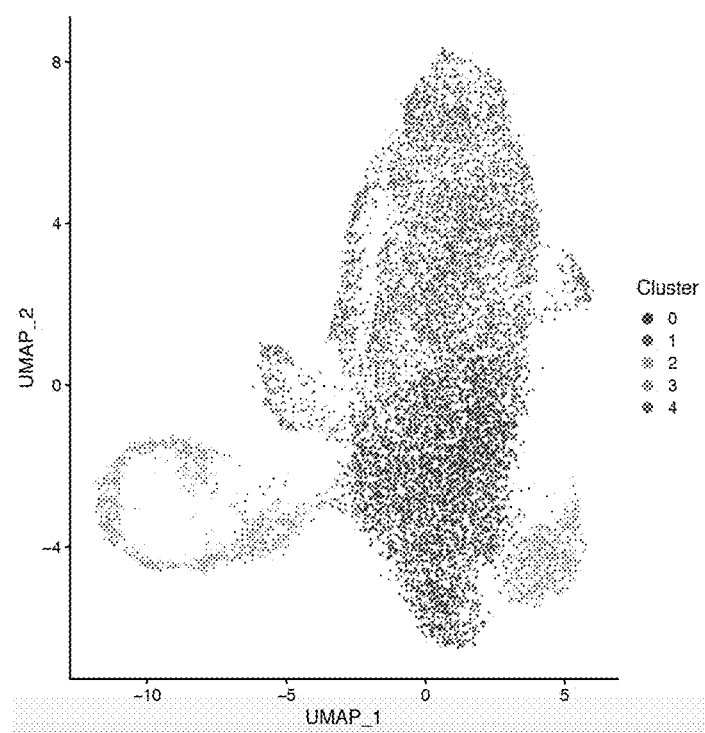
FIGS. 37A-37D— Discovery of distinct homeostatic and pathogenic Th17 populations in the spleen.
Figure 37B:
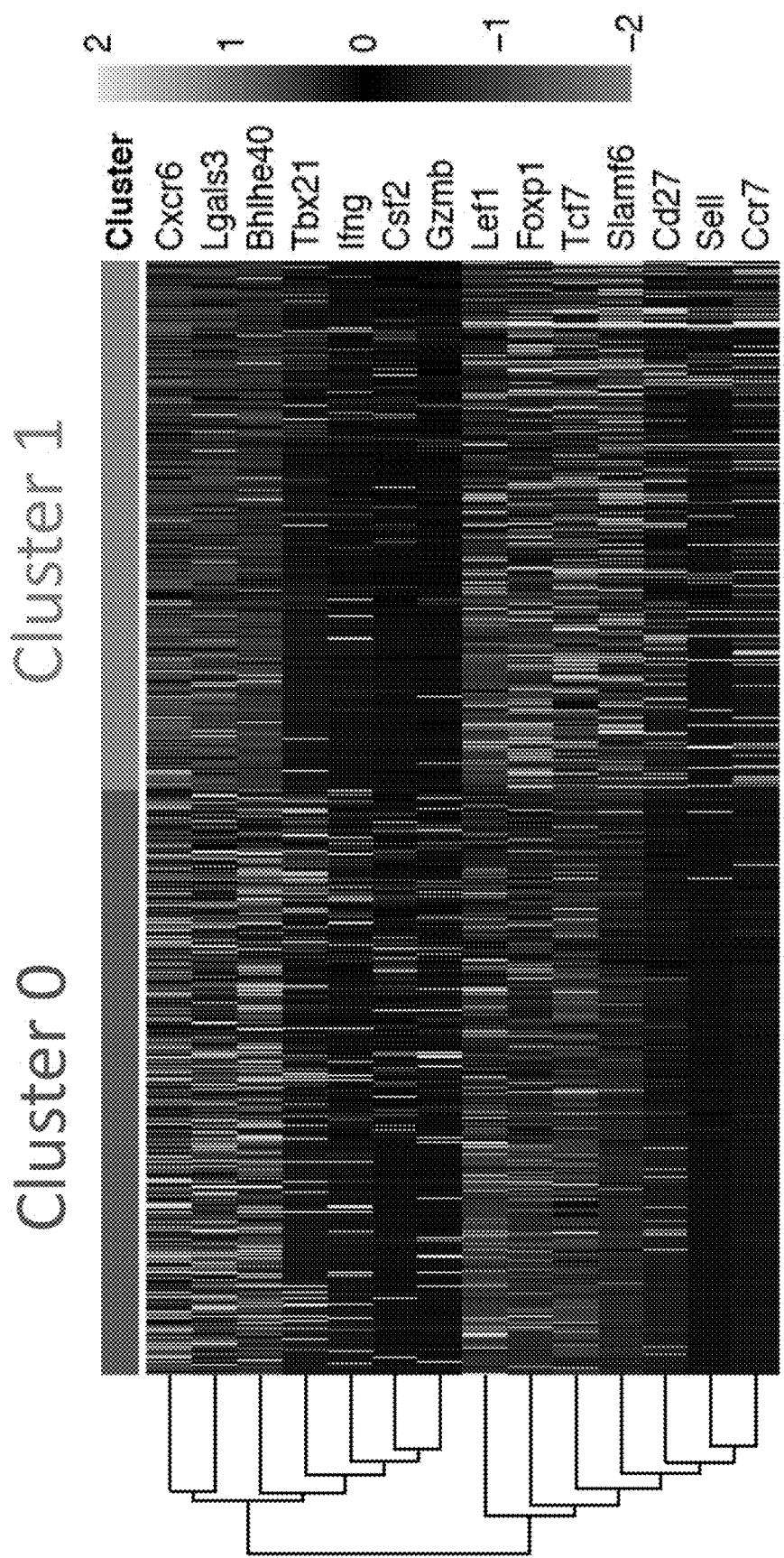
Figure 37C:
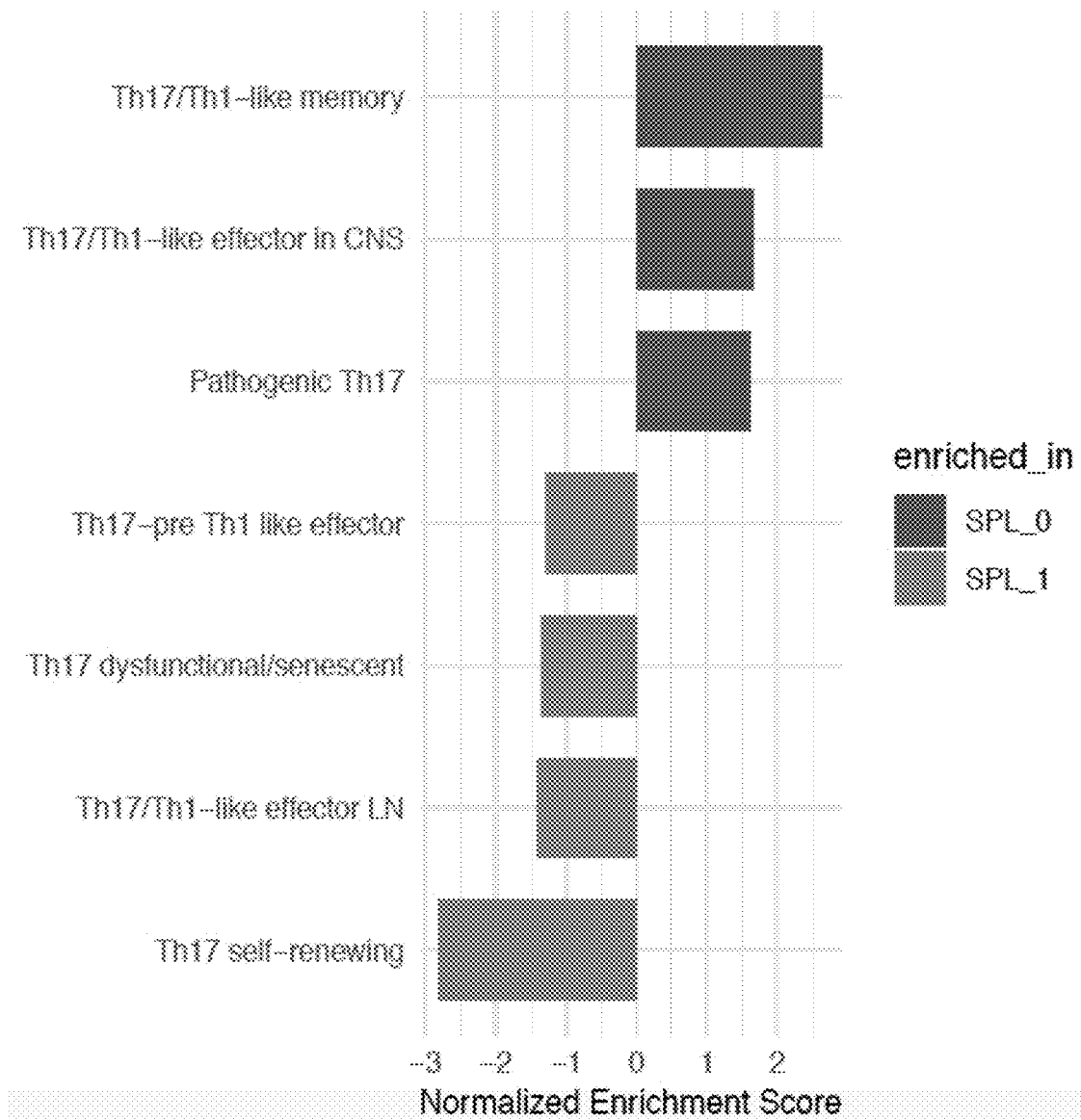
Figure 37D:
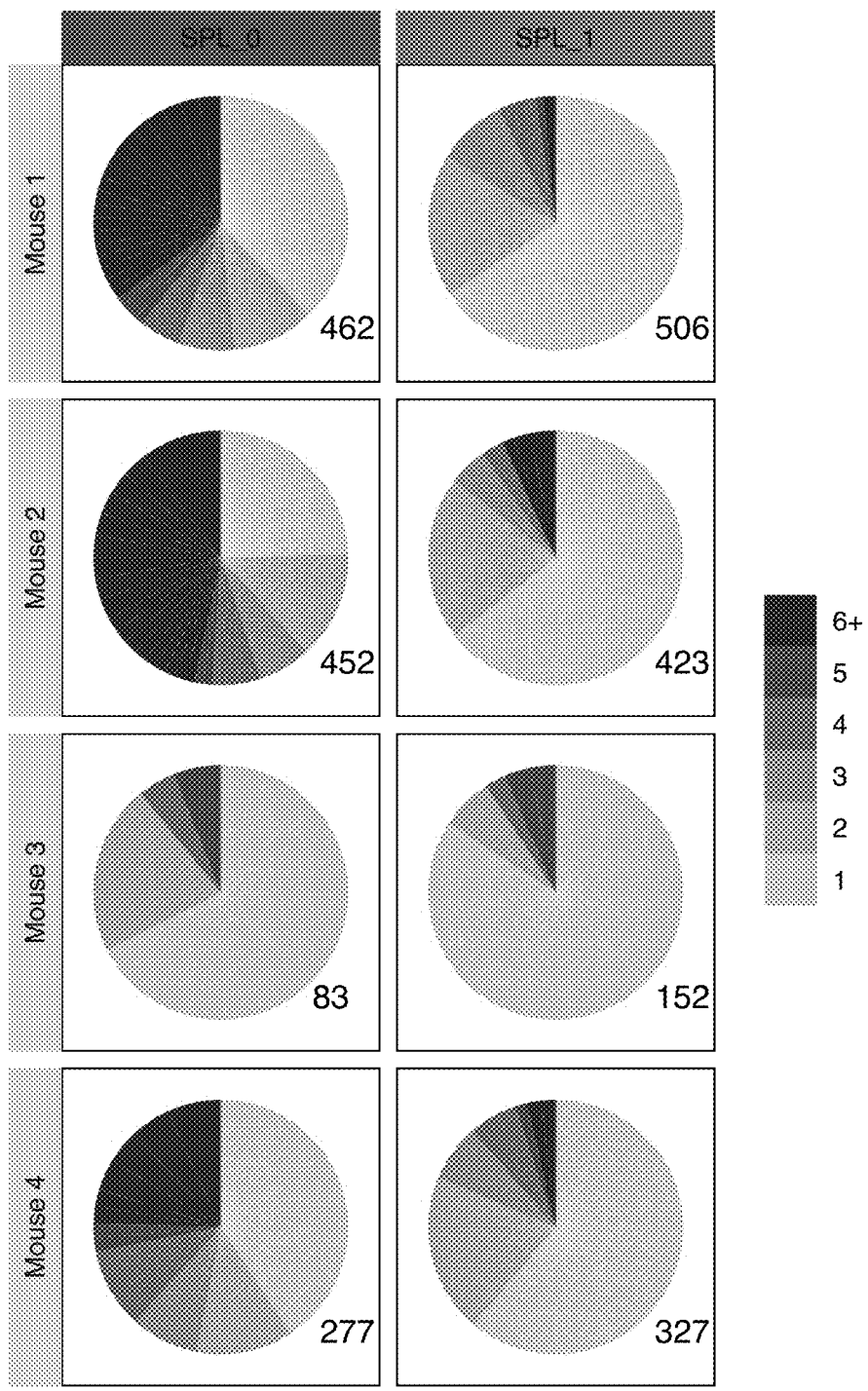

Applicants studied autoimmunity by using mice treated to induce experimental autoimmune encephalomyelitis (EAE) (FIG. 32). Applicants identified functionally distinct encephalitogenic Th17 cell subpopulations (CNS_0, CNS_1, CNS_2, CNS_3, and CNS_4) (FIG. 33). Applicants used the mouse model and single-cell RNA-seq to profile tissue specific Th17 cells during EAE (FIG. 34). Applicants discovered two ecosystems of Th17 cell migration during EAE (FIG. 35). One ecosystem was localized to the spleen, draining lymph node and central nervous system. Comparison of all of the tissues showed that the most dramatic changes were observed in the spleen during EAE (FIG. 36).

Figure 38:
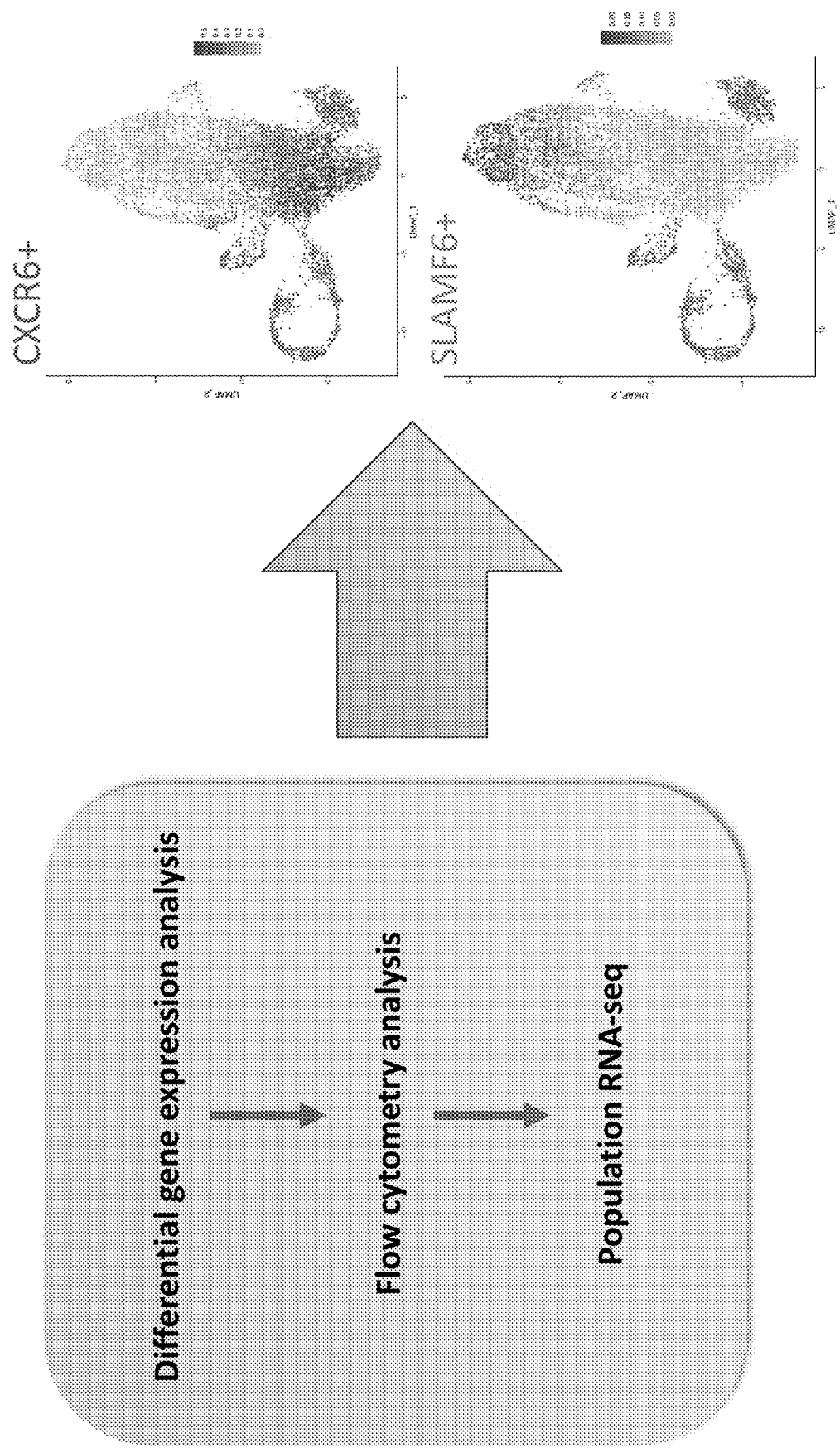
FIG. 38— Validation of CXCR6 and SLAMF6 as surface markers for SPL_0 and SPL_1 populations.
Figure 39:
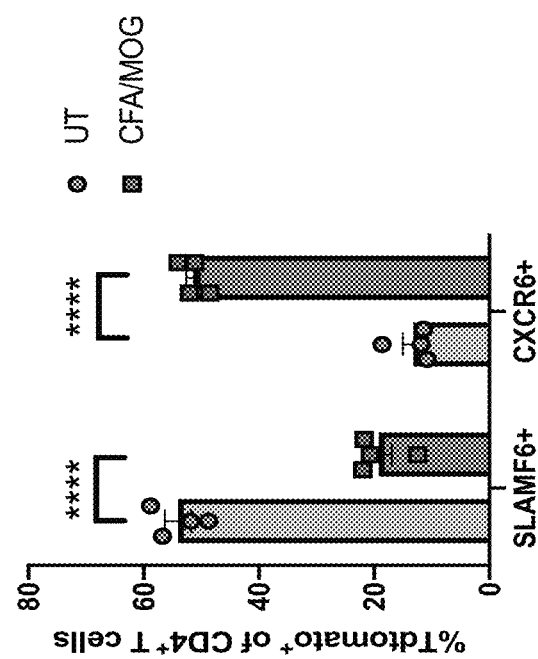
FIG. 39— Appearance of the CXCR6+ population during EAE.
Figure 39:
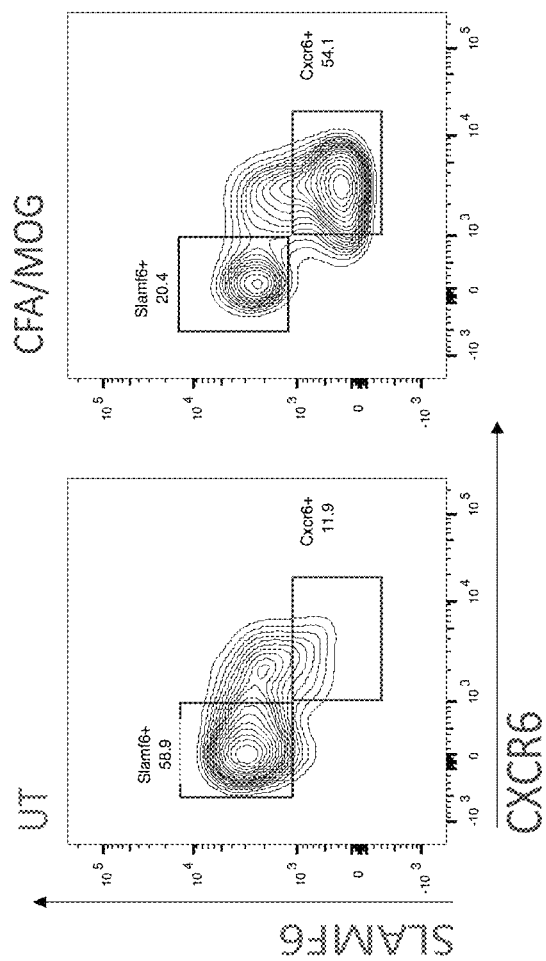
Figure 40:
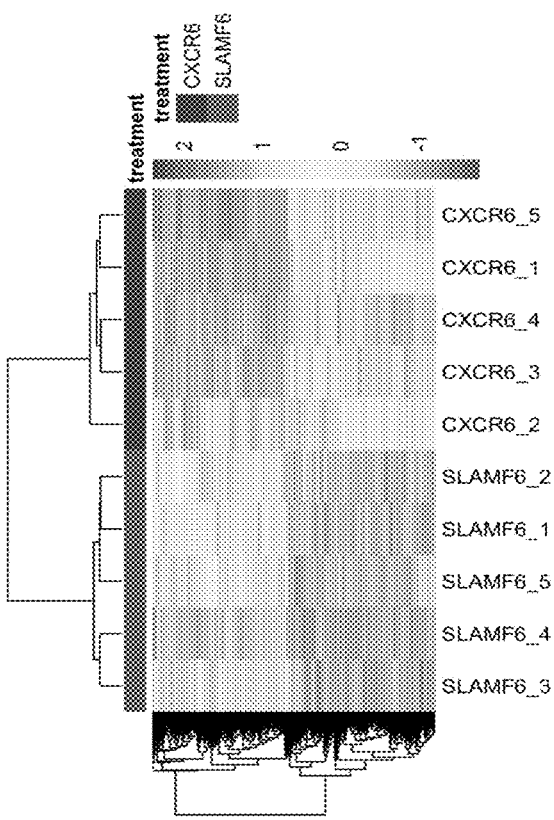
FIG. 40— Vastly distinct chromatin landscape of the CXCR6+ and SLAMF6+ subpopulations.
Figure 40:
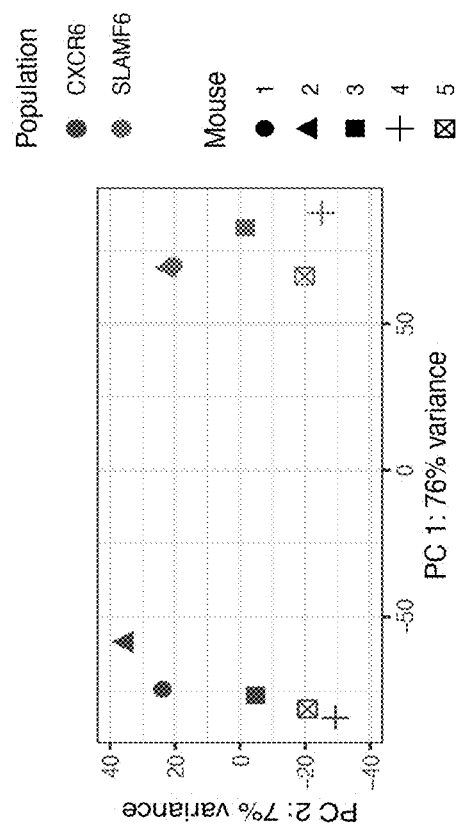
Figure 41:
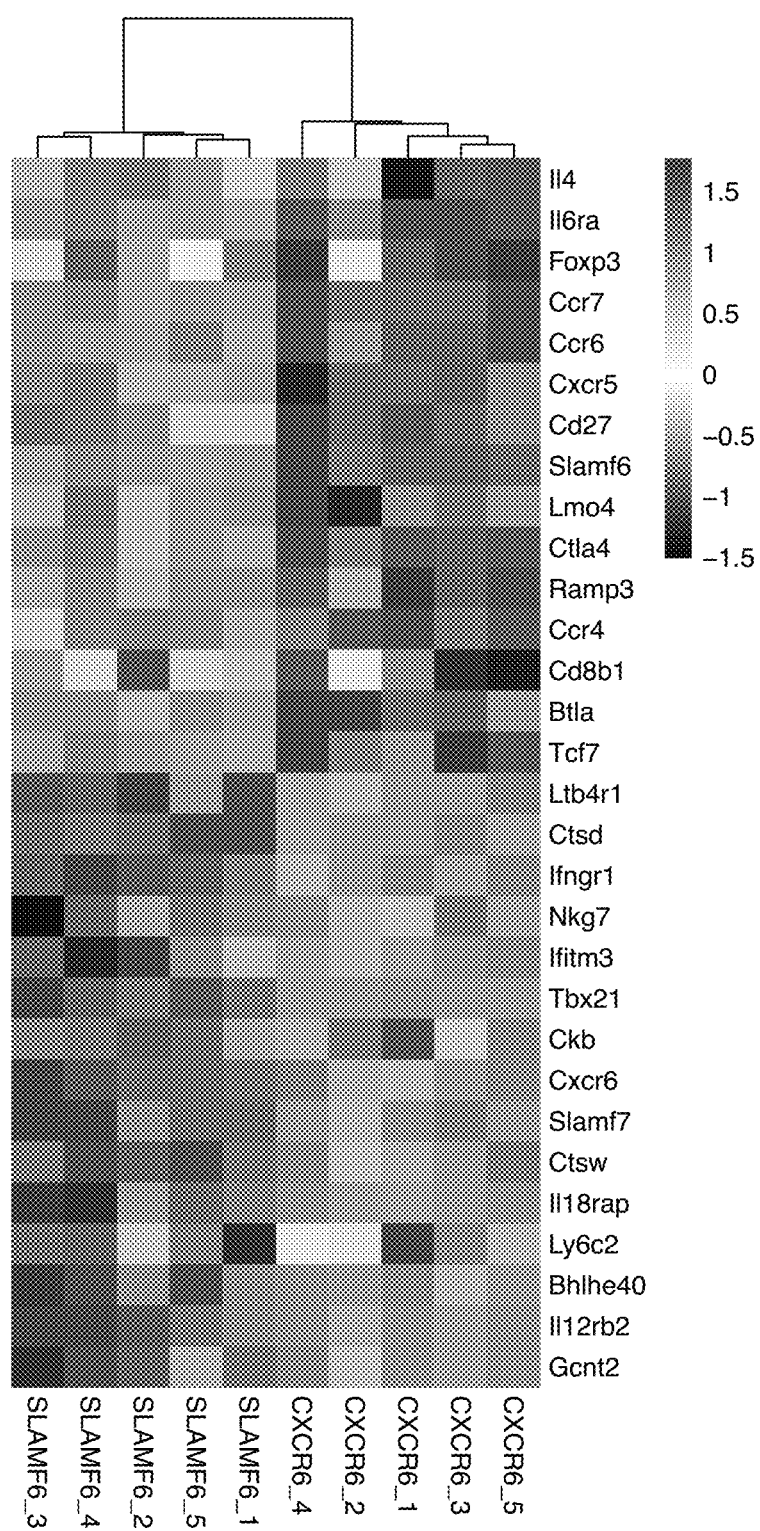
FIG. 41— Heat map showing gene expression in SPL_0 and SPL_1 populations.
Figure 42A:
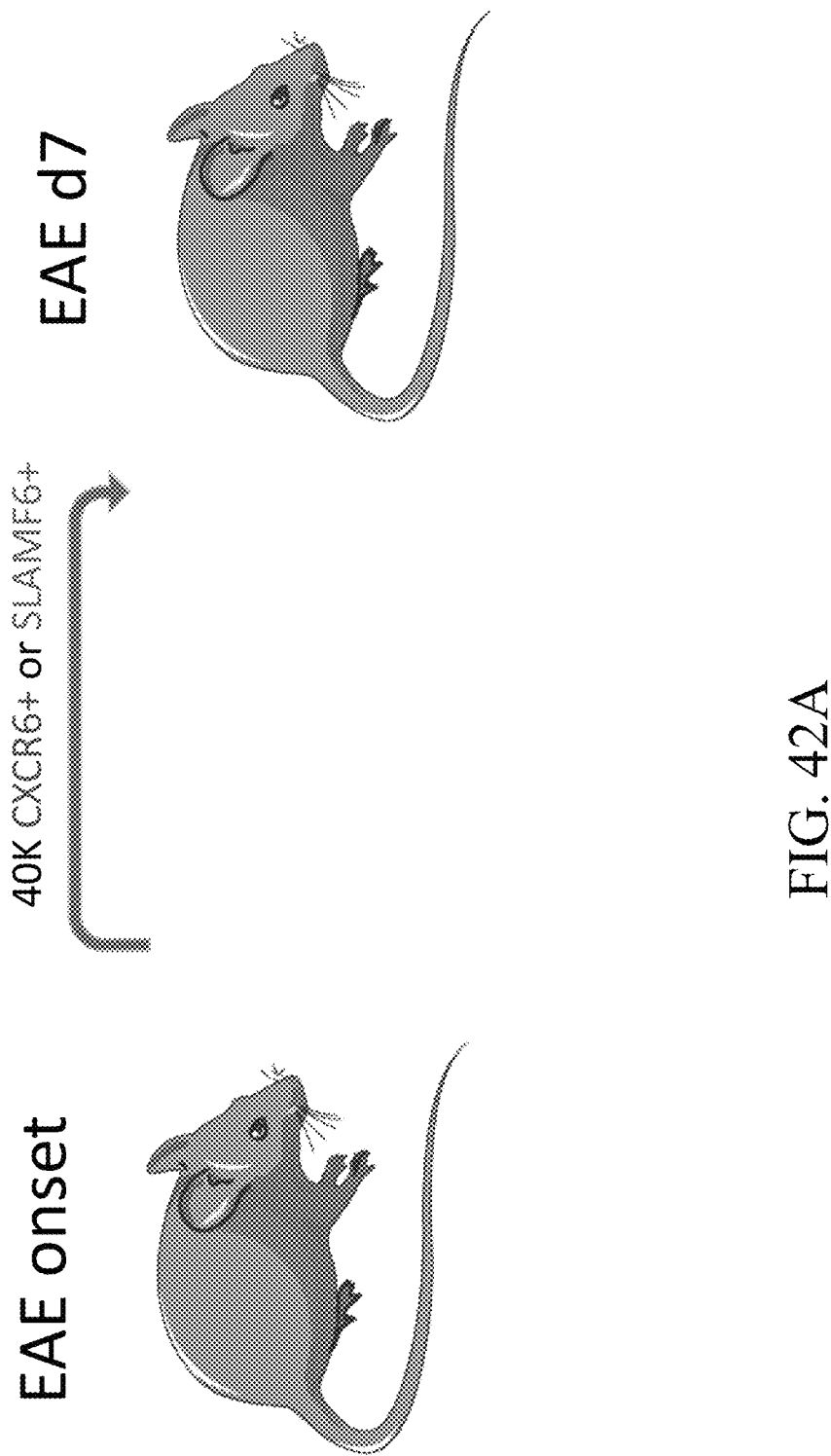
FIGS. 42A-42B— FIG. 42A. Experimental set-up for testing whether the CXCR6+ population influences EAE disease.
Figure 42B:
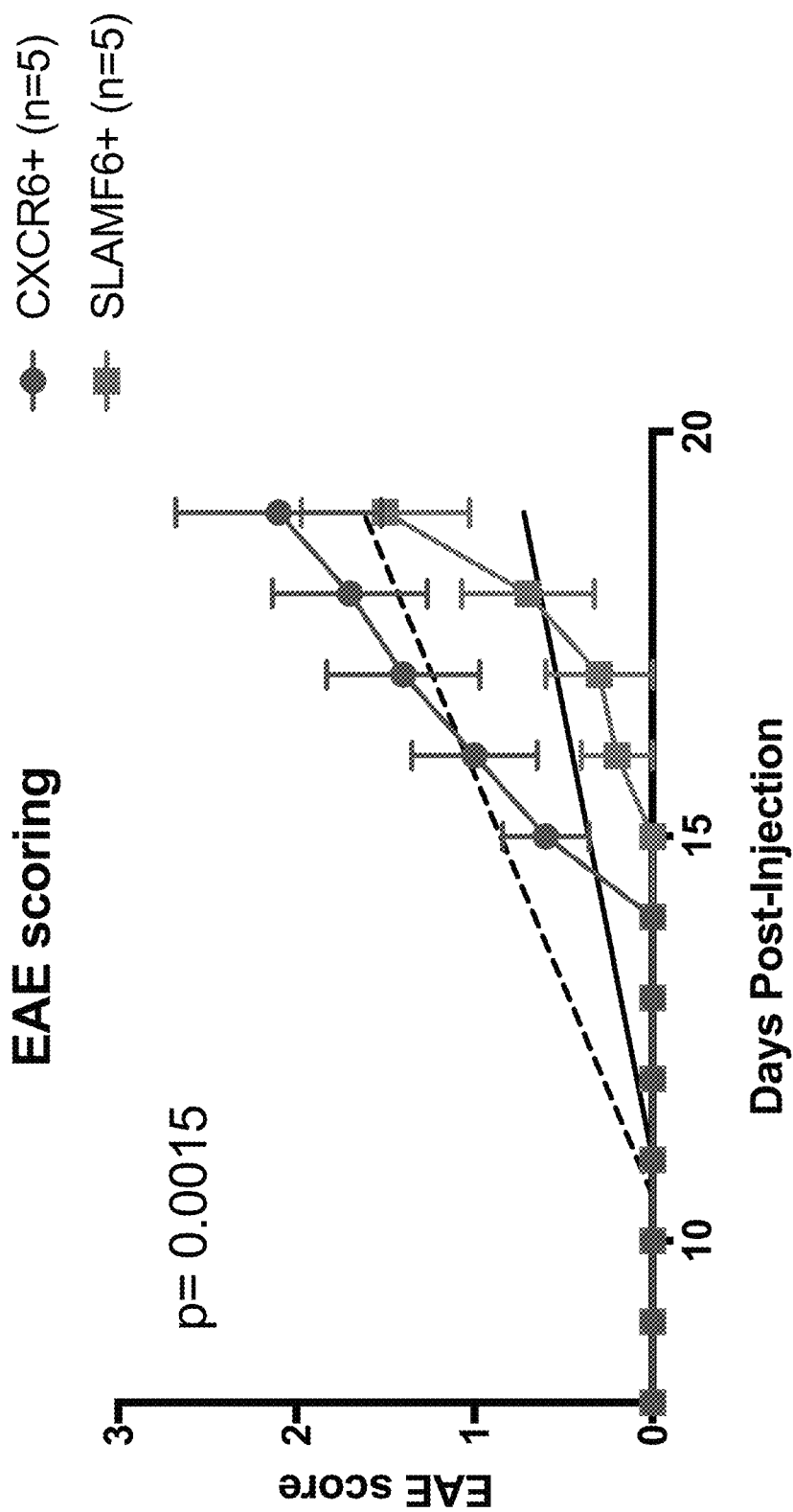
Figure 43:
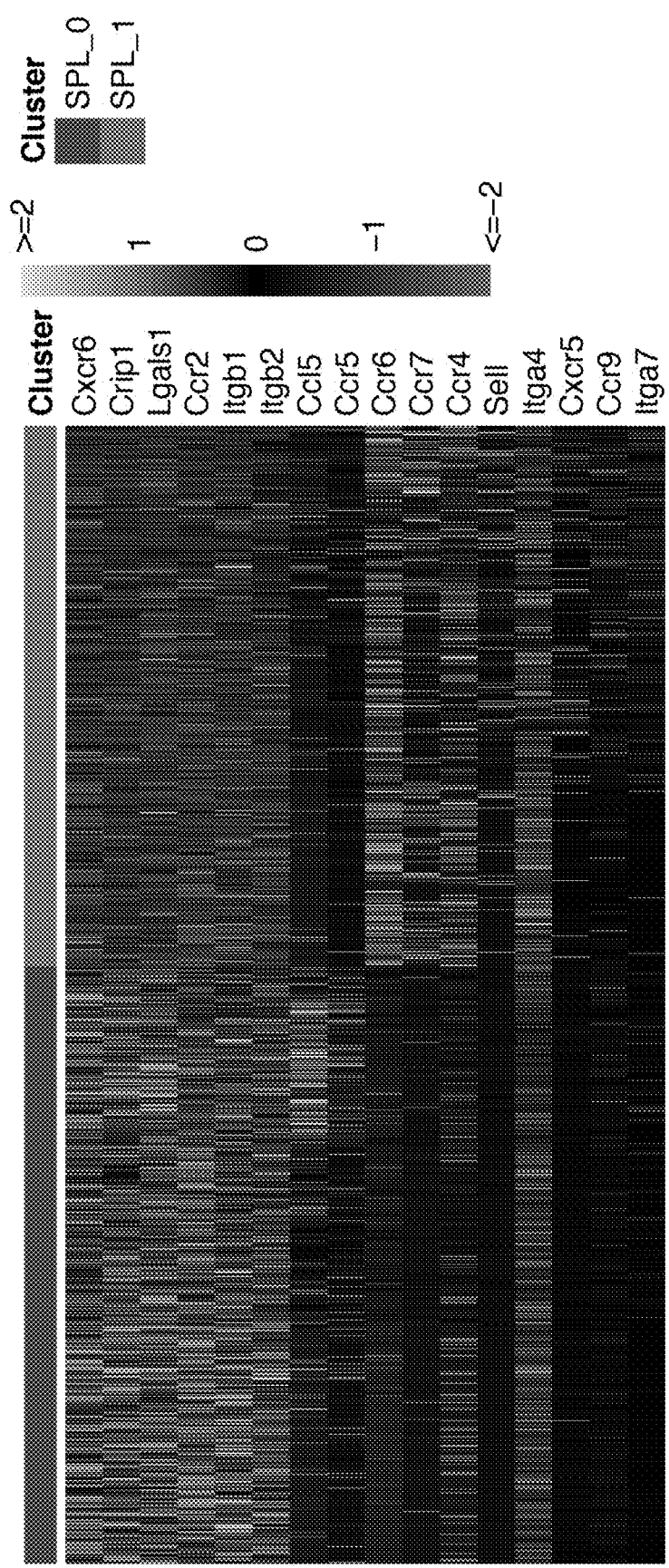
FIG. 43— Distinct expression of migratory molecules in SPL_0 and SPL_1 populations.
Figure 44:
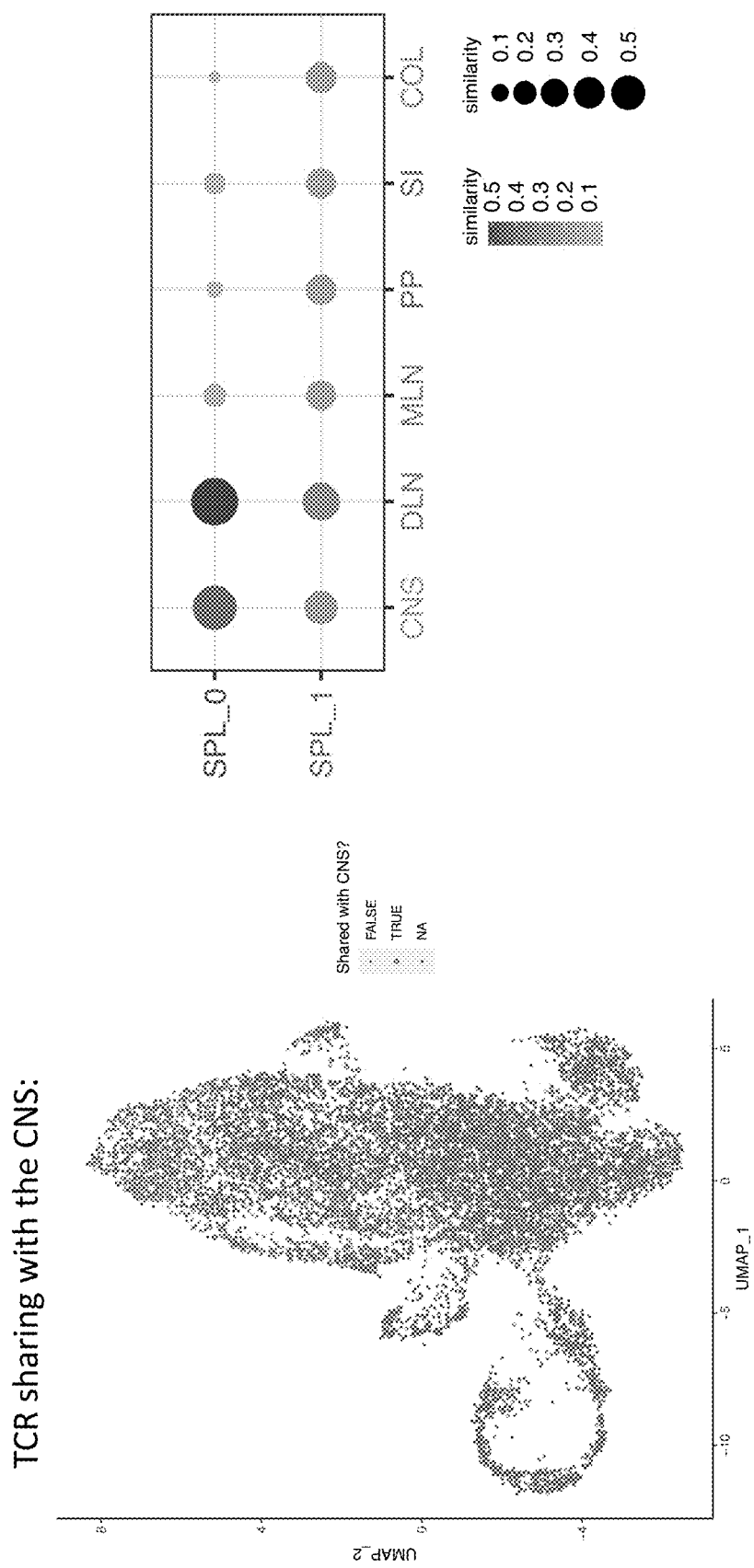
FIG. 44— Distinct migratory behavior of the CXCR6+ and SLAMF6+ subpopulations.
Figure 45:
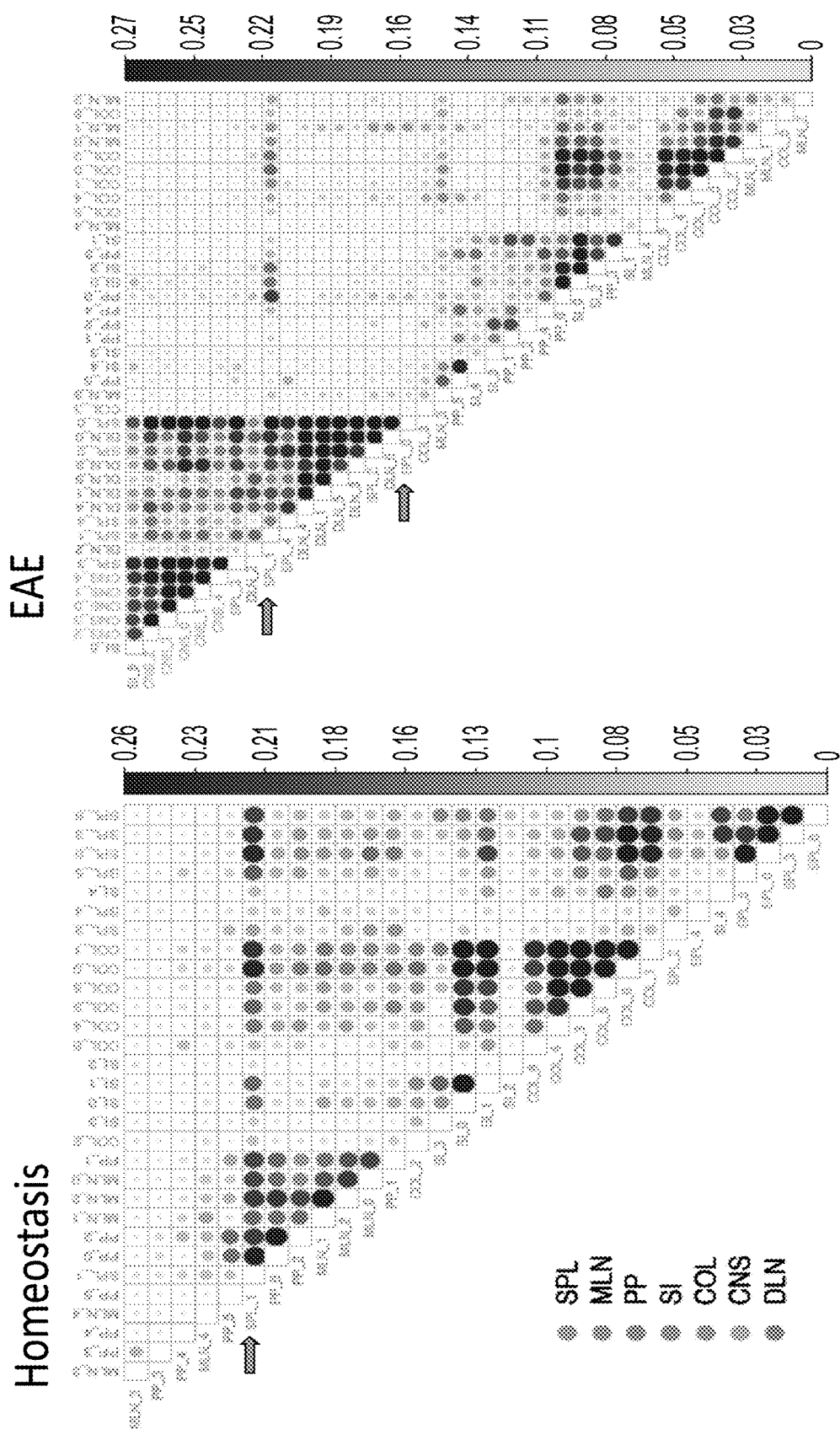
FIG. 45— Correlation analysis of tissue Th17 cell clusters based on TCR clonality.
Figure 46:
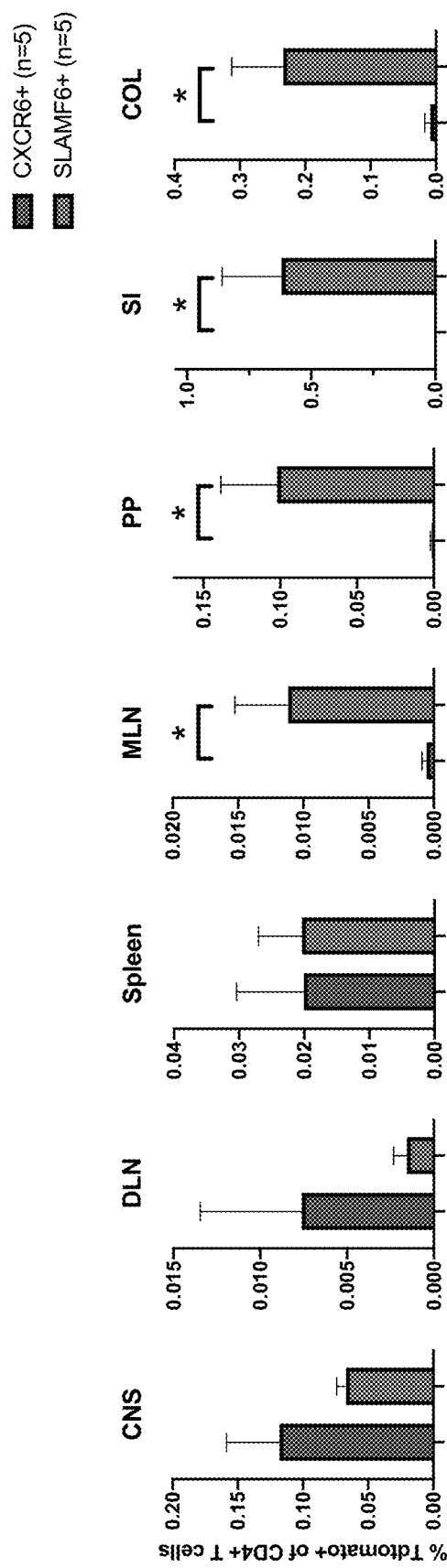
FIG. 46— Distinct migratory behavior of SPL_0 and SPL_1 in vivo.
Figure 47A:
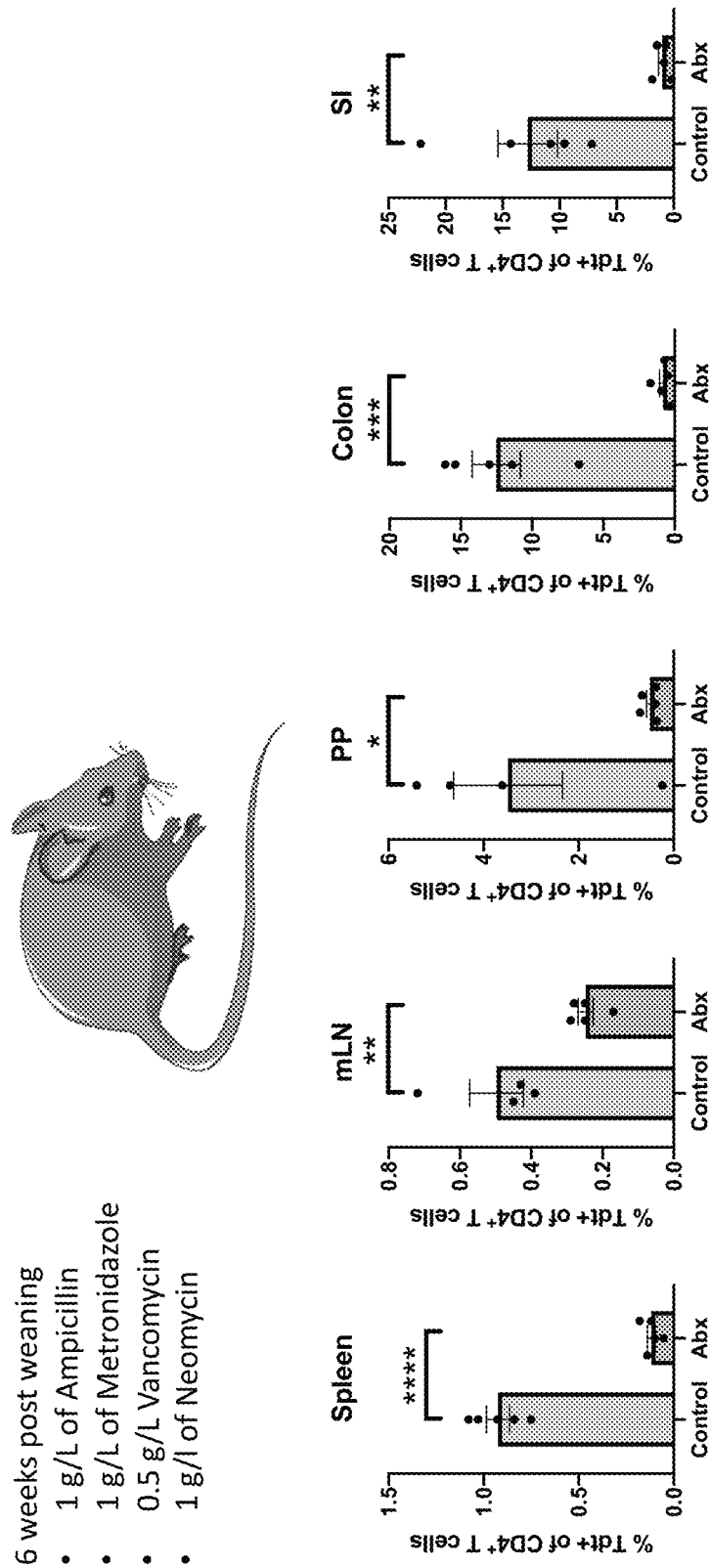
FIGS. 47A-47B— FIG. 47A. Microbiota dependency of the SLAMF6+ subpopulation shown by antibiotic (Abx) treatment and elimination of Th17 cells.
Figure 47B:
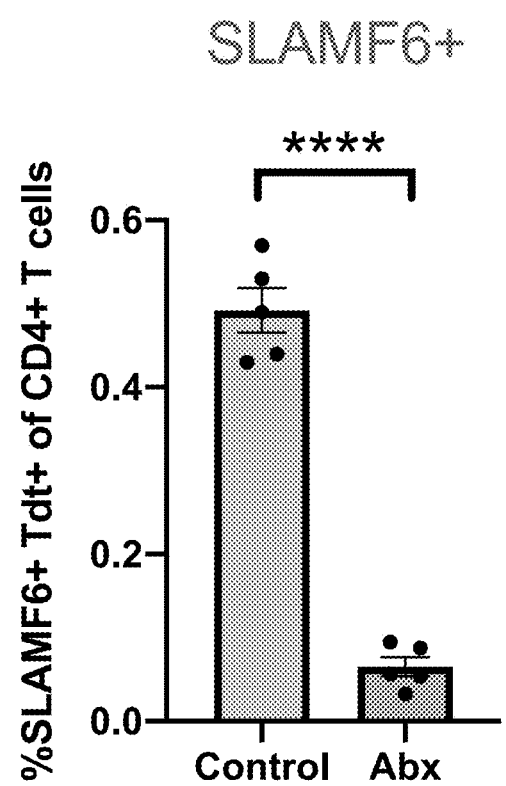
Figure 48:
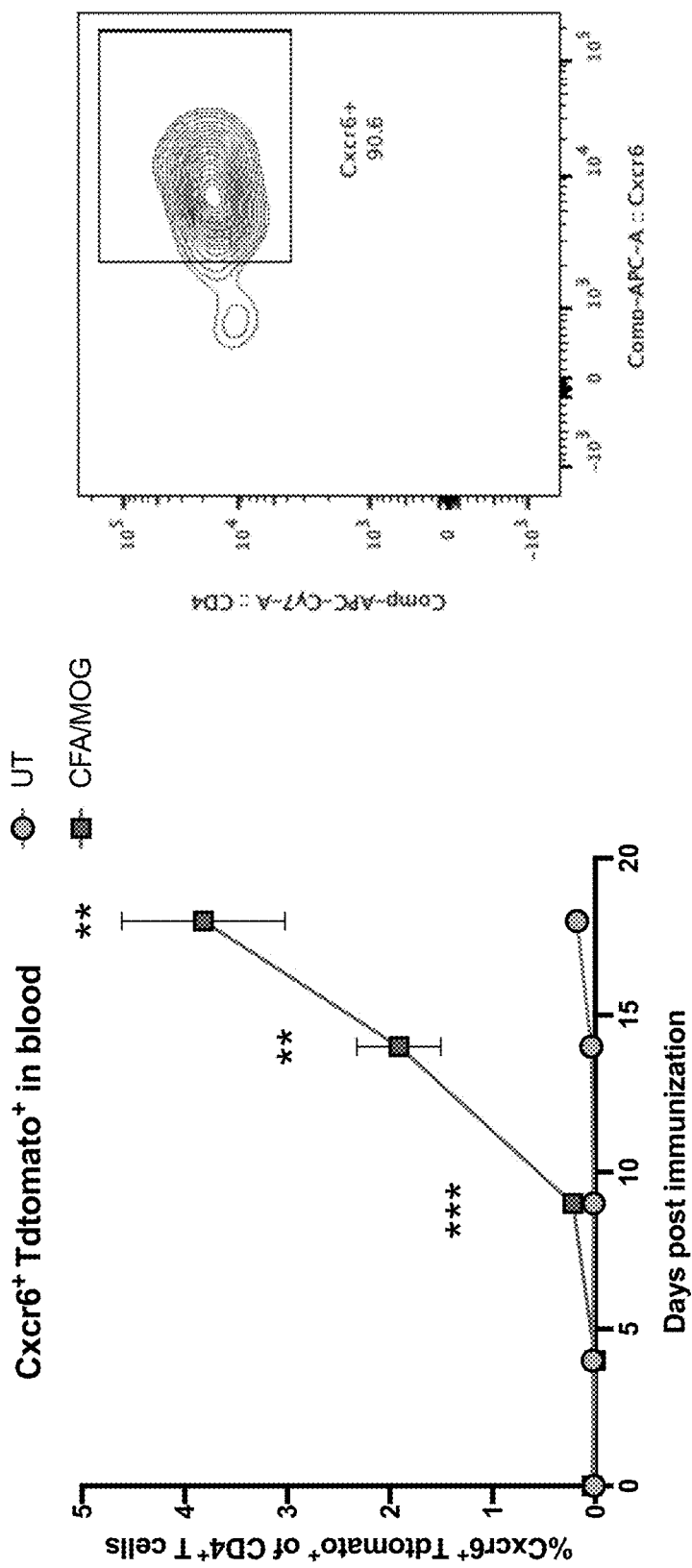
FIG. 48— Detection of Tdt+ Cxcr6+ cells in the blood of EAE mice to show how CXCR6+ cells migrate to the CNS.
Figure 49:
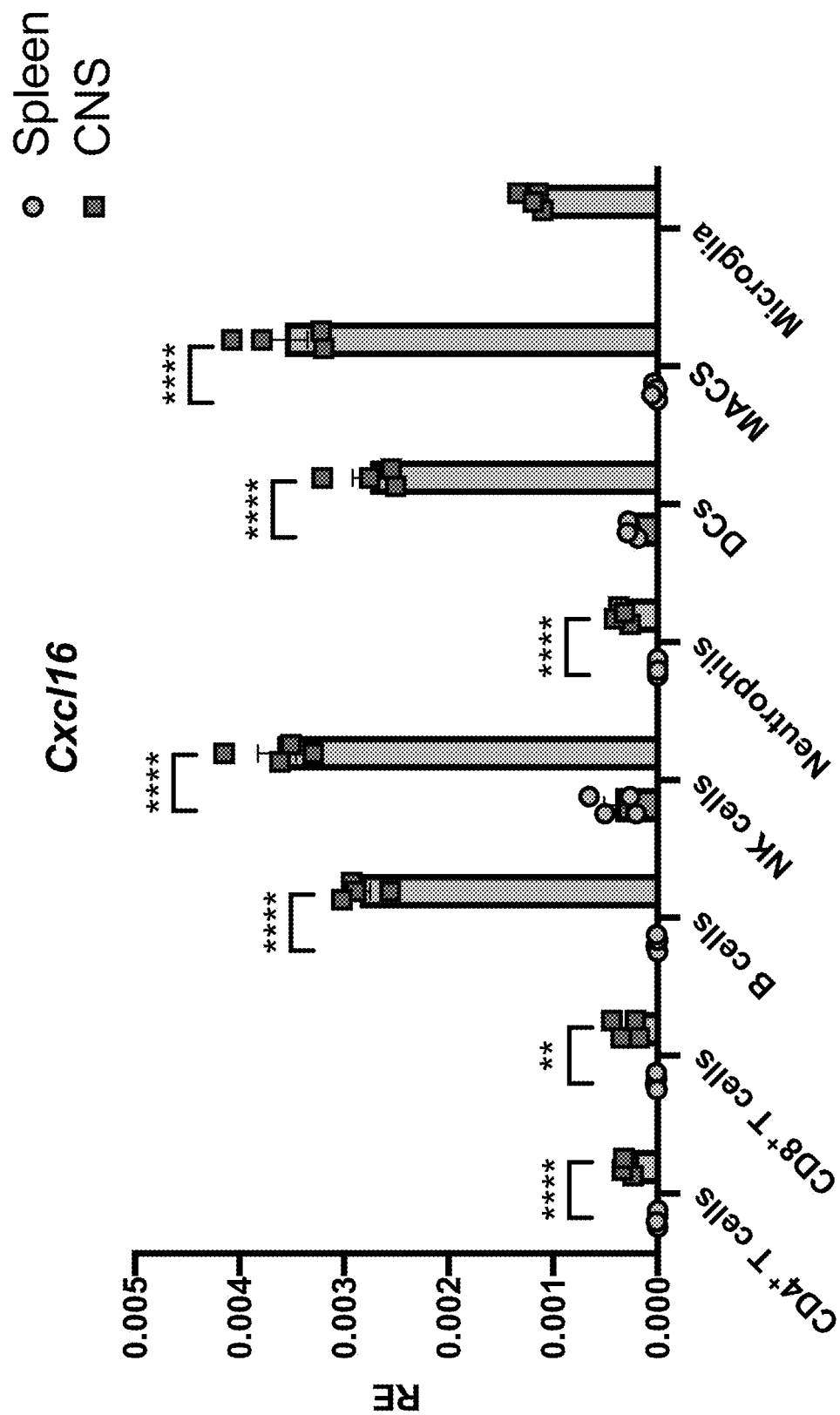
FIG. 49— Higher expression of Cxcl16 in the CNS than in the spleen.
Figure 50:
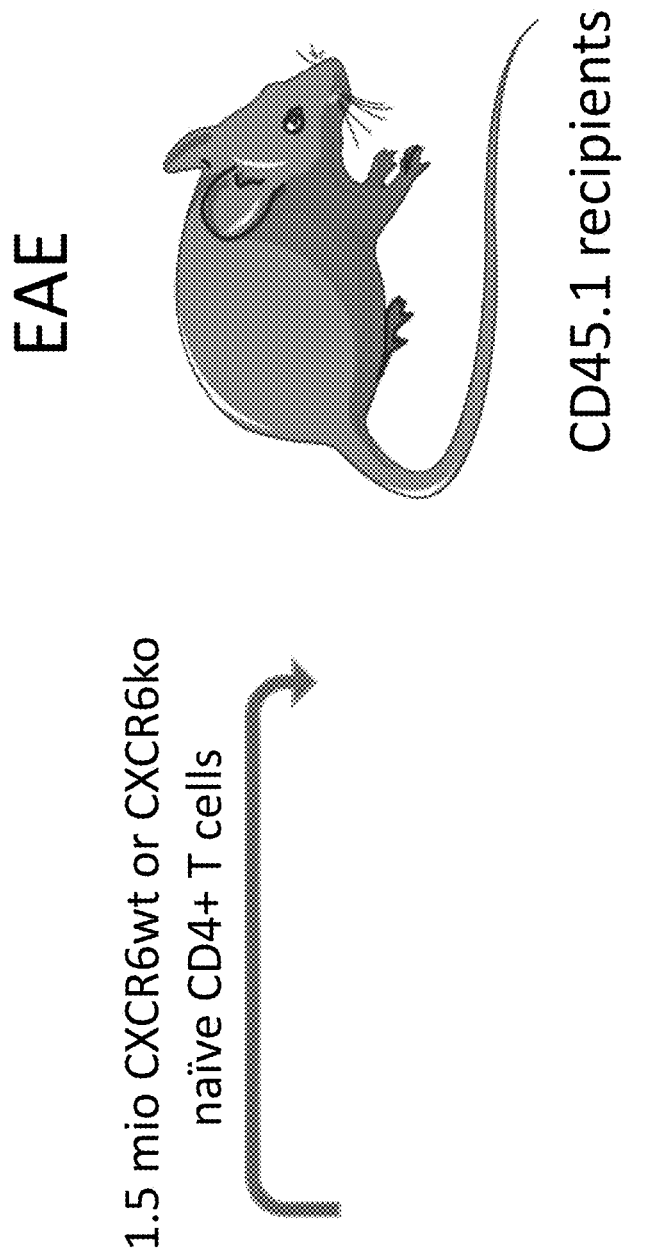
FIG. 50— Experimental set-up to determine whether the CXCR6+ subpopulation has a functional role in the pathogenic spleen population.
Figure 51:
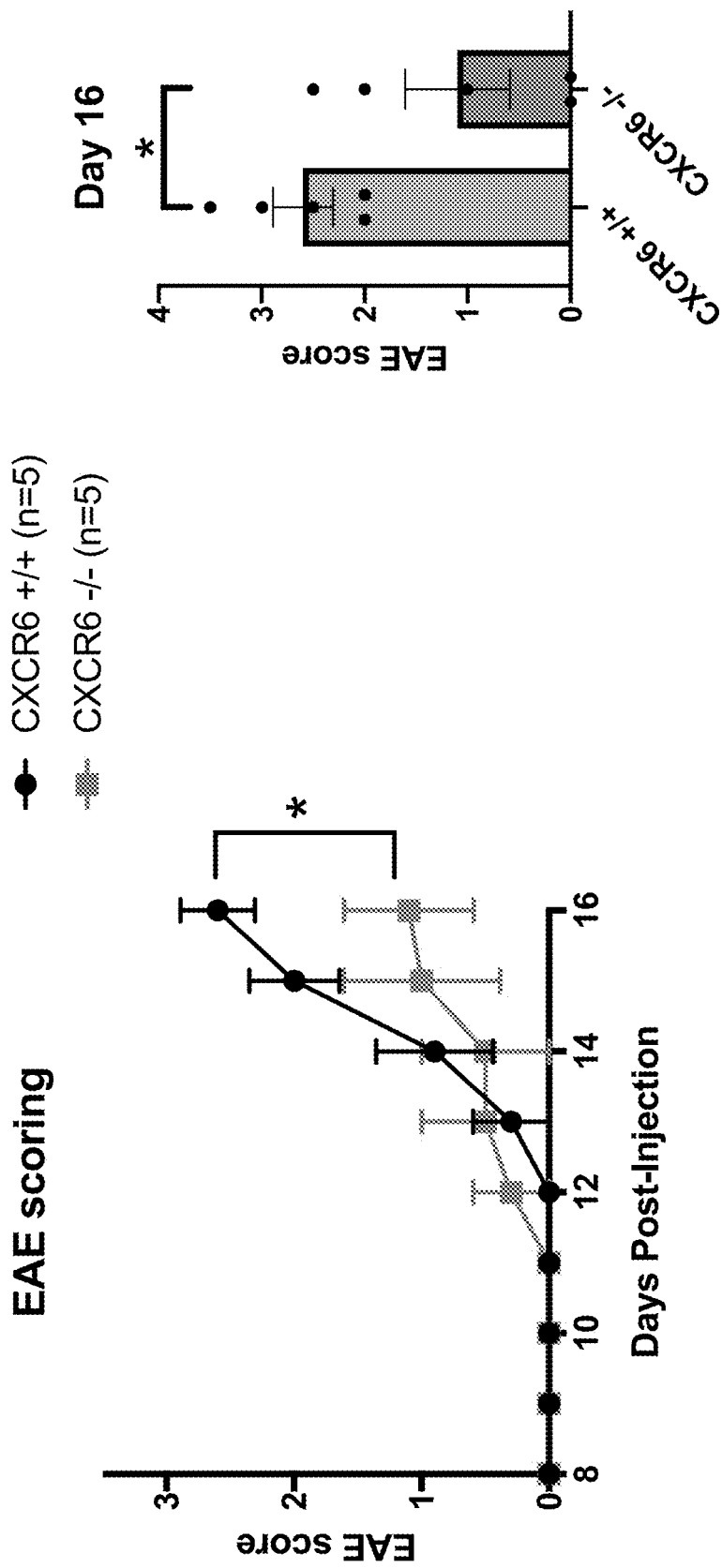
FIG. 51— CXCR6−/− cell recipients display attenuated EAE disease.
Figure 52:
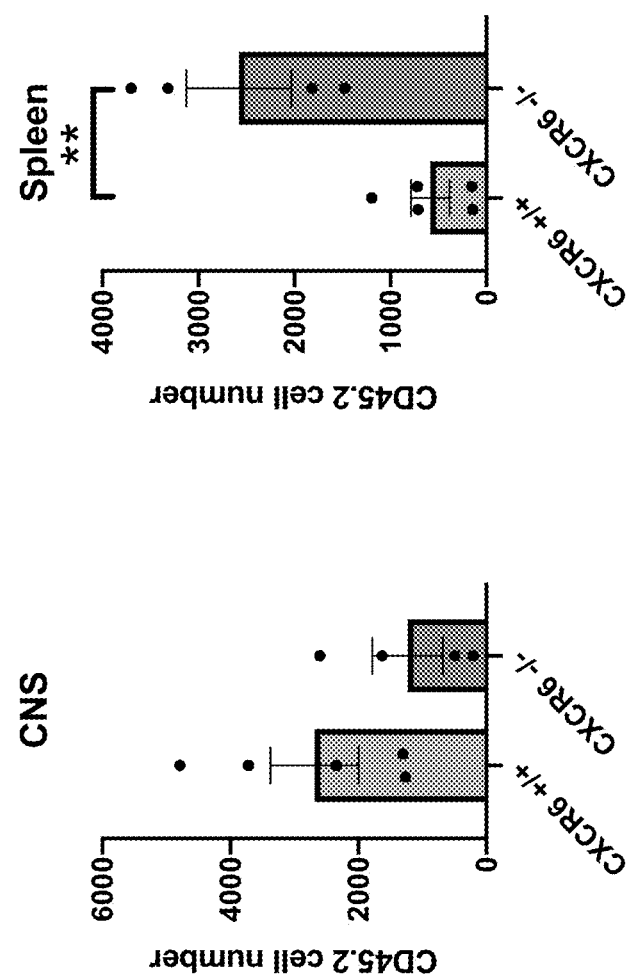
FIG. 52— CXCR6-deficient encephalitogenic CD4+ T cells are less pathogenic.
Figure 53:
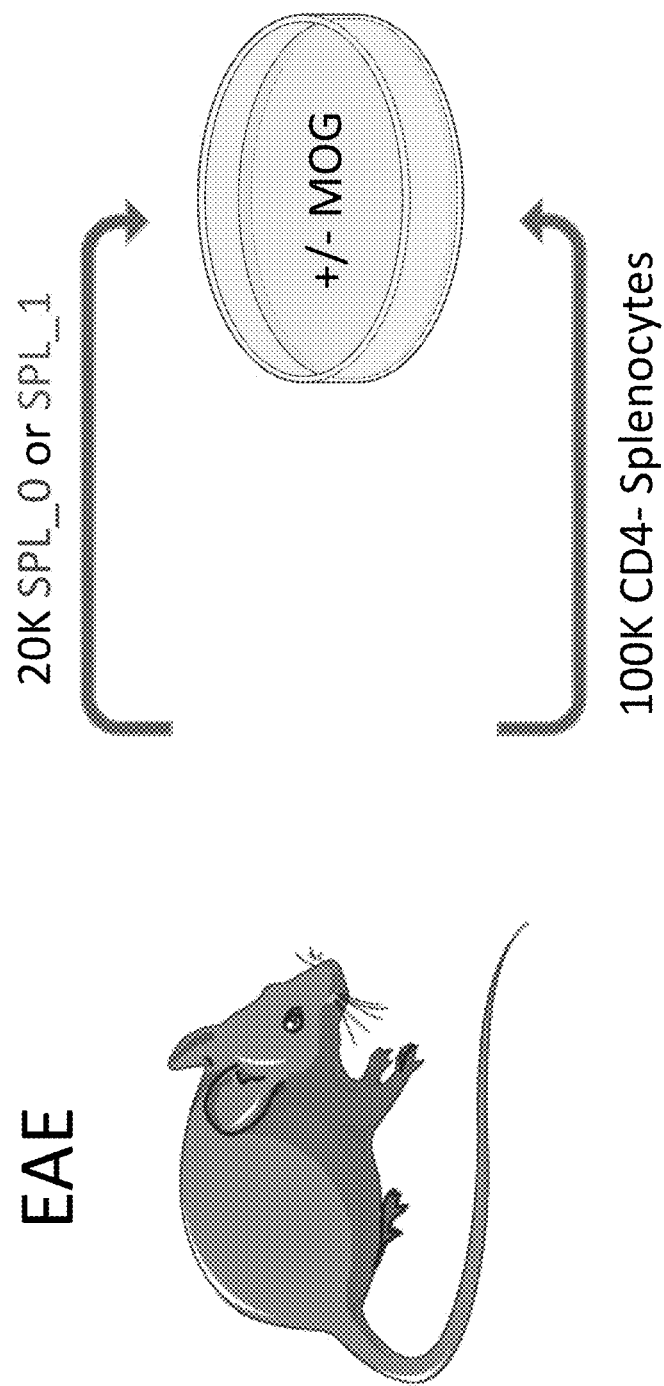
FIG. 53— Experimental set-up for determining whether the CXCR6+ and SLAMF6+ subpopulations differently respond in the spleen to MOG.
Figure 54A:
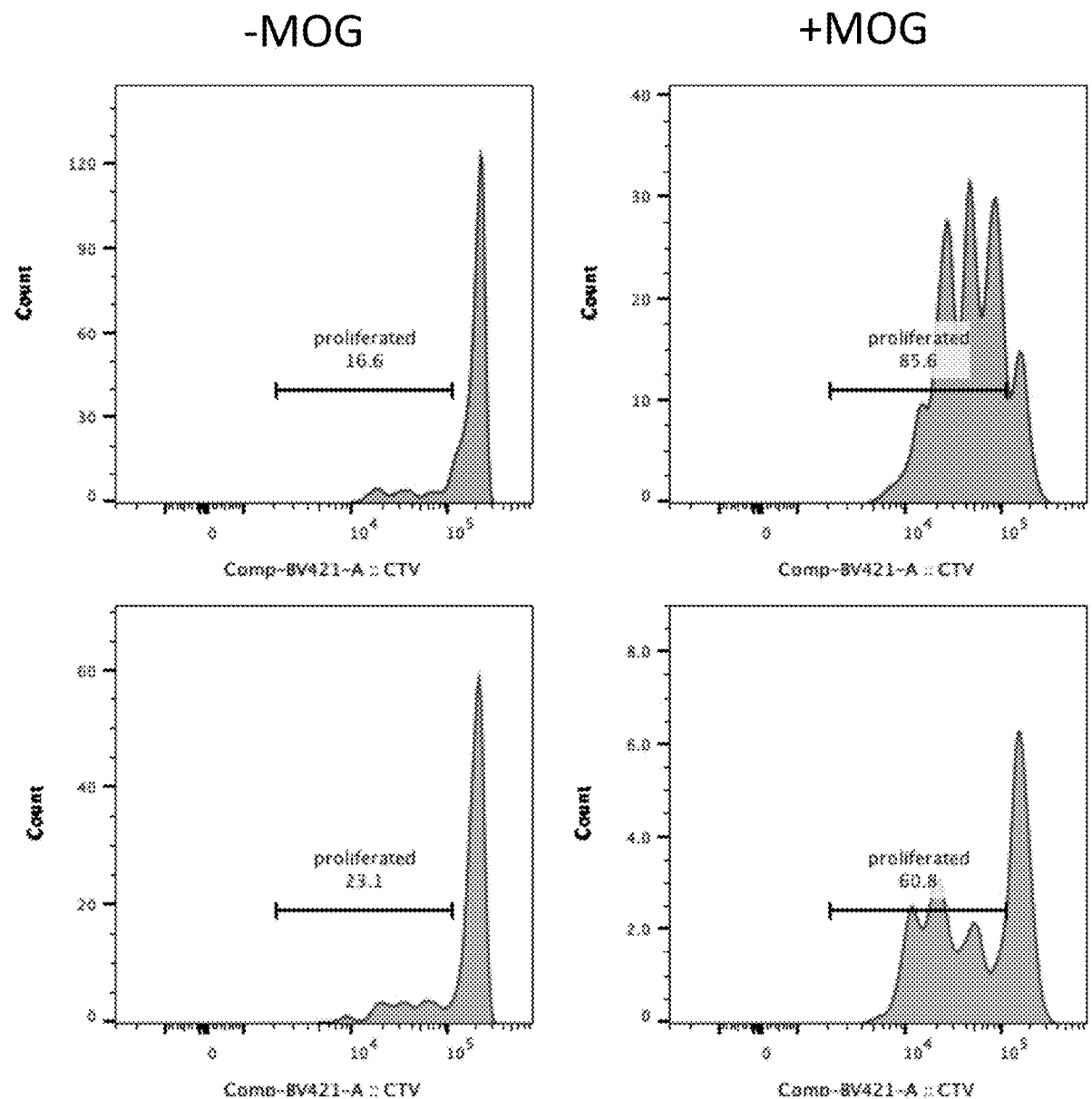
FIGS. 54A-54B— The SPL_0 population proliferates more than SPL_1 population.
Figure 54B:
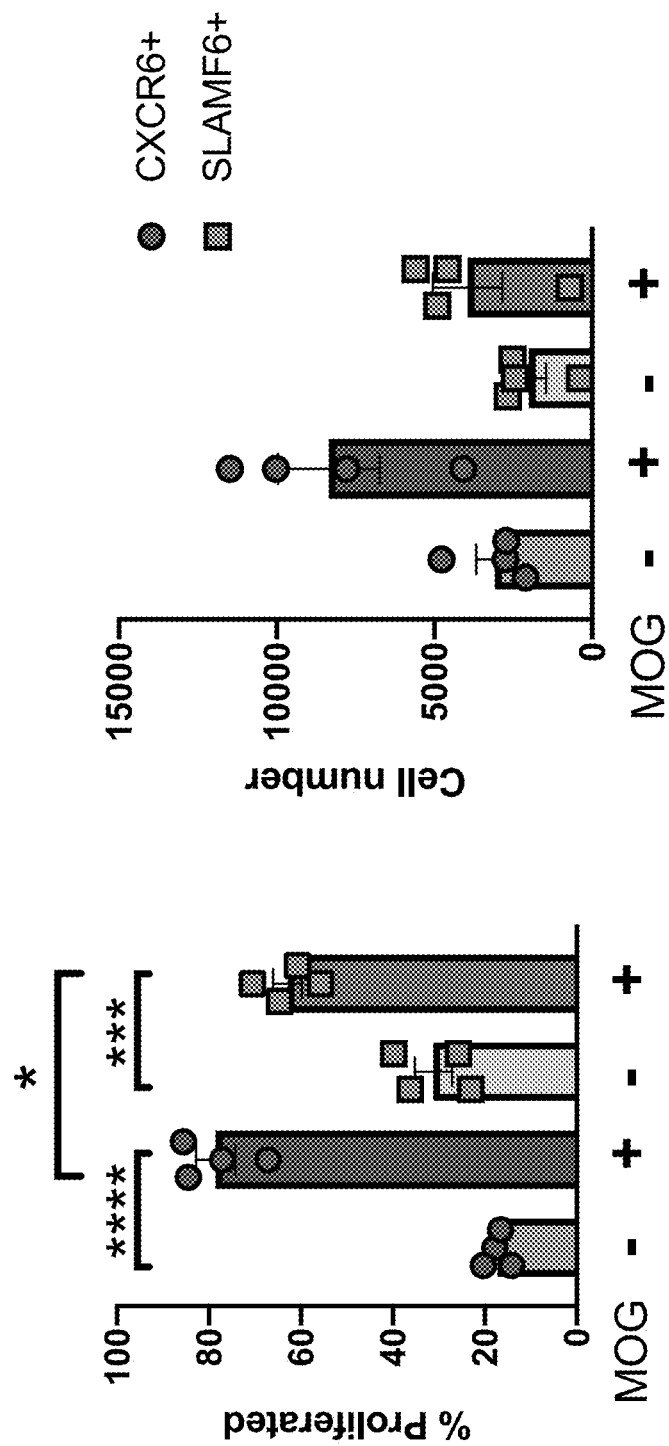
Figure 55A:
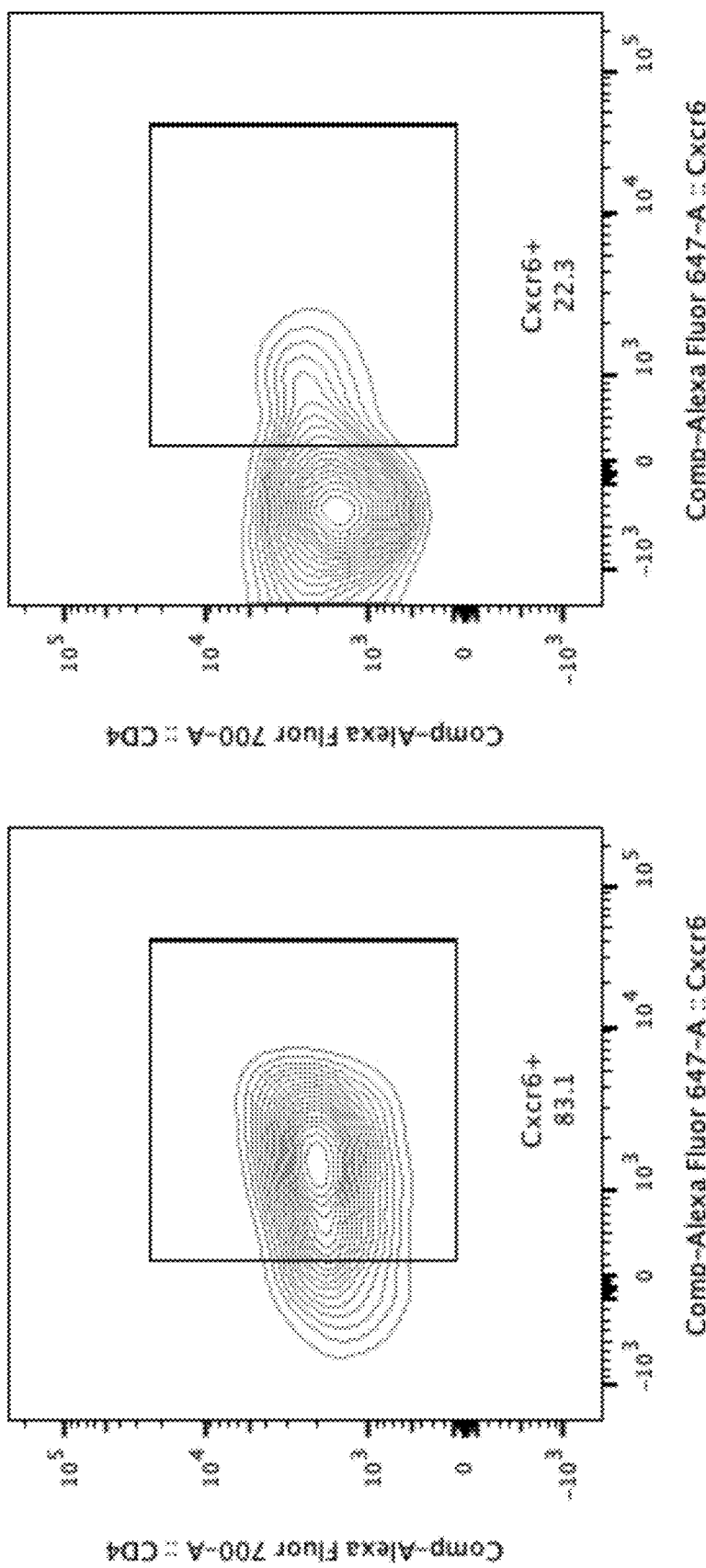
FIGS. 55A-55B— SPL_0 cells and SPL_1 cells are stable in vitro.
Figure 55B:
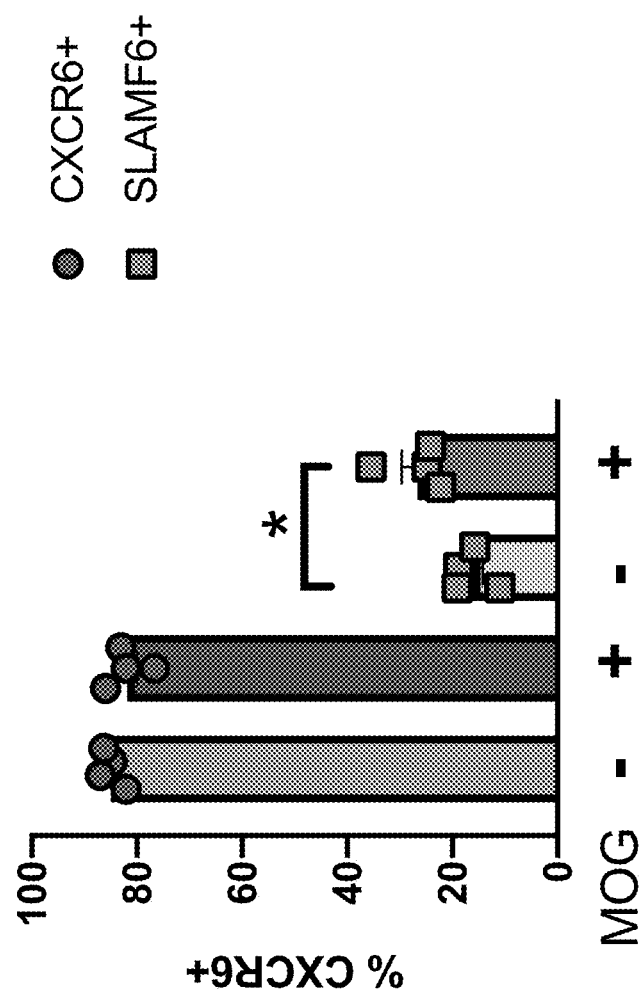
Figure 56A:
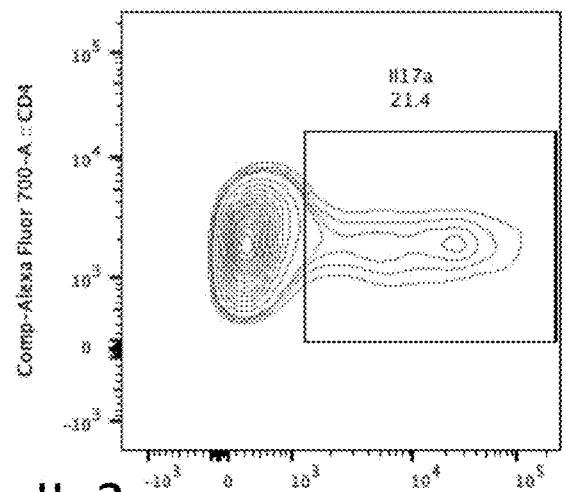
FIGS. 56A-56B— Higher expression of IL-2 and IL-17A in the SPL_1 population.
Figure 56A:
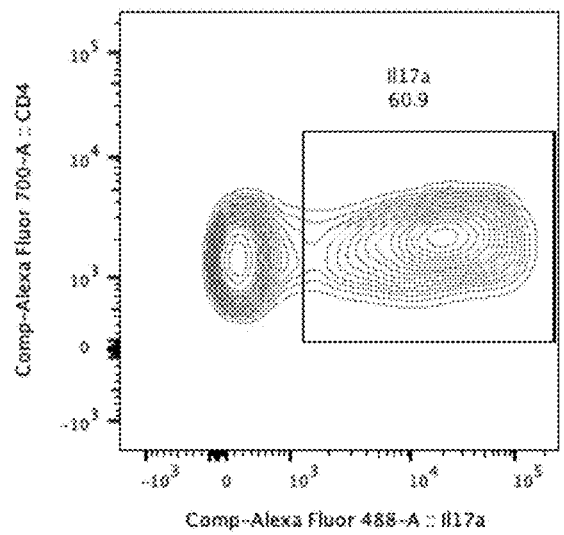
Figure 56A:
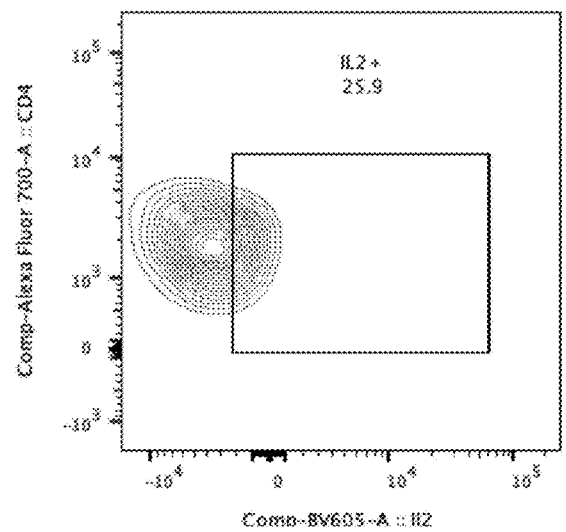
Figure 56A:
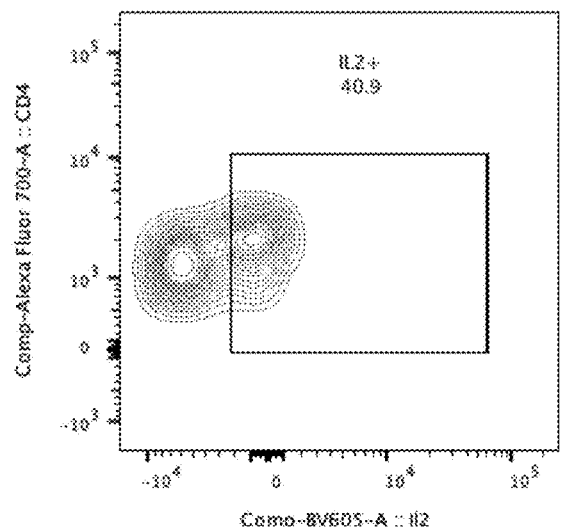
Figure 56B:
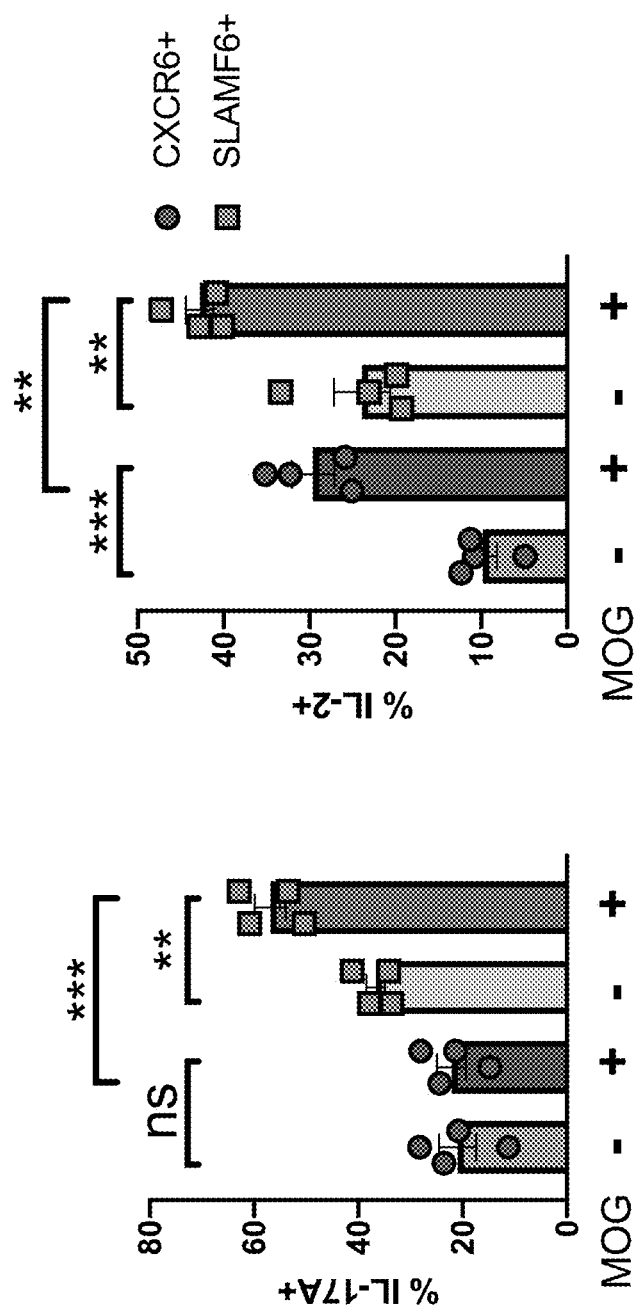
Figure 57A:
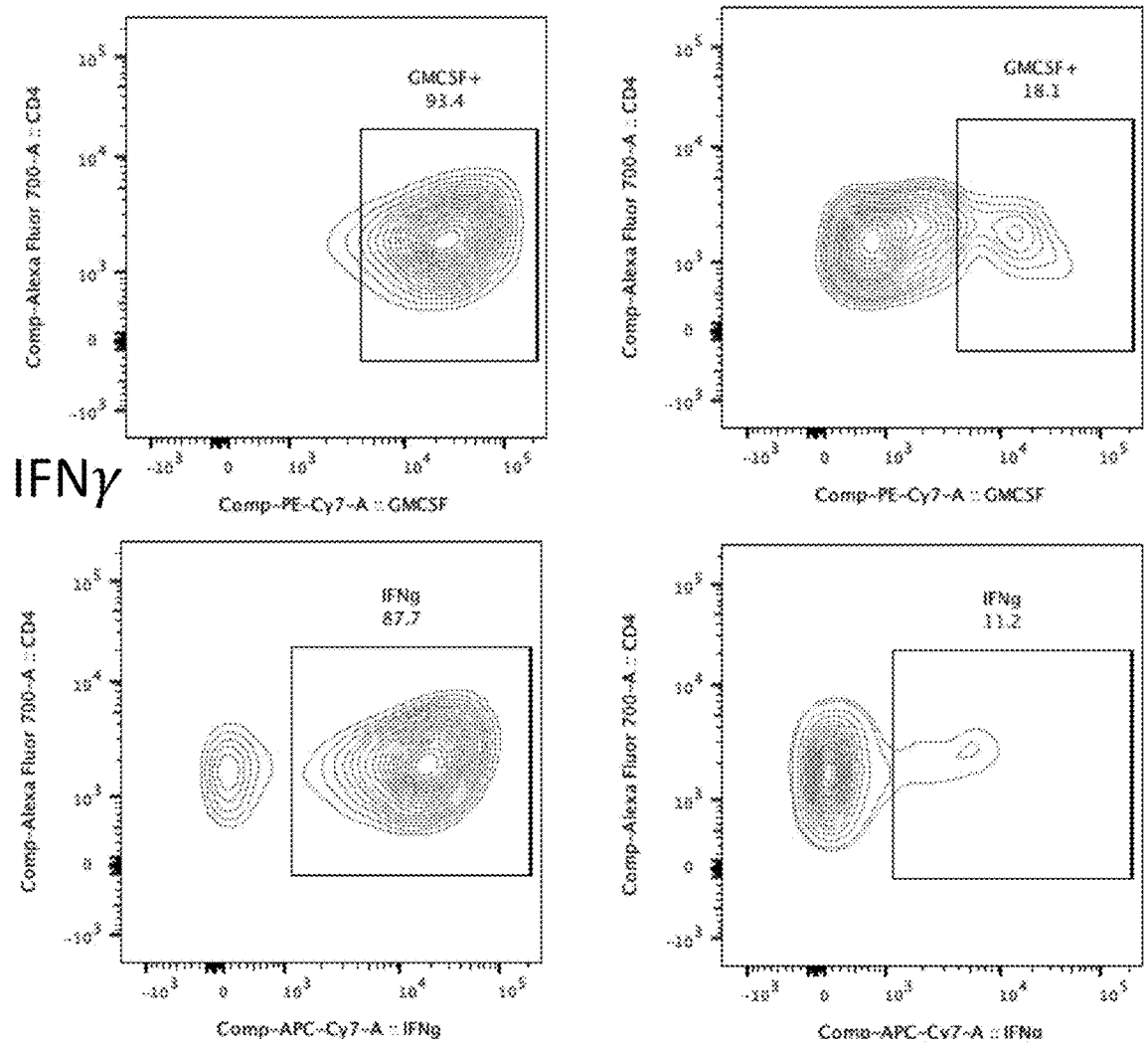
FIGS. 57A-57B— Higher expression of GM-CSF and IFNγ in the SPL_0 population.
Figure 57B:
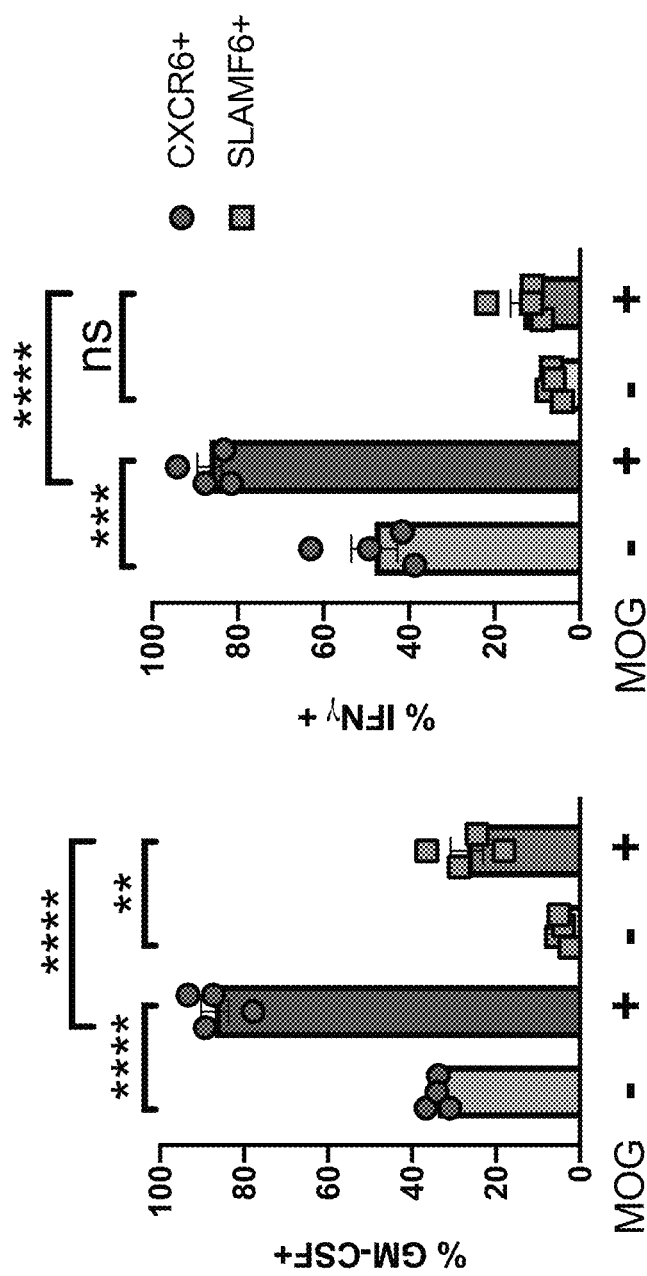
Figure 58A:
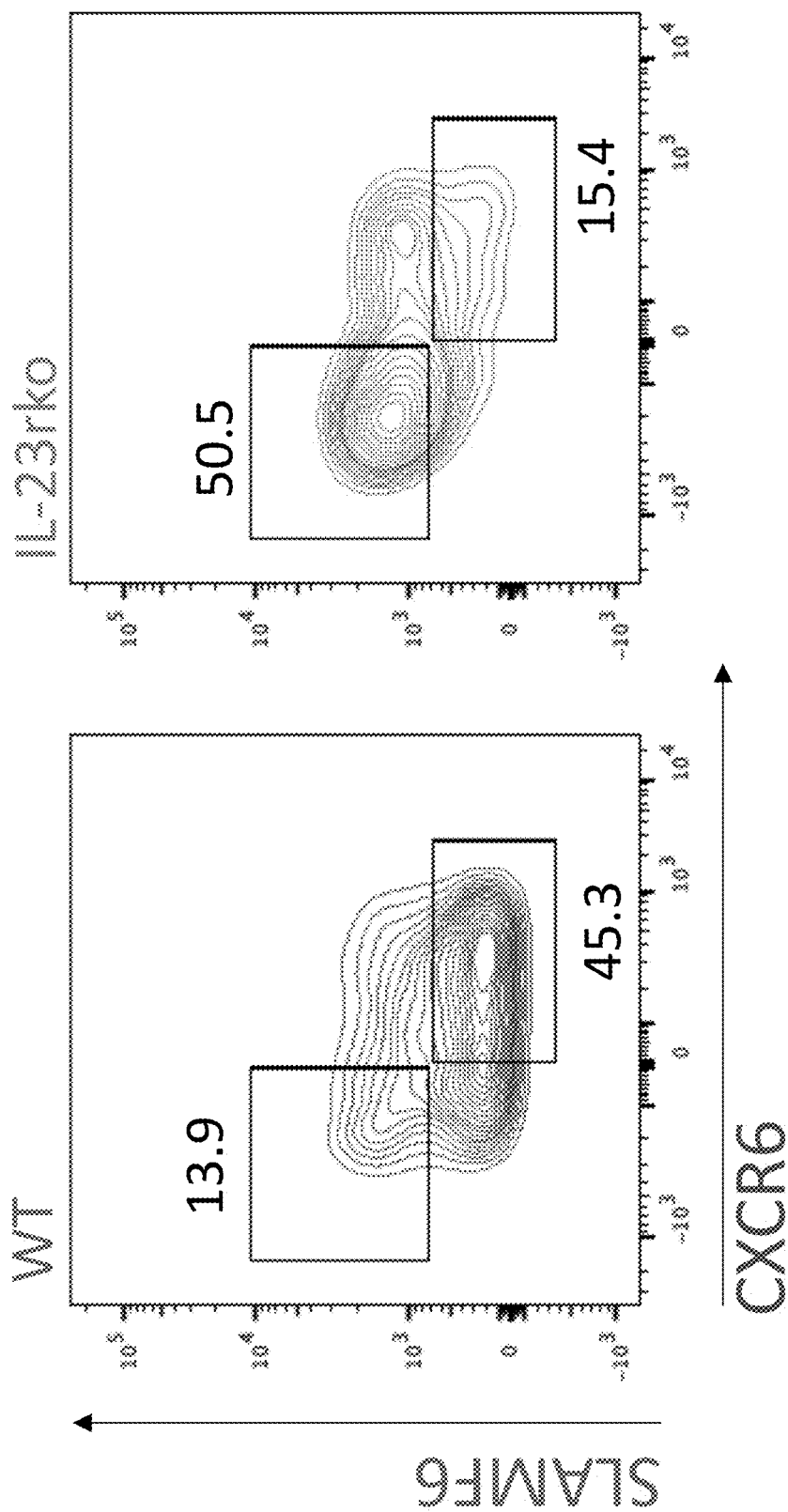
FIGS. 58A-58B— IL-23r signaling is required for the generation of the CXCR6+ population.
Figure 58B:
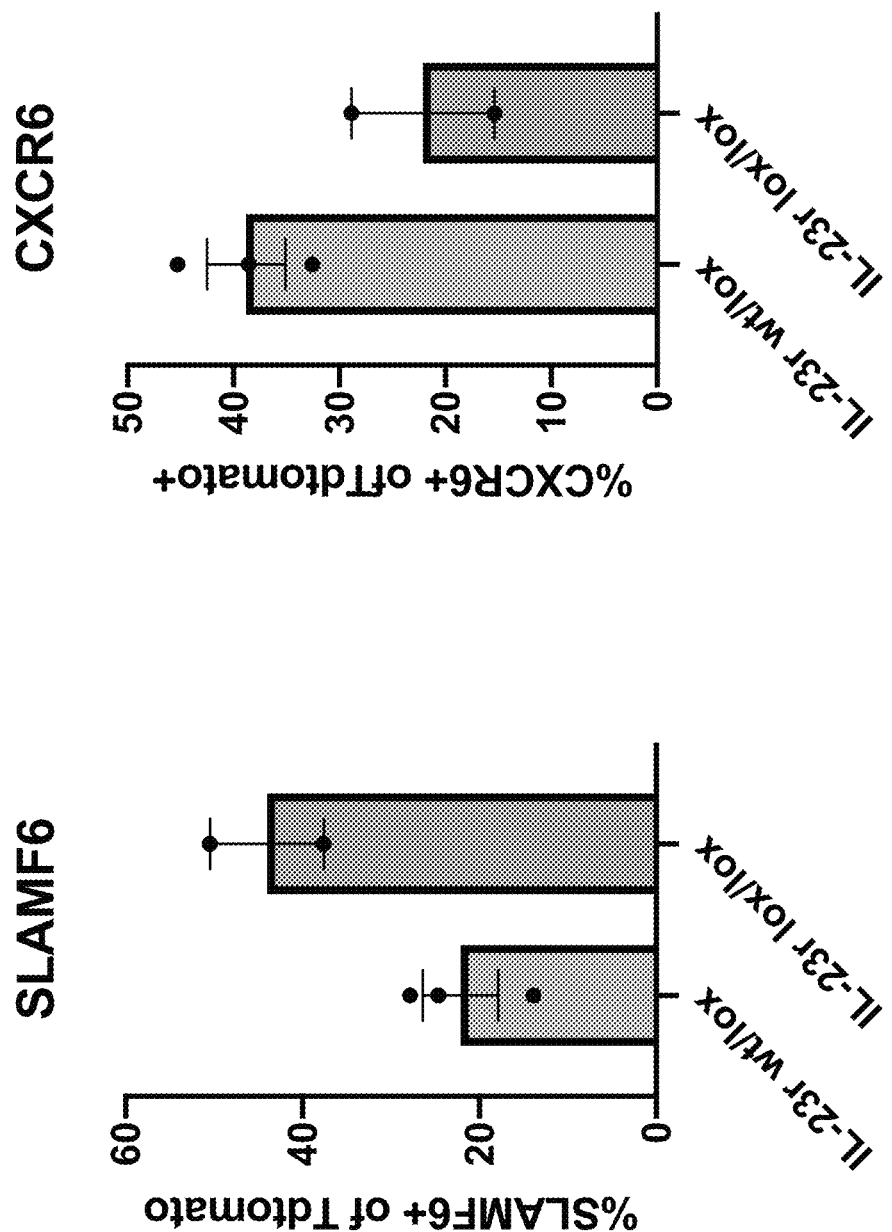
Figure 59:
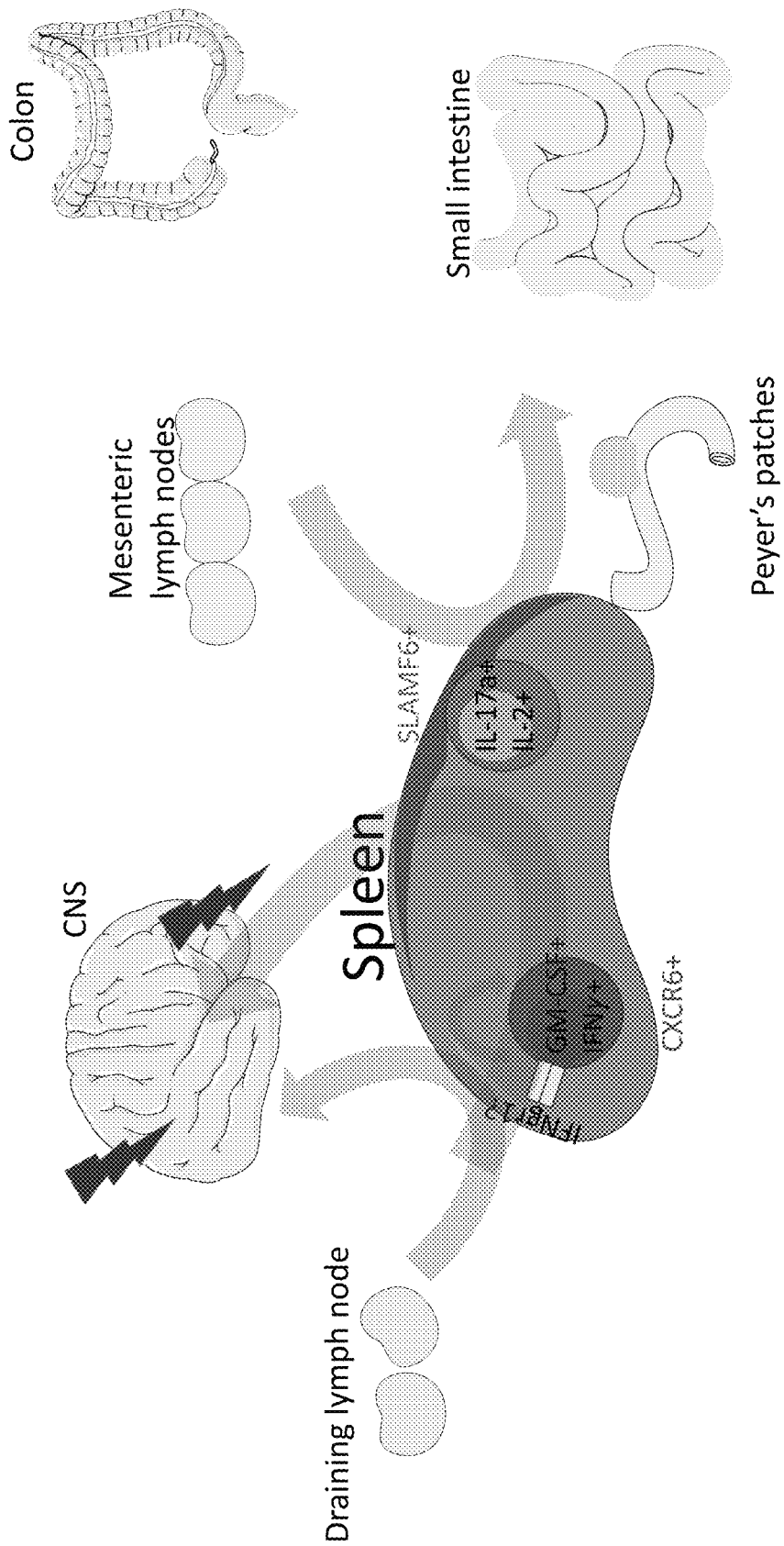
FIG. 59— Model of tissue specific Th17 cell subsets.

Applicants discovered two clusters in the EAE spleen; a pathogenic (SPL_0) and a stem-like (SPL_1) population (FIG. 37). Applicants can identify, quantitate and isolate SPL_0 and SPL_1 using the surface marker CXCR6 (SPL_0) and SLAMF6 (SPL_1) (FIG. 38). The CXCR6 population appears during EAE induction (FIG. 39). Applicants further characterized the CXCR6+ and SLAMF6+ populations (FIGS. 40 and 41). Applicants determined that the CXCR6+ population influences EAE disease by using adoptive cell transfer of the CXCR6+ and SLAMF6+ populations (FIG. 42). Applicants identified distinct migratory behaviors of SPL_0 and SPL_1 in vivo (FIGS. 43, 44 and 46). The CXCR6+ population strongly localizes to the CNS and DLN. During homeostasis there is correlation across tissues for the SLAMF6 cluster and during EAE there is correlation for the CXCR6 cluster in the spleen, CNS and DLN (FIG. 45). The SLAMF6+ subpopulation is dependent on the microbiota in the mesenteric lymph nodes (mLN), Peyer's patches (PP), colon and small intestine (SI) because treatment with antibiotics eliminates the subpopulation in those tissues (FIG. 47). The CXCR6+ cells migrate to the CNS through the blood in EAE mice (FIG. 48) in response to higher expression of the chemokine CXCL16 in the CNS during EAE (FIG. 49). Applicants determined that the CXCR6+ population has a functional role in EAE disease by using adoptive cell transfer of CXCR6 wild type and knockout naïve CD4+ T cells (FIGS. 50-52). Applicants determined that the CXCR6+ and SLAMVF6+ populations respond differently in the spleen to MOG (FIGS. 53-57). Applicants determined that IL-23r, which is required to differentiate pathogenic Th17 cells, is required for the generation of the CXCR6+ population (FIG. 58). Applicants provide a model for the CXCR6+ and SLAMVF6+ populations across tissues (FIG. 59). The results have implications for autoimmune disease therapies, such as specific targeting of the SPL_0 population.

Tables

TABLE 1

| UT tissue vs Spleen | | | |
|---|---|---|---|
| up_MLN | up_PP | up_SI | up_Colon |
| Ccl20 | Il22 | Rgs1 | Hspa1a |
| Lag3 | Ccl20 | Jun | Rgs1 |
| Rgs1 | Rgs1 | Gzmb | Il22 |
| Tnfrsf4 | Lag3 | Hspa1a | Jun |
| Ctla4 | Hspa1a | Asb2 | Dusp1 |
| Gzmb | Ctla4 | Ccr9 | Il17f |
| Ccr1 | Il1r2 | Il17f | Fos |
| Ccr9 | Tnfsf8 | Il22 | Junb |
| Icos | Pard6g | Dusp1 | Tnfaip3 |
| Sccpdh | Tnfrsf4 | Igha | Ccl20 |
| Serpina3g | Junb | Fos | Bhlhe40 |
| Pard6g | Crem | Junb | Ifng |
| Rps27rt | Il17f | Abi3 | Gadd45b |
| Il17f | Ccr9 | Gzma | Cd69 |
| Asb2 | Bhlhe40 | Fgl2 | Ctla4 |
| Gadd45b | Lilr4b | Gngt2 | Fosb |
| Lgmn | Gm42418 | Tcrg-C2 | Gem |
| Isg15 | Tcrg-C1 | Sdc4 | Nr4a1 |
| Il1r2 | Ccr1 | Ccl20 | Hspa1b |
| Sdc4 | Kit | Igkc | Sdc4 |
| Rps12-ps3 | Nfil3 | Tnfaip3 | Gzmb |
| Irf4 | Sccpdh | Ctla4 | Klf6 |
| Tnfsf8 | Nr4a1 | Gem | Asb2 |
| Cpe | Tnfaip3 | Cd69 | Ppp1r15a |
| Il22 | Asb2 | Tcrg-C4 | Furin |
| Gm12840 | Ifng | Ifng | Lag3 |
| Nfil3 | Cd83 | Lag3 | Rgs2 |
| Cd83 | Tpi1 | Gm20069 | Ccr1 |
| Mmd | Gadd45b | Hic1 | Ehd1 |
| Gm45716 | Il17a | Tcrg-C1 | Jund |
| Kdm6b | Lgals7 | Lilr4b | Gm26825 |
| Tnfaip3 | Gm45716 | Gadd45b | Cdkn1a |

TABLE 1-continued

| UT tissue vs Spleen | | | |
|---|---|---|---|
| up_MLN | up_PP | up_SI | up_Colon |
| Fgl2 | Gm12840 | Ehd1 | Il17a |
| Ahr | Hif1a | Fosb | Fgl2 |
| Abi3 | Gem | Hspa1b | Ckb |
| Rps12 | Kdm6b | Jchain | Tnfsf8 |
| Furin | Gzmb | Gm26825 | Lilr4b |
| Ffar2 | Lztfl1 | Furin | Dennd4a |
| Rpl36a-ps1 | Furin | Ccr1 | Sytl3 |
| Rpl9-ps6 | Hspa1b | Il17a | Nfil3 |
| Rpl27-ps3 | Zeb2 | Zeb2 | Abi3 |
| Junb | Bcl2a1d | Bhlhe40 | Zeb2 |
| AW112010 | Ahr | Ckb | Fosl2 |
| Fabp5 | Icos | Prrt1 | Crem |
| Gm42418 | IL17A-GFP-wg | Lztfl1 | Gngt2 |
| Ctsb | Gngt2 | Gm45716 | Zfp36l1 |
| Bcl2a1b | Serpina3g | Gm42418 | Il1r2 |
| Rpl27 | Zfp36l1 | Ccr5 | Nfkbia |
| Nt5e | Ehd1 | AW112010 | Slc15a3 |
| Bcl2a1d | AC160336.1 | Gcnt2 | Lgals7 |
| Dennd4a | Srgn | Ppp1r15a | AC163354.1 |
| Ehd1 | Irf4 | Osgin1 | Ccr5 |
| Ptms | Abi3 | Ppp1r14c | Tnfrsf9 |
| Gngt2 | Fosl2 | Gimap7 | Gm42418 |
| Rpl10 | Skil | AC163354.1 | Tcrg-C1 |
| AC160336.1 | Tgif1 | Ffar2 | Gm12840 |
| Plin2 | Ptms | 4930453N24Rik | Gcnt2 |
| Skil | Batf | Nfkbiz | Smox |
| Susd3 | Hic1 | Susd3 | Ubald2 |
| Crem | Bcl2a1b | Rbm24 | Kdm6b |
| Gm2000 | Nt5e | Gadd45g | Zfp36 |
| Rpl13a-ps1 | Rnaset2a | Naga | Icos |
| Tcrg-C1 | Pdcd1 | Crem | Ppp1r14c |
| Cst7 | Rps27rt | IL17A-GFP-wg | Nfkbiz |
| Tnfrsf1b | Tox | Cst7 | Tcrg-C2 |
| Zfp36l1 | Rps12-ps3 | Lilrb4a | Ly6g5b |
| Plac8 | AW112010 | 4930503L19Rik | 4930453N24Rik |
| Gm11808 | Ctsb | Cish | Odc1 |
| Lilr4b | Plekho1 | Pim1 | Gm45716 |
| Kit | Il21 | Cpe | Tnfrsf4 |
| Adam19 | Sdc4 | Dennd4a | Slc3a2 |
| Srgn | Dennd4a | Plin2 | Pim1 |
| Rps27 | Mrps6 | Slc3a2 | Igkc |
| Il2rb | Tbc1d4 | Bcl2a1d | Vps37b |
| Nr4a1 | Rpl9-ps6 | Nrip1 | Tnfsf11 |
| Jchain | Rgs2 | Mmd | Lilrb4a |
| Pim1 | Pim1 | Fosl2 | Gm20594 |
| Bcl3 | Prkca | Tiparp | IL17A-GFP-wg |
| Uba52 | Adam19 | Zfp36l1 | Cish |
| Ttc39b | Ubald2 | Camk2n1 | Plk3 |
| Smco4 | Vps37b | Gm20594 | Tcrg-C4 |
| Ifi27l2a | Mmd | Rapsn | Tgif1 |
| Mrps6 | Nrip1 | Tnfsf8 | Hif1a |
| Nfkbia | Gm26917 | Jund | Camk2n1 |
| Tgif1 | Art2b | Smim3 | Csrnp1 |
| Lztfl1 | Dgat1 | Gm26917 | Bcl2a1d |
| Il21r | Rgs10 | Klf6 | Susd3 |
| Cited4 | Fabp5 | Dgat1 | Dgat1 |
| Jun | Gapdh | Kit | Ahr |
| Gm20069 | Ckb | Nr4a1 | Nmrk1 |
| Il2ra | Rpl27-ps3 | Smco4 | Pnrc1 |
| Gem | Inpp4b | Plac8 | Mxd1 |
| Hic1 | Gm26825 | Dok1 | Jchain |
| Ly6a | Cpe | Bcl2a1b | Cpe |
| Sh2d2a | Rpl36a-ps1 | Actn2 | Igha |
| Gm10269 | Tnfsf11 | Mdfic | Cxcr6 |
| Hsp90aa1 | Sh2d2a | Cited4 | Rbpj |
| Wdr89 | Tnfrsf9 | Nfil3 | Tiparp |
| Ccr5 | Sdf4 | St6galnac2 | Serpina3g |
| Nrip1 | Fgl2 | Plk3 | Bcl2a1b |
| Gm20594 | Ecm1 | Smox | Trafl |
| Timp2 | Ccr5 | Sytl3 | Hic1 |
| Batf | Klrb1c | P2rx7 | Hsp90aa1 |
| Twsg1 | Gm20069 | Nabp1 | Ubc |
| Fosl2 | Ikzf2 | Icos | Clk1 |
| Art2b | Cst7 | Ucp2 | AC160336.1 |
| Plekho1 | Izumo1r | Cd72 | 4930503L19Rik |
| Ckb | Rpl10 | H2-Q4 | Gm26917 |

TABLE 1-continued

UT tissue vs Spleen

| up_MLN | up_PP | up_SI | up_Colon |
|---|---|---|---|
| Odc1 | Aldoa | Cpd | Gm26532 |
| Il21 | Smco4 | Metrnl | Mmd |
| Lgals7 | Rpl10-ps3 | Irak3 | Hilpda |
| Rpl10-ps3 | Timp2 | Itgb5 | Plin2 |
| Gm26917 | Il21r | Vps37b | Cd28 |
| Rgs10 | Jun | Prelid2 | AW112010 |
| Rnaset2a | Cxcr4 | Lgals7 | Kit |
| Oas1a | Rnaset2b | Skil | Gadd45g |
| Laptm4b | Ramp3 | Mxd1 | Mmp9 |
| Zeb2 | Il2rb | Tox | Smim3 |
| Ifit1 | Plk3 | Sh3gl3 | Ppp1r16b |
| Gimap7 | Hsp90aa1 | Cmc2 | Dusp5 |
| Izumo1r | Odc1 | Cd86 | Prrt1 |
| Grn | Lilrb4a | Gstp1 | Skil |
| Gm6525 | Twsg1 | Selenom | Got1 |
| Glrx | Tcrg-C2 | Tnfrsf1b | Trps1 |
| Arhgap31 | Gm11808 | Serpina3g | Ecm1 |
| Ikzf3 | Ttc39b | Bcl3 | Sh2d2a |
| Ccnd2 | Bcl3 | H2-Q6 | Nkg7 |
| Lilrb4a | Nmrk1 | Ociad2 | H2-Q4 |
| Mmp9 | Tnfsf11 | Tnfsf11 | Nabp1 |
| Ppp1r15a | Rpl13a-ps1 | Tox2 | Fam110a |
| Abcg1 | Stx11 | Il12rb1 | Phlda1 |
| Tnf | Rps12 | Runx1 | Srgn |
| Pdcd1 | Rpl27 | Wbp1 | Nfkbid |
| Egr1 | Gm20594 | Lmo4 | Ermn |
| Vmp1 | Susd3 | Ablim3 | Tpi1 |
| Comt | Ptpn22 | Ddx5 | Pkd1 |
| Tnfsf11 | Dusp1 | Tmem140 | Irf4 |
| Icam1 | Trib2 | Gbp8 | Lmna |
| Rpl9 | Egr1 | Sh2d2a | Ptms |
| Usp18 | Pde5a | AU020206 | Tob2 |
| Malt1 | St13 | Adam19 | Metrnl |
| Vps37b | Vmp1 | Ahr | Havcr2 |
| Sbno2 | Cdkn1a | Podnl1 | Ucp2 |
| Inpp4b | Slc3a2 | Mmp9 | Mrps6 |
| ligp1 | Arhgap31 | Ppp1r16b | Hist1h1c |
| Usp50 | AW011738 | Id2 | Tnf |
| Selenom | Gm2000 | Ubald2 | Samsn1 |
| Rpl9-ps1 | Fam162a | Rgs2 | Glrx |
| Prdm1 | Angptl2 | Kdm6b | Btg1 |
| Bst2 | Samsn1 | Blk | Cst7 |
| Nipal1 | Dynlt3 | Hist1h1c | H2-Q6 |
| Hspa5 | Tnfrsf1b | Serpinb6a | Gapdh |
| Ifng | Gimap5 | Samsn1 | Coq10b |
| Trim30a | Sh3gl3 | Gm20186 | Pim3 |
| Gm48236 | Vps54 | Capg | Plcxd2 |
| Rpl7a | Ffar2 | BC018473 | Gm20186 |
| Rpl7a-ps5 | Rnf19a | Hsp90aa1 | Cd44 |
| Egr2 | Prelid2 | B4galnt4 | Rpl27-ps3 |
| IL17A-GFP-wg | AC163354.1 | Dhrs3 | Gm11808 |
| Rnaset2b | Mif | Tnfrsf9 | Il12rb1 |
| Med7 | Mxd1 | Rpl9-ps6 | Il21r |
| Gm47283 | Casp4 | Btg1 | Ddx5 |
| Gm8186 | Mdfic | Art2b | Cpd |
| Tbc1d4 | Malt1 | Itm2b | F2rl2 |
| Rps29 | Tcrg-C4 | Ifi27 | Actn2 |
| Tgtp1 | Camk2n1 | Coro2a | Hspa5 |
| Ctss | Rilpl2 | Cxcr6 | Map3k8 |
| Ube2l6 | Arhgef3 | Efhd2 | Aldoa |
| Peak1 | Nfkbia | Nkg7 | Capg |
| Hspe1 | Dennd2d | Arhgap31 | Icam1 |
| Maf | Itm2c | Cebpb | Btg2 |
| Got1 | Chchd10 | Ctsb | Malat1 |
| Bhlhe40 | Rbm24 | Rab37 | Rpl9-ps6 |
| Samsn1 | Plac8 | Cd38 | Cd40lg |
| Gm5239 | Litaf | Malat1 | Runx1 |
| Il17a | Stat4 | Aldh7a1 | Ctsb |
| Slc3a2 | Cd200 | Sla | Litaf |
| Gm5547 | Nfkbid | B930036N10Rik | Ccnd2 |
| Rilpl2 | Nfkbiz | Gfi1 | Mdfic |
| Rasa1 | Egr2 | Pigp | Ifrd1 |
| Gm9856 | Pdcd1lg2 | Msi2 | St6galnac2 |
| AU020206 | RasIl1a | Gbp6 | BC018473 |
| Stat1 | Hspa5 | Litaf | Tnfrsf1b |
| Hsp90ab1 | Ece1 | Slc16a6 | Ctla2a |
| Sdf4 | Fyn | Pde5a | Ramp3 |
| Gm10076 | Sytl3 | Coq10b | Acot7 |
| Prg4 | Rps27 | Nr3c1 | Casp4 |
| Hsph1 | Ldlrad4 | Rpl13a-ps1 | B930036N10Rik |
| Tcrg-C4 | Gm10269 | St6galnac3 | Prr7 |
| Nfkbiz | Dhrs3 | Tab2 | Uba52 |
| Gm9493 | Msi2 | Nedd9 | Gm20069 |
| F2r | Prrt1 | Il2ra | AU020206 |
| Trib2 | Gm8186 | Vmn1r13 | Batf |
| St13 | Wdr89 | Chchd10 | Gbp6 |
| AW011738 | AU020206 | Itm2c | Rps12-ps3 |
| Itm2c | Slc41a1 | Inpp4b | Dnajb1 |
| Irf7 | Pkm | Traf1 | 2010111I01Rik |
| Gnl3 | Havcr2 | Mgat5 | Wnk1 |
| Naga | Gm6525 | Sat1 | Nedd9 |
| Gbp4 | Tox2 | Cd247 | Prdm1 |
| Notch1 | Ppp1r14c | Csrnp1 | Spty2d1 |
| Ubald2 | Plin2 | Comt | Rpl27 |
| Plk3 | Map3k8 | Unc119 | Aebp2 |
| Wdfy1 | Stx6 | Cyp4f16 | Arhgap31 |
| Gadd45g | Naga | Mynn | Rbm24 |
| Il23r | Sla | Cerk | Dusp6 |
| Tnfrsf9 | P2rx7 | Ptk2b | H2-Q7 |
| Pigp | Abhd17c | Rcbtb2 | Arl5a |
| 4930503L19Rik | Sap18b | Cd3e | Rps12 |
| Havcr2 | Rpl9 | Ikzf3 | Adam19 |
| Vmn1r13 | Hsp90ab1 | Arl5a | Cd83 |
| Arhgap39 | Prdm1 | Cd3g | Vmn1r13 |
| Arl5a | Ppp1r16b | Aebp2 | Ikzf3 |
| Gm9803 | Il2ra | Sh2b1 | Ttc39b |
| Ppp1r14c | Nfatc1 | Ramp3 | Atf4 |
| Gm49368 | Gpr183 | Grina | Gng2 |
| Nr3c1 | Rabgap1l | Got1 | Zc3h12a |
| Rtp4 | Ccnd2 | Gm12840 | Itgb5 |
| Mdfic | Got1 | Tmem176b | Comt |
| Ldlrad4 | Med7 | Pi4k2a | Ubb |
| Zfp36 | Gm47283 | Il1r2 | Tmem176b |
| Socs3 | Maf | Lgmn | Wbp1 |
| | Vmn1r13 | Mapkapk3 | Nrip1 |
| Etv6 | Icam1 | Pnrc1 | Nr3c1 |
| Mast4 | Pnrc1 | Lpxn | Egr1 |
| Rpl9-ps1 | Gpr183 | Zfp36 | Akap13 |
| Malat1 | Dusp6 | Cd4 | |
| Smim3 | D16Ertd472e | Rps27rt | |
| Arhgap39 | Azin1 | Rpl10 | |
| Nfkb2 | Ptger4 | Slc38a2 | |
| Pnrc1 | Hilpda | Rrad | |
| Sbno2 | Rrad | Rpl13a-ps1 | |
| Il23r | Il23r | Tgfb1 | |
| Aebp2 | Ecm1 | Ndfip1 | |
| Arid5b | Ttc39b | Smco4 | |
| Cxcr5 | Ubc | Cd6 | |
| 1700012B07Rik | Rab11fip1 | Sap18b | |
| Ucp2 | Lncpint | Smad7 | |
| Rps29 | Gpr171 | Grn | |
| Mapkapk2 | Srgn | Bcl3 | |
| Rbpj | Dtx3 | Pkm | |
| Gimap7 | Pde3b | Lncpint | |
| Uba52 | Acot7 | Rabgap1l | |
| Cycs | Gm11808 | Ipmk | |
| Cd247 | Rpl27-ps3 | Cebpb | |
| Tmem256 | Hsph1 | Rnaset2a | |
| Cflar | Lamtor4 | Mapkapk3 | |
| Cisd2 | Ndufa1 | Stx11 | |
| Gm20186 | Sap18b | Pde4b | |
| Marcksl1 | Dus2 | Ier5 | |
| Wdfy1 | Rab8b | Fabp5 | |
| Cd38 | Serpinb1a | Vgll4 | |
| Vcpkmt | Ubb | Picalm | |
| 4930503L19Rik | Man2a2 | Slc2a3 | |
| Gpr174 | Rpl10 | Gstp1 | |
| Sypl | Rps12 | Ccnl1 | |
| Pfkl | Plekhf1 | Gpr65 | |
| Gm48236 | Prdm1 | Emb | |
| Comt | Ube2e3 | Gm48236 | |
| Bmp2k | | Tmem256 | |

TABLE 1-continued

UT tissue vs Spleen

| up_MLN | up_PP | up_SI | up_Colon |
|---|---|---|---|
| Mapkapk3 | Pim3 | Msi2 | |
| Gm19585 | Ccnd2 | Tmem176a | |
| Ftl1-ps1 | Srsf5 | Pi4k2a | |
| Rtl8a | Acpp | Hsph1 | |
| Aldh7a1 | Cfap36 | Ppp1r10 | |
| St6galnac3 | Ppp1r10 | Sla | |
| Vsig10 | Hspa5 | Aypi1 | |
| Nrgn | Gm47283 | Hsp90ab1 | |
| Phactr2 | Pkp3 | Rasgrp1 | |
| Il1r1 | Dnajb13 | F2r | |
| Cd4 | Nfkbia | Unc119 | |
| Icam1 | Ptms | Sdf4 | |
| Tspan5 | Znrf1 | Acpp | |
| Slc29a1 | Tob2 | Gpr183 | |
| Azin1 | Gpr183 | Gbp4 | |
| Hspe1 | Mrps6 | Ier2 | |
| Zap70 | Ybx1 | Gbp8 | |
| Tiparp | Dexi | Birc3 | |
| Traf1 | 2010111I01Rik | Kcnk5 | |
| Relb | Phlda1 | Il2ra | |
| Peak1 | Ppt2 | Srsf5 | |
| Pde4b | Tmem256 | D16Ertd472e | |
| Pgam1 | BC037034 | Mapkapk2 | |
| Cerk | Rtl8a | Antxr2 | |
| Tnf | Cisd2 | Pkp3 | |
| Gcnt2 | Dnajb1 | Aldh7a1 | |
| Rpl7a | Ppm1h | Il2rb | |
| Arl5a | Rnase4 | Man2a2 | |
| Gm5239 | Stat4 | Pold4 | |
| Grn | Odc1 | Il21 | |
| Gm5547 | Tgif1 | Tab2 | |
| Sec61g | Grn | Gm47283 | |
| Nab2 | | Tmem154 | |
| Neu3 | | Itpr1 | |
| Cish | | Tubb2a | |
| Plscr1 | | Selenom | |
| Raf1 | | Txk | |
| Fam3c | | Prdx6 | |
| Med15 | | Stat3 | |
| Ndfip1 | | Ptp4a1 | |
| Trbc1 | | Gpr171 | |
| Sec14l1 | | Serpinb6a | |
| Elk3 | | Arid5a | |
| Gm9803 | | Gch1 | |
| Snrpg | | Cd82 | |
| Pde3b | | Ptk2b | |
| Hdac4 | | Fth1 | |
| 1500011K16Rik | | Il1r1 | |
| Cstb | | Maf | |
| Hpcal1 | | Grcc10 | |
| Notch1 | | Cd38 | |
| Sesn3 | | Bcl2l1 | |
| Ccdc28b | | Grina | |
| Ctla2a | | Cyp4f16 | |
| Dus2 | | Angptl2 | |
| Rpl38 | | Itm2b | |
| Gm9493 | | Rpl10-ps3 | |
| Pold4 | | Abhd17c | |
| | | Siah2 | |
| | | Orai1 | |
| | | Rab11fip1 | |
| | | Slc16a6 | |
| | | Il27 | |
| | | Stx6 | |
| | | Ccr2 | |
| | | Eif4e3 | |
| | | Inpp4b | |
| | | Ece1 | |
| | | Coro2a | |
| | | Vps54 | |
| | | Rhoh | |
| | | Gm5547 | |
| | | Rora | |
| | | Atp2b4 | |
| | | Cstb | |
| | | Cxcr4 | |
| | | Twsg1 | |
| | | Lamc1 | |
| | | Sbno2 | |
| | | Gm5239 | |
| | | Meis3 | |
| | | Gm8797 | |
| | | Dnajb9 | |
| | | Myl12a | |
| | | St13 | |
| | | B4galnt4 | |
| | | Tox2 | |
| | | Msmo1 | |
| | | Gm14005 | |
| | | Slamf1 | |
| | | Dok1 | |
| | | Rnaset2b | |
| | | Rab8b | |

TABLE 2

UT tissue vs Spleen

| down_mLN | down_PP | down_SI | down_colon |
|---|---|---|---|
| Itgb1 | Klf2 | Klf2 | Klf2 |
| Igkc | S100a4 | Itgb1 | Itgb1 |
| Igha | Lgals3 | S100a4 | Rasgrp2 |
| S100a4 | Itgb1 | Slamf6 | Stmn2 |
| Ube2c | Crip1 | Atp1b3 | Atp1b3 |
| Crip1 | S100a6 | Cdc25b | S1pr1 |
| Stmn1 | Rasgrp2 | S1pr4 | Cdc25b |
| H2afx | Stmn2 | Ass1 | Klf3 |
| S100a6 | Emp3 | Ramp1 | Gzma |
| Fut7 | Igha | S1pr1 | S1pr4 |
| Klf2 | Sgk1 | Ighm | Slamf6 |
| Cdc20 | Igkc | Crip1 | Rtp4 |
| Ccnb2 | S1pr4 | Rasgrp2 | 1500009L16Rik |
| Lgals1 | Lgals1 | Klf3 | Il7r |
| Crip2 | Ramp1 | Ms4a4b | Sgk1 |
| Stmn2 | 1500009L16Rik | Ube2c | Acsbg1 |
| Rrm2 | Lfng | Sgk1 | Ighm |
| Lgals3 | Ube2c | Stmn2 | Lef1 |
| Emp3 | Cdc25b | Lef1 | Tspan32 |
| Hmgb2 | Vim | Cd9 | Ccr6 |
| Cenpa | Tppp3 | Ccr7 | Ifi27l2a |
| Tppp3 | Glipr2 | Cenpa | Ube2c |
| Birc5 | Rasa3 | Ccnb2 | Prkcq |
| Pclaf | Ass1 | Ifi27l2a | Klhl6 |
| Lmna | Ccnb2 | Lfng | Trat1 |
| Cks1b | Ms4a4b | Pdlim1 | Pycard |
| Ggt1 | Fut7 | Emp3 | Pdlim1 |
| Top2a | Ggt1 | Lgals3 | Dtx1 |
| Mki67 | Atp1b3 | Rgcc | Ccnb2 |
| Tacc3 | Pycard | S100a6 | Tnfrsf25 |
| Prc1 | Anxa6 | Prkcq | Cd7 |
| Cdc25b | Stmn1 | Tcf7 | Ccr7 |
| Gzma | Birc5 | Id3 | Fut7 |
| Anxa2 | Rrm2 | Stmn1 | Rasa3 |
| Klrk1 | Adgre5 | Rasa3 | Ripor2 |
| Cdca8 | S1pr1 | Acsbg1 | Stk38 |
| Cenpe | Rtp4 | Birc5 | Ggt1 |
| Anxa1 | Tsc22d3 | Fut7 | Birc5 |
| BC018473 | Cd48 | Il7r | Tcf7 |
| Rasgrp2 | Itgb7 | AB124611 | H2afx |
| S100a10 | S100a10 | 1500009L16Rik | Cenpa |
| Hsd11b1 | Pclaf | Pglyrp1 | Hmgb2 |
| Nrm | Trat1 | Ripor2 | Id3 |
| Cdca3 | Il7r | Kcnn4 | Cdc42se1 |
| Ndc80 | Crip2 | Klhl6 | Cd9 |
| Kif22 | H2afx | Cdc20 | AB124611 |
| Atp1b3 | Jaml | Stk38 | Itga4 |
| AB124611 | Tnfrsf25 | Tspan32 | Dgka |
| Klf3 | Klf3 | Tppp3 | Kcnn4 |

TABLE 2-continued

UT tissue vs Spleen

| down_mLN | down_PP | down_SI | down_colon |
|---|---|---|---|
| Cdk1 | Racgap1 | Dgka | Add3 |
| Adgre5 | Acsbg1 | Cd27 | Actn1 |
| Cdkn3 | Cdc42ep3 | Lgals1 | Ass1 |
| Ahnak | Klhl6 | Evl | Cmah |
| Jaml | Klrk1 | Tnfrsf25 | Il6ra |
| Ccna2 | Lsp1 | Il6ra | Txndc5 |
| Fbxo5 | Anxa1 | S100a10 | Crip1 |
| Prkcq | Add3 | Ccr6 | Rrm2 |
| Vim | Ahnak | Adgre5 | Ifi203 |
| Tmpo | Cd7 | H2afx | Tmem71 |
| Lsp1 | Cenpa | Hmgb2 | Gm2682 |
| Asf1b | Nrm | Ggt1 | Evl |
| Glipr2 | Pdlim1 | Pycard | Pclaf |
| G430095P16Rik | Capn2 | Rrm2 | Ehd3 |
| Racgap1 | Ccna2 | Cmah | Il17ra |
| Tagln2 | Anxa2 | Flna | Stmn1 |
| Ass1 | Gna15 | Gramd3 | Tppp3 |
| Anxa6 | Dok2 | Izumo1r | Ccna2 |
| Ramp1 | Lmna | Cd7 | Pglyrp1 |
| Tyms | Cdc20 | Glipr2 | Emp3 |
| Cks2 | Esyt1 | Klrk1 | Cdc20 |
| 1500009L16Rik | Stk38 | Actn1 | Rarg |
| Sema4a | Hmgb2 | Prdx4 | Nrp1 |
| Rgcc | Lrrc25 | Rarg | Lfng |
| Hist1h1e | Hsd11b1 | Pclaf | Ifit1 |
| Rarg | Tspo | Cks1b | Ddit4 |
| S1pr4 | Cited2 | Arl4c | Samhd1 |
| St3gal6 | Tuba1a | Crip2 | Pik3ip1 |
| Spc24 | Txndc5 | Cxcr3 | Racgap1 |
| Cd48 | AB124611 | Ddit4 | Slfn1 |
| Sgk1 | Top2a | Anxa1 | Prdx4 |
| Mid1ip1 | Lbr | Icam2 | Icam2 |
| Tsc22d3 | Pglyrp1 | Cdkn3 | Hexb |
| Cited2 | Ripor2 | Sike1 | Phf11c |
| S1pr1 | Prkcq | Cited2 | Fam69a |
| Rnf115 | Sema4a | Gm2682 | Mndal |
| Hmgb3 | Flna | Samhd1 | Cenpe |
| Myo1g | Ccr6 | Cenpe | Sike1 |
| Trat1 | Prdx4 | Kbtbd11 | Trim12a |
| Lmnb1 | Lmnb1 | Racgap1 | BC147527 |
| Ripor2 | Kif22 | Sema4a | Mki67 |
| Esyt1 | Cdca3 | Trat1 | Ms4a4b |
| Il7r | Mki67 | Rps19 | Ifi209 |
| Acsbg1 | Rarg | Cdc42se1 | Rsrp1 |
| Mpnd | E2f2 | Cdca3 | Arhgap45 |
| Itgb2 | Nqo2 | Il17ra | Tnfaip8l2 |
| Pglyrp1 | Myo1g | Nrp1 | 2810001G20Rik |
| Cd9 | Asf1b | F2rl1 | Hmgn2 |
| Serpinb1a | Cxcr3 | Arl5c | Cdca3 |
| Gna15 | Pttg1 | Kif22 | Igf2bp3 |
| Adam8 | Cdkn3 | Cd48 | Gramd3 |
| Kif23 | Cenpe | Mki67 | Fnta |
| Capn2 | Selplg | Tmem71 | Cks1b |
| Ltb4r1 | Cd47 | Lsp1 | Crip2 |
| Cdkn2c | Cks1b | Atp2b1 | Cd48 |
| Lfng | Iqgap2 | Cdk1 | Mrps5 |
| Atp1a1 | Rcsd1 | Cldnd1 | E2f2 |
| Pycard | Nebl | Cks2 | Cdkn3 |
| Rbms1 | Plec | Gprin3 | Sp100 |
| Glud1 | 1700097N02Rik | Ccna2 | Lsp1 |
| Incenp | Prc1 | G430095P16Rik | G430095P16Rik |
| Cdc42ep3 | Tmem71 | Nsg2 | Cd27 |
| Gm2682 | Il17ra | Tob1 | Rps19 |
| H2afv | Cdk1 | Tacc3 | A430078G23Rik |
| Arl5c | G430095P16Rik | Add3 | Cnp |
| Lockd | Tacc3 | Itga4 | Kif22 |
| Tnfrsf25 | Tagln2 | 2310001H17Rik | Al467606 |
| Lbr | Mndal | Top2a | Sema4a |
| Cd7 | Dock2 | Cdca8 | Fbxo5 |
| Plec | Sike1 | Tmsb10 | Itgb7 |
| Anp32e | Trpv2 | Ehd3 | Adk |
| Rasa3 | Rbms1 | Prc1 | Sh2d1a |
| Reep4 | Cmtm7 | 1700097N02Rik | Phf11b |
| Knstrn | Nrp1 | Iqgap2 | Cd47 |
| Dap | St3gal6 | Fam69a | Cdk1 |
| Safb | Card19 | Asf1b | F2rl1 |
| Txndc5 | Axin2 | Rtp4 | Iqgap2 |
| Cdkn2d | Fbxo5 | E2f2 | Rom1 |
| Riox2 | Ifi203 | Slfn1 | Madd |
| Mrps5 | Arl5c | Spn | Gm10073 |
| Lrrc25 | Ccr7 | Ifit1 | Rnf167 |
| Iqgap2 | Kcnab2 | Plec | Kbtbd11 |
| E2f2 | Tmpo | Lmna | Faah |
| Hmgn5 | Cnp | Adk | Ccr9 |
| Bub3 | Cdc42se1 | Rbms1 | H2afv |
| Pdlim1 | Jchain | Nrm | Tnfrsf26 |
| Tspo | Arl4c | Mir142hg | Nqo2 |
| Tcf19 | Mrps5 | Cd47 | Asf1b |
| Bin2 | Rom1 | Al467606 | Mllt11 |
| Stk38 | Al467606 | Txndc5 | Axin2 |
| Rab8a | Rala | Xrn2 | Cdca8 |
| Apbb1ip | Lef1 | Gna15 | Nsg2 |
| Itgb2 | Cdkn2d | Rala | Spn |
| Nebl | Fnta | Spc24 | Lbr |
| Myo1f | Tubb4b | Knstrn | B3galt4 |
| Rom1 | Sit1 | Hexb | Ndc80 |
| Prdx4 | Reep5 | Dap | Cd1d1 |
| Cxcr3 | Knstrn | Rom1 | Rflnb |
| Atp2b1 | Flt3l | Cd2 | Tacc3 |
| Mad2l1 | Tcf19 | Ndc80 | Top2a |
| Nqo2 | Gm2682 | Tnfrsf26 | Lrrc8a |
| Trpv2 | Myo1f | Nebl | Kcnq1ot1 |
| Sike1 | 4930523C07Rik | Slc17a9 | Knstrn |
| Prkag1 | Spc24 | Mrps5 | Xrn2 |
| Amdhd2 | Tob1 | Hmgb3 | Btla |
| Dok2 | Galnt12 | Anp32e | Snhg20 |
| | Ndc80 | Kcnab2 | Flna |
| | Fam69a | BC147527 | Hmgb3 |
| | Cmah | Dusp2 | Xaf1 |
| | Kbtbd11 | Satb1 | S100a10 |
| | Mpnd | Ltb | Prkd2 |
| | Cdca8 | Glipr1 | Cxcr3 |
| | Gata3 | Ccr4 | Pttg1 |
| | Ifit1 | Tmod3 | Anp32e |
| | Sp100 | Fbxo5 | Ms4a6b |
| | Ttc13 | Scpep1 | Selenoh |
| | Grap | Kif23 | Hp1bp3 |
| | Twf2 | Smc2 | Ttc13 |
| | Selenoh | Ttc13 | Phgdh |
| | Tyms | Snrpd3 | Kif21b |
| | Spn | Capn2 | Prc1 |
| | Adam8 | Nqo2 | Gna15 |
| | BC147527 | Gm9844 | Rbm38 |
| | Glipr1 | Marcksl1 | Slc17a9 |
| | Atp2b1 | Axin2 | Arhgap15 |
| | Ddx58 | Card19 | Glipr2 |
| | Hexb | Gclm | Lamp1 |
| | S100a13 | Nfic | Mitd1 |
| | Me2 | Rps20 | Ifi206 |
| | Snrpd3 | Ifi209 | Anxa1 |
| | Fli1 | Phf11b | Traf3ip3 |
| | Bin2 | Snhg20 | Rp9 |
| | Rgcc | Carhsp1 | Trim35 |
| | Ywhaq | Mpnd | Spc24 |
| | H2afv | Mllt11 | Top2b |
| | Prkd2 | H2afv | Aqp3 |
| | Slc17a9 | H2afz | Psen2 |
| | Apbb1ip | Lockd | Rplp0 |
| | Smc2 | Lbr | Sptbn1 |
| | Slc25a24 | Dck | Pym1 |
| | Tuba4a | Faah | Bin2 |
| | 2810001G20Rik | Prkd2 | Hsd11b1 |
| | Mid1ip1 | Itgb7 | Ccr4 |
| | Ifi209 | Tmpo | Scpep1 |
| | Rad21 | Tspo | Rpsa |
| | Def6 | Rflnb | Arl5c |
| | Arhgdib | Anxa6 | Epsti1 |
| | Klf6 | Hmgn2 | Lmnb1 |
| | Lrrc8a | Sp100 | Rps20 |
| | Nfic | Myo1g | Sp110 |
| | Tmod3 | Tpm4 | Dock2 |
| | Crlf3 | Fas | Bzw2 |

TABLE 2-continued

UT tissue vs Spleen

| down_mLN | down_PP | down_SI | down_colon |
|---|---|---|---|
| | Ccnd3 | Rpsa | |
| | Tspan32 | Sptbn1 | |
| | Pag1 | Ahnak | |
| | Cks2 | Rplp0 | |
| | Irf7 | B4galt1 | |
| | Cry1 | Bin2 | |
| | Kif23 | Crlf3 | |
| | Anapc5 | Cry1 | |
| | Calm1 | A430078G23Rik | |
| | Glud1 | 2810001G20Rik | |
| | Scpep1 | Ifi203 | |
| | Riox2 | Fnta | |
| | Tnfaip8l2 | Add1 | |
| | A430078G23Rik | Ablim1 | |
| | Ly6a | Tnfaip8l1 | |
| | Thy1 | Dgkz | |
| | Phf11c | Igf2bp3 | |
| | Hmgn5 | Pik3ip1 | |
| | Il6ra | Selenoh | |
| | Cldnd1 | Lmnb1 | |
| | Hmgn2 | Madd | |
| | Id3 | Plp2 | |
| | Sesn1 | Osbpl9 | |
| | Triobp | Pttg1 | |
| | Sun1 | Arhgdib | |
| | Tpst2 | Btla | |
| | Kcnn4 | Sun1 | |
| | Txnip | | |
| | Idh3a | | |
| | Rgs14 | | |
| | Abhd8 | | |
| | Xrn2 | | |
| | Entpd5 | | |
| | Usp1 | | |
| | Hist1h1e | | |
| | Ppdpf | | |
| | Samhd1 | | |
| | Atp2a3 | | |
| | Carhsp1 | | |
| | Faah | | |
| | Itgb2 | | |
| | Igf2bp3 | | |
| | Ctsd | | |
| | Dgka | | |
| | Ltb4r1 | | |
| | Irf2bpl | | |
| | Gprin3 | | |
| | Tmem59 | | |
| | Bst2 | | |
| | Mad2l1 | | |
| | Add1 | | |
| | 2210011C24Rik | | |
| | Acat1 | | |
| | Ccr4 | | |
| | Mark2 | | |
| | Gucd1 | | |

TABLE 3

Tissue specific genes upregulated in EAE-vs-Untreated

| SI | colon | spleen | PP | mLN |
|---|---|---|---|---|
| Zfp36l2 | Cd7 | AA467197 | S100a4 | Ccl5 |
| Serinc3 | Ccl5 | Plac8 | Klf2 | Lgals3 |
| Gzma | Ctsw | Ifitm2 | Vim | Rbm3 |
| Ccl5 | Klf2 | Ifitm1 | Tsc22d3 | Ifngr1 |
| Tsc22d3 | Rbm3 | Ifitm3 | Fabp2 | S100a4 |
| Klf2 | Zfp36l2 | Bhlhe40 | S100a6 | Nkg7 |
| Fkbp5 | Trat1 | Nkg7 | Ifngr1 | Cirbp |
| Ddit4 | Serpinb1a | Ifngr1 | Crip1 | AA467197 |
| Serpina3g | Il7r | Ermn | Rbm3 | Ifitm2 |
| Vars | Acsbg1 | Ctsw | Txnip | Dnajc15 |
| Tcrg-C2 | Cirbp | Ggt1 | Bcl2 | Bbc3 |
| Nfkbia | | Pglyrp1 | Ltb4r1 | Txnip |
| Bcl2 | | Klrd1 | Ccl5 | Bhlhe40 |
| Il7r | | Sema4a | Ccr2 | Tsc22d3 |
| Cirbp | | Gramd3 | Serpinb1a | Sytl3 |
| Rbm3 | | Il18rap | Cirbp | 1500011B03Rik |
| Ccl20 | | Ccr2 | Cxcr6 | S100a6 |
| Acp5 | | Zyx | Tcrg-C1 | Lilr4b |
| Bbc3 | | 2810001G20Rik | Tmem176b | Bcl2 |
| 2810474O19Rik | | AC163354.1 | Rgs1 | Vim |
| Apobec3 | | Serpinb6b | Lilr4b | Ctsw |
| Gimap5 | | Itgb1 | Acsbg1 | Zfp36l2 |
| | | Rasl11a | Lgals3 | Crip1 |
| | | Sytl3 | Il18r1 | 2810474O19Rik |
| | | Klrc1 | Il7r | Klf2 |
| | | Cxcr6 | Ddit4 | Ccr2 |
| | | Id2 | Id2 | Ermn |
| | | Bbc3 | Actn2 | Id2 |
| | | Ostf1 | Arl4c | Il7r |
| | | Car5b | Gm5914 | Gm5914 |
| | | Paox | Ccr9 | 1700097N02Rik |
| | | Gcnt2 | Selplg | Mir142hg |
| | | Furin | Rasgrp2 | Lfng |
| | | Slc2a3 | Emp3 | Ddit4 |
| | | Lilr4b | Nkg7 | Atp1b3 |
| | | Rom1 | Anxa6 | Acsbg1 |
| | | Satb1 | Serpina3g | Glipr2 |
| | | Il2rb | Aqp3 | Pik3ip1 |

TABLE 3-continued

Tissue specific genes upregulated in EAE-vs-Untreated

| SI | colon | spleen | PP | mLN |
|---|---|---|---|---|
|  |  | Hcst | Cd7 | Tmem203 |
|  |  | Lgals3 | Pdcd4 | Gm14005 |
|  |  | Nptn | Il17re | Ltb4r1 |
|  |  | Ly6a | Bbc3 | BC018473 |
|  |  | Serpinb9 | Tmem176a | Serpinb1a |
|  |  | Dnajc15 | Glipr2 | Dusp2 |
|  |  | Anxa1 | Dusp2 | Zyx |
|  |  | Ctsd | Cish | Gimap5 |
|  |  | Crip1 | Zfp36l2 | Ahnak |
|  |  | Gzmb | 1500011B03Rik | Ostf1 |
|  |  | Atp8b4 | Rnf166 | Gm8369 |
|  |  | Cox17 | Socs2 | S1pr4 |
|  |  |  | Rora | Cdkn2d |
|  |  |  | Dnajc15 | Lgals1 |
|  |  |  | Plekhf1 | Cd47 |
|  |  |  | Stk24 | Tmem71 |
|  |  |  | Gm8369 | Fam204a |
|  |  |  | Cd47 | Gna13 |
|  |  |  | Lsp1 | Smim4 |
|  |  |  | Lztfl1 | Rasgrp2 |
|  |  |  | 2810474O19Rik | Il18rap |
|  |  |  | St6galnac1 | 1500009L16Rik |
|  |  |  | S1pr4 | 1810058I24Rik |
|  |  |  | Ctla2a | Ifitm3 |
|  |  |  | BC018473 | Pofut2 |
|  |  |  | St6galnac2 | Anxa2 |
|  |  |  | Pofut2 | Cd48 |
|  |  |  | Pik3ip1 | Ifitm1 |
|  |  |  | Ccdc88c | Il22 |
|  |  |  | Trat1 | Gm29243 |
|  |  |  | Ahnak | Gadd45g |
|  |  |  | Cytip | St6galnac2 |
|  |  |  | Sytl3 | Arl6ip5 |
|  |  |  | Ctsw | Cd200 |
|  |  |  | Gzma | Ass1 |
|  |  |  | Ostf1 | Ccdc88c |
|  |  |  | Sit1 | Snhg9 |
|  |  |  | Atp1b3 | Htatip2 |
|  |  |  | Ass1 | Pim1 |
|  |  |  | Ly6a | Cd7 |
|  |  |  | Lfng | H1f0 |
|  |  |  | Lgals1 | Card19 |
|  |  |  | Itgb7 | St6galnac1 |
|  |  |  | Tnfrsf25 | Eci2 |
|  |  |  | Lmo4 | Zfp672 |
|  |  |  | Coro2a | Zfp87 |
|  |  |  | Reep5 | Rab27a |
|  |  |  | Pim1 | Plp2 |
|  |  |  | Nop53 | Fkbp5 |
|  |  |  | Adgre5 | AU020206 |
|  |  |  | Cdkn2d | Zfp787 |
|  |  |  | Tpst2 | Cenpw |
|  |  |  | Adam19 | Pnpla2 |
|  |  |  | Cd48 | Efhd2 |
|  |  |  | Mapkapk3 | Mzt1 |
|  |  |  | Fgl2 | Serinc3 |
|  |  |  | Ifng | Mrpl57 |
|  |  |  | AC163354.1 | Etfbkmt |
|  |  |  | Mbd2 | Arl2bp |
|  |  |  | Arhgap9 | Reep5 |
|  |  |  | Cyb5a | Serpina3g |
|  |  |  | Emb | Hcst |
|  |  |  | Prelid2 | Il18r1 |
|  |  |  | Serinc3 | Flt3l |
|  |  |  | IL17A-GFP-wg | 2310039H08Rik |
|  |  |  | Tmem203 | Cenpa |
|  |  |  | Fabp5 | Anxa1 |
|  |  |  | Rab27a | Cish |
|  |  |  | S1pr1 | Cysltr1 |
|  |  |  | Ermn | Klhdc1 |
|  |  |  | Eno1 | Avpi1 |
|  |  |  | Ctsc |  |
|  |  |  | Smim4 |  |
|  |  |  | 1810058I24Rik |  |
|  |  |  | Esyt1 |  |
|  |  |  | Bhlhe40 |  |

TABLE 3-continued

Tissue specific genes upregulated in EAE-vs-Untreated

| SI | colon | spleen | PP | mLN |
|---|---|---|---|---|
| | | | Ppp3ca | |
| | | | Eef2 | |
| | | | Atp2b4 | |
| | | | Rap1b | |
| | | | Ttc39b | |
| | | | Anxa2 | |
| | | | Atxn1 | |
| | | | Gna15 | |
| | | | Sema4d | |
| | | | Zfp87 | |
| | | | Cdk6 | |
| | | | Gm29243 | |
| | | | Ramp3 | |
| | | | Gm5547 | |
| | | | Zfp672 | |
| | | | Tecpr1 | |
| | | | Efhd2 | |
| | | | Rpl24 | |
| | | | Pcif1 | |
| | | | Gm14005 | |
| | | | Ptger4 | |
| | | | Dexi | |
| | | | Thy1 | |
| | | | Rnf138 | |
| | | | Il22 | |
| | | | Grap2 | |
| | | | Gclc | |
| | | | Runx3 | |
| | | | Tab2 | |
| | | | Ginm1 | |
| | | | Gimap5 | |
| | | | Crmp1 | |
| | | | Nebl | |
| | | | Klf13 | |
| | | | Rnf19b | |
| | | | Klk8 | |

TABLE 4

Tissue specific genes downregulated in EAE-v-Untreated

| SI | colon | spleen | PP | mLN |
|---|---|---|---|---|
| Hspa1a | Hspa1a | Ifi27l2a | Sostdc1 | Ifi27l2a |
| Igkc | Ccl20 | Izumo1r | Pdcd1 | Isg15 |
| Igha | Il10 | Tcrg-C2 | Izumo1r | Ccl20 |
| Jchain | Tnfrsf9 | Timp2 | Art2b | Lag3 |
| Ifi27l2a | Lgals7 | Ikzf2 | Rnaset2a | Ifit1 |
| Isg15 | Lag3 | Slamf6 | Tbc1d4 | Izumo1r |
| Stmn1 | Hspa1b | Cd27 | Cd83 | Art2b |
| Lag3 | Gzmb | Ccr6 | Cd27 | Tbc1d4 |
| Gadd45g | Tnfrsf4 | Tnfsf8 | Cxcr5 | Stat1 |
| Gngt2 | Il17f | Tbc1d4 | Id3 | Rtp4 |
| Gm20069 | Izumo1r | Nav2 | Prkca | Ighm |
| Ifit1 | Mmp9 | Cldnd1 | Ubac2 | Asb2 |
| Hmgn2 | Gm45716 | Tspan32 | Rnaset2b | Il17f |
| Gzmb | Mmd | Rtp4 | Ikzf2 | Cpe |
| Malat1 | Ifi27l2a | Lag3 | Ifi27l2a | Iigp1 |
| Cpe | Lgmn | Ighm | Dynll1 | Usp18 |
| | Cd27 | Trbc1 | Pard6g | Sccpdh |
| | Il1r2 | Cd9 | Ephx1 | Ikzf2 |
| | Pdcd1 | Ctss | Tox | Ccnd2 |
| | Lmna | Ctla4 | Lag3 | Cd27 |
| | Slc15a3 | Jaml | Ptprc | Bst2 |
| | Ptms | Iigp1 | Icam2 | Ifi203 |
| | Malat1 | St3gal6 | Eif4a2 | Eif4a2 |
| | Foxp3 | Ccr7 | Il6st | Mndal |
| | Tox | Klf3 | Ighm | Ifi47 |
| | Cd81 | Rgs10 | Malt1 | Il27ra |
| | Ehd1 | Zbtb20 | St13 | Xaf1 |
| | Jchain | Id3 | Ptpn11 | Pard6g |
| | Sccpdh | Nt5e | Hspa5 | Malat1 |
| | Gm26825 | Asb2 | Gstp3 | Id3 |
| Havcr2 | Hmgn1 | Angptl2 | Irf7 | |
| Cpe | Tox | Evl | Hspa5 | |
| Ighm | Adk | 2310001H17Rik | Cd83 | |
| Ccnd2 | Maf | Tcf7 | Ifi209 | |
| Ecm1 | Lmo4 | Isg15 | Rorc | |
| Dnajb1 | Ifit1 | Calr | Zfp36l1 | |
| Hsp90aa1 | Ar | Klrb1c | Gm12840 | |
| Msmo1 | Ndufa4 | Tpi1 | Zbp1 | |
| Ikzf2 | Aqp3 | Rgcc | Acyp1 | |
| Samsn1 | Il6ra | Sec14l1 | Pdia6 | |
| Fgl2 | Chd3 | Fam162a | Evl | |
| Sdc4 | Stat1 | Isyna1 | Rnaset2a | |
| Isg15 | Tcrg-C4 | Hnrnpc | Trim30a | |
| | Rflnb | Batf | Hnrnpc | |
| | Bcl2 | Sept7 | St13 | |
| | Arl5c | Pcbd2 | Chd3 | |
| | Ikzf3 | Sccpdh | Ifi27 | |
| | Isg15 | Eea1 | Galm | |
| | Mtss1 | Zfp36l1 | Jun | |
| | Art2b | Il27ra | Pdcd1 | |
| | Cpe | Gadd45b | Isg20 | |
| | Foxp1 | Ifi27 | Phf11c | |
| | Ifi203 | Tnfsf8 | Ccr9 | |
| | | Rbms2 | Gbp2 | |
| | | Sh2d1a | Tesc | |
| | | Stat1 | Pde6d | |
| | | Ivns1abp | Hsp90b1 | |
| | | Aldoa | Calr | |
| | | Pdia6 | Irf9 | |
| | | Hivep2 | Gadd45b | |

TABLE 4-continued

Tissue specific genes downregulated in EAE-v-Untreated

| SI | colon | spleen | PP | mLN |
|---|---|---|---|---|
| | | | Phactr2 | Slfn5 |
| | | | Vamp5 | Prg4 |
| | | | Elavl1 | Clec2d |
| | | | Gm42722 | Ptms |
| | | | Lig1 | Tnfsf8 |
| | | | Hexa | Rnaset2b |
| | | | Dennd2d | Tgtp1 |
| | | | Kdm6b | Gm47283 |
| | | | Tspan32 | Phactr2 |
| | | | Orai1 | Nav2 |
| | | | Hsbp1 | Gm20069 |
| | | | Cd74 | Creg1 |
| | | | Acyp1 | Ivns1abp |
| | | | Cyfip1 | Sh2d1a |
| | | | Nfatc1 | Cd5 |
| | | | Hsp90b1 | AC149090.1 |
| | | | Pacsin1 | BC147527 |
| | | | Cdk2ap2 | Arhgap39 |
| | | | Tnfrsf9 | Icam2 |
| | | | Egr2 | Mrps6 |
| | | | Ctsb | Rgs10 |
| | | | Mrps6 | Pdia4 |
| | | | Il21 | Malt1 |
| | | | Ptger2 | Hic1 |
| | | | Asb2 | Dynll1 |
| | | | Pfkp | Smco4 |
| | | | Dbi | Rgcc |
| | | | Tuba1b | Mmd |
| | | | Pfkl | Ctsb |
| | | | Ndufa3 | Gbp4 |
| | | | Rnf19a | Pml |
| | | | Smarcb1 | Glrx |
| | | | H2-Q2 | Actn1 |
| | | | Malat1 | H2-Q2 |
| | | | Plekho1 | Fos |
| | | | Itgb3bp | Tox |
| | | | Smc4 | Isyna1 |
| | | | Smco4 | Ptpn7 |
| | | | Stx11 | Ttc3 |
| | | | Ptms | Hsph1 |
| | | | Cd9 | Phf11b |
| | | | Decr1 | Cyb5b |
| | | | Itpkb | Hsp90aa1 |
| | | | Bbip1 | Hspe1 |
| | | | Dguok | Rbm5 |
| | | | Baz1a | Igtp |
| | | | Slc9a9 | Hexa |
| | | | Ap1s2 | Dbnl |
| | | | Top1 | Nt5e |
| | | | Ndufc1 | Sdc4 |
| | | | Hmgn2 | Mitd1 |
| | | | Tubb2a | Gimap7 |
| | | | Hmgn1 | |
| | | | Hsp90ab1 | |
| | | | Hsp90aa1 | |
| | | | Ptges3 | |
| | | | Galm | |
| | | | Coa3 | |
| | | | Rasl11a | |
| | | | Mmd | |
| | | | Chtf8 | |
| | | | Ppil3 | |
| | | | Zranb2 | |
| | | | Mrps21 | |
| | | | Meaf6 | |
| | | | Clec2d | |
| | | | Trim8 | |
| | | | Zap70 | |

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A method of shifting T cell balance in an in vitro population of cells comprising migratory Th17 cells capable of migration to a central nervous system (CNS), wherein the population of cells is obtained from a spleen of a mouse model induced to have experimental autoimmune encephalomyelitis (EAE), said method comprising contacting the population of cells comprising migratory Th17 cells with a genetic modifying agent targeting a Cxcr6 gene or gene transcripts and capable of reducing expression of Cxcr6, wherein the migratory Th17 cells express a gene signature comprising Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a, or Crip1.

2. The method of claim 1, wherein the migratory Th17 cells are shifted towards non-pathogenic Th17 cells and/or are shifted away from pathogenic Th17 cells.

3. The method of claim 1, wherein the genetic modifying agent comprises a CRISPR system, a RNAi system, a zinc finger nuclease system, a TALE system, or a meganuclease.

4. The method of claim 1, wherein the population of cells further comprises naïve T cells and/or Th1 cells.

5. The method of claim 1, further comprising detecting in single Th17 cells the expression of a gene signature comprising Cxcr6, AA467197, Bhlhe40, Nkg7, Ifngr1, Ccr2, Id2, Ostf1, Lgals1, S100a10, Hcst, Lgals3, Cd2, Vim, S100a6, Arl6ip5, Selplg, Ctsw, Cd48, S100a4, Ms4a4b, Anxa1, Itgb1, Sema4a, or Crip1, wherein the single Th17 cells are single migratory Th17 cells contacted by the genetic modifying agent.

6. The method of claim 5, wherein the gene signature is detected by single cell RNA-seq, immunofluorescence, or fluorescence activated cell sorting (FACS).

7. The method of claim 5, wherein the migratory Th17 cells expressing the gene signature are quantitated.

8. The method of claim 1, further comprising detecting in single Th17 cells the expression of a gene signature comprising Slamf6, Ccr6, Rps29, Ifi2712a, Rps28, Rps20, Rpl12, Rplp1, Tnfsf8, Il6ra, Timp2, Sell, Nav2, Tcf7, Saraf, Tmem176b, Tbc1d4, Ccr7, Izumo1r, Asap1, Lamp1, 5830411N06Rik, Ndufa4, Ctss, or Adk, wherein the single Th17 cells are single migratory Th17 cells contacted by the genetic modifying agent.

9. The method of claim 8, wherein the gene signature is detected by single cell RNA-seq, immunofluorescence, or fluorescence activated cell sorting (FACS).

10. The method of claim 8, wherein the migratory Th17 cells expressing the gene signature are quantitated.

11. The method of claim 3, wherein the CRISPR system comprises a CRISPR-Cas base editing system, a prime editor system, or a CAST system.

12. The method of claim 11, wherein the CRISPR system comprises a guide molecule configured to bind to a target sequence of the Cxcr6 gene.

13. The method of claim 11, wherein the CRISPR system comprises a guide molecule configured to bind to a target sequence of a Cxcr6 transcript.

14. The method of claim 5, wherein the detecting is detecting the expression of Cxcr6.

15. The method of claim 8, wherein the detecting is detecting the expression of Slamf6.

* * * * *